(12) United States Patent
Ahituv et al.

(10) Patent No.: US 11,730,828 B2
(45) Date of Patent: Aug. 22, 2023

(54) GENE THERAPY FOR HAPLOINSUFFICIENCY

(71) Applicant: The Regents of the University of California, Oakland, CA (US)

(72) Inventors: Nadav Ahituv, San Francisco, CA (US); Navneet Matharu, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 275 days.

(21) Appl. No.: 16/479,177

(22) PCT Filed: Feb. 7, 2018

(86) PCT No.: PCT/US2018/017186
§ 371 (c)(1),
(2) Date: Jul. 18, 2019

(87) PCT Pub. No.: WO2018/148256
PCT Pub. Date: Aug. 16, 2018

(65) Prior Publication Data
US 2019/0351074 A1    Nov. 21, 2019

Related U.S. Application Data

(60) Provisional application No. 62/455,988, filed on Feb. 7, 2017.

(51) Int. Cl.
| | | |
|---|---|---|
| *C07H 21/02* | (2006.01) | |
| *A61K 48/00* | (2006.01) | |
| *A61P 3/04* | (2006.01) | |
| *A01K 67/027* | (2006.01) | |
| *C12N 9/22* | (2006.01) | |
| *C12N 15/113* | (2010.01) | |
| *C12N 15/86* | (2006.01) | |
| *C12N 15/10* | (2006.01) | |

(52) U.S. Cl.
CPC ...... *A61K 48/0066* (2013.01); *A01K 67/0276* (2013.01); *A61K 48/0016* (2013.01); *A61P 3/04* (2018.01); *C12N 9/22* (2013.01); *C12N 15/102* (2013.01); *C12N 15/113* (2013.01); *C12N 15/86* (2013.01); *A01K 2217/077* (2013.01); *A01K 2227/105* (2013.01); *A01K 2267/0362* (2013.01); *C12N 2310/20* (2017.05)

(58) Field of Classification Search
CPC .................. C12N 15/113; C12N 2310/20
See application file for complete search history.

(56) References Cited

U.S. PATENT DOCUMENTS

| | | | |
|---|---|---|---|
| 2016/0039893 A1 | 2/2016 | Neutzner et al. | |
| 2016/0324987 A1* | 11/2016 | Wang | A61K 9/127 |
| 2016/0338327 A1* | 11/2016 | Kurrasch | C12N 15/113 |
| 2016/0355797 A1 | 12/2016 | Konermann et al. | |

FOREIGN PATENT DOCUMENTS

| | | | |
|---|---|---|---|
| CN | 105358568 A | 2/2016 | |
| EP | 3045537 A1 | 7/2016 | |
| EP | 3510152 A1 | 7/2019 | |
| WO | 2014/204723 A9 | 12/2014 | |
| WO | 2014/204729 A1 | 12/2014 | |
| WO | 2015/089486 A2 | 6/2015 | |
| WO | WO 2016/049163 A2 * | 3/2016 | .......... C12N 15/113 |
| WO | 2016083360 A1 | 6/2016 | |
| WO | 2016/187717 A1 | 12/2016 | |

OTHER PUBLICATIONS

Jin et al. "Generation of genetically modified mice using CRISPR/Cas9 and haploid embryonic stem cell systems." Zoological Research 37, No. 4 (2016): 205.
Li et al., "An episomal CRISPR/Cas9 system to derive vector-free gene modified mammalian cells," *Protein Cell*, Sep. 2016, 7(9):689-691.
PCT/US2018/017186, "International Search Report and Written Opinion" dated Jun. 6, 2018, 16 pages.
EP18750827.0 , "Extended European Search Report", dated Nov. 20, 2020, 15 pages.
JP2019-542540 , "Office Action", dated Jan. 19, 2022, 5 pages.
Matharu et al., "Crispr-Mediated Activation of a Promoter or Enhancer Rescues Obesity Caused by Haploin Sufficiency", Science, vol. 363, Issue 6424, XP0557 48390, Dec. 13, 2018, pp. 1-30.
PCT/US2018/017186 , "Invitation to Pay Add'l Fees and Partial Search Report", dated Apr. 10, 2018, 3 pages.

* cited by examiner

*Primary Examiner* — Amy H Bowman
(74) *Attorney, Agent, or Firm* — Kilpatrick Townsend & Stockton LLP

(57) ABSTRACT

Methods and compositions are provided for activating transcription in a mammalian cell.

8 Claims, 22 Drawing Sheets

Specification includes a Sequence Listing.

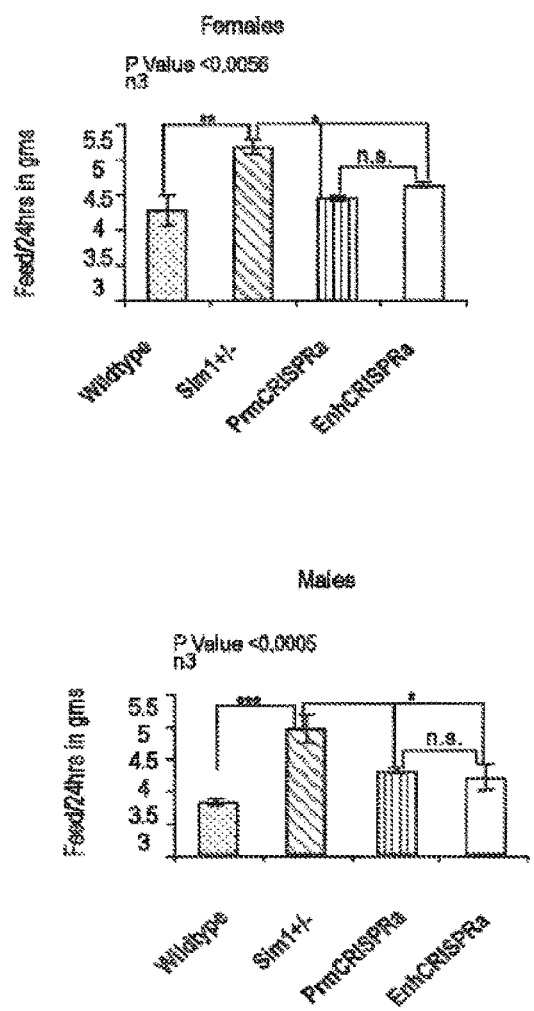
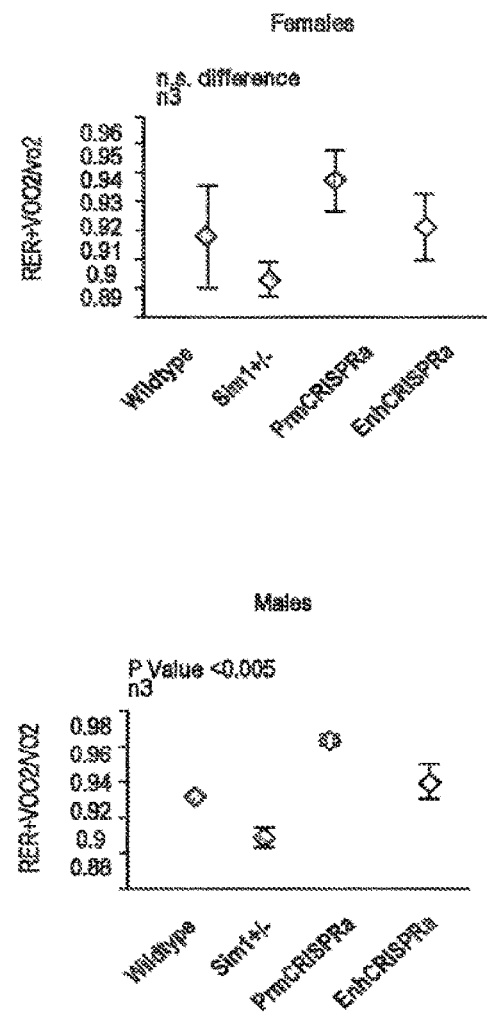
FIG. 2c                    FIG. 2d

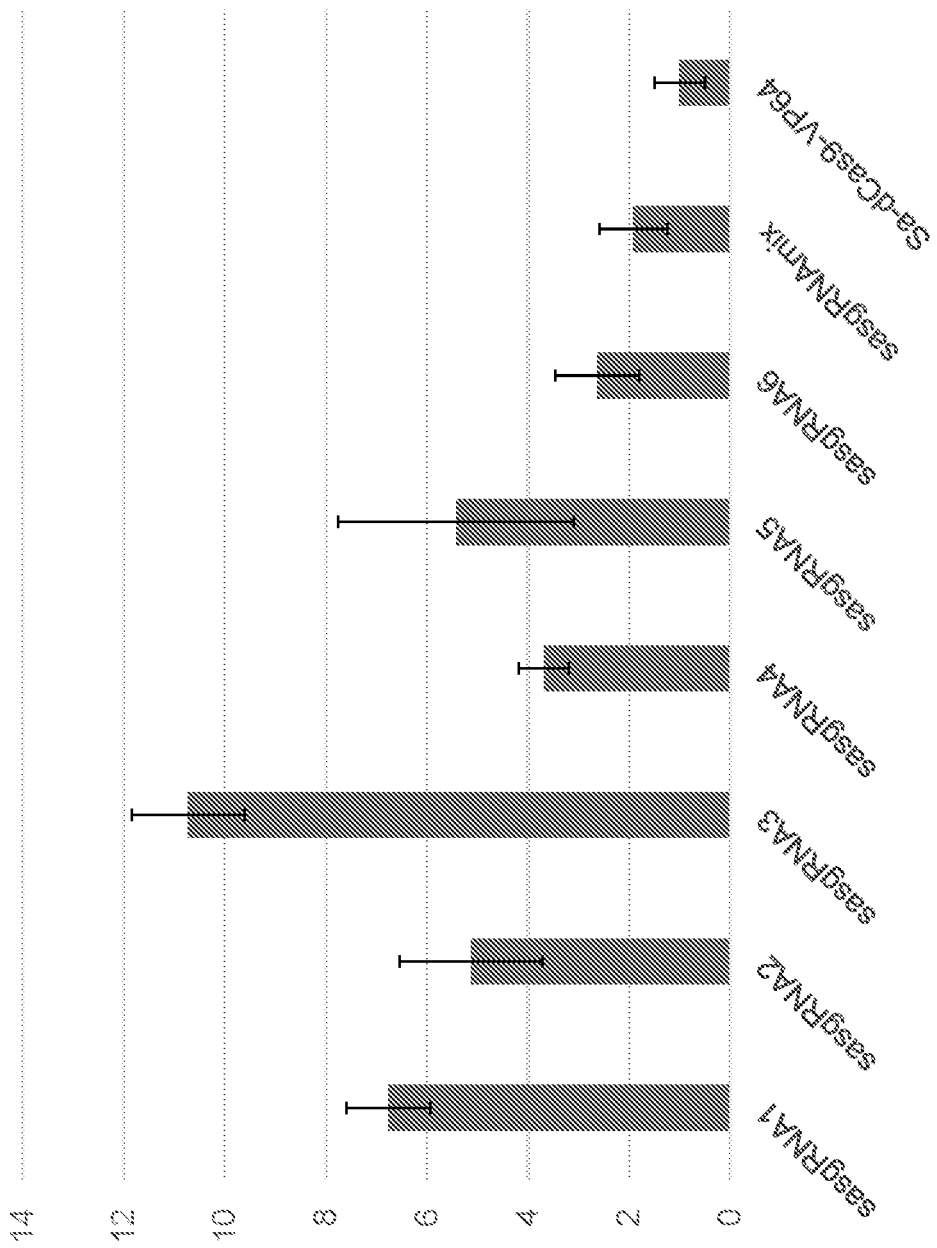

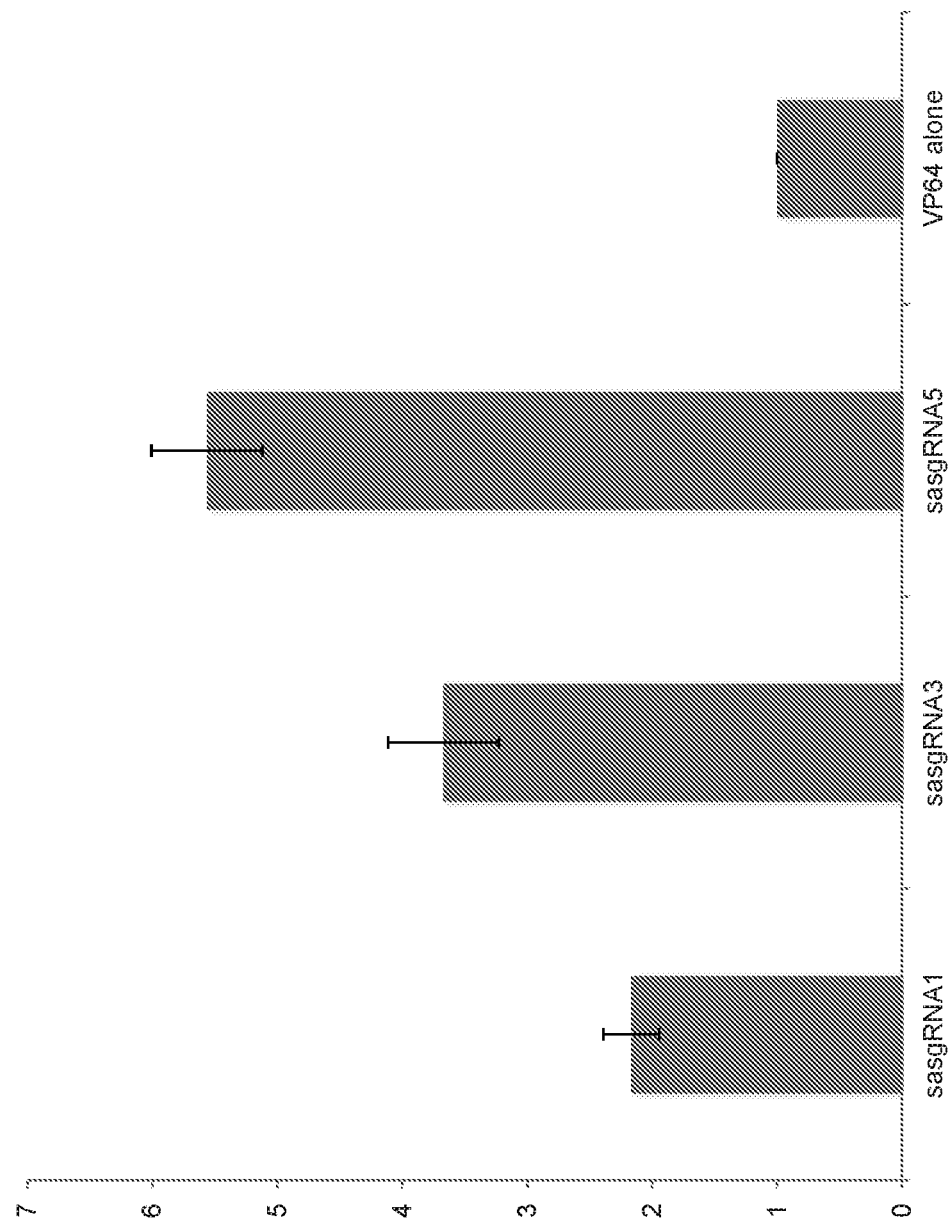

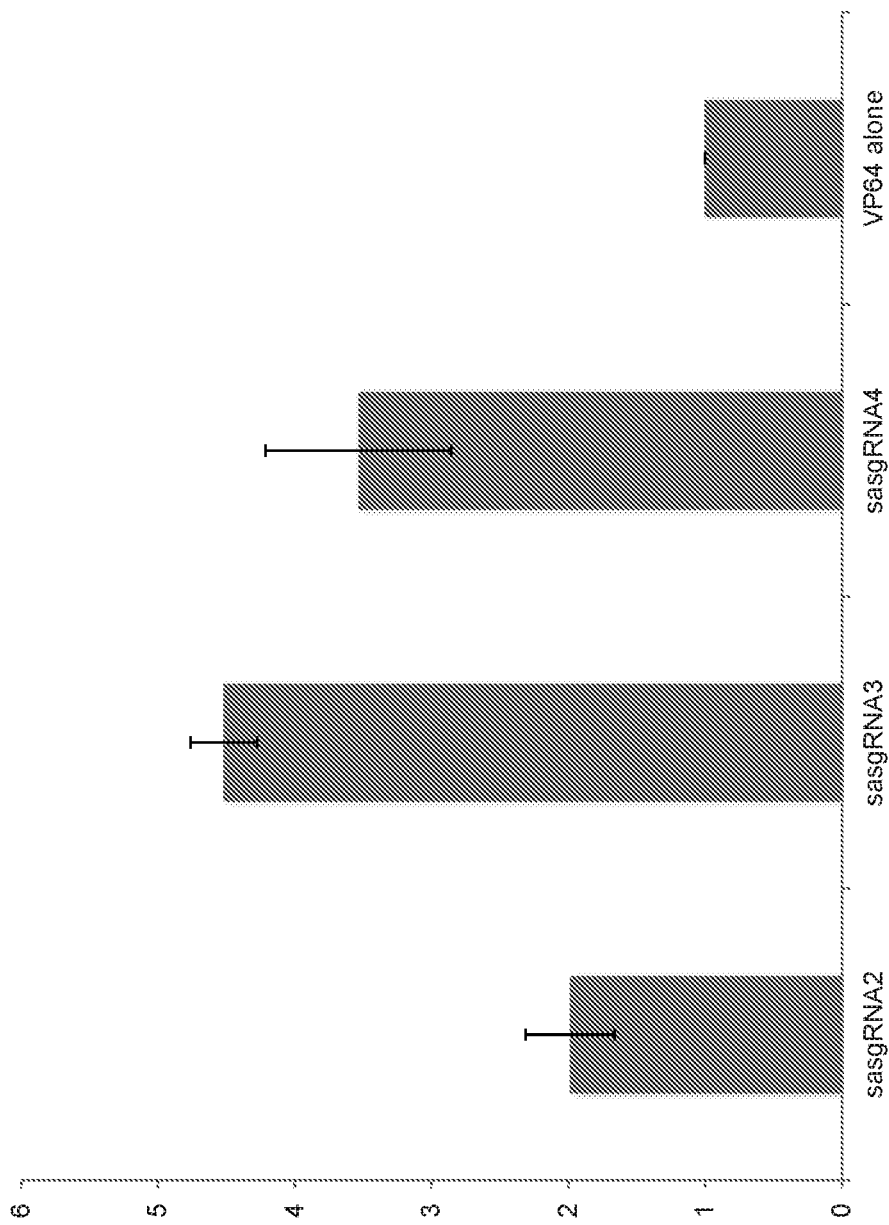

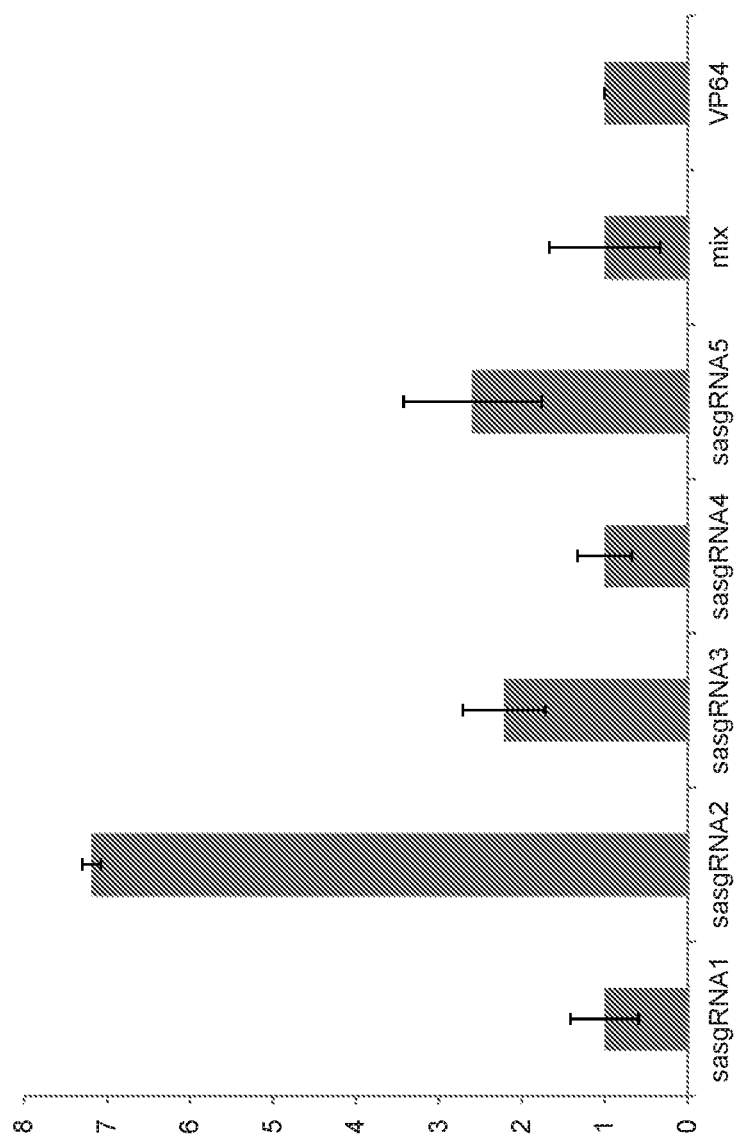

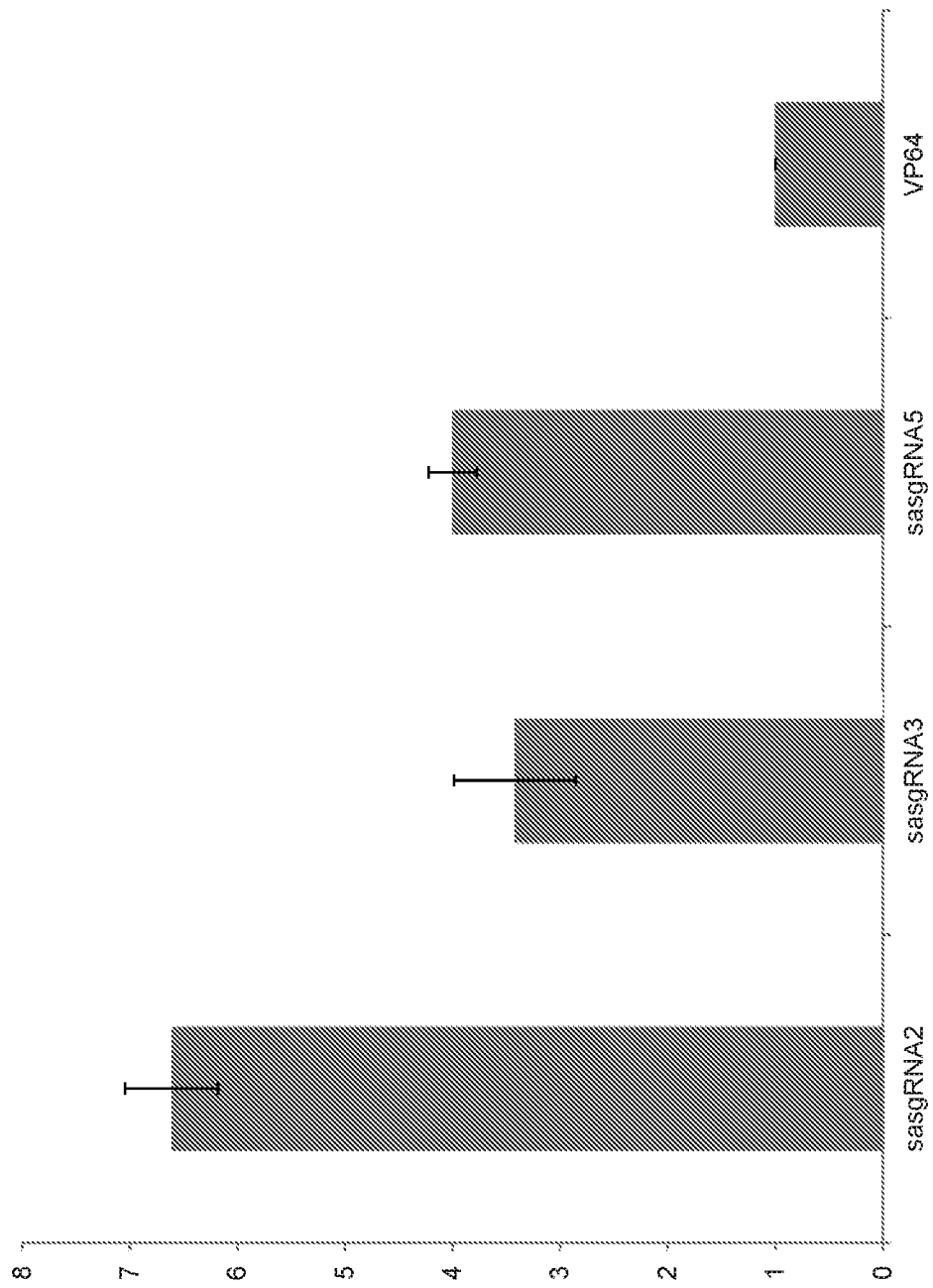

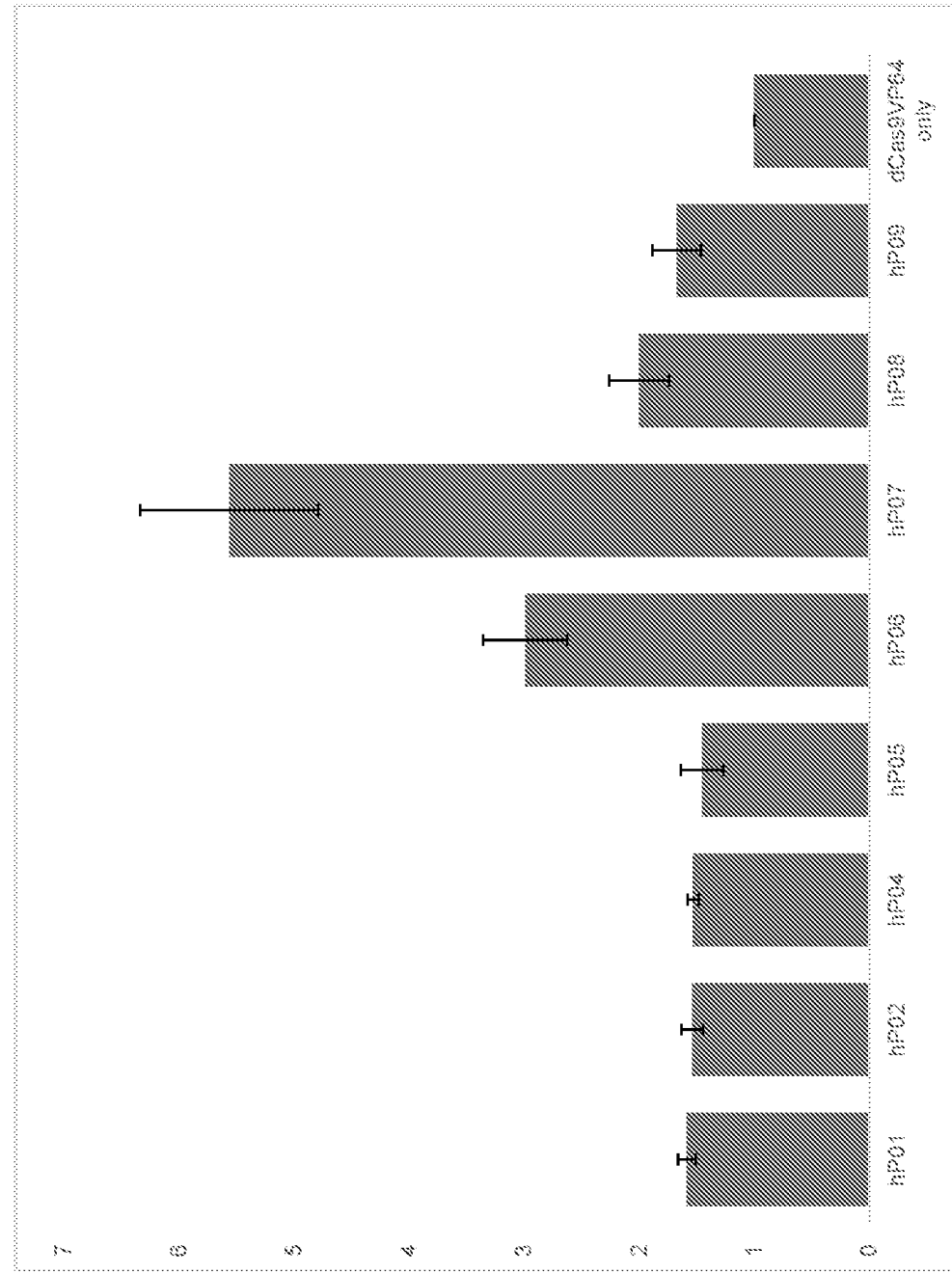

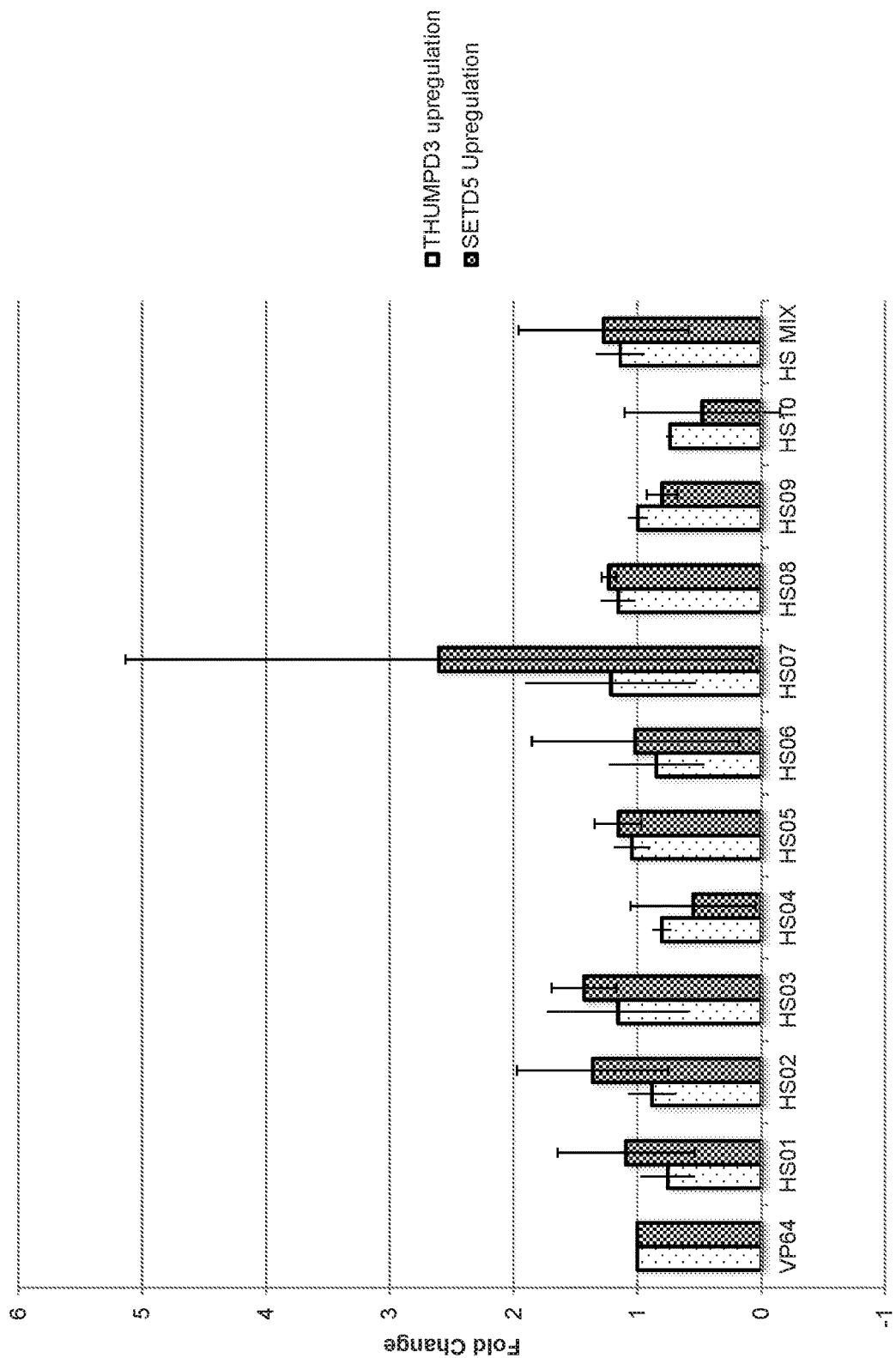

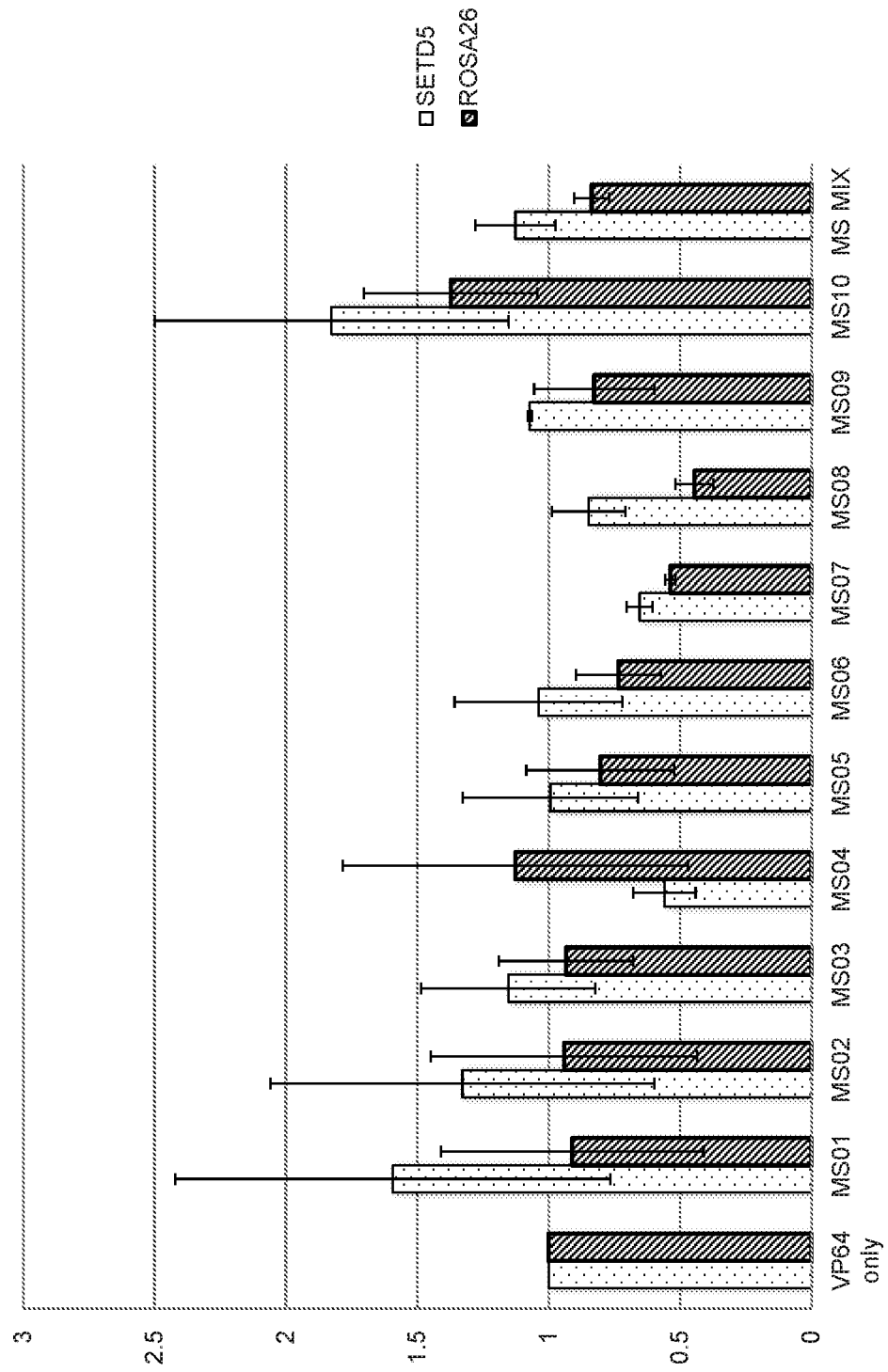

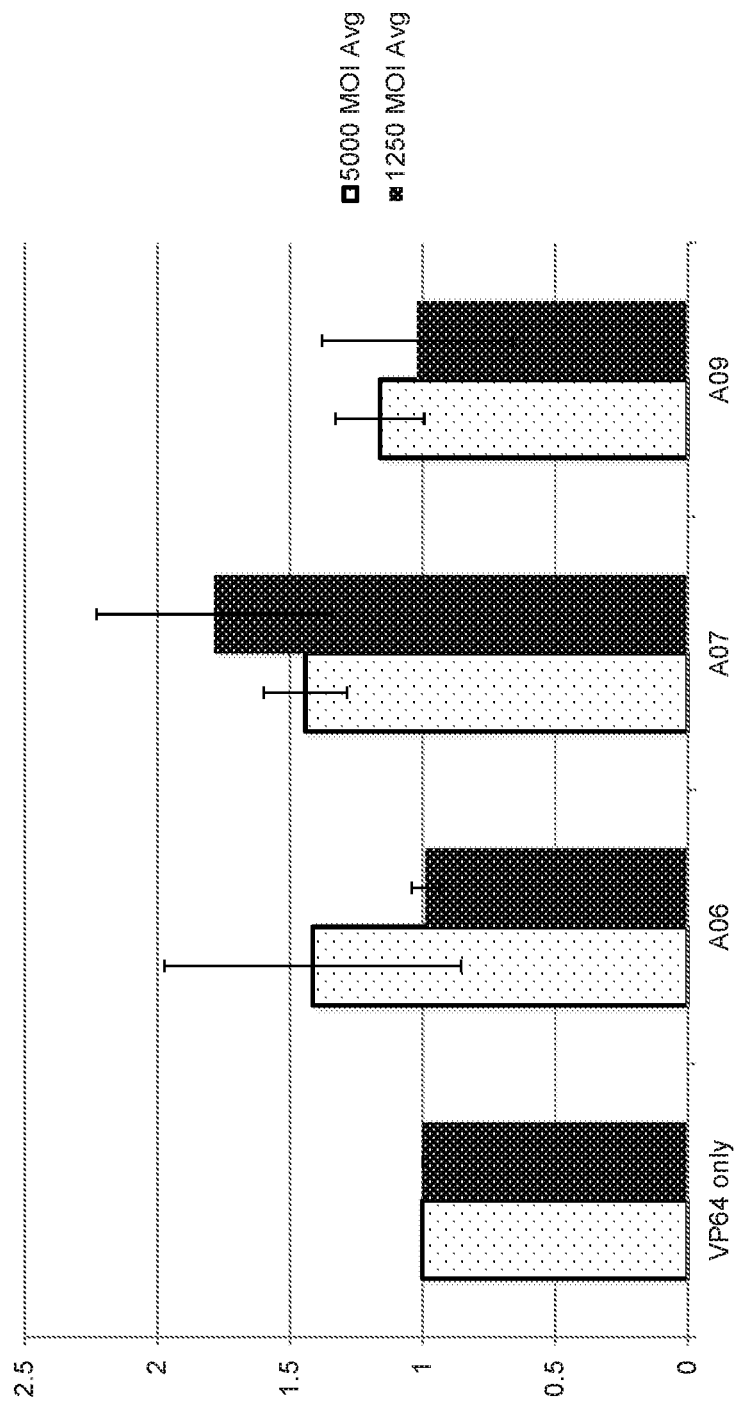

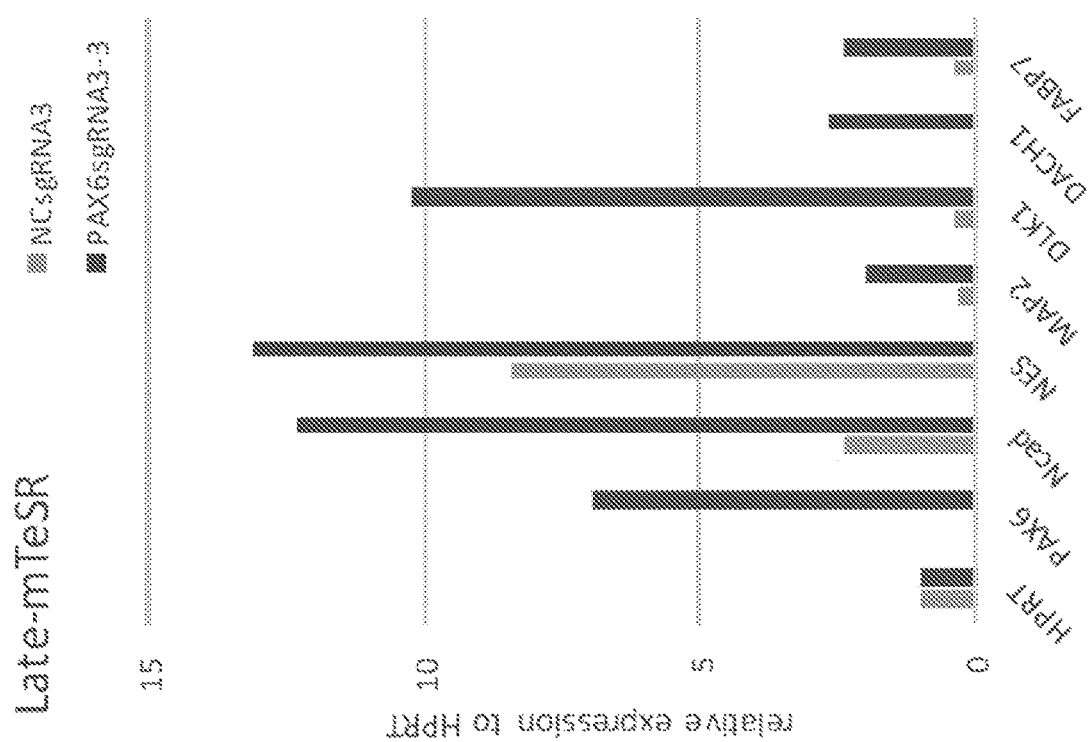

SEQUENCE LISTING

```
<160> NUMBER OF SEQ ID NOS: 95

<210> SEQ ID NO 1
<211> LENGTH: 20
<212> TYPE: DNA
<213> ORGANISM: Artificial Sequence
<220> FEATURE:
<223> OTHER INFORMATION: Synthetic construct

<400> SEQUENCE: 1
gacacggaat tcattgccag                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic construct

<400> SEQUENCE: 2
ctgcgggtta ggtctaccgg                                               20

<210> SEQ ID NO 3
<211> LENGTH: 20
<212> TYPE: DNA
<213> ORGANISM: Artificial Sequence
<220> FEATURE:
<223> OTHER INFORMATION: Synthetic construct

<400> SEQUENCE: 3
gttgagcgct cagtccagcg                                               20

<210> SEQ ID NO 4
<211> LENGTH: 20
<212> TYPE: DNA
<213> ORGANISM: Artificial Sequence
<220> FEATURE:
<223> OTHER INFORMATION: Synthetic construct
```

-continued

```
<400> SEQUENCE: 4
tcccgacgtc gtgcgcgacc                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic construct

<400> SEQUENCE: 5
gctctgaatc ttactacccg                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic construct

<400> SEQUENCE: 6
gctgttaact aaagacaggg                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic construct

<400> SEQUENCE: 7
gtggtctggg tgatctcatg                                               20

<210> SEQ ID NO 8
<211> LENGTH: 21
<212> TYPE: DNA
<213> ORGANISM: Artificial Sequence
<220> FEATURE:
<223> OTHER INFORMATION: Synthetic construct

<400> SEQUENCE: 8
gacaaaggaa catctgagag g                                             21

<210> SEQ ID NO 9
<211> LENGTH: 20
<212> TYPE: DNA
<213> ORGANISM: Artificial Sequence
<220> FEATURE:
<223> OTHER INFORMATION: Synthetic construct

<400> SEQUENCE: 9
gtgatctcat ggggaagagg                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic construct

<400> SEQUENCE: 10
ggctttgatc gtggtctggg                                               20

<210> SEQ ID NO 11
<211> LENGTH: 20
```

```
<212> TYPE: DNA
<213> ORGANISM: Artificial Sequence
<220> FEATURE:
<223> OTHER INFORMATION: Synthetic construct

<400> SEQUENCE: 11
gcgagcccag tcgcgtgggg                                          20

<210> SEQ ID NO 12
<211> LENGTH: 20
<212> TYPE: DNA
<213> ORGANISM: Artificial Sequence
<220> FEATURE:
<223> OTHER INFORMATION: Synthetic construct

<400> SEQUENCE: 12
gccaagaatt ggccaaaggg                                          20

<210> SEQ ID NO 13
<211> LENGTH: 159
<212> TYPE: PRT
<213> ORGANISM: Homo sapiens

<400> SEQUENCE: 13
```

Glu Lys Cys Leu Ser Val Ala Cys Leu Asp Lys Asn Glu Leu Ser Asp
1               5                   10                  15

His Leu Asp Ala Met Asp Ser Asn Leu Asp Asn Leu Gln Thr Met Leu
            20                  25                  30

Ser Ser His Gly Phe Ser Val Asp Thr Ser Ala Leu Leu Asp Leu Phe
        35                  40                  45

Ser Pro Ser Val Thr Val Pro Asp Met Ser Leu Pro Asp Leu Asp Ser
    50                  55                  60

Ser Leu Ala Ser Ile Gln Glu Leu Leu Ser Pro Gln Glu Pro Pro Arg
65                  70                  75                  80

Pro Pro Glu Ala Glu Asn Ser Ser Pro Asp Ser Gly Lys Gln Leu Val
                85                  90                  95

His Tyr Thr Ala Gln Pro Leu Phe Leu Leu Asp Pro Gly Ser Val Asp
            100                 105                 110

Thr Gly Ser Asn Asp Leu Pro Val Leu Phe Glu Leu Gly Glu Gly Ser
        115                 120                 125

Tyr Phe Ser Glu Gly Asp Gly Phe Ala Glu Asp Pro Thr Ile Ser Leu
    130                 135                 140

Leu Thr Gly Ser Glu Pro Pro Lys Ala Lys Asp Pro Thr Val Ser
145                 150                 155

```
<210> SEQ ID NO 14
<211> LENGTH: 11
<212> TYPE: PRT
<213> ORGANISM: Unknown
<220> FEATURE:
<223> OTHER INFORMATION: Herpes simplex virus

<400> SEQUENCE: 14
```

Asp Ala Leu Asp Asp Phe Asp Leu Asp Met Leu
1               5                   10

```
<210> SEQ ID NO 15
<211> LENGTH: 50
<212> TYPE: PRT
<213> ORGANISM: Artificial Sequence
<220> FEATURE:
<223> OTHER INFORMATION: Synthetic construct
```

<400> SEQUENCE: 15

Asp Ala Leu Asp Asp Phe Asp Leu Asp Met Leu Gly Ser Asp Ala Leu
1               5                   10                  15

Asp Asp Phe Asp Leu Asp Met Leu Gly Ser Asp Ala Leu Asp Asp Phe
            20                  25                  30

Asp Leu Asp Met Leu Gly Ser Asp Ala Leu Asp Asp Phe Asp Leu Asp
        35                  40                  45

Met Leu
    50

<210> SEQ ID NO 16
<211> LENGTH: 261
<212> TYPE: PRT
<213> ORGANISM: Homo sapiens

<400> SEQUENCE: 16

Ser Gln Tyr Leu Pro Asp Thr Asp Asp Arg His Arg Ile Glu Glu Lys
1               5                   10                  15

Arg Lys Arg Thr Tyr Glu Thr Phe Lys Ser Ile Met Lys Lys Ser Pro
            20                  25                  30

Phe Ser Gly Pro Thr Asp Pro Arg Pro Pro Arg Ile Ala Val
            35                  40                  45

Pro Ser Arg Ser Ser Ala Ser Val Pro Lys Pro Ala Pro Gln Pro Tyr
50                  55                  60

Pro Phe Thr Ser Ser Leu Ser Thr Ile Asn Tyr Asp Glu Phe Pro Thr
65                  70                  75                  80

Met Val Phe Pro Ser Gly Gln Ile Ser Gln Ala Ser Ala Leu Ala Pro
                85                  90                  95

Ala Pro Pro Gln Val Leu Pro Gln Ala Pro Ala Pro Ala Pro Ala Pro
            100                 105                 110

Ala Met Val Ser Ala Leu Ala Gln Ala Pro Ala Pro Val Pro Val Leu
        115                 120                 125

Ala Pro Gly Pro Pro Gln Ala Val Ala Pro Pro Ala Pro Lys Pro Thr
130                 135                 140

Gln Ala Gly Glu Gly Thr Leu Ser Glu Ala Leu Leu Gln Leu Gln Phe
145                 150                 155                 160

Asp Asp Glu Asp Leu Gly Ala Leu Leu Gly Asn Ser Thr Asp Pro Ala
                165                 170                 175

Val Phe Thr Asp Leu Ala Ser Val Asp Asn Ser Glu Phe Gln Gln Leu
            180                 185                 190

Leu Asn Gln Gly Ile Pro Val Ala Pro His Thr Thr Glu Pro Met Leu
        195                 200                 205

Met Glu Tyr Pro Glu Ala Ile Thr Arg Leu Val Thr Gly Ala Gln Arg
    210                 215                 220

Pro Pro Asp Pro Ala Pro Ala Pro Leu Gly Ala Pro Gly Leu Pro Asn
225                 230                 235                 240

Gly Leu Leu Ser Gly Asp Glu Asp Phe Ser Ser Ile Ala Asp Met Asp
                245                 250                 255

Phe Ser Ala Leu Leu
            260

<210> SEQ ID NO 17
<211> LENGTH: 318
<212> TYPE: PRT
<213> ORGANISM: Mus musculus

<400> SEQUENCE: 17

```
Met Glu Leu Leu Ser Pro Pro Leu Arg Asp Ile Asp Leu Thr Gly Pro
1               5                   10                  15

Asp Gly Ser Leu Cys Ser Phe Glu Thr Ala Asp Asp Phe Tyr Asp Asp
            20                  25                  30

Pro Cys Phe Asp Ser Pro Asp Leu Arg Phe Phe Glu Asp Leu Asp Pro
        35                  40                  45

Arg Leu Val His Met Gly Ala Leu Leu Lys Pro Glu Glu His Ala His
    50                  55                  60

Phe Pro Thr Ala Val His Pro Gly Pro Gly Ala Arg Glu Asp Glu His
65                  70                  75                  80

Val Arg Ala Pro Ser Gly His His Gln Ala Gly Arg Cys Leu Leu Trp
                85                  90                  95

Ala Cys Lys Ala Cys Lys Arg Lys Thr Thr Asn Ala Asp Arg Arg Lys
            100                 105                 110

Ala Ala Thr Met Arg Glu Arg Arg Arg Leu Ser Lys Val Asn Glu Ala
        115                 120                 125

Phe Glu Thr Leu Lys Arg Cys Thr Ser Ser Asn Pro Asn Gln Arg Leu
130                 135                 140

Pro Lys Val Glu Ile Leu Arg Asn Ala Ile Arg Tyr Ile Glu Gly Leu
145                 150                 155                 160

Gln Ala Leu Leu Arg Asp Gln Asp Ala Ala Pro Gly Ala Ala Ala Ala
                165                 170                 175

Phe Tyr Ala Pro Gly Pro Leu Pro Pro Gly Arg Gly Ser Glu His Tyr
            180                 185                 190

Ser Gly Asp Ser Asp Ala Ser Ser Pro Arg Ser Asn Cys Ser Asp Gly
        195                 200                 205

Met Met Asp Tyr Ser Gly Pro Pro Ser Gly Pro Arg Arg Gln Asn Gly
    210                 215                 220

Tyr Asp Thr Ala Tyr Tyr Ser Glu Ala Ala Arg Glu Ser Arg Pro Gly
225                 230                 235                 240

Lys Ser Ala Ala Val Ser Ser Leu Asp Cys Leu Ser Ser Ile Val Glu
                245                 250                 255

Arg Ile Ser Thr Asp Ser Pro Ala Ala Pro Ala Leu Leu Leu Ala Asp
            260                 265                 270

Ala Pro Pro Glu Ser Pro Pro Gly Pro Pro Glu Gly Ala Ser Leu Ser
        275                 280                 285

Asp Thr Glu Gln Gly Thr Gln Thr Pro Ser Pro Asp Ala Ala Pro Gln
    290                 295                 300

Cys Pro Ala Gly Ser Asn Pro Asn Ala Ile Tyr Gln Val Leu
305                 310                 315
```

<210> SEQ ID NO 18
<211> LENGTH: 190
<212> TYPE: PRT
<213> ORGANISM: Unknown
<220> FEATURE:
<223> OTHER INFORMATION: Epstein-Barr virus

<400> SEQUENCE: 18

```
Arg Asp Ser Arg Glu Gly Met Phe Leu Pro Lys Pro Glu Ala Gly Ser
1               5                   10                  15

Ala Ile Ser Asp Val Phe Glu Gly Arg Glu Val Cys Gln Pro Lys Arg
            20                  25                  30
```

```
Ile Arg Pro Phe His Pro Pro Gly Ser Pro Trp Ala Asn Arg Pro Leu
            35                  40                  45

Pro Ala Ser Leu Ala Pro Thr Pro Thr Gly Pro Val His Glu Pro Val
 50                  55                  60

Gly Ser Leu Thr Pro Ala Pro Val Pro Gln Pro Leu Asp Pro Ala Pro
 65                  70                  75                  80

Ala Val Thr Pro Glu Ala Ser His Leu Leu Glu Asp Pro Asp Glu Glu
                 85                  90                  95

Thr Ser Gln Ala Val Lys Ala Leu Arg Glu Met Ala Asp Thr Val Ile
                100                 105                 110

Pro Gln Lys Glu Glu Ala Ala Ile Cys Gly Gln Met Asp Leu Ser His
                115                 120                 125

Pro Pro Pro Arg Gly His Leu Asp Glu Leu Thr Thr Thr Leu Glu Ser
            130                 135                 140

Met Thr Glu Asp Leu Asn Leu Asp Ser Pro Leu Thr Pro Glu Leu Asn
145                 150                 155                 160

Glu Ile Leu Asp Thr Phe Leu Asn Asp Glu Cys Leu Leu His Ala Met
                165                 170                 175

His Ile Ser Thr Gly Leu Ser Ile Phe Asp Thr Ser Leu Phe
                180                 185                 190

<210> SEQ ID NO 19
<211> LENGTH: 366
<212> TYPE: PRT
<213> ORGANISM: Homo sapiens

<400> SEQUENCE: 19

Met Asp Ser Asp Glu Met Val Glu Ala Val Glu Gly His Leu
  1               5                  10                  15

Asp Asp Asp Gly Leu Pro His Gly Phe Cys Thr Val Thr Tyr Ser Ser
                 20                  25                  30

Thr Asp Arg Phe Glu Gly Asn Phe Val His Gly Glu Lys Asn Gly Arg
             35                  40                  45

Gly Lys Phe Phe Phe Phe Asp Gly Ser Thr Leu Glu Gly Tyr Tyr Val
 50                  55                  60

Asp Asp Ala Leu Gln Gly Gln Gly Val Tyr Thr Tyr Glu Asp Gly Gly
 65                  70                  75                  80

Val Leu Gln Gly Thr Tyr Val Asp Gly Glu Leu Asn Gly Pro Ala Gln
                 85                  90                  95

Glu Tyr Asp Thr Asp Gly Arg Leu Ile Phe Lys Gly Gln Tyr Lys Asp
                100                 105                 110

Asn Ile Arg His Gly Val Cys Trp Ile Tyr Tyr Pro Asp Gly Gly Ser
            115                 120                 125

Leu Val Gly Glu Val Asn Glu Asp Gly Glu Met Thr Gly Glu Lys Ile
            130                 135                 140

Ala Tyr Val Tyr Pro Asp Glu Arg Thr Ala Leu Tyr Gly Lys Phe Ile
145                 150                 155                 160

Asp Gly Glu Met Ile Glu Gly Lys Leu Ala Thr Leu Met Ser Thr Glu
                165                 170                 175

Glu Gly Arg Pro His Phe Glu Leu Met Pro Gly Asn Ser Val Tyr His
            180                 185                 190

Phe Asp Lys Ser Thr Ser Ser Cys Ile Ser Thr Asn Ala Leu Leu Pro
            195                 200                 205

Asp Pro Tyr Glu Ser Glu Arg Val Tyr Val Ala Glu Ser Leu Ile Ser
        210                 215                 220
```

```
Ser Ala Gly Glu Gly Leu Phe Ser Lys Val Ala Val Gly Pro Asn Thr
225                 230                 235                 240

Val Met Ser Phe Tyr Asn Gly Val Arg Ile Thr His Gln Glu Val Asp
            245                 250                 255

Ser Arg Asp Trp Ala Leu Asn Gly Asn Thr Leu Ser Leu Asp Glu Glu
        260                 265                 270

Thr Val Ile Asp Val Pro Glu Pro Tyr Asn His Val Ser Lys Tyr Cys
    275                 280                 285

Ala Ser Leu Gly His Lys Ala Asn His Ser Phe Thr Pro Asn Cys Ile
290                 295                 300

Tyr Asp Met Phe Val His Pro Arg Phe Gly Pro Ile Lys Cys Ile Arg
305                 310                 315                 320

Thr Leu Arg Ala Val Glu Ala Asp Glu Glu Leu Thr Val Ala Tyr Gly
            325                 330                 335

Tyr Asp His Ser Pro Pro Gly Lys Ser Gly Pro Glu Ala Pro Glu Trp
        340                 345                 350

Tyr Gln Val Glu Leu Lys Ala Phe Gln Ala Thr Gln Lys
    355                 360                 365

<210> SEQ ID NO 20
<211> LENGTH: 531
<212> TYPE: PRT
<213> ORGANISM: Artificial Sequence
<220> FEATURE:
<223> OTHER INFORMATION: Synthetic construct

<400> SEQUENCE: 20

Glu Ala Ser Gly Ser Gly Arg Ala Asp Ala Leu Asp Asp Phe Asp Leu
1               5                   10                  15

Asp Met Leu Gly Ser Asp Ala Leu Asp Asp Phe Asp Leu Asp Met Leu
            20                  25                  30

Gly Ser Asp Ala Leu Asp Asp Phe Asp Leu Asp Met Leu Gly Ser Asp
        35                  40                  45

Ala Leu Asp Asp Phe Asp Leu Asp Met Leu Ile Asn Ser Arg Ser Ser
50                  55                  60

Gly Ser Pro Lys Lys Lys Arg Lys Val Gly Ser Gln Tyr Leu Pro Asp
65                  70                  75                  80

Thr Asp Asp Arg His Arg Ile Glu Glu Lys Arg Lys Arg Thr Tyr Glu
            85                  90                  95

Thr Phe Lys Ser Ile Met Lys Lys Ser Pro Phe Ser Gly Pro Thr Asp
        100                 105                 110

Pro Arg Pro Pro Arg Arg Ile Ala Val Pro Ser Arg Ser Ser Ala
        115                 120                 125

Ser Val Pro Lys Pro Ala Pro Gln Pro Tyr Pro Phe Thr Ser Ser Leu
    130                 135                 140

Ser Thr Ile Asn Tyr Asp Glu Phe Pro Thr Met Val Phe Pro Ser Gly
145                 150                 155                 160

Gln Ile Ser Gln Ala Ser Ala Leu Ala Pro Ala Pro Pro Gln Val Leu
            165                 170                 175

Pro Gln Ala Pro Ala Pro Ala Pro Ala Pro Ala Met Val Ser Ala Leu
        180                 185                 190

Ala Gln Ala Pro Ala Pro Val Pro Val Leu Ala Pro Gly Pro Pro Gln
    195                 200                 205

Ala Val Ala Pro Pro Ala Pro Lys Pro Thr Gln Ala Gly Glu Gly Thr
210                 215                 220
```

```
Leu Ser Glu Ala Leu Leu Gln Leu Gln Phe Asp Asp Glu Asp Leu Gly
225                 230                 235                 240

Ala Leu Leu Gly Asn Ser Thr Asp Pro Ala Val Phe Thr Asp Leu Ala
                245                 250                 255

Ser Val Asp Asn Ser Glu Phe Gln Gln Leu Leu Asn Gln Gly Ile Pro
                260                 265                 270

Val Ala Pro His Thr Thr Glu Pro Met Leu Met Glu Tyr Pro Glu Ala
                275                 280                 285

Ile Thr Arg Leu Val Thr Gly Ala Gln Arg Pro Pro Asp Pro Ala Pro
            290                 295                 300

Ala Pro Leu Gly Ala Pro Gly Leu Pro Asn Gly Leu Leu Ser Gly Asp
305                 310                 315                 320

Glu Asp Phe Ser Ser Ile Ala Asp Met Asp Phe Ser Ala Leu Leu Gly
                325                 330                 335

Ser Gly Ser Gly Ser Arg Asp Ser Arg Glu Gly Met Phe Leu Pro Lys
                340                 345                 350

Pro Glu Ala Gly Ser Ala Ile Ser Asp Val Phe Glu Gly Arg Glu Val
            355                 360                 365

Cys Gln Pro Lys Arg Ile Arg Pro Phe His Pro Pro Gly Ser Pro Trp
        370                 375                 380

Ala Asn Arg Pro Leu Pro Ala Ser Leu Ala Pro Thr Pro Thr Gly Pro
385                 390                 395                 400

Val His Glu Pro Val Gly Ser Leu Thr Pro Ala Pro Val Pro Gln Pro
                405                 410                 415

Leu Asp Pro Ala Pro Ala Val Thr Pro Glu Ala Ser His Leu Leu Glu
                420                 425                 430

Asp Pro Asp Glu Glu Thr Ser Gln Ala Val Lys Ala Leu Arg Glu Met
            435                 440                 445

Ala Asp Thr Val Ile Pro Gln Lys Glu Glu Ala Ala Ile Cys Gly Gln
450                 455                 460

Met Asp Leu Ser His Pro Pro Pro Arg Gly His Leu Asp Glu Leu Thr
465                 470                 475                 480

Thr Thr Leu Glu Ser Met Thr Glu Asp Leu Asn Leu Asp Ser Pro Leu
                485                 490                 495

Thr Pro Glu Leu Asn Glu Ile Leu Asp Thr Phe Leu Asn Asp Glu Cys
                500                 505                 510

Leu Leu His Ala Met His Ile Ser Thr Gly Leu Ser Ile Phe Asp Thr
                515                 520                 525

Ser Leu Phe
        530

<210> SEQ ID NO 21
<211> LENGTH: 377
<212> TYPE: PRT
<213> ORGANISM: Homo sapiens

<400> SEQUENCE: 21

Lys Phe Ser Ala Lys Arg Leu Pro Ser Thr Arg Leu Gly Thr Phe Leu
1               5                   10                  15

Glu Asn Arg Val Asn Asp Phe Leu Arg Arg Gln Asn His Pro Glu Ser
                20                  25                  30

Gly Glu Val Thr Val Arg Val Val His Ala Ser Asp Lys Thr Val Glu
            35                  40                  45

Val Lys Pro Gly Met Lys Ala Arg Phe Val Asp Ser Gly Glu Met Ala
```

```
                50                  55                  60
Glu Ser Phe Pro Tyr Arg Thr Lys Ala Leu Phe Ala Phe Glu Glu Ile
 65                  70                  75                  80

Asp Gly Val Asp Leu Cys Phe Phe Gly Met His Val Gln Glu Tyr Gly
                 85                  90                  95

Ser Asp Cys Pro Pro Asn Gln Arg Arg Val Tyr Ile Ser Tyr Leu
            100                 105                 110

Asp Ser Val His Phe Arg Pro Lys Cys Leu Arg Thr Ala Val Tyr
            115                 120                 125

His Glu Ile Leu Ile Gly Tyr Leu Glu Tyr Val Lys Lys Leu Gly Tyr
            130                 135                 140

Thr Thr Gly His Ile Trp Ala Cys Pro Ser Glu Gly Asp Asp Tyr
145                 150                 155                 160

Ile Phe His Cys His Pro Pro Asp Gln Lys Ile Pro Lys Pro Lys Arg
                165                 170                 175

Leu Gln Glu Trp Tyr Lys Lys Met Leu Asp Lys Ala Val Ser Glu Arg
                180                 185                 190

Ile Val His Asp Tyr Lys Asp Ile Phe Lys Gln Ala Thr Glu Asp Arg
                195                 200                 205

Leu Thr Ser Ala Lys Glu Leu Pro Tyr Phe Glu Gly Asp Phe Trp Pro
210                 215                 220

Asn Val Leu Glu Glu Ser Ile Lys Glu Leu Glu Gln Glu Glu Glu
225                 230                 235                 240

Arg Lys Arg Glu Glu Asn Thr Ser Asn Glu Ser Thr Asp Val Thr Lys
                245                 250                 255

Gly Asp Ser Lys Asn Ala Lys Lys Asn Asn Lys Thr Ser Lys
                260                 265                 270

Asn Lys Ser Ser Leu Ser Arg Gly Asn Lys Lys Pro Gly Met Pro
                275                 280                 285

Asn Val Ser Asn Asp Leu Ser Gln Lys Leu Tyr Ala Thr Met Glu Lys
                290                 295                 300

His Lys Glu Val Phe Phe Val Ile Arg Leu Ile Ala Gly Pro Ala Ala
305                 310                 315                 320

Asn Ser Leu Pro Pro Ile Val Asp Pro Asp Pro Leu Ile Pro Cys Asp
                325                 330                 335

Leu Met Asp Gly Arg Asp Ala Phe Leu Thr Leu Ala Arg Asp Lys His
                340                 345                 350

Leu Glu Phe Ser Ser Leu Arg Arg Ala Gln Trp Ser Thr Met Cys Met
                355                 360                 365

Leu Val Glu Leu His Thr Gln Ser Gln
                370                 375

<210> SEQ ID NO 22
<211> LENGTH: 2136
<212> TYPE: PRT
<213> ORGANISM: Homo sapiens

<400> SEQUENCE: 22

Met Ser Arg Ser Arg His Ala Arg Pro Ser Arg Leu Val Arg Lys Glu
 1               5                  10                  15

Asp Val Asn Lys Lys Lys Lys Asn Ser Gln Leu Arg Lys Thr Thr Lys
                20                  25                  30

Gly Ala Asn Lys Asn Val Ala Ser Val Lys Thr Leu Ser Pro Gly Lys
                35                  40                  45
```

-continued

```
Leu Lys Gln Leu Ile Gln Glu Arg Asp Val Lys Lys Thr Glu Pro
     50                  55                  60
Lys Pro Pro Val Pro Val Arg Ser Leu Leu Thr Arg Ala Gly Ala Ala
 65                  70                  75                  80
Arg Met Asn Leu Asp Arg Thr Glu Val Leu Phe Gln Asn Pro Glu Ser
                 85                  90                  95
Leu Thr Cys Asn Gly Phe Thr Met Ala Leu Arg Ser Thr Ser Leu Ser
            100                 105                 110
Arg Arg Leu Ser Gln Pro Pro Leu Val Val Ala Lys Ser Lys Lys Val
        115                 120                 125
Pro Leu Ser Lys Gly Leu Glu Lys Gln His Asp Cys Asp Tyr Lys Ile
130                 135                 140
Leu Pro Ala Leu Gly Val Lys His Ser Glu Asn Asp Ser Val Pro Met
145                 150                 155                 160
Gln Asp Thr Gln Val Leu Pro Asp Ile Glu Thr Leu Ile Gly Val Gln
                165                 170                 175
Asn Pro Ser Leu Leu Lys Gly Lys Ser Gln Glu Thr Thr Gln Phe Trp
            180                 185                 190
Ser Gln Arg Val Glu Asp Ser Lys Ile Asn Ile Pro Thr His Ser Gly
        195                 200                 205
Pro Ala Ala Glu Ile Leu Pro Gly Pro Leu Glu Gly Thr Arg Cys Gly
210                 215                 220
Glu Gly Leu Phe Ser Glu Glu Thr Leu Asn Asp Thr Ser Gly Ser Pro
225                 230                 235                 240
Lys Met Phe Ala Gln Asp Thr Val Cys Ala Pro Phe Pro Gln Arg Ala
                245                 250                 255
Thr Pro Lys Val Thr Ser Gln Gly Asn Pro Ser Ile Gln Leu Glu Glu
            260                 265                 270
Leu Gly Ser Arg Val Glu Ser Leu Lys Leu Ser Asp Ser Tyr Leu Asp
        275                 280                 285
Pro Ile Lys Ser Glu His Asp Cys Tyr Pro Thr Ser Ser Leu Asn Lys
290                 295                 300
Val Ile Pro Asp Leu Asn Leu Arg Asn Cys Leu Ala Leu Gly Gly Ser
305                 310                 315                 320
Thr Ser Pro Thr Ser Val Ile Lys Phe Leu Leu Ala Gly Ser Lys Gln
                325                 330                 335
Ala Thr Leu Gly Ala Lys Pro Asp His Gln Glu Ala Phe Glu Ala Thr
            340                 345                 350
Ala Asn Gln Gln Glu Val Ser Asp Thr Thr Ser Phe Leu Gly Gln Ala
        355                 360                 365
Phe Gly Ala Ile Pro His Gln Trp Glu Leu Pro Gly Ala Asp Pro Val
370                 375                 380
His Gly Glu Ala Leu Gly Glu Thr Pro Asp Leu Pro Glu Ile Pro Gly
385                 390                 395                 400
Ala Ile Pro Val Gln Gly Glu Val Phe Gly Thr Ile Leu Asp Gln Gln
                405                 410                 415
Glu Thr Leu Gly Met Ser Gly Ser Val Val Pro Asp Leu Pro Val Phe
            420                 425                 430
Leu Pro Val Pro Pro Asn Pro Ile Ala Thr Phe Asn Ala Pro Ser Lys
        435                 440                 445
Trp Pro Glu Pro Gln Ser Thr Val Ser Tyr Gly Leu Ala Val Gln Gly
450                 455                 460
Ala Ile Gln Ile Leu Pro Leu Gly Ser Gly His Thr Pro Gln Ser Ser
```

-continued

```
                465                 470                 475                 480
            Ser Asn Ser Glu Lys Asn Ser Leu Pro Pro Val Met Ala Ile Ser Asn
                            485                 490                 495
            Val Glu Asn Glu Lys Gln Val His Ile Ser Phe Leu Pro Ala Asn Thr
                            500                 505                 510
            Gln Gly Phe Pro Leu Ala Pro Glu Arg Gly Leu Phe His Ala Ser Leu
                            515                 520                 525
            Gly Ile Ala Gln Leu Ser Gln Ala Gly Pro Ser Lys Ser Asp Arg Gly
                            530                 535                 540
            Ser Ser Gln Val Ser Val Thr Ser Thr Val His Val Val Asn Thr Thr
            545                 550                 555                 560
            Val Val Thr Met Pro Val Pro Met Val Ser Thr Ser Ser Ser Ser Tyr
                                565                 570                 575
            Thr Thr Leu Leu Pro Thr Leu Glu Lys Lys Arg Lys Arg Cys Gly
                            580                 585                 590
            Val Cys Glu Pro Cys Gln Gln Lys Thr Asn Cys Gly Glu Cys Thr Tyr
                            595                 600                 605
            Cys Lys Asn Arg Lys Asn Ser His Gln Ile Cys Lys Lys Arg Lys Cys
                            610                 615                 620
            Glu Glu Leu Lys Lys Lys Pro Ser Val Val Val Pro Leu Glu Val Ile
            625                 630                 635                 640
            Lys Glu Asn Lys Arg Pro Gln Arg Glu Lys Lys Pro Lys Val Leu Lys
                            645                 650                 655
            Ala Asp Phe Asp Asn Lys Pro Val Asn Gly Pro Lys Ser Glu Ser Met
                            660                 665                 670
            Asp Tyr Ser Arg Cys Gly His Gly Glu Glu Gln Lys Leu Glu Leu Asn
                            675                 680                 685
            Pro His Thr Val Glu Asn Val Thr Lys Asn Glu Asp Ser Met Thr Gly
                            690                 695                 700
            Ile Glu Val Glu Lys Trp Thr Gln Asn Lys Lys Ser Gln Leu Thr Asp
            705                 710                 715                 720
            His Val Lys Gly Asp Phe Ser Ala Asn Val Pro Glu Ala Glu Lys Ser
                            725                 730                 735
            Lys Asn Ser Glu Val Asp Lys Lys Arg Thr Lys Ser Pro Lys Leu Phe
                            740                 745                 750
            Val Gln Thr Val Arg Asn Gly Ile Lys His Val His Cys Leu Pro Ala
                            755                 760                 765
            Glu Thr Asn Val Ser Phe Lys Lys Phe Asn Ile Glu Glu Phe Gly Lys
                            770                 775                 780
            Thr Leu Glu Asn Asn Ser Tyr Lys Phe Leu Lys Asp Thr Ala Asn His
            785                 790                 795                 800
            Lys Asn Ala Met Ser Ser Val Ala Thr Asp Met Ser Cys Asp His Leu
                            805                 810                 815
            Lys Gly Arg Ser Asn Val Leu Val Phe Gln Gln Pro Gly Phe Asn Cys
                            820                 825                 830
            Ser Ser Ile Pro His Ser Ser His Ser Ile Ile Asn His His Ala Ser
                            835                 840                 845
            Ile His Asn Glu Gly Asp Gln Pro Lys Thr Pro Glu Asn Ile Pro Ser
                            850                 855                 860
            Lys Glu Pro Lys Asp Gly Ser Pro Val Gln Pro Ser Leu Leu Ser Leu
            865                 870                 875                 880
            Met Lys Asp Arg Arg Leu Thr Leu Glu Gln Val Val Ala Ile Glu Ala
                            885                 890                 895
```

```
Leu Thr Gln Leu Ser Glu Ala Pro Ser Glu Asn Ser Ser Pro Ser Lys
        900                 905                 910

Ser Glu Lys Asp Glu Glu Ser Glu Gln Arg Thr Ala Ser Leu Leu Asn
        915                 920                 925

Ser Cys Lys Ala Ile Leu Tyr Thr Val Arg Lys Asp Leu Gln Asp Pro
        930                 935                 940

Asn Leu Gln Gly Glu Pro Pro Lys Leu Asn His Cys Pro Ser Leu Glu
945                 950                 955                 960

Lys Gln Ser Ser Cys Asn Thr Val Val Phe Asn Gly Gln Thr Thr Thr
                965                 970                 975

Leu Ser Asn Ser His Ile Asn Ser Ala Thr Asn Gln Ala Ser Thr Lys
        980                 985                 990

Ser His Glu Tyr Ser Lys Val Thr Asn Ser Leu Ser Leu Phe Ile Pro
        995                 1000                1005

Lys Ser Asn Ser Ser Lys Ile Asp Thr Asn Lys Ser Ile Ala Gln
    1010                1015                1020

Gly Ile Ile Thr Leu Asp Asn Cys Ser Asn Asp Leu His Gln Leu
    1025                1030                1035

Pro Pro Arg Asn Asn Glu Val Glu Tyr Cys Asn Gln Leu Leu Asp
    1040                1045                1050

Ser Ser Lys Lys Leu Asp Ser Asp Asp Leu Ser Cys Gln Asp Ala
    1055                1060                1065

Thr His Thr Gln Ile Glu Glu Asp Val Ala Thr Gln Leu Thr Gln
    1070                1075                1080

Leu Ala Ser Ile Ile Lys Ile Asn Tyr Ile Lys Pro Glu Asp Lys
    1085                1090                1095

Lys Val Glu Ser Thr Pro Thr Ser Leu Val Thr Cys Asn Val Gln
    1100                1105                1110

Gln Lys Tyr Asn Gln Glu Lys Gly Thr Ile Gln Lys Pro Pro
    1115                1120                1125

Ser Ser Val His Asn Asn His Gly Ser Ser Leu Thr Lys Gln Lys
    1130                1135                1140

Asn Pro Thr Gln Lys Lys Thr Lys Ser Thr Pro Ser Arg Asp Arg
    1145                1150                1155

Arg Lys Lys Lys Pro Thr Val Val Ser Tyr Gln Glu Asn Asp Arg
    1160                1165                1170

Gln Lys Trp Glu Lys Leu Ser Tyr Met Tyr Gly Thr Ile Cys Asp
    1175                1180                1185

Ile Trp Ile Ala Ser Lys Phe Gln Asn Phe Gly Gln Phe Cys Pro
    1190                1195                1200

His Asp Phe Pro Thr Val Phe Gly Lys Ile Ser Ser Ser Thr Lys
    1205                1210                1215

Ile Trp Lys Pro Leu Ala Gln Thr Arg Ser Ile Met Gln Pro Lys
    1220                1225                1230

Thr Val Phe Pro Pro Leu Thr Gln Ile Lys Leu Gln Arg Tyr Pro
    1235                1240                1245

Glu Ser Ala Glu Glu Lys Val Lys Val Glu Pro Leu Asp Ser Leu
    1250                1255                1260

Ser Leu Phe His Leu Lys Thr Glu Ser Asn Gly Lys Ala Phe Thr
    1265                1270                1275

Asp Lys Ala Tyr Asn Ser Gln Val Gln Leu Thr Val Asn Ala Asn
    1280                1285                1290
```

```
Gln Lys Ala His Pro Leu Thr Gln Pro Ser Ser Pro Pro Asn Gln
    1295                1300                1305

Cys Ala Asn Val Met Ala Gly Asp Asp Gln Ile Arg Phe Gln Gln
    1310                1315                1320

Val Val Lys Glu Gln Leu Met His Gln Arg Leu Pro Thr Leu Pro
    1325                1330                1335

Gly Ile Ser His Glu Thr Pro Leu Pro Glu Ser Ala Leu Thr Leu
    1340                1345                1350

Arg Asn Val Asn Val Val Cys Ser Gly Gly Ile Thr Val Val Ser
    1355                1360                1365

Thr Lys Ser Glu Glu Glu Val Cys Ser Ser Ser Phe Gly Thr Ser
    1370                1375                1380

Glu Phe Ser Thr Val Asp Ser Ala Gln Lys Asn Phe Asn Asp Tyr
    1385                1390                1395

Ala Met Asn Phe Phe Thr Asn Pro Thr Lys Asn Leu Val Ser Ile
    1400                1405                1410

Thr Lys Asp Ser Glu Leu Pro Thr Cys Ser Cys Leu Asp Arg Val
    1415                1420                1425

Ile Gln Lys Asp Lys Gly Pro Tyr Tyr Thr His Leu Gly Ala Gly
    1430                1435                1440

Pro Ser Val Ala Ala Val Arg Glu Ile Met Glu Asn Arg Tyr Gly
    1445                1450                1455

Gln Lys Gly Asn Ala Ile Arg Ile Glu Ile Val Val Tyr Thr Gly
    1460                1465                1470

Lys Glu Gly Lys Ser Ser His Gly Cys Pro Ile Ala Lys Trp Val
    1475                1480                1485

Leu Arg Arg Ser Ser Asp Glu Glu Lys Val Leu Cys Leu Val Arg
    1490                1495                1500

Gln Arg Thr Gly His His Cys Pro Thr Ala Val Met Val Val Leu
    1505                1510                1515

Ile Met Val Trp Asp Gly Ile Pro Leu Pro Met Ala Asp Arg Leu
    1520                1525                1530

Tyr Thr Glu Leu Thr Glu Asn Leu Lys Ser Tyr Asn Gly His Pro
    1535                1540                1545

Thr Asp Arg Arg Cys Thr Leu Asn Glu Asn Arg Thr Cys Thr Cys
    1550                1555                1560

Gln Gly Ile Asp Pro Glu Thr Cys Gly Ala Ser Phe Ser Phe Gly
    1565                1570                1575

Cys Ser Trp Ser Met Tyr Phe Asn Gly Cys Lys Phe Gly Arg Ser
    1580                1585                1590

Pro Ser Pro Arg Arg Phe Arg Ile Asp Pro Ser Ser Pro Leu His
    1595                1600                1605

Glu Lys Asn Leu Glu Asp Asn Leu Gln Ser Leu Ala Thr Arg Leu
    1610                1615                1620

Ala Pro Ile Tyr Lys Gln Tyr Ala Pro Val Ala Tyr Gln Asn Gln
    1625                1630                1635

Val Glu Tyr Glu Asn Val Ala Arg Glu Cys Arg Leu Gly Ser Lys
    1640                1645                1650

Glu Gly Arg Pro Phe Ser Gly Val Thr Ala Cys Leu Asp Phe Cys
    1655                1660                1665

Ala His Pro His Arg Asp Ile His Asn Met Asn Asn Gly Ser Thr
    1670                1675                1680

Val Val Cys Thr Leu Thr Arg Glu Asp Asn Arg Ser Leu Gly Val
```

-continued

```
        1685                1690                1695

Ile Pro Gln Asp Glu Gln Leu His Val Leu Pro Leu Tyr Lys Leu
    1700                1705                1710

Ser Asp Thr Asp Glu Phe Gly Ser Lys Glu Gly Met Glu Ala Lys
    1715                1720                1725

Ile Lys Ser Gly Ala Ile Glu Val Leu Ala Pro Arg Arg Lys Lys
    1730                1735                1740

Arg Thr Cys Phe Thr Gln Pro Val Pro Arg Ser Gly Lys Lys Arg
    1745                1750                1755

Ala Ala Met Met Thr Glu Val Leu Ala His Lys Ile Arg Ala Val
    1760                1765                1770

Glu Lys Lys Pro Ile Pro Arg Ile Lys Arg Lys Asn Asn Ser Thr
    1775                1780                1785

Thr Thr Asn Asn Ser Lys Pro Ser Ser Leu Pro Thr Leu Gly Ser
    1790                1795                1800

Asn Thr Glu Thr Val Gln Pro Glu Val Lys Ser Glu Thr Glu Pro
    1805                1810                1815

His Phe Ile Leu Lys Ser Ser Asp Asn Thr Lys Thr Tyr Ser Leu
    1820                1825                1830

Met Pro Ser Ala Pro His Pro Val Lys Glu Ala Ser Pro Gly Phe
    1835                1840                1845

Ser Trp Ser Pro Lys Thr Ala Ser Ala Thr Pro Ala Pro Leu Lys
    1850                1855                1860

Asn Asp Ala Thr Ala Ser Cys Gly Phe Ser Glu Arg Ser Ser Thr
    1865                1870                1875

Pro His Cys Thr Met Pro Ser Gly Arg Leu Ser Gly Ala Asn Ala
    1880                1885                1890

Ala Ala Ala Asp Gly Pro Gly Ile Ser Gln Leu Gly Glu Val Ala
    1895                1900                1905

Pro Leu Pro Thr Leu Ser Ala Pro Val Met Glu Pro Leu Ile Asn
    1910                1915                1920

Ser Glu Pro Ser Thr Gly Val Thr Glu Pro Leu Thr Pro His Gln
    1925                1930                1935

Pro Asn His Gln Pro Ser Phe Leu Thr Ser Pro Gln Asp Leu Ala
    1940                1945                1950

Ser Ser Pro Met Glu Glu Asp Glu Gln His Ser Glu Ala Asp Glu
    1955                1960                1965

Pro Pro Ser Asp Glu Pro Leu Ser Asp Asp Pro Leu Ser Pro Ala
    1970                1975                1980

Glu Glu Lys Leu Pro His Ile Asp Glu Tyr Trp Ser Asp Ser Glu
    1985                1990                1995

His Ile Phe Leu Asp Ala Asn Ile Gly Gly Val Ala Ile Ala Pro
    2000                2005                2010

Ala His Gly Ser Val Leu Ile Glu Cys Ala Arg Arg Glu Leu His
    2015                2020                2025

Ala Thr Thr Pro Val Glu His Pro Asn Arg Asn His Pro Thr Arg
    2030                2035                2040

Leu Ser Leu Val Phe Tyr Gln His Lys Asn Leu Asn Lys Pro Gln
    2045                2050                2055

His Gly Phe Glu Leu Asn Lys Ile Lys Phe Glu Ala Lys Glu Ala
    2060                2065                2070

Lys Asn Lys Lys Met Lys Ala Ser Glu Gln Lys Asp Gln Ala Ala
    2075                2080                2085
```

```
Asn Glu Gly Pro Glu Gln Ser Ser Glu Val Asn Glu Leu Asn Gln
    2090            2095                2100

Ile Pro Ser His Lys Ala Leu Thr Leu Thr His Asp Asn Val Val
    2105            2110                2115

Thr Val Ser Pro Tyr Ala Leu Thr His Val Ala Gly Pro Tyr Asn
    2120            2125                2130

His Trp Val
    2135

<210> SEQ ID NO 23
<211> LENGTH: 552
<212> TYPE: PRT
<213> ORGANISM: Mus musculus

<400> SEQUENCE: 23

Gly Met Asp Val Thr Leu Leu Glu Ala Arg Asp Arg Val Gly Gly Arg
1               5                   10                  15

Val Ala Thr Phe Arg Lys Gly Asn Tyr Val Ala Asp Leu Gly Ala Met
            20                  25                  30

Val Val Thr Gly Leu Gly Gly Asn Pro Met Ala Val Val Ser Lys Gln
        35                  40                  45

Val Asn Met Glu Leu Ala Lys Ile Lys Gln Lys Cys Pro Leu Tyr Glu
    50                  55                  60

Ala Asn Gly Gln Ala Val Pro Lys Glu Lys Asp Glu Met Val Glu Gln
65                  70                  75                  80

Glu Phe Asn Arg Leu Leu Glu Ala Thr Ser Tyr Leu Ser His Gln Leu
                85                  90                  95

Asp Phe Asn Val Leu Asn Asn Lys Pro Val Ser Leu Gly Gln Ala Leu
            100                 105                 110

Glu Val Val Ile Gln Leu Gln Glu Lys His Val Lys Asp Glu Gln Ile
        115                 120                 125

Glu His Trp Lys Lys Ile Val Lys Thr Gln Glu Glu Leu Lys Glu Leu
    130                 135                 140

Leu Asn Lys Met Val Asn Leu Lys Glu Lys Ile Lys Glu Leu His Gln
145                 150                 155                 160

Gln Tyr Lys Glu Ala Ser Glu Val Lys Pro Pro Arg Asp Ile Thr Ala
                165                 170                 175

Glu Phe Leu Val Lys Ser Lys His Arg Asp Leu Thr Ala Leu Cys Lys
            180                 185                 190

Glu Tyr Asp Glu Leu Ala Glu Thr Gln Gly Lys Leu Glu Glu Lys Leu
        195                 200                 205

Gln Glu Leu Glu Ala Asn Pro Pro Ser Asp Val Tyr Leu Ser Ser Arg
    210                 215                 220

Asp Arg Gln Ile Leu Asp Trp His Phe Ala Asn Leu Glu Phe Ala Asn
225                 230                 235                 240

Ala Thr Pro Leu Ser Thr Leu Ser Leu Lys His Trp Asp Gln Asp Asp
                245                 250                 255

Asp Phe Glu Phe Thr Gly Ser His Leu Thr Val Arg Asn Gly Tyr Ser
            260                 265                 270

Cys Val Pro Val Ala Leu Ala Glu Gly Leu Asp Ile Lys Leu Asn Thr
        275                 280                 285

Ala Val Arg Gln Val Arg Tyr Thr Ala Ser Gly Cys Glu Val Ile Ala
    290                 295                 300

Val Asn Thr Arg Ser Thr Ser Gln Thr Phe Ile Tyr Lys Cys Asp Ala
```

```
              305                 310                 315                 320
Val Leu Cys Thr Leu Pro Leu Gly Val Leu Lys Gln Gln Pro Pro Ala
             325                 330                 335

Val Gln Phe Val Pro Leu Pro Glu Trp Lys Thr Ser Ala Val Gln
         340                 345                 350

Arg Met Gly Phe Gly Asn Leu Asn Lys Val Val Leu Cys Phe Asp Arg
             355                 360                 365

Val Phe Trp Asp Pro Ser Val Asn Leu Phe Gly His Val Gly Ser Thr
         370                 375                 380

Thr Ala Ser Arg Gly Glu Leu Phe Leu Phe Trp Asn Leu Tyr Lys Ala
385                 390                 395                 400

Pro Ile Leu Leu Ala Leu Val Ala Gly Glu Ala Gly Ile Met Glu
             405                 410                 415

Asn Ile Ser Asp Asp Val Ile Val Gly Arg Cys Leu Ala Ile Leu Lys
             420                 425                 430

Gly Ile Phe Gly Ser Ser Ala Val Pro Gln Pro Lys Glu Thr Val Val
             435                 440                 445

Ser Arg Trp Arg Ala Asp Pro Trp Ala Arg Gly Ser Tyr Ser Tyr Val
450                 455                 460

Ala Ala Gly Ser Ser Gly Asn Asp Tyr Asp Leu Met Ala Gln Pro Ile
465                 470                 475                 480

Thr Pro Gly Pro Ser Ile Pro Gly Ala Pro Gln Pro Ile Pro Arg Leu
             485                 490                 495

Phe Phe Ala Gly Glu His Thr Ile Arg Asn Tyr Pro Ala Thr Val His
             500                 505                 510

Gly Ala Leu Leu Ser Gly Leu Arg Glu Ala Gly Arg Ile Ala Asp Gln
             515                 520                 525

Phe Leu Gly Ala Met Tyr Thr Leu Pro Arg Gln Ala Thr Pro Gly Val
         530                 535                 540

Pro Ala Gln Gln Ser Pro Ser Met
545                 550

<210> SEQ ID NO 24
<211> LENGTH: 191
<212> TYPE: PRT
<213> ORGANISM: Homo sapiens

<400> SEQUENCE: 24

Met Gly Gly Ser Gly Ser Arg Leu Ser Lys Glu Leu Leu Ala Glu Tyr
1               5                  10                  15

Gln Asp Leu Thr Phe Leu Thr Lys Gln Glu Ile Leu Leu Ala His Arg
             20                  25                  30

Arg Phe Cys Glu Leu Leu Pro Gln Glu Gln Arg Ser Val Glu Ser Ser
         35                  40                  45

Leu Arg Ala Gln Val Pro Phe Glu Gln Ile Leu Ser Leu Pro Glu Leu
     50                  55                  60

Lys Ala Asn Pro Phe Lys Glu Arg Ile Cys Arg Val Phe Ser Thr Ser
65                  70                  75                  80

Pro Ala Lys Asp Ser Leu Ser Phe Glu Asp Phe Leu Asp Leu Leu Ser
                 85                  90                  95

Val Phe Ser Asp Thr Ala Thr Pro Asp Ile Lys Ser His Tyr Ala Phe
             100                 105                 110

Arg Ile Phe Asp Phe Asp Asp Gly Thr Leu Asn Arg Glu Asp Leu
         115                 120                 125
```

```
Ser Arg Leu Val Asn Cys Leu Thr Gly Glu Gly Glu Asp Thr Arg Leu
130                 135                 140

Ser Ala Ser Glu Met Lys Gln Leu Ile Asp Asn Ile Leu Glu Glu Ser
145                 150                 155                 160

Asp Ile Asp Arg Asp Gly Thr Ile Asn Leu Ser Glu Phe Gln His Val
                165                 170                 175

Ile Ser Arg Ser Pro Asp Phe Ala Ser Ser Phe Lys Ile Val Leu
                180                 185                 190
```

<210> SEQ ID NO 25
<211> LENGTH: 654
<212> TYPE: PRT
<213> ORGANISM: Homo sapiens

<400> SEQUENCE: 25

```
Met Asn Gln Pro Gln Arg Met Ala Pro Val Gly Thr Asp Lys Glu Leu
1               5                   10                  15

Ser Asp Leu Leu Asp Phe Ser Met Met Phe Pro Leu Pro Val Thr Asn
                20                  25                  30

Gly Lys Gly Arg Pro Ala Ser Leu Ala Gly Ala Gln Phe Gly Gly Ser
                35                  40                  45

Gly Leu Glu Asp Arg Pro Ser Ser Gly Ser Trp Gly Ser Gly Asp Gln
50                  55                  60

Ser Ser Ser Ser Phe Asp Pro Ser Arg Thr Phe Ser Glu Gly Thr His
65                  70                  75                  80

Phe Thr Glu Ser His Ser Ser Leu Ser Ser Ser Thr Phe Leu Gly Pro
                85                  90                  95

Gly Leu Gly Gly Lys Ser Gly Glu Arg Gly Ala Tyr Ala Ser Phe Gly
                100                 105                 110

Arg Asp Ala Gly Val Gly Gly Leu Thr Gln Ala Gly Phe Leu Ser Gly
                115                 120                 125

Glu Leu Ala Leu Asn Ser Pro Gly Pro Leu Ser Pro Ser Gly Met Lys
130                 135                 140

Gly Thr Ser Gln Tyr Tyr Pro Ser Tyr Ser Gly Ser Ser Arg Arg Arg
145                 150                 155                 160

Ala Ala Asp Gly Ser Leu Asp Thr Gln Pro Lys Lys Val Arg Lys Val
                165                 170                 175

Pro Pro Gly Leu Pro Ser Ser Val Tyr Pro Ser Ser Gly Glu Asp
                180                 185                 190

Tyr Gly Arg Asp Ala Thr Ala Tyr Pro Ser Ala Lys Thr Pro Ser Ser
                195                 200                 205

Thr Tyr Pro Ala Pro Phe Tyr Val Ala Asp Gly Ser Leu His Pro Ser
210                 215                 220

Ala Glu Leu Trp Ser Pro Gly Gln Ala Gly Phe Gly Pro Met Leu
225                 230                 235                 240

Gly Gly Gly Ser Ser Pro Leu Pro Leu Pro Pro Gly Ser Gly Pro Val
                245                 250                 255

Gly Ser Ser Gly Ser Ser Thr Phe Gly Gly Leu His Gln His Glu
                260                 265                 270

Arg Met Gly Tyr Gln Leu His Gly Ala Glu Val Asn Gly Gly Leu Pro
                275                 280                 285

Ser Ala Ser Ser Phe Ser Ala Pro Gly Ala Thr Tyr Gly Gly Val
                290                 295                 300

Ser Ser His Thr Pro Pro Val Ser Gly Ala Asp Ser Leu Leu Gly Ser
305                 310                 315                 320
```

```
Arg Gly Thr Thr Ala Gly Ser Ser Gly Asp Ala Leu Gly Lys Ala Leu
                325                 330                 335

Ala Ser Ile Tyr Ser Pro Asp His Ser Ser Asn Asn Phe Ser Ser Ser
                340                 345                 350

Pro Ser Thr Pro Val Gly Ser Pro Gln Gly Leu Ala Gly Thr Ser Gln
                355                 360                 365

Trp Pro Arg Ala Gly Ala Pro Gly Ala Leu Ser Pro Ser Tyr Asp Gly
            370                 375                 380

Gly Leu His Gly Leu Gln Ser Lys Ile Glu Asp His Leu Asp Glu Ala
385                 390                 395                 400

Ile His Val Leu Arg Ser His Ala Val Gly Thr Ala Gly Asp Met His
                405                 410                 415

Thr Leu Leu Pro Gly His Gly Ala Leu Ala Ser Gly Phe Thr Gly Pro
                420                 425                 430

Met Ser Leu Gly Gly Arg His Ala Gly Leu Val Gly Gly Ser His Pro
            435                 440                 445

Glu Asp Gly Leu Ala Gly Ser Thr Ser Leu Met His Asn His Ala Ala
    450                 455                 460

Leu Pro Ser Gln Pro Gly Thr Leu Pro Asp Leu Ser Arg Pro Pro Asp
465                 470                 475                 480

Ser Tyr Ser Gly Leu Gly Arg Ala Gly Ala Thr Ala Ala Ala Ser Glu
                485                 490                 495

Ile Lys Arg Glu Glu Lys Glu Asp Glu Glu Asn Thr Ser Ala Ala Asp
                500                 505                 510

His Ser Glu Glu Glu Lys Lys Glu Leu Lys Ala Pro Arg Ala Arg Thr
            515                 520                 525

Ser Pro Asp Glu Asp Glu Asp Asp Leu Leu Pro Pro Glu Gln Lys Ala
    530                 535                 540

Glu Arg Glu Lys Glu Arg Arg Val Ala Asn Asn Ala Arg Glu Arg Leu
545                 550                 555                 560

Arg Val Arg Asp Ile Asn Glu Ala Phe Lys Glu Leu Gly Arg Met Cys
                565                 570                 575

Gln Leu His Leu Asn Ser Glu Lys Pro Gln Thr Lys Leu Leu Ile Leu
                580                 585                 590

His Gln Ala Val Ser Val Ile Leu Asn Leu Glu Gln Gln Val Arg Glu
            595                 600                 605

Arg Asn Leu Asn Pro Lys Ala Ala Cys Leu Lys Arg Arg Glu Glu Glu
    610                 615                 620

Lys Val Ser Gly Val Val Gly Asp Pro Gln Met Val Leu Ser Ala Pro
625                 630                 635                 640

His Pro Gly Leu Ser Glu Ala His Asn Pro Ala Gly His Met
                645                 650

<210> SEQ ID NO 26
<211> LENGTH: 1663
<212> TYPE: PRT
<213> ORGANISM: Homo sapiens

<400> SEQUENCE: 26

Met Gly Pro Thr Ser Gly Pro Ser Leu Leu Leu Leu Leu Thr His
1               5                   10                  15

Leu Pro Leu Ala Leu Gly Ser Pro Met Tyr Ser Ile Ile Thr Pro Asn
                20                  25                  30

Ile Leu Arg Leu Glu Ser Glu Glu Thr Met Val Leu Glu Ala His Asp
```

```
                35                  40                  45
Ala Gln Gly Asp Val Pro Val Thr Val Thr Val His Asp Phe Pro Gly
 50                  55                  60
Lys Lys Leu Val Leu Ser Ser Glu Lys Thr Val Leu Thr Pro Ala Thr
 65                  70                  75                  80
Asn His Met Gly Asn Val Thr Phe Thr Ile Pro Ala Asn Arg Glu Phe
                 85                  90                  95
Lys Ser Glu Lys Gly Arg Asn Lys Phe Val Thr Val Gln Ala Thr Phe
                100                 105                 110
Gly Thr Gln Val Val Glu Lys Val Leu Val Ser Leu Gln Ser Gly
                115                 120                 125
Tyr Leu Phe Ile Gln Thr Asp Lys Thr Ile Tyr Thr Pro Gly Ser Thr
                130                 135                 140
Val Leu Tyr Arg Ile Phe Thr Val Asn His Lys Leu Leu Pro Val Gly
145                 150                 155                 160
Arg Thr Val Met Val Asn Ile Glu Asn Pro Glu Gly Ile Pro Val Lys
                165                 170                 175
Gln Asp Ser Leu Ser Ser Gln Asn Gln Leu Gly Val Leu Pro Leu Ser
                180                 185                 190
Trp Asp Ile Pro Glu Leu Val Asn Met Gly Gln Trp Lys Ile Arg Ala
                195                 200                 205
Tyr Tyr Glu Asn Ser Pro Gln Gln Val Phe Ser Thr Glu Phe Glu Val
                210                 215                 220
Lys Glu Tyr Val Leu Pro Ser Phe Glu Val Ile Val Glu Pro Thr Glu
225                 230                 235                 240
Lys Phe Tyr Tyr Ile Tyr Asn Glu Lys Gly Leu Glu Val Thr Ile Thr
                245                 250                 255
Ala Arg Phe Leu Tyr Gly Lys Lys Val Glu Gly Thr Ala Phe Val Ile
                260                 265                 270
Phe Gly Ile Gln Asp Gly Glu Gln Arg Ile Ser Leu Pro Glu Ser Leu
                275                 280                 285
Lys Arg Ile Pro Ile Glu Asp Gly Ser Gly Glu Val Val Leu Ser Arg
                290                 295                 300
Lys Val Leu Leu Asp Gly Val Gln Asn Pro Arg Ala Glu Asp Leu Val
305                 310                 315                 320
Gly Lys Ser Leu Tyr Val Ser Ala Thr Val Ile Leu His Ser Gly Ser
                325                 330                 335
Asp Met Val Gln Ala Glu Arg Ser Gly Ile Pro Ile Val Thr Ser Pro
                340                 345                 350
Tyr Gln Ile His Phe Thr Lys Thr Pro Lys Tyr Phe Lys Pro Gly Met
                355                 360                 365
Pro Phe Asp Leu Met Val Phe Val Thr Asn Pro Asp Gly Ser Pro Ala
                370                 375                 380
Tyr Arg Val Pro Val Ala Val Gln Gly Glu Asp Thr Val Gln Ser Leu
385                 390                 395                 400
Thr Gln Gly Asp Gly Val Ala Lys Leu Ser Ile Asn Thr His Pro Ser
                405                 410                 415
Gln Lys Pro Leu Ser Ile Thr Val Arg Thr Lys Lys Gln Glu Leu Ser
                420                 425                 430
Glu Ala Glu Gln Ala Thr Arg Thr Met Gln Ala Leu Pro Tyr Ser Thr
                435                 440                 445
Val Gly Asn Ser Asn Asn Tyr Leu His Leu Ser Val Leu Arg Thr Glu
                450                 455                 460
```

Leu Arg Pro Gly Glu Thr Leu Asn Val Asn Phe Leu Arg Met Asp
465                 470                 475                 480

Arg Ala His Glu Ala Lys Ile Arg Tyr Tyr Thr Tyr Leu Ile Met Asn
            485                 490                 495

Lys Gly Arg Leu Leu Lys Ala Gly Arg Gln Val Arg Glu Pro Gly Gln
                500                 505                 510

Asp Leu Val Val Leu Pro Leu Ser Ile Thr Thr Asp Phe Ile Pro Ser
            515                 520                 525

Phe Arg Leu Val Ala Tyr Tyr Thr Leu Ile Gly Ala Ser Gly Gln Arg
    530                 535                 540

Glu Val Val Ala Asp Ser Val Trp Val Asp Val Lys Asp Ser Cys Val
545                 550                 555                 560

Gly Ser Leu Val Val Lys Ser Gly Gln Ser Glu Asp Arg Gln Pro Val
                565                 570                 575

Pro Gly Gln Gln Met Thr Leu Lys Ile Glu Gly Asp His Gly Ala Arg
            580                 585                 590

Val Val Leu Val Ala Val Asp Lys Gly Val Phe Val Leu Asn Lys Lys
            595                 600                 605

Asn Lys Leu Thr Gln Ser Lys Ile Trp Asp Val Glu Lys Ala Asp
    610                 615                 620

Ile Gly Cys Thr Pro Gly Ser Gly Lys Asp Tyr Ala Gly Val Phe Ser
625                 630                 635                 640

Asp Ala Gly Leu Thr Phe Thr Ser Ser Gly Gln Gln Thr Ala Gln
            645                 650                 655

Arg Ala Glu Leu Gln Cys Pro Gln Pro Ala Ala Arg Arg Arg Arg Ser
            660                 665                 670

Val Gln Leu Thr Glu Lys Arg Met Asp Lys Val Gly Lys Tyr Pro Lys
            675                 680                 685

Glu Leu Arg Lys Cys Cys Glu Asp Gly Met Arg Glu Asn Pro Met Arg
    690                 695                 700

Phe Ser Cys Gln Arg Arg Thr Arg Phe Ile Ser Leu Gly Glu Ala Cys
705                 710                 715                 720

Lys Lys Val Phe Leu Asp Cys Cys Asn Tyr Ile Thr Glu Leu Arg Arg
                725                 730                 735

Gln His Ala Arg Ala Ser His Leu Gly Leu Ala Arg Ser Asn Leu Asp
            740                 745                 750

Glu Asp Ile Ile Ala Glu Asn Ile Val Ser Arg Ser Glu Phe Pro
    755                 760                 765

Glu Ser Trp Leu Trp Asn Val Glu Asp Leu Lys Glu Pro Pro Lys Asn
    770                 775                 780

Gly Ile Ser Thr Lys Leu Met Asn Ile Phe Leu Lys Asp Ser Ile Thr
785                 790                 795                 800

Thr Trp Glu Ile Leu Ala Val Ser Met Ser Asp Lys Lys Gly Ile Cys
            805                 810                 815

Val Ala Asp Pro Phe Glu Val Thr Val Met Gln Asp Phe Phe Ile Asp
            820                 825                 830

Leu Arg Leu Pro Tyr Ser Val Val Arg Asn Glu Gln Val Glu Ile Arg
    835                 840                 845

Ala Val Leu Tyr Asn Tyr Arg Gln Asn Gln Glu Leu Lys Val Arg Val
    850                 855                 860

Glu Leu Leu His Asn Pro Ala Phe Cys Ser Leu Ala Thr Thr Lys Arg
865                 870                 875                 880

```
Arg His Gln Gln Thr Val Thr Ile Pro Pro Lys Ser Ser Leu Ser Val
                885                 890                 895

Pro Tyr Val Ile Val Pro Leu Lys Thr Gly Leu Gln Glu Val Glu Val
                900                 905                 910

Lys Ala Ala Val Tyr His His Phe Ile Ser Asp Gly Val Arg Lys Ser
                915                 920                 925

Leu Lys Val Val Pro Glu Gly Ile Arg Met Asn Lys Thr Val Ala Val
                930                 935                 940

Arg Thr Leu Asp Pro Glu Arg Leu Gly Arg Glu Gly Val Gln Lys Glu
945                 950                 955                 960

Asp Ile Pro Pro Ala Asp Leu Ser Asp Gln Val Pro Asp Thr Glu Ser
                965                 970                 975

Glu Thr Arg Ile Leu Leu Gln Gly Thr Pro Val Ala Gln Met Thr Glu
                980                 985                 990

Asp Ala Val Asp Ala Glu Arg Leu Lys His Leu Ile Val Thr Pro Ser
                995                 1000                1005

Gly Cys Gly Glu Gln Asn Met Ile Gly Met Thr Pro Thr Val Ile
                1010                1015                1020

Ala Val His Tyr Leu Asp Glu Thr Glu Gln Trp Glu Lys Phe Gly
                1025                1030                1035

Leu Glu Lys Arg Gln Gly Ala Leu Glu Leu Ile Lys Lys Gly Tyr
                1040                1045                1050

Thr Gln Gln Leu Ala Phe Arg Gln Pro Ser Ser Ala Phe Ala Ala
                1055                1060                1065

Phe Val Lys Arg Ala Pro Ser Thr Trp Leu Thr Ala Tyr Val Val
                1070                1075                1080

Lys Val Phe Ser Leu Ala Val Asn Leu Ile Ala Ile Asp Ser Gln
                1085                1090                1095

Val Leu Cys Gly Ala Val Lys Trp Leu Ile Leu Glu Lys Gln Lys
                1100                1105                1110

Pro Asp Gly Val Phe Gln Glu Asp Ala Pro Val Ile His Gln Glu
                1115                1120                1125

Met Ile Gly Gly Leu Arg Asn Asn Asn Glu Lys Asp Met Ala Leu
                1130                1135                1140

Thr Ala Phe Val Leu Ile Ser Leu Gln Glu Ala Lys Asp Ile Cys
                1145                1150                1155

Glu Glu Gln Val Asn Ser Leu Pro Gly Ser Ile Thr Lys Ala Gly
                1160                1165                1170

Asp Phe Leu Glu Ala Asn Tyr Met Asn Leu Gln Arg Ser Tyr Thr
                1175                1180                1185

Val Ala Ile Ala Gly Tyr Ala Leu Ala Gln Met Gly Arg Leu Lys
                1190                1195                1200

Gly Pro Leu Leu Asn Lys Phe Leu Thr Thr Ala Lys Asp Lys Asn
                1205                1210                1215

Arg Trp Glu Asp Pro Gly Lys Gln Leu Tyr Asn Val Glu Ala Thr
                1220                1225                1230

Ser Tyr Ala Leu Leu Ala Leu Leu Gln Leu Lys Asp Phe Asp Phe
                1235                1240                1245

Val Pro Pro Val Val Arg Trp Leu Asn Glu Gln Arg Tyr Tyr Gly
                1250                1255                1260

Gly Gly Tyr Gly Ser Thr Gln Ala Thr Phe Met Val Phe Gln Ala
                1265                1270                1275

Leu Ala Gln Tyr Gln Lys Asp Ala Pro Asp His Gln Glu Leu Asn
```

```
              1280                1285                1290
Leu Asp Val Ser Leu Gln Leu Pro Ser Arg Ser Lys Ile Thr
             1295                1300                1305
His Arg Ile His Trp Glu Ser Ala Ser Leu Leu Arg Ser Glu Glu
             1310                1315                1320
Thr Lys Glu Asn Glu Gly Phe Thr Val Thr Ala Glu Gly Lys Gly
             1325                1330                1335
Gln Gly Thr Leu Ser Val Val Thr Met Tyr His Ala Lys Ala Lys
             1340                1345                1350
Asp Gln Leu Thr Cys Asn Lys Phe Asp Leu Lys Val Thr Ile Lys
             1355                1360                1365
Pro Ala Pro Glu Thr Glu Lys Arg Pro Gln Asp Ala Lys Asn Thr
             1370                1375                1380
Met Ile Leu Glu Ile Cys Thr Arg Tyr Arg Gly Asp Gln Asp Ala
             1385                1390                1395
Thr Met Ser Ile Leu Asp Ile Ser Met Met Thr Gly Phe Ala Pro
             1400                1405                1410
Asp Thr Asp Asp Leu Lys Gln Leu Ala Asn Gly Val Asp Arg Tyr
             1415                1420                1425
Ile Ser Lys Tyr Glu Leu Asp Lys Ala Phe Ser Asp Arg Asn Thr
             1430                1435                1440
Leu Ile Ile Tyr Leu Asp Lys Val Ser His Ser Glu Asp Asp Cys
             1445                1450                1455
Leu Ala Phe Lys Val His Gln Tyr Phe Asn Val Glu Leu Ile Gln
             1460                1465                1470
Pro Gly Ala Val Lys Val Tyr Ala Tyr Asn Leu Glu Glu Ser
             1475                1480                1485
Cys Thr Arg Phe Tyr His Pro Glu Lys Glu Asp Gly Lys Leu Asn
             1490                1495                1500
Lys Leu Cys Arg Asp Glu Leu Cys Arg Cys Ala Glu Glu Asn Cys
             1505                1510                1515
Phe Ile Gln Lys Ser Asp Asp Lys Val Thr Leu Glu Glu Arg Leu
             1520                1525                1530
Asp Lys Ala Cys Glu Pro Gly Val Asp Tyr Val Tyr Lys Thr Arg
             1535                1540                1545
Leu Val Lys Val Gln Leu Ser Asn Asp Phe Asp Glu Tyr Ile Met
             1550                1555                1560
Ala Ile Glu Gln Thr Ile Lys Ser Gly Ser Asp Glu Val Gln Val
             1565                1570                1575
Gly Gln Gln Arg Thr Phe Ile Ser Pro Ile Lys Cys Arg Glu Ala
             1580                1585                1590
Leu Lys Leu Glu Glu Lys Lys His Tyr Leu Met Trp Gly Leu Ser
             1595                1600                1605
Ser Asp Phe Trp Gly Glu Lys Pro Asn Leu Ser Tyr Ile Ile Gly
             1610                1615                1620
Lys Asp Thr Trp Val Glu His Trp Pro Glu Glu Asp Glu Cys Gln
             1625                1630                1635
Asp Glu Glu Asn Gln Lys Gln Cys Gln Asp Leu Gly Ala Phe Thr
             1640                1645                1650
Glu Ser Met Val Val Phe Gly Cys Pro Asn
             1655                1660

<210> SEQ ID NO 27
```

<211> LENGTH: 442
<212> TYPE: PRT
<213> ORGANISM: Homo sapiens

<400> SEQUENCE: 27

```
Met Tyr Gln Ser Leu Ala Met Ala Ala Asn His Gly Pro Pro Pro Gly
1               5                   10                  15

Ala Tyr Glu Ala Gly Gly Pro Gly Ala Phe Met His Gly Ala Gly Ala
            20                  25                  30

Ala Ser Ser Pro Val Tyr Val Pro Thr Pro Arg Val Pro Ser Ser Val
        35                  40                  45

Leu Gly Leu Ser Tyr Leu Gln Gly Gly Ala Gly Ser Ala Ser Gly
50                  55                  60

Gly Ala Ser Gly Gly Ser Ser Gly Gly Ala Ala Ser Gly Ala Gly Pro
65                  70                  75                  80

Gly Thr Gln Gln Gly Ser Pro Gly Trp Ser Gln Ala Gly Ala Asp Gly
                85                  90                  95

Ala Ala Tyr Thr Pro Pro Pro Val Ser Pro Arg Phe Ser Phe Pro Gly
            100                 105                 110

Thr Thr Gly Ser Leu Ala Ala Ala Ala Ala Ala Ala Ala Ala Arg Glu
        115                 120                 125

Ala Ala Ala Tyr Ser Ser Gly Gly Gly Ala Ala Gly Ala Gly Leu Ala
130                 135                 140

Gly Arg Glu Gln Tyr Gly Arg Ala Gly Phe Ala Gly Ser Tyr Ser Ser
145                 150                 155                 160

Pro Tyr Pro Ala Tyr Met Ala Asp Val Gly Ala Ser Trp Ala Ala Ala
                165                 170                 175

Ala Ala Ala Ser Ala Gly Pro Phe Asp Ser Pro Val Leu His Ser Leu
            180                 185                 190

Pro Gly Arg Ala Asn Pro Ala Ala Arg His Pro Asn Leu Asp Met Phe
        195                 200                 205

Asp Asp Phe Ser Glu Gly Arg Glu Cys Val Asn Cys Gly Ala Met Ser
210                 215                 220

Thr Pro Leu Trp Arg Arg Asp Gly Thr Gly His Tyr Leu Cys Asn Ala
225                 230                 235                 240

Cys Gly Leu Tyr His Lys Met Asn Gly Ile Asn Arg Pro Leu Ile Lys
                245                 250                 255

Pro Gln Arg Arg Leu Ser Ala Ser Arg Arg Val Gly Leu Ser Cys Ala
            260                 265                 270

Asn Cys Gln Thr Thr Thr Thr Thr Leu Trp Arg Arg Asn Ala Glu Gly
        275                 280                 285

Glu Pro Val Cys Asn Ala Cys Gly Leu Tyr Met Lys Leu His Gly Val
290                 295                 300

Pro Arg Pro Leu Ala Met Arg Lys Glu Gly Ile Gln Thr Arg Lys Arg
305                 310                 315                 320

Lys Pro Lys Asn Leu Asn Lys Ser Lys Thr Pro Ala Ala Pro Ser Gly
                325                 330                 335

Ser Glu Ser Leu Pro Pro Ala Ser Gly Ala Ser Ser Asn Ser Ser Asn
            340                 345                 350

Ala Thr Thr Ser Ser Ser Glu Glu Met Arg Pro Ile Lys Thr Glu Pro
        355                 360                 365

Gly Leu Ser Ser His Tyr Gly His Ser Ser Val Ser Gln Thr Phe
370                 375                 380

Ser Val Ser Ala Met Ser Gly His Gly Pro Ser Ile His Pro Val Leu
```

```
385                 390                 395                 400
Ser Ala Leu Lys Leu Ser Pro Gln Gly Tyr Ala Ser Pro Val Ser Gln
                405                 410                 415

Ser Pro Gln Thr Ser Ser Lys Gln Asp Ser Trp Asn Ser Leu Val Leu
            420                 425                 430

Ala Asp Ser His Gly Asp Ile Ile Thr Ala
        435                 440

<210> SEQ ID NO 28
<211> LENGTH: 393
<212> TYPE: PRT
<213> ORGANISM: Homo sapiens

<400> SEQUENCE: 28

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320
```

```
Lys Pro Leu Asp Gly Glu Tyr Phe Thr Leu Gln Ile Arg Gly Arg Glu
            325                 330                 335

Arg Phe Glu Met Phe Arg Glu Leu Asn Glu Ala Leu Glu Leu Lys Asp
        340                 345                 350

Ala Gln Ala Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
        370                 375                 380

Phe Lys Thr Glu Gly Pro Asp Ser Asp
385                 390

<210> SEQ ID NO 29
<211> LENGTH: 785
<212> TYPE: PRT
<213> ORGANISM: Homo sapiens

<400> SEQUENCE: 29

Met Ser Asp Gln Asp His Ser Met Asp Glu Met Thr Ala Val Val Lys
1               5                   10                  15

Ile Glu Lys Gly Val Gly Gly Asn Asn Gly Gly Asn Gly Asn Gly Gly
            20                  25                  30

Gly Ala Phe Ser Gln Ala Arg Ser Ser Thr Gly Ser Ser Ser Ser
        35                  40                  45

Thr Gly Gly Gly Gln Glu Ser Gln Pro Ser Pro Leu Ala Leu Leu
    50                  55                  60

Ala Ala Thr Cys Ser Arg Ile Glu Ser Pro Asn Glu Asn Ser Asn Asn
65                  70                  75                  80

Ser Gln Gly Pro Ser Gln Ser Gly Thr Gly Glu Leu Asp Leu Thr
                85                  90                  95

Ala Thr Gln Leu Ser Gln Gly Ala Asn Gly Trp Gln Ile Ile Ser Ser
            100                 105                 110

Ser Ser Gly Ala Thr Pro Thr Ser Lys Glu Gln Ser Gly Ser Ser Thr
        115                 120                 125

Asn Gly Ser Asn Gly Ser Glu Ser Ser Lys Asn Arg Thr Val Ser Gly
    130                 135                 140

Gly Gln Tyr Val Val Ala Ala Pro Asn Leu Gln Asn Gln Gln Val
145                 150                 155                 160

Leu Thr Gly Leu Pro Gly Val Met Pro Asn Ile Gln Tyr Gln Val Ile
                165                 170                 175

Pro Gln Phe Gln Thr Val Asp Gly Gln Gln Leu Gln Phe Ala Ala Thr
            180                 185                 190

Gly Ala Gln Val Gln Gln Asp Gly Ser Gly Gln Ile Gln Ile Ile Pro
        195                 200                 205

Gly Ala Asn Gln Gln Ile Ile Thr Asn Arg Gly Ser Gly Gly Asn Ile
    210                 215                 220

Ile Ala Ala Met Pro Asn Leu Leu Gln Gln Ala Val Pro Leu Gln Gly
225                 230                 235                 240

Leu Ala Asn Asn Val Leu Ser Gly Gln Thr Gln Tyr Val Thr Asn Val
                245                 250                 255

Pro Val Ala Leu Asn Gly Asn Ile Thr Leu Leu Pro Val Asn Ser Val
            260                 265                 270

Ser Ala Ala Thr Leu Thr Pro Ser Ser Gln Ala Val Thr Ile Ser Ser
        275                 280                 285

Ser Gly Ser Gln Glu Ser Gly Ser Gln Pro Val Thr Ser Gly Thr Thr
    290                 295                 300
```

-continued

| | | | | | | | | | | | | |
|---|---|---|---|---|---|---|---|---|---|---|---|---|
|Ile|Ser|Ser|Ala|Ser|Leu|Val|Ser|Ser|Gln|Ala|Ser|Ser|Ser|Ser|Phe|
|305| | | | |310| | | | |315| | | | |320|

Phe Thr Asn Ala Asn Ser Tyr Ser Thr Thr Thr Thr Ser Asn Met
               325               330           335

Gly Ile Met Asn Phe Thr Thr Ser Gly Ser Ser Gly Thr Asn Ser Gln
340                   345               350

Gly Gln Thr Pro Gln Arg Val Ser Gly Leu Gln Gly Ser Asp Ala Leu
     355                 360               365

Asn Ile Gln Gln Asn Gln Thr Ser Gly Gly Ser Leu Gln Ala Gly Gln
370                   375               380

Gln Lys Glu Gly Glu Gln Asn Gln Gln Thr Gln Gln Gln Ile Leu
385                   390               395           400

Ile Gln Pro Gln Leu Val Gln Gly Gln Ala Leu Gln Ala Leu Gln
         405               410               415

Ala Ala Pro Leu Ser Gly Gln Thr Phe Thr Thr Gln Ala Ile Ser Gln
420                   425               430

Glu Thr Leu Gln Asn Leu Gln Leu Gln Ala Val Pro Asn Ser Gly Pro
     435                 440               445

Ile Ile Ile Arg Thr Pro Thr Val Gly Pro Asn Gly Gln Val Ser Trp
450                   455               460

Gln Thr Leu Gln Leu Gln Asn Leu Gln Val Gln Asn Pro Gln Ala Gln
465                   470               475           480

Thr Ile Thr Leu Ala Pro Met Gln Gly Val Ser Leu Gly Gln Thr Ser
         485               490               495

Ser Ser Asn Thr Thr Leu Thr Pro Ile Ala Ser Ala Ala Ser Ile Pro
         500               505               510

Ala Gly Thr Val Thr Val Asn Ala Ala Gln Leu Ser Ser Met Pro Gly
     515                 520               525

Leu Gln Thr Ile Asn Leu Ser Ala Leu Gly Thr Ser Gly Ile Gln Val
     530                 535               540

His Pro Ile Gln Gly Leu Pro Leu Ala Ile Ala Asn Ala Pro Gly Asp
545                   550               555           560

His Gly Ala Gln Leu Gly Leu His Gly Ala Gly Gly Asp Gly Ile His
         565               570               575

Asp Asp Thr Ala Gly Gly Glu Glu Gly Glu Asn Ser Pro Asp Ala Gln
         580               585               590

Pro Gln Ala Gly Arg Arg Thr Arg Arg Glu Ala Cys Thr Cys Pro Tyr
     595                 600               605

Cys Lys Asp Ser Glu Gly Arg Gly Ser Gly Asp Pro Gly Lys Lys Lys
         610               615               620

Gln His Ile Cys His Ile Gln Gly Cys Gly Lys Val Tyr Gly Lys Thr
625                   630               635           640

Ser His Leu Arg Ala His Leu Arg Trp His Thr Gly Glu Arg Pro Phe
         645               650               655

Met Cys Thr Trp Ser Tyr Cys Gly Lys Arg Phe Thr Arg Ser Asp Glu
         660               665               670

Leu Gln Arg His Lys Arg Thr His Thr Gly Glu Lys Lys Phe Ala Cys
     675                 680               685

Pro Glu Cys Pro Lys Arg Phe Met Arg Ser Asp His Leu Ser Lys His
     690                 695               700

Ile Lys Thr His Gln Asn Lys Lys Gly Gly Pro Gly Val Ala Leu Ser
705                   710               715           720

```
Val Gly Thr Leu Pro Leu Asp Ser Gly Ala Gly Ser Gly
            725             730             735

Thr Ala Thr Pro Ser Ala Leu Ile Thr Thr Asn Met Val Ala Met Glu
            740                 745                 750

Ala Ile Cys Pro Glu Gly Ile Ala Arg Leu Ala Asn Ser Gly Ile Asn
            755                 760                 765

Val Met Gln Val Ala Asp Leu Gln Ser Ile Asn Ile Ser Gly Asn Gly
770                 775                 780

Phe
785

<210> SEQ ID NO 30
<211> LENGTH: 473
<212> TYPE: PRT
<213> ORGANISM: Homo sapiens

<400> SEQUENCE: 30

Met Gly Arg Lys Lys Ile Gln Ile Thr Arg Ile Met Asp Glu Arg Asn
1               5                   10                  15

Arg Gln Val Thr Phe Thr Lys Arg Lys Phe Gly Leu Met Lys Lys Ala
                20                  25                  30

Tyr Glu Leu Ser Val Leu Cys Asp Cys Glu Ile Ala Leu Ile Ile Phe
            35                  40                  45

Asn Ser Thr Asn Lys Leu Phe Gln Tyr Ala Ser Thr Asp Met Asp Lys
        50                  55                  60

Val Leu Leu Lys Tyr Thr Glu Tyr Asn Glu Pro His Glu Ser Arg Thr
65                  70                  75                  80

Asn Ser Asp Ile Val Glu Thr Leu Arg Lys Lys Gly Leu Asn Gly Cys
                85                  90                  95

Asp Ser Pro Asp Pro Asp Ala Asp Ser Val Gly His Ser Pro Glu
            100                 105                 110

Ser Glu Asp Lys Tyr Arg Lys Ile Asn Glu Asp Ile Asp Leu Met Ile
        115                 120                 125

Ser Arg Gln Arg Leu Cys Ala Val Pro Pro Pro Asn Phe Glu Met Pro
130                 135                 140

Val Ser Ile Pro Val Ser Ser His Asn Ser Leu Val Tyr Ser Asn Pro
145                 150                 155                 160

Val Ser Ser Leu Gly Asn Pro Asn Leu Leu Pro Leu Ala His Pro Ser
                165                 170                 175

Leu Gln Arg Asn Ser Met Ser Pro Gly Val Thr His Arg Pro Pro Ser
            180                 185                 190

Ala Gly Asn Thr Gly Gly Leu Met Gly Gly Asp Leu Thr Ser Gly Ala
        195                 200                 205

Gly Thr Ser Ala Gly Asn Gly Tyr Gly Asn Pro Arg Asn Ser Pro Gly
    210                 215                 220

Leu Leu Val Ser Pro Gly Asn Leu Asn Lys Asn Met Gln Ala Lys Ser
225                 230                 235                 240

Pro Pro Pro Met Asn Leu Gly Met Asn Asn Arg Lys Pro Asp Leu Arg
                245                 250                 255

Val Leu Ile Pro Pro Gly Ser Lys Asn Thr Met Pro Ser Val Ser Glu
            260                 265                 270

Asp Val Asp Leu Leu Leu Asn Gln Arg Ile Asn Asn Ser Gln Ser Ala
        275                 280                 285

Gln Ser Leu Ala Thr Pro Val Val Ser Val Ala Thr Pro Thr Leu Pro
    290                 295                 300
```

Gly Gln Gly Met Gly Gly Tyr Pro Ser Ala Ile Ser Thr Thr Tyr Gly
305                 310                 315                 320

Thr Glu Tyr Ser Leu Ser Ser Ala Asp Leu Ser Ser Leu Ser Gly Phe
            325                 330                 335

Asn Thr Ala Ser Ala Leu His Leu Gly Ser Val Thr Gly Trp Gln Gln
        340                 345                 350

Gln His Leu His Asn Met Pro Pro Ser Ala Leu Ser Gln Leu Gly Ala
    355                 360                 365

Cys Thr Ser Thr His Leu Ser Gln Ser Ser Asn Leu Ser Leu Pro Ser
370                 375                 380

Thr Gln Ser Leu Asn Ile Lys Ser Glu Pro Val Ser Pro Pro Arg Asp
385                 390                 395                 400

Arg Thr Thr Thr Pro Ser Arg Tyr Pro Gln His Thr Arg His Glu Ala
                405                 410                 415

Gly Arg Ser Pro Val Asp Ser Leu Ser Ser Cys Ser Ser Ser Tyr Asp
            420                 425                 430

Gly Ser Asp Arg Glu Asp His Arg Asn Glu Phe His Ser Pro Ile Gly
        435                 440                 445

Leu Thr Arg Pro Ser Pro Asp Glu Arg Glu Ser Pro Ser Val Lys Arg
    450                 455                 460

Met Arg Leu Ser Glu Gly Trp Ala Thr
465                 470

<210> SEQ ID NO 31
<211> LENGTH: 353
<212> TYPE: PRT
<213> ORGANISM: Unknown
<220> FEATURE:
<223> OTHER INFORMATION: Human T-lymphotrophic virus

<400> SEQUENCE: 31

Met Ala His Phe Pro Gly Phe Gly Gln Ser Leu Leu Phe Gly Tyr Pro
1               5                   10                  15

Val Tyr Val Phe Gly Asp Cys Val Gln Gly Asp Trp Cys Pro Ile Ser
            20                  25                  30

Gly Gly Leu Cys Ser Ala Arg Leu His Arg His Ala Leu Leu Ala Thr
        35                  40                  45

Cys Pro Glu His Gln Ile Thr Trp Asp Pro Ile Asp Gly Arg Val Ile
    50                  55                  60

Gly Ser Ala Leu Gln Phe Leu Ile Pro Arg Leu Pro Ser Phe Pro Thr
65                  70                  75                  80

Gln Arg Thr Ser Lys Thr Leu Lys Val Leu Thr Pro Pro Ile Thr His
                85                  90                  95

Thr Thr Pro Asn Ile Pro Pro Ser Phe Leu Gln Ala Met Arg Lys Tyr
            100                 105                 110

Ser Pro Phe Arg Asn Gly Tyr Met Glu Pro Thr Leu Gly Gln His Leu
        115                 120                 125

Pro Thr Leu Ser Phe Pro Asp Pro Gly Leu Arg Pro Gln Asn Leu Tyr
    130                 135                 140

Thr Leu Trp Gly Gly Ser Val Val Cys Met Tyr Leu Tyr Gln Leu Ser
145                 150                 155                 160

Pro Pro Ile Thr Trp Pro Leu Leu Pro His Val Ile Phe Cys His Pro
                165                 170                 175

Gly Gln Leu Gly Ala Phe Leu Thr Asn Val Pro Tyr Lys Arg Ile Glu
            180                 185                 190

```
Glu Leu Leu Tyr Lys Ile Ser Leu Thr Thr Gly Ala Leu Ile Ile Leu
            195                 200                 205

Pro Glu Asp Cys Leu Pro Thr Thr Leu Phe Gln Pro Ala Arg Ala Pro
210                 215                 220

Val Thr Leu Thr Ala Trp Gln Asn Gly Leu Leu Pro Phe His Ser Thr
225                 230                 235                 240

Leu Thr Thr Pro Gly Leu Ile Trp Thr Phe Thr Asp Gly Thr Pro Met
            245                 250                 255

Ile Ser Gly Pro Cys Pro Lys Asp Gly Gln Pro Ser Leu Val Leu Gln
            260                 265                 270

Ser Ser Ser Phe Ile Phe His Lys Phe Gln Thr Lys Ala Tyr His Pro
            275                 280                 285

Ser Phe Leu Leu Ser His Gly Leu Ile Gln Tyr Ser Ser Phe His Ser
            290                 295                 300

Leu His Leu Leu Phe Glu Glu Tyr Thr Asn Ile Pro Ile Ser Leu Leu
305                 310                 315                 320

Phe Asn Glu Lys Glu Ala Asp Asp Asn Asp His Glu Pro Gln Ile Ser
            325                 330                 335

Pro Gly Gly Leu Glu Pro Pro Ser Glu Lys His Phe Arg Glu Thr Glu
            340                 345                 350

Val

<210> SEQ ID NO 32
<211> LENGTH: 505
<212> TYPE: PRT
<213> ORGANISM: Homo sapiens

<400> SEQUENCE: 32

Met Gly Glu Thr Leu Gly Asp Ser Pro Ile Asp Pro Glu Ser Asp Ser
1               5                   10                  15

Phe Thr Asp Thr Leu Ser Ala Asn Ile Ser Gln Glu Met Thr Met Val
            20                  25                  30

Asp Thr Glu Met Pro Phe Trp Pro Thr Asn Phe Gly Ile Ser Ser Val
        35                  40                  45

Asp Leu Ser Val Met Glu Asp His Ser His Ser Phe Asp Ile Lys Pro
50                  55                  60

Phe Thr Thr Val Asp Phe Ser Ser Ile Ser Thr Pro His Tyr Glu Asp
65                  70                  75                  80

Ile Pro Phe Thr Arg Thr Asp Pro Val Val Ala Asp Tyr Lys Tyr Asp
                85                  90                  95

Leu Lys Leu Gln Glu Tyr Gln Ser Ala Ile Lys Val Glu Pro Ala Ser
            100                 105                 110

Pro Pro Tyr Tyr Ser Glu Lys Thr Gln Leu Tyr Asn Lys Pro His Glu
            115                 120                 125

Glu Pro Ser Asn Ser Leu Met Ala Ile Glu Cys Arg Val Cys Gly Asp
130                 135                 140

Lys Ala Ser Gly Phe His Tyr Gly Val His Ala Cys Glu Gly Cys Lys
145                 150                 155                 160

Gly Phe Phe Arg Arg Thr Ile Arg Leu Lys Leu Ile Tyr Asp Arg Cys
                165                 170                 175

Asp Leu Asn Cys Arg Ile His Lys Lys Ser Arg Asn Lys Cys Gln Tyr
            180                 185                 190

Cys Arg Phe Gln Lys Cys Leu Ala Val Gly Met Ser His Asn Ala Ile
            195                 200                 205
```

```
Arg Phe Gly Arg Met Pro Gln Ala Glu Lys Glu Lys Leu Leu Ala Glu
            210                 215                 220

Ile Ser Ser Asp Ile Asp Gln Leu Asn Pro Glu Ser Ala Asp Leu Arg
225                 230                 235                 240

Ala Leu Ala Lys His Leu Tyr Asp Ser Tyr Ile Lys Ser Phe Pro Leu
                245                 250                 255

Thr Lys Ala Lys Ala Arg Ala Ile Leu Thr Gly Lys Thr Thr Asp Lys
                260                 265                 270

Ser Pro Phe Val Ile Tyr Asp Met Asn Ser Leu Met Met Gly Glu Asp
            275                 280                 285

Lys Ile Lys Phe Lys His Ile Thr Pro Leu Gln Glu Gln Ser Lys Glu
290                 295                 300

Val Ala Ile Arg Ile Phe Gln Gly Cys Gln Phe Arg Ser Val Glu Ala
305                 310                 315                 320

Val Gln Glu Ile Thr Glu Tyr Ala Lys Ser Ile Pro Gly Phe Val Asn
                325                 330                 335

Leu Asp Leu Asn Asp Gln Val Thr Leu Leu Lys Tyr Gly Val His Glu
            340                 345                 350

Ile Ile Tyr Thr Met Leu Ala Ser Leu Met Asn Lys Asp Gly Val Leu
            355                 360                 365

Ile Ser Glu Gly Gln Gly Phe Met Thr Arg Glu Phe Leu Lys Ser Leu
370                 375                 380

Arg Lys Pro Phe Gly Asp Phe Met Glu Pro Lys Phe Glu Phe Ala Val
385                 390                 395                 400

Lys Phe Asn Ala Leu Glu Leu Asp Asp Ser Asp Leu Ala Ile Phe Ile
                405                 410                 415

Ala Val Ile Ile Leu Ser Gly Asp Arg Pro Gly Leu Leu Asn Val Lys
            420                 425                 430

Pro Ile Glu Asp Ile Gln Asp Asn Leu Leu Gln Ala Leu Glu Leu Gln
            435                 440                 445

Leu Lys Leu Asn His Pro Glu Ser Ser Gln Leu Phe Ala Lys Leu Leu
450                 455                 460

Gln Lys Met Thr Asp Leu Arg Gln Ile Val Thr Glu His Val Gln Leu
465                 470                 475                 480

Leu Gln Val Ile Lys Lys Thr Glu Thr Asp Met Ser Leu His Pro Leu
                485                 490                 495

Leu Gln Glu Ile Tyr Lys Asp Leu Tyr
            500                 505

<210> SEQ ID NO 33
<211> LENGTH: 366
<212> TYPE: PRT
<213> ORGANISM: Homo sapiens

<400> SEQUENCE: 33

Met Asp Ser Asp Asp Glu Met Val Glu Glu Ala Val Glu Gly His Leu
1               5                   10                  15

Asp Asp Asp Gly Leu Pro His Gly Phe Cys Thr Val Thr Tyr Ser Ser
            20                  25                  30

Thr Asp Arg Phe Glu Gly Asn Phe Val His Gly Glu Lys Asn Gly Arg
        35                  40                  45

Gly Lys Phe Phe Phe Asp Gly Ser Thr Leu Glu Gly Tyr Tyr Val
    50                  55                  60

Asp Asp Ala Leu Gln Gly Gln Gly Val Tyr Thr Tyr Glu Asp Gly Gly
```

```
            65                  70                  75                  80
        Val Leu Gln Gly Thr Tyr Val Asp Gly Glu Leu Asn Gly Pro Ala Gln
                        85                  90                  95
        Glu Tyr Asp Thr Asp Gly Arg Leu Ile Phe Lys Gly Gln Tyr Lys Asp
                       100                 105                 110
        Asn Ile Arg His Gly Val Cys Trp Ile Tyr Tyr Pro Asp Gly Gly Ser
                       115                 120                 125
        Leu Val Gly Glu Val Asn Glu Asp Gly Glu Met Thr Gly Glu Lys Ile
                   130                 135                 140
        Ala Tyr Val Tyr Pro Asp Glu Arg Thr Ala Leu Tyr Gly Lys Phe Ile
        145                 150                 155                 160
        Asp Gly Glu Met Ile Glu Gly Lys Leu Ala Thr Leu Met Ser Thr Glu
                       165                 170                 175
        Glu Gly Arg Pro His Phe Glu Leu Met Pro Gly Asn Ser Val Tyr His
                       180                 185                 190
        Phe Asp Lys Ser Thr Ser Ser Cys Ile Ser Thr Asn Ala Leu Leu Pro
                       195                 200                 205
        Asp Pro Tyr Glu Ser Glu Arg Val Tyr Val Ala Glu Ser Leu Ile Ser
                   210                 215                 220
        Ser Ala Gly Glu Gly Leu Phe Ser Lys Val Ala Val Gly Pro Asn Thr
        225                 230                 235                 240
        Val Met Ser Phe Tyr Asn Gly Val Arg Ile Thr His Gln Glu Val Asp
                       245                 250                 255
        Ser Arg Asp Trp Ala Leu Asn Gly Asn Thr Leu Ser Leu Asp Glu Glu
                       260                 265                 270
        Thr Val Ile Asp Val Pro Glu Pro Tyr Asn His Val Ser Lys Tyr Cys
                   275                 280                 285
        Ala Ser Leu Gly His Lys Ala Asn His Ser Phe Thr Pro Asn Cys Ile
        290                 295                 300
        Tyr Asp Met Phe Val His Pro Arg Phe Gly Pro Ile Lys Cys Ile Arg
        305                 310                 315                 320
        Thr Leu Arg Ala Val Glu Ala Asp Glu Glu Leu Thr Val Ala Tyr Gly
                       325                 330                 335
        Tyr Asp His Ser Pro Pro Gly Lys Ser Gly Pro Glu Ala Pro Glu Trp
                       340                 345                 350
        Tyr Gln Val Glu Leu Lys Ala Phe Gln Ala Thr Gln Gln Lys
                   355                 360                 365

<210> SEQ ID NO 34
<211> LENGTH: 21
<212> TYPE: DNA
<213> ORGANISM: Artificial Sequence
<220> FEATURE:
<223> OTHER INFORMATION: Synthetic construct

<400> SEQUENCE: 34
gtcaaagggg catatggaag g                                              21

<210> SEQ ID NO 35
<211> LENGTH: 20
<212> TYPE: DNA
<213> ORGANISM: Artificial Sequence
<220> FEATURE:
<223> OTHER INFORMATION: Synthetic construct

<400> SEQUENCE: 35
gggaagaaag ccccacttgg                                                20
```

<210> SEQ ID NO 36
<211> LENGTH: 20
<212> TYPE: DNA
<213> ORGANISM: Artificial Sequence
<220> FEATURE:
<223> OTHER INFORMATION: Synthetic construct

<400> SEQUENCE: 36
gcccagtcgc gtgggggggg                                              20

<210> SEQ ID NO 37
<211> LENGTH: 20
<212> TYPE: DNA
<213> ORGANISM: Artificial Sequence
<220> FEATURE:
<223> OTHER INFORMATION: Synthetic construct

<400> SEQUENCE: 37
ggagcgcgag tgtcactcgg                                              20

<210> SEQ ID NO 38
<211> LENGTH: 21
<212> TYPE: DNA
<213> ORGANISM: Mus musculus

<400> SEQUENCE: 38
gctcactgta ggacccgagc c                                            21

<210> SEQ ID NO 39
<211> LENGTH: 21
<212> TYPE: DNA
<213> ORGANISM: Mus musculus

<400> SEQUENCE: 39
gacgcggcgc tcattggcca a                                            21

<210> SEQ ID NO 40
<211> LENGTH: 21
<212> TYPE: DNA
<213> ORGANISM: Mus musculus

<400> SEQUENCE: 40
cgagccgcga gcccagtcgc g                                            21

<210> SEQ ID NO 41
<211> LENGTH: 21
<212> TYPE: DNA
<213> ORGANISM: Mus musculus

<400> SEQUENCE: 41 tcccccccccc ccccccacgcg a                                          21

<210> SEQ ID NO 42
<211> LENGTH: 21
<212> TYPE: DNA
<213> ORGANISM: Mus musculus

<400> SEQUENCE: 42
gtcactcacc ccgattggcc a                                            21

<210> SEQ ID NO 43
<211> LENGTH: 21
<212> TYPE: DNA

```
<213> ORGANISM: Mus musculus

<400> SEQUENCE: 43
cgcgagccca gtcgcgtggg g                                              21

<210> SEQ ID NO 44
<211> LENGTH: 21
<212> TYPE: DNA
<213> ORGANISM: Mus musculus

<400> SEQUENCE: 44
gttggcttat ccaaacatct c                                              21

<210> SEQ ID NO 45
<211> LENGTH: 21
<212> TYPE: DNA
<213> ORGANISM: Mus musculus

<400> SEQUENCE: 45
atgttaagca agggtaatag a                                              21

<210> SEQ ID NO 46
<211> LENGTH: 21
<212> TYPE: DNA
<213> ORGANISM: Mus musculus

<400> SEQUENCE: 46
ctgtgaaagg aatacaattc a                                              21

<210> SEQ ID NO 47
<211> LENGTH: 21
<212> TYPE: DNA
<213> ORGANISM: Mus musculus

<400> SEQUENCE: 47
gccaattctt ggcaaccgag c                                              21

<210> SEQ ID NO 48
<211> LENGTH: 21
<212> TYPE: DNA
<213> ORGANISM: Mus musculus

<400> SEQUENCE: 48
gaattggcca aagggagggg t                                              21

<210> SEQ ID NO 49
<211> LENGTH: 21
<212> TYPE: DNA
<213> ORGANISM: Mus musculus

<400> SEQUENCE: 49
aattagcaga cagcttggta c                                              21

<210> SEQ ID NO 50
<211> LENGTH: 21
<212> TYPE: DNA
<213> ORGANISM: Mus musculus

<400> SEQUENCE: 50
ctggctgatt cccgaggatt t                                              21

<210> SEQ ID NO 51
<211> LENGTH: 21
```

```
<212> TYPE: DNA
<213> ORGANISM: Mus musculus

<400> SEQUENCE: 51
cactgaatac ggattggtca g                                        21

<210> SEQ ID NO 52
<211> LENGTH: 21
<212> TYPE: DNA
<213> ORGANISM: Mus musculus

<400> SEQUENCE: 52
gatgtctcag aaccactgaa t                                        21

<210> SEQ ID NO 53
<211> LENGTH: 21
<212> TYPE: DNA
<213> ORGANISM: Mus musculus

<400> SEQUENCE: 53
aaccactgaa tacggattgg t                                        21

<210> SEQ ID NO 54
<211> LENGTH: 21
<212> TYPE: DNA
<213> ORGANISM: Mus musculus

<400> SEQUENCE: 54
accaatccgt attcagtggt t                                        21

<210> SEQ ID NO 55
<211> LENGTH: 21
<212> TYPE: DNA
<213> ORGANISM: Homo sapiens

<400> SEQUENCE: 55
ggcgcggggc ggacggggcg a                                        21

<210> SEQ ID NO 56
<211> LENGTH: 21
<212> TYPE: DNA
<213> ORGANISM: Homo sapiens

<400> SEQUENCE: 56
gcgccccggg aacgcgtggg g                                        21

<210> SEQ ID NO 57
<211> LENGTH: 21
<212> TYPE: DNA
<213> ORGANISM: Homo sapiens

<400> SEQUENCE: 57
cgccccgcgc cgcgcgggga g                                        21

<210> SEQ ID NO 58
<211> LENGTH: 21
<212> TYPE: DNA
<213> ORGANISM: Homo sapiens

<400> SEQUENCE: 58
tccgccccgc gccgcgcggg g                                        21

<210> SEQ ID NO 59
```

```
<211> LENGTH: 21
<212> TYPE: DNA
<213> ORGANISM: Homo sapiens

<400> SEQUENCE: 59
ggaacgcgtg gggcggagct t                                              21

<210> SEQ ID NO 60
<211> LENGTH: 21
<212> TYPE: DNA
<213> ORGANISM: Homo sapiens

<400> SEQUENCE: 60
gccccgcgcc gcgcggggag g                                              21

<210> SEQ ID NO 61
<211> LENGTH: 21
<212> TYPE: DNA
<213> ORGANISM: Homo sapiens

<400> SEQUENCE: 61
tgcgccccgg gaacgcgtgg g                                              21

<210> SEQ ID NO 62
<211> LENGTH: 21
<212> TYPE: DNA
<213> ORGANISM: Homo sapiens

<400> SEQUENCE: 62
gaacgcgtgg ggcggagctt c                                              21

<210> SEQ ID NO 63
<211> LENGTH: 21
<212> TYPE: DNA
<213> ORGANISM: Homo sapiens

<400> SEQUENCE: 63
gcggcgcggg gcggacgggg c                                              21

<210> SEQ ID NO 64
<211> LENGTH: 21
<212> TYPE: DNA
<213> ORGANISM: Homo sapiens

<400> SEQUENCE: 64
cccgtccgcc ccgcgccgcg c                                              21

<210> SEQ ID NO 65
<211> LENGTH: 21
<212> TYPE: DNA
<213> ORGANISM: Homo sapiens

<400> SEQUENCE: 65
ggcccactcg ccgccaatca g                                              21

<210> SEQ ID NO 66
<211> LENGTH: 21
<212> TYPE: DNA
<213> ORGANISM: Homo sapiens

<400> SEQUENCE: 66
ggaagccgcc ggggccgcct a                                              21
```

```
<210> SEQ ID NO 67
<211> LENGTH: 21
<212> TYPE: DNA
<213> ORGANISM: Homo sapiens

<400> SEQUENCE: 67
tgattggcgg cgagtgggcc a                                              21

<210> SEQ ID NO 68
<211> LENGTH: 21
<212> TYPE: DNA
<213> ORGANISM: Homo sapiens

<400> SEQUENCE: 68
gccgccaatc agcggaagcc g                                              21

<210> SEQ ID NO 69
<211> LENGTH: 21
<212> TYPE: DNA
<213> ORGANISM: Homo sapiens

<400> SEQUENCE: 69
ggcggcttcc gctgattggc g                                              21

<210> SEQ ID NO 70
<211> LENGTH: 21
<212> TYPE: DNA
<213> ORGANISM: Homo sapiens

<400> SEQUENCE: 70
ccgccaatca gcggaagccg c                                              21

<210> SEQ ID NO 71
<211> LENGTH: 21
<212> TYPE: DNA
<213> ORGANISM: Homo sapiens

<400> SEQUENCE: 71
agccgccggg gccgcctaga g                                              21

<210> SEQ ID NO 72
<211> LENGTH: 21
<212> TYPE: DNA
<213> ORGANISM: Homo sapiens

<400> SEQUENCE: 72
gcttccgctg attggcggcg a                                              21

<210> SEQ ID NO 73
<211> LENGTH: 21
<212> TYPE: DNA
<213> ORGANISM: Homo sapiens

<400> SEQUENCE: 73
cggcgagtgg gccaatgggt g                                              21

<210> SEQ ID NO 74
<211> LENGTH: 21
<212> TYPE: DNA
<213> ORGANISM: Homo sapiens

<400> SEQUENCE: 74
ccaatgggtg cggggcggtg g                                              21
```

<210> SEQ ID NO 75
<211> LENGTH: 21
<212> TYPE: DNA
<213> ORGANISM: Mus musculus

<400> SEQUENCE: 75
ggctgccggg gccgcctaaa g                                      21

<210> SEQ ID NO 76
<211> LENGTH: 21
<212> TYPE: DNA
<213> ORGANISM: Mus musculus

<400> SEQUENCE: 76
ggaggctgcc ggggccgcct a                                      21

<210> SEQ ID NO 77
<211> LENGTH: 21
<212> TYPE: DNA
<213> ORGANISM: Mus musculus

<400> SEQUENCE: 77
gccgccaatc agcggaggct g                                      21

<210> SEQ ID NO 78
<211> LENGTH: 21
<212> TYPE: DNA
<213> ORGANISM: Mus musculus

<400> SEQUENCE: 78
ccgccaatca gcggaggctg c                                      21

<210> SEQ ID NO 79
<211> LENGTH: 21
<212> TYPE: DNA
<213> ORGANISM: Mus musculus

<400> SEQUENCE: 79
tggccggtgc gccgccaatc a                                      21

<210> SEQ ID NO 80
<211> LENGTH: 21
<212> TYPE: DNA
<213> ORGANISM: Mus musculus

<400> SEQUENCE: 80
ggccggtgcg ccgccaatca g                                      21

<210> SEQ ID NO 81
<211> LENGTH: 21
<212> TYPE: DNA
<213> ORGANISM: Mus musculus

<400> SEQUENCE: 81
cggcgcaccg gccaataagt g                                      21

<210> SEQ ID NO 82
<211> LENGTH: 21
<212> TYPE: DNA
<213> ORGANISM: Mus musculus

<400> SEQUENCE: 82
ataagtgtgg ggcggtgggc g                                      21

```
<210> SEQ ID NO 83
<211> LENGTH: 21
<212> TYPE: DNA
<213> ORGANISM: Mus musculus

<400> SEQUENCE: 83
ccaataagtg tggggcggtg g                                              21

<210> SEQ ID NO 84
<211> LENGTH: 21
<212> TYPE: DNA
<213> ORGANISM: Mus musculus

<400> SEQUENCE: 84
caataagtgt ggggcggtgg g                                              21

<210> SEQ ID NO 85
<211> LENGTH: 20
<212> TYPE: DNA
<213> ORGANISM: Mus musculus

<400> SEQUENCE: 85
cctttctatg acctagtcgg                                                20

<210> SEQ ID NO 86
<211> LENGTH: 20
<212> TYPE: DNA
<213> ORGANISM: Mus musculus

<400> SEQUENCE: 86
cagaatcagt aacgcactgt                                                20

<210> SEQ ID NO 87
<211> LENGTH: 20
<212> TYPE: DNA
<213> ORGANISM: Mus musculus

<400> SEQUENCE: 87
gaaaccagga gagataaccc                                                20

<210> SEQ ID NO 88
<211> LENGTH: 20
<212> TYPE: DNA
<213> ORGANISM: Mus musculus

<400> SEQUENCE: 88
ggaccccaga tattctggaa                                                20

<210> SEQ ID NO 89
<211> LENGTH: 20
<212> TYPE: DNA
<213> ORGANISM: Mus musculus

<400> SEQUENCE: 89
ttattgttga cttaacgaag                                                20

<210> SEQ ID NO 90
<211> LENGTH: 20
<212> TYPE: DNA
<213> ORGANISM: Mus musculus

<400> SEQUENCE: 90
```

```
aaaaagaagc aaatagctaa                                              20

<210> SEQ ID NO 91
<211> LENGTH: 20
<212> TYPE: DNA
<213> ORGANISM: Mus musculus

<400> SEQUENCE: 91
agaatcagta acgcactgta                                              20

<210> SEQ ID NO 92
<211> LENGTH: 27
<212> TYPE: DNA
<213> ORGANISM: Mus musculus

<400> SEQUENCE: 92
tgttggttta ttggacccca gatattc                                      27

<210> SEQ ID NO 93
<211> LENGTH: 27
<212> TYPE: DNA
<213> ORGANISM: Mus musculus

<400> SEQUENCE: 93
tgttggagaa aattaactta gtgcata                                      27

<210> SEQ ID NO 94
<211> LENGTH: 27
<212> TYPE: DNA
<213> ORGANISM: Mus musculus

<400> SEQUENCE: 94
tgttggtata actgccacta gagggct                                      27

<210> SEQ ID NO 95
<211> LENGTH: 19
<212> TYPE: DNA
<213> ORGANISM: Homo sapiens

<400> SEQUENCE: 95
aggagccggg acccaccgg                                               19
```

GENE THERAPY FOR HAPLOINSUFFICIENCY

CROSS-REFERENCE TO RELATED APPLICATIONS

This application is a 35 U.S.C. § 371 U.S. National Phase application from PCT/US2018/017186, filed Feb. 7, 2018, which claims benefit of priority to U.S. Provisional Application No. 62/455,988, filed Feb. 7, 2017, the contents of which are hereby incorporated by reference in their entireties for all purposes.

STATEMENT AS TO RIGHTS TO INVENTIONS MADE UNDER FEDERALLY SPONSORED RESEARCH AND DEVELOPMENT

This invention was made with government support under grant No. R01 DK090382 awarded by The National Institutes of Health. The government has certain rights in the invention.

REFERENCE TO SUBMISSION OF A SEQUENCE LISTING

This application includes a Sequence Listing as a text file named "081906-224410PC-1072775_SequenceListing.txt" created Feb. 6, 2018 and containing 107 kilobytes. The material contained in this text file is incorporated by reference in its entirety for all purposes.

FIELD OF INVENTION

The present disclosure relates generally to methods and compositions for activating transcription in mammalian cells.

BACKGROUND OF THE INVENTION

Genomic alterations resulting in reduced transcription or activity of one or more genes or gene products are a causative factor in a myriad of mammalian diseases. One such genomic alteration is haploinsufficiency, in which there is only one functional copy of a gene and that single copy does not produce enough of the gene product to produce a wild-type phenotype. Other diseases are caused by genomic alterations in one or both copies of a gene that alter the gene product so that it exhibits a reduction, but not elimination, in activity. In still other diseases, genomic alterations reduce transcription or reduce transcript stability of one or both copies of a gene, such that there is insufficient gene product to produce a wild-type phenotype. Numerous approaches have been attempted to treat such diseases by augmenting the amount or activity of the one or more genes reduced in transcription or activity. Such approaches include delivery into the genome of a wild-type copy of the one or more genes. Recently, targeted introduction into a genome has been demonstrated using methods and compositions based on clustered regularly interspaced short palindromic repeats (CRISPR), Zinc Finger Nucleases (ZFNs) (see, Urnov et al., *Nat. Rev. Genet.*, 11:636-646 (2010) or transcription activator-like effector nucleases (TALENs) (see, Joung and Sander, *Nat. Rev. Mol. Cell Biol.*, 1:49-55 (2013). Other approaches for increasing transcription of one or more target genes include the use of antisense oligomers that promote constitutive splicing (see, US 2016/0298121). However, there remains a need for alternative methods and compositions for increasing the transcription of target genes to treat diseases caused by their reduced transcription, amount, or activity.

BRIEF SUMMARY OF THE INVENTION

The present invention is directed to methods and compositions for increasing transcription of target genes in a mammalian (e.g., human) subject. The inventors have discovered that such increased transcription can be achieved with a transcription-activating guide-RNA (gRNA) construct (e.g., as part of a dCAS9/gRNA complex) targeted to a promoter or enhancer region of a gene. Moreover, the inventors have discovered that transcriptional activation in amounts and for periods of time that are sufficient to treat a disease can be achieved with a non-integrating vector. In some cases, the methods and compositions for transcriptional activation do not covalently modify the genome of the host mammal by endonuclease cleavage, nicking, and/or repair. In some cases, the non-integrating vector is an episomal vector, such as an adeno associated viral vector.

In one aspect, the present invention provides a method of treating a haploinsufficiency disease in a mammalian subject, the method comprising contacting a cell of the subject with a composition comprising: i) a guide RNA, wherein the guide RNA comprises: a) a targeting region that, under conditions present in a nucleus of the cell, specifically hybridizes to a promoter region or an enhancer region operably linked to a wild-type copy of a haploinsufficient gene; and b) a CRISPR nuclease-binding region that specifically binds a CRISPR nuclease under conditions present in a nucleus of the cell or a region that specifically binds to the CRISPR nuclease-binding region; and ii) the CRISPR nuclease, —wherein the contacting forms a complex comprising the CRISPR nuclease bound to the guide RNA, wherein the targeting region of the guide RNA in the complex is hybridized to the promoter or enhancer; —wherein the complex comprises a catalytically inactive CRISPR nuclease and a transcriptional activation domain, and—wherein the complex activates transcription of the wild-type copy of the haploinsufficient gene in an amount and for a duration sufficient to treat the haploinsufficiency disease in the subject. In some embodiments, the mammalian subject is treated with a host cell obtained from the subject. In one embodiment, the mammalian subject is treated with a host cell obtained from a different (distinct) mammalian subject. In some embodiments, the host cell is an isolated mammalian host cell. In another embodiment, the host cell comprises an isolated mammalian host cell having one functional copy of a target gene.

In some embodiments, the contacting comprises contacting the cell with an episomal vector encoding the guide RNA or the CRISPR nuclease. In some embodiments, the contacting comprises contacting the cell with an episomal vector encoding the guide RNA and the CRISPR nuclease. In some embodiments, the contacting comprises contacting the cell with an episomal vector encoding the guide RNA and a second episomal vector encoding the CRISPR nuclease. In some embodiments, the episomal vector(s) are non-integrating. In some embodiments, the episomal vector(s) are non-replicating. In some embodiments, the episomal vector(s) are adeno-associated virus (AAV) vectors. In some embodiments, the episomal vector(s) independently comprise a first and a second end, wherein the first end and second end each independently comprise an AAV inverted terminal repeat.

In some embodiments, the CRISPR nuclease comprises (i) a nuclease domain that has been modified to eliminate nuclease and nicking activity and (ii) a transcriptional activation domain. In some embodiments, the CRISPR nuclease comprises a Cas9 or Cpf1 nuclease. In some embodiments, the modification comprises a mutation at positions corresponding to D10 and H840 of *S. pyogenes* Cas9. In some embodiments, the CRISPR nuclease comprises a D10A, H840A *S. pyogenes* dCas9. In some embodiments, the CRISPR nuclease comprises a *S. aureus* dCas9. In some embodiments the *S. aureus* dCas9 comprises one or more mutations in one of the following residues: E782, K929, N968, R1015. In some embodiments, the guide RNA comprises a dead guide sequence.

In some embodiments, the guide RNA comprises a transcriptional activation binding domain, wherein the transcriptional activation binding domain specifically binds a composition comprising one or more transcriptional activation domains. In some embodiments, the complex comprising the CRISPR nuclease bound to the guide RNA further comprises a transcriptional activation domain selected from the group consisting of HSF1, VP16, VP64, p65, MyoD1, RTA, SET7/9, VPR, histone acetyltransferase p300, an hydroxylase catalytic domain of a TET family protein (e.g., TET1 hydroxylase catalytic domain), LSD1, CIB1, AD2, CR3, EKLF1, GATA4, PRVIE, p53, SP1, MEF2C, TAX, and PPARγ. In some embodiments, the CRISPR nuclease is a CRISPR nuclease-VP64 fusion polypeptide.

In some embodiments, the guide RNA comprises a scaffold region. In some embodiments, the scaffold region comprises an ms2, f6, PP7, com, or L7a ligand sequence. In some embodiments, the scaffold region of the guide RNA in the complex is bound to a transcriptional activation domain fused to an MCP polypeptide, a COM polypeptide, a PCP polypeptide, or an L7a polypeptide. In some embodiments, the haploinsufficient gene is SIM1, Leptin, Leptin receptor, MC4R, SCN2A, SETD5, PAX6, PKD1, MC3R, POMC, STAT3, STAT5, SOCS3, GHR, NPY, NPY1R, NPY2R, NPY5R, PYY, AMPK (PRKAA1, PRKAA2, PRKAB1, PRKAB2, PRKAG1, PRKAG2, PRKAG3), OXT, JAK2, SHP2, NOS3, NROB2, BRS3, CARTPT, FABP4, HTR2C, IL6, NHLH2, NMU, NPB, NPBWRI, PNPLA2, UCP3, ADIPOQ, APOA5, ARNT2, ASIP, C1QTNF2, C3AR1, CCK, CPT1B, CSF2, DGAT1, DGAT2, GHRL, GHSR, HSD11B1, HTR7, INSIG1, INSIG2, LIPC, NMURI, NMUR2, NPBWR2, NTS, PPARGC1A, PPY, RETN, SIRT1, TGFBR2, WDTC1, or FOXO1.

In some embodiments, the targeting region of the guide RNA is encoded by or specifically hybridizes to: SEQ ID NO:1 (GACACGGAATTCATTGCCAG), SEQ ID NO:2 (CTGCGGGTTAGGTCTACCGG), SEQ ID NO:3 (GTTGAGCGCTCAGTCCAGCG), SEQ ID NO:4 (TCCCGACGTCGTGCGCGACC), or SEQ ID NO:5 (GCTCTGAATCTTACTACCCG). In some embodiments, the targeting region of the guide RNA is encoded by or specifically hybridizes to: SEQ ID NO:6 (GCTGTTAACTAAAGACAGGG), SEQ ID NO:7 (GTGGTCTGGGTGATCTCATG), SEQ ID NO:8 (GACAAAGGAACATCTGAGAGG), SEQ ID NO:9 (GTGATCTCATGGGGAAGAGG), or SEQ ID NO:10 (GGCTTTGATCGTGGTCTGGG). In some embodiments, the targeting region of the guide RNA is encoded by or specifically hybridizes to: SEQ ID NO: 11 (GCGAGCCCAGTCGCGTGGGG), or SEQ ID NO:12 (GCCAAGAATTGGCCAAAGGG), SEQ ID NO:34 (GTCAAAGGGGCATATGGAAGG), SEQ ID NO:35 (GGGAAGAAAGCCCCACTTGG), SEQ ID NO:36 (GCCCAGTCGCGTGGGGGGGG), or SEQ ID NO:37 (GGAGCGCGAGTGTCACTCGG). In another embodiment, the targeting region of the guide RNA is encoded by or specifically hybridizes to: SEQ ID NO:38 (GCTCACTGTAGGACCCGAGCC), SEQ ID NO:39 (GACGCGGCGCTCATTGGCCAA), SEQ ID NO:40 (CGAGCCGCGAGCCCAGTCGCG), SEQ ID NO:41 (TCCCCCCCCCCCCCCACGCGA), SEQ ID NO:42 (GTCACTCACCCCGATTGGCCA), or SEQ ID NO:43 (CGCGAGCCCAGTCGCGTGGGG). In some embodiments, the targeting region of the guide RNA is encoded by or specifically hybridizes to: SEQ ID NO:44 (GTTGGCTTATCCAAACATCTC), SEQ ID NO:45 (ATGTTAAGCAAGGGTAATAGA), SEQ ID NO:46 (CTGTGAAAGGAATACAATTCA), SEQ ID NO: 47 (GCCAATTCTTGGCAACCGAGC), SEQ ID NO:48 (GAATTGGCCAAAGGGAGGGGT), or SEQ ID NO:49 (AATTAGCAGACAGCTTGGTAC). In some embodiments, the targeting region of the guide RNA is encoded by or specifically hybridizes to: SEQ ID NO:50 (CTGGCTGATTCCCGAGGATTT), SEQ ID NO: 51 (CACTGAATACGGATTGGTCAG), SEQ ID NO:52 (GATGTCTCAGAACCACTGAAT), SEQ ID NO:53 (AACCACTGAATACGGATTGGT), or SEQ ID NO:54 (ACCAATCCGTATTCAGTGGTT). In some embodiments, the targeting region of the guide RNA is encoded by or specifically hybridizes to: SEQ ID NO:55 (GGCGCGGGGCGGACGGGGCGA), SEQ ID NO:56 (GCGCCCGGGAACGCGTGGGG), SEQ ID NO:57 (CGCCCCGCGCCGCGCGGGGAG), SEQ ID NO:58 (TCCGCCCCGCGCCGCGCGGGG), SEQ ID NO:59 (GGAACGCGTGGGGCGGAGCTT), SEQ ID NO:60 (GCCCCGCGCCGCGCGGGGAGG), SEQ ID NO:61 (TGCGCCCCGGGAACGCGTGGG), SEQ ID NO:62 (GAACGCGTGGGGCGGAGCTTC), SEQ ID NO:63 (GCGGCGCGGGGCGGACGGGGC), or SEQ ID NO:64 (CCCGTCCGCCCCGCGCCGCGC). In some embodiments, the targeting region of the guide RNA is encoded by or specifically hybridizes to: SEQ ID NO:65 (GGCCCACTCGCCGCCAATCAG), SEQ ID NO:66 (GGAAGCCGCCGGGGCCGCCTA), SEQ ID NO:67 (TGATTGGCGGCGAGTGGGCCA), SEQ ID NO:68: (GCCGCCAATCAGCGGAAGCCG), SEQ ID NO:69: (GGCGGCTTCCGCTGATTGGCG), SEQ ID NO:70: (CCGCCAATCAGCGGAAGCCGC), SEQ ID NO:71: (AGCCGCCGGGGCCGCCTAGAG), SEQ ID NO:72: (GCTTCCGCTGATTGGCGGCGA), SEQ ID NO:73: (CGGCGAGTGGGCCAATGGGTG), or SEQ ID NO:74: (CCAATGGGTGCGGGCGGTGG). In some embodiments, the targeting region of the guide RNA is encoded by or specifically hybridizes to: SEQ ID NO:75 (GGCTGCCGGGGCCGCCTAAAG), SEQ ID NO:76 (GGAGGCTGCCGGGGCCGCCTA), SEQ ID NO:77 (GCCGCCAATCAGCGGAGGCTG), SEQ ID NO:78 (CCGCCAATCAGCGGAGGCTGC), SEQ ID NO:79 (TGGCCGGTGCGCCGCCAATCA), SEQ ID NO:80 (GGCCGGTGCGCCGCCAATCAG), SEQ ID NO:81 (CGGCGCACCGGCCAATAAGTG), SEQ ID NO:82 (ATAAGTGTGGGGCGGTGGGCG), SEQ ID NO:83 (CCAATAAGTGTGGGGCGGTGG), or SEQ ID NO:84 (CAATAAGTGTGGGGCGGTGG). In some embodiments, the targeting region of the guide RNA is encoded by or specifically hybridizes to: SEQ ID NO:85 (CCTTTCTATGACCTAGTCGG), SEQ ID NO:86 (CAGAATCAGTAACGCACTGT), SEQ ID NO:87 (GAAACCAGGAGAGATAACCC), SEQ ID NO:88 (GGACCCCAGATATTCTGGAA), SEQ ID NO:89 (TTAT- TGTTGACTTAACGAAG), SEQ ID NO:90 (AAAAAGAAGCAAATAGCTAA), or SEQ ID NO:91 (AGAATCAGTAACGCACTGTA). In some embodiments, the targeting region of the guide RNA is encoded by or specifically hybridizes to: SEQ ID NO:92 (TGTTGGTTT-ATTGGACCCCAGATATTC), SEQ ID NO:93 (TGTTG-GAGAAAATTAACTTAGTGCATA), or SEQ ID NO:94 (TGTTGGTATAACTGCCACTAGAGGGCT). In some embodiments, the targeting region of the guide RNA is encoded by or specifically hybridizes to SEQ ID NO:95 (AGGAGCCGGGACCCACCGG).

In some embodiments, the cell is a non-dividing cell. In some embodiments, the cell is a neuron. In some embodiments, the cell is a hypothalamus cell. In some embodiments, the contacting comprises injection of nucleic acid encoding the guide RNA and/or the CRISPR nuclease into a region of a brain containing a hypothalamus. In some embodiments, the contacting comprises injection of an adeno-associated viral vector comprising nucleic acid encoding the guide RNA and/or the CRISPR nuclease into a region of a brain containing a hypothalamus. In some embodiments, the haploinsufficiency disease is selected from Table 1. In some embodiments, the haploinsufficiency disease is selected from obesity, autism, epilepsy, intellectual disability, aniridia, and polycystic kidney disease. In some embodiments, the haploinsufficiency disease is obesity.

In another aspect, the present invention provides a mammalian host cell comprising: I.) a genome comprising at least one functional copy of a target gene, wherein the functional cop(y/ies) in the absence of transcriptional activation by a heterologous complex do not produce enough of a corresponding gene product to produce a wild-type phenotype in an organism; and II.) the heterologous complex, wherein the heterologous complex comprises: a) a guide RNA, wherein the guide RNA comprises: i.) a targeting region that specifically hybridizes to a promoter region or an enhancer region operably linked to the functional cop(y/ies) of the target gene under conditions present in a nucleus of the cell; and ii.) a CRISPR nuclease-binding region that specifically binds a CRISPR nuclease under conditions present in a nucleus of the cell; and b) the CRISPR nuclease, —wherein the guide RNA of the heterologous complex comprising the CRISPR nuclease bound to the guide RNA is hybridized to the promoter or enhancer; —wherein the CRISPR nuclease is catalytically inactive, and—wherein the complex activates transcription of the functional cop(y/ies) of the target gene in an amount and for a duration sufficient to produce a wild-type phenotype when the host cell is present in an organism.

In some embodiments, the genome comprises a single functional copy of the target gene. In some embodiments, the single functional copy of the target gene comprises a haploinsufficient gene. In some embodiments, the genome comprises less than two functional copies of the target gene.

BRIEF DESCRIPTION OF THE DRAWINGS

FIGS. 2A-D Body composition and metabolic analyses of Sim1 CRISPRa transgenic mice. A, Estimated percent fat in wild-type littermates, Sim1$^{+/-}$, H11P$^{CAG\text{-}dCas9\text{-}VP64}$ X ROSA26$^{Sim1Pr\text{-}sgRNA}$ (PrmCRISPRa) and H11P$^{CAG\text{-}dCas9\text{-}VP64}$ X ROSA26$^{SCE2En\text{-}sgRNA}$ (EnhCRISPRa) as determined by Dual Energy X-ray Absorptiometry (DEXA) or Echo Magnetic Resonance Imaging (EchoMRI), with their corresponding body weight measurements. The mean values+s.d. were obtained from 3 females and 3 males. B, Metabolic chamber energy expenditure analyses for 3 males and 3 females for all four genotypes determined over a 4 day period. C, Food intake for all four genotypes determined over a 4 day period. Mean values±s.d. were obtained from 3 females and 3 males. *=p-value<0.001; ***=p-value<0.0005; n.s=non-significant (ANOVA, Tukey test). D, Respiratory exchange ratio (RER; VCO2/VO2) for all four genotypes obtained from 3 females and 3 males and plotted as mean values±s.d.

FIG. 7A-7B: CRISPRa Sim1 overexpression in vitro. FIG. 7A, shows an exemplary S. aureus CRISPRa system targeting the Sim1 promoter (Pr) by transfection of various sgRNA's (SEQ ID NOS:38-43) into Neuro-2A (N2A) cells. Results are expressed as mRNA fold-increase normalized to Sa-dCas9-VP64. The mean values±s.d. were obtained from 3 independent experiments. FIG. 7B, shows an exemplary S. aureus CRISPRa in N2A cells targeting the Sim1 promoter (Pr) after infection of AAV's containing select sgRNA's (SEQ ID NOS:38, 40, or 42) into N2A cells. Results are expressed as mRNA fold-increase normalized to VP64 alone. The mean values±s.d. were obtained from 3 independent experiments.

FIG. 8A-8B: CRISPRa Sim1 overexpression in vitro. FIG. 8A, shows an exemplary S. aureus CRISPRa system targeting the Sim1 SCE2 enhancer (Enh) by transfection of various sgRNA's (SEQ ID NOS:44-49) into N2A cells. Results are expressed as mRNA fold-increase normalized to Sa-dCas9-VP64. The mean values±s.d. were obtained from 3 independent experiments. FIG. 8B, shows an exemplary S. aureus CRISPRa system targeting the Sim1 SCE2 enhancer (Enh) after infection of AAV's containing select sgRNA's (SEQ ID NOS:45, 46, or 47) into N2A cells. Results are expressed as mRNA fold-increase normalized to VP64 alone. The mean values±s.d. were obtained from 3 independent experiments.

FIG. 9A-9B: CRISPRa Mc4r overexpression in vitro. FIG. 9A, shows an exemplary S. aureus CRISPRa system targeting the Mc4r promoter (Pr) by transfection of various sgRNA's (SEQ ID NOS:50-54) into N2A cells. Results are expressed as mRNA fold-increase normalized to VP64. The mean values±s.d. were obtained from 3 independent experiments. FIG. 9B, shows an exemplary S. aureus CRISPRa system targeting the Mc4r promoter (Pr) after infection of AAV's containing select sgRNA's (SEQ ID NOS:51, 52, or 54) into N2A cells. Results are expressed as mRNA fold-increase normalized to VP64. The mean values±s.d. were obtained from 3 independent experiments.

FIG. 10: CRISPRa PKD1 overexpression in vitro. An exemplary S. aureus CRISPRa system targeting the PKD1 promoter (Pr) by transfection of human promoter sgRNA's (SEQ ID NOS:55-64) into human HEK293T cells. Results are expressed as mRNA fold-increase normalized to dCas9-VP64. The mean values±s.d. were obtained from 3 independent experiments.

FIG. 11A-11B: CRISPRa SETD5 overexpression in vitro. FIG. 11A, shows an exemplary S. aureus CRISPRa system targeting the SETD5 promoter (Pr) or THUMPD3 by transfection of human promoter sgRNA's (SEQ ID NOS:65-74) into human HEK293T cells. HS MIX refers to transfection of an equimolar concentration of each of HS01-HS10 into human HEK293T cells. Results are expressed as mRNA fold-increase normalized to VP64 alone. The mean values±s.d. were obtained from 3 independent experiments. FIG. 11B, shows an exemplary S. aureus CRISPRa system targeting the SETD5 promoter (Pr) or ROSA26 by transfection of mouse promoter sgRNA's (SEQ ID NOS:75-84) into mouse Neuro-2A cells. MS MIX refers to transfection of an equimolar concentration of each of MS01-MS10 into mouse Neuro-2A cells. Results are expressed as mRNA fold-increase normalized to VP64 alone. The mean values±s.d. were obtained from 3 independent experiments.

FIG. 12A-12B: CRISPRa Scn2A overexpression in vitro. FIG. 12A, shows an exemplary S. pyogenes (Sp) Cas9 CRISPRa system targeting the Scn2a promoter (Pr) by transfection of various sgRNA's (SEQ ID NOS:85-91) into N2A cells. Results are expressed as mRNA fold-increase normalized to VP64 alone. The mean values±s.d. were obtained from 3 independent experiments. FIG. 12B, shows an exemplary S. aureus CRISPRa system targeting the Scn2a promoter (Pr) after infection of AAV's containing select sgRNA's (SEQ ID NOS:92-94) into N2A cells. Two different multiplicity of infection (MOI) were used: 5,000 and 1,250 viral genome (vg/ml). Results are expressed as mRNA fold-increase normalized to VP64 alone. The mean values±s.d. were obtained from 3 independent experiments.

FIG. 13: CRISPRa PAX6 overexpression in vitro. shows an exemplary S. pyogenes (Sp) Cas9 CRISPRa system targeting the PAX6 promoter (Pr) by lentiviral delivery of human promoter sgRNA (SEQ ID NO:95) into human H1-ESC cells differentiated into neurons. Results are expressed as relative expression to HPRT. The mean values±s.d. were obtained from 3 independent experiments. Additional neuronal markers are shown to demonstrate that PAX6 CRISPRa leads to neural induction of H1-ESCs.

DEFINITIONS

Figure 1A:
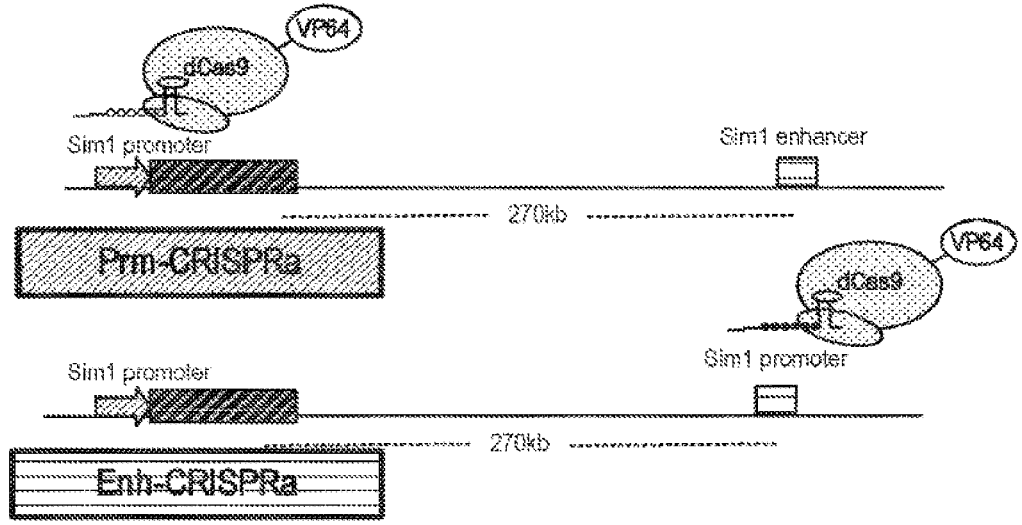
FIGS. 1A-F: Transgenic CRISPRa Sim1 overexpression in vitro and in vivo. A, Schema of the mouse Sim1 genomic locus. B, CRISPRa in Neuro-2A cells targeting the Sim1 promoter (Pr) or enhancer (Enh). Results are expressed as mRNA fold-increase normalized to beta-actin using the ΔΔCT method. The mean values±s.d. were obtained from 3 independent experiments. *=p-value<0.001 ***=p-value<0.0005 (ANOVA, Tukey test). C, Schema showing the various mouse lines and mouse transgenic CRISPRa concept. D, Weekly weight measurements of wild-type littermates, Sim1$^{+/-}$, H11P$^{CAG\text{-}dCas9\text{-}VP64}$ X ROSA26$^{Sim1Pr\text{-}sgRNA}$ and H11P$^{CAG\text{-}dCas9\text{-}VP64}$ X ROSA26$^{SCE2En\text{-}sgRNA}$. At least 10 male and female mice were measured per genotype. Mean values±s.d are shown. E-F, Pictures showing 20 week old mice for each genotype: Sim1$^{+/-}$, H11P$^{CAG\text{-}dCas9\text{-}VP64}$ X ROSA26$^{Sim1Pr\text{-}sgRNA}$ and wild-type littermate (E) and Sim1$^{+/-}$, H11P$^{CAG\text{-}dCas9\text{-}VP64}$ X ROSA26$^{SCE2En\text{-}sgRNA}$ and wild-type littermate (F). Length and weight of each mice are depicted above and below respectively.

As used in this specification and the appended claims, the singular forms "a," "an," and "the" include plural reference unless the context clearly dictates otherwise.

"Treating" refers to any indicia of success in the treatment or amelioration or prevention of the disease, condition, or disorder, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with a disease, condition or disorder as described herein. The term "therapeutic effect" refers to the reduction, elimination, or prevention of the disease, symptoms of the disease, or side effects of the disease in the subject. "Treating" or "treatment" using the methods of the present invention includes preventing the onset of symptoms in a subject that can be at increased risk of a disease or disorder associated with a disease, condition or disorder as described herein, but does not yet experience or exhibit symptoms, inhibiting the symptoms of a disease or disorder (slowing or arresting its development), providing relief from the symptoms or side-effects of a disease (including palliative treatment), and relieving the symptoms of a disease (causing regression). Treatment can be prophylactic (to prevent or delay the onset of the disease, or to prevent the manifestation of clinical or subclinical symptoms thereof) or therapeutic suppression or alleviation of symptoms after the manifestation of the disease or condition. The term "treatment," as used herein, includes preventative (e.g., prophylactic), curative or palliative treatment.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologues, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al, Mol. Cell. Probes 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter.

A "reporter gene" encodes proteins that are readily detectable due to their biochemical characteristics, such as enzymatic activity or chemifluorescent features. One specific example of such a reporter is green fluorescent protein. Fluorescence generated from this protein can be detected with various commercially-available fluorescent detection systems. Other reporters can be detected by staining. The reporter can also be an enzyme that generates a detectable signal when contacted with an appropriate substrate. The reporter can be an enzyme that catalyzes the formation of a detectable product. Suitable enzymes include, but are not limited to, proteases, nucleases, lipases, phosphatases and hydrolases. The reporter can encode an enzyme whose substrates are substantially impermeable to eukaryotic plasma membranes, thus making it possible to tightly control signal formation. Specific examples of suitable reporter genes that encode enzymes include, but are not limited to, CAT (chloramphenicol acetyl transferase; Alton and Vapnek (1979) Nature 282: 864-869); luciferase (lux); β-galactosidase; LacZ; β.-glucuronidase; and alkaline phosphatase (Toh, et al. (1980) Eur. J. Biochem. 182: 231-238; and Hall et al. (1983) J. Mol. Appl. Gen. 2: 101), each of which are incorporated by reference herein in its entirety. Other suitable reporters include those that encode for a particular epitope that can be detected with a labeled antibody that specifically recognizes the epitope.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups {e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. In some cases, conservatively modified variants of a CRISPR nuclease such as Cas9 or a guide RNA such as a small guide RNA (sgRNA) can have an increased stability, assembly, or activity as described in WO 2016/011080, the contents of which are hereby incorporated by reference in the entirety for all purposes including, without limitation, the sgRNAs, sgRNA scaffolds, sgRNA libraries, and sgRNA binding regions described therein.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins, W. H. Freeman and Co., N. Y. (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the left most residue, which is numbered 1, in an unmodified wild-type polypeptide sequence.

As used in herein, the terms "identical" or percent "identity," in the context of describing two or more polynucleotide or amino acid sequences, refer to two or more sequences or subsequences that are the same or have a specified percentage of amino acid residues or nucleotides that are the same. For example, a core small guide RNA (sgRNA) sequence responsible for assembly and activity of a sgRNA:nuclease complex has at least 80% identity, preferably 85%, 90%, 91%, 92%, 93, 94%, 95%, 96%, 97%, 98%, 99%, or 100%) identity, to a reference sequence, when compared and aligned for maximum correspondence over a comparison window, or designated region as measured using one of the following sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Examples of algorithms that are suitable for determining percent sequence identity and sequence similarity are the BLAST and BLAST 2.0 algorithms, which are described in Altschul et al, (1990) J. Mol. Biol. 215: 403-410 and Altschul et al. (1977) Nucleic Acids Res. 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, Proc. Natl. Acad. Sci. USA 89: 10915 (1989)).

The BLAST algorithm also performs a statistical analysis of the similarity between two sequences {see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence. Yet another indication that two polypeptides are substantially identical is that the two polypeptides retain identical or substantially similar activity.

A "translocation sequence" or "transduction sequence" refers to a peptide or protein (or active fragment or domain thereof) sequence that directs the movement of a protein from one cellular compartment to another, or from the extracellular space through the cell or plasma membrane into the cell. Translocation sequences that direct the movement of a protein from the extracellular space through the cell or plasma membrane into the cell are "cell penetration peptides." Translocation sequences that localize to the nucleus of a cell are termed "nuclear localization" sequences, signals, domains, peptides, or the like.

Examples of translocation sequences include, without limitation, the TAT transduction domain (see, e.g., S. Schwarze et al, Science 285 (Sep. 3, 1999); penetratins or penetratin peptides (D. Derossi et al, Trends in Cell Biol. 8, 84-87); Herpes simplex virus type 1 VP22 (A. Phelan et al., Nature Biotech. 16, 440-443 (1998), and polycationic (e.g., poly-arginine) peptides (Cell Mol. Life Sci. 62 (2005) 1839-1849). Further translocation sequences are known in the art. Translocation peptides can be fused (e.g. at the amino or carboxy terminus), conjugated, or coupled to a compound of the present invention, to, among other things, produce a conjugate compound that may easily pass into target cells, or through the blood brain barrier and into target cells.

As used herein, the term "CRISPR" refers to any one of the naturally occurring Clustered Regularly Interspaced Short Palindromic Repeat systems or loci, or a derivative thereof. CRISPR loci can be found in the genomes of many bacteria and archaea. There are four types of CRISPR systems (e.g., Type I, Type II, Type III, and Type U).

A CRISPR locus can comprise polynucleotide sequences encoding for CRISPR Associated Genes (Cas) genes. Cas genes can be involved in the biogenesis and/or the interference stages of crRNA function. Cas genes can be named according to the organism from which they are derived. For example, Cas genes in *Staphylococcus epidermidis* can be referred to as Csm-type, Cas genes in *Streptococcus thermophilus* can be referred to as Csn-type, and Cas genes in *Pyrococcus furiosus* can be referred to as Cmr-type.

As used herein, the term CRISPR nuclease refers to a polypeptide of, or derived from, a nuclease encoded in any one of the four types of CRISPR loci: Type I, Type II, Type III, and Type U, wherein the natural sequence of the polypeptide exhibits RNA-guided nuclease activity. A CRISPR nuclease can be catalytically inactive. Catalytically inactive CRISPR nucleases do not exhibit nuclease or nickase activity when in complex with an RNA-guide and bound to a nucleic acid target containing a target domain and, in certain embodiments, a PAM sequence. The catalytically inactive CRISPR nuclease can be catalytically inactive due to one or more mutations of the CRISPR nuclease polypeptide sequence, or due to forming a complex with a guide RNA that is sufficient to provide RNA-guided targeting, but insufficient to support catalytic activity (i.e., nuclease or nicking activity). For example, the CRISPR nuclease can be a wild-type CRISPR nuclease (e.g., a Cas9 or Cpf1 nuclease) in complex with a dead guide sequence. For example, Cpf1 is a Class II CRISPR-Cas system and is described in Zetsche et al., *Cell*, 163:759-771 (2015). Dead guide sequences and their use are further described in, e.g., WO 2016/094872, which is hereby incorporated by reference for all purposes, including dead guide sequences, complexes between CRISPR nucleases and dead guide sequences, and methods and compositions for making and using such dead guide sequences and complexes containing them.

In certain embodiments, a CRISPR nuclease meets one or both of the following criteria: it has at least 20, 30, 40, 50, 55, 60, 65, 70, 75, 80, 81, 82, 83, 84, 85, 86, 87, 88, 89, 90, 91, 92, 93, 94, 95, 96, 97, 98, 99, or 100% homology with, or it differs by no more than 1, 2, 3, 4, 5, 6, 7, 8, 9, 10, 11, 12, 13, 14, 15, 16, 17, 18, 19, 20, 25, 30, 35, 40, 35, 50, 55, 60, 65, 70, 75, 80, 85, 90, 95, 100, 150, 200, 250, 300, 350 or 400, amino acid residues from, the amino acid sequence of a reference sequences, e.g., a naturally occurring CRISPR nuclease. Additional CRISPR nucleases include, without limitation, one or more CRISPR nucleases described in WO 2016/154579.

In certain embodiments, a CRISPR nuclease contains (i.e., is covalently or non-covalently linked to) one or more additional polypeptides or nucleic acids. For example, the CRISPR nuclease can be fused at an amino or carboxy-terminus to one or more transcriptional activation domain polypeptides, one or more DNA-binding polypeptides, one or more affinity tags (e.g., in complex with one or more affinity tag ligands, such as affinity tag ligand-transcriptional activation domain fusion protein(s)), nuclear localization sequences, or a combination thereof.

Exemplary DNA-binding polypeptides include, but are not limited to, the programmable DNA binding domains described in Bolukbasi et al., Nature Methods 12, 1150-1156 (2015), the contents of which are hereby incorporated by reference in the entirety including, e.g., the programmable DNA-binding domains (pDBD), Cas9 variants, and Cas9-pDBD chimeras described therein. Exemplary transcriptional activation domain polypeptides include, but are not limited to, an activation domain of, or combinations of activation domains of, one or more of the following:

```
heat shock transcription factor 1 (HSF1), e.g.,
                                                                    SEQ ID NO: 13
(EKCLSVACLDKNELSDHLDAMDSNLDNLQTMLSSHGFSVDTSALLDLFSPSVTV

PDMSLPDLDSSLASIQELLSPQEPPRPPEAENSSPDSGKQLVHYTAQPLFLLDPGS

VDTGSNDLPVLFELGEGSYFSEGDGFAEDPTISLLTGSEPPKAKDPTVS)
``` viral protein 16 (VP16), e.g.,                               SEQ ID NO: 14
(DALDDFDLDML);

tetrameric VP16 (VP64), e.g.,                        SEQ ID NO: 15
(DALDDFDLDMLGSDALDDFDLDMLGSDALDDFDLDMLGSDALDDFDLDML)

the p65 NF-Kβ transactivating subunit (p65), e.g.,       SEQ ID NO: 16
(SQYLPDTDDRHRIEEKRKRTYETFKSIMKKSPFSGPTDPRPPPRRIAVPSRSSASV

PKPAPQPYPFTSSLSTINYDEFPTMVFPSGQISQASALAPAPPQVLPQAPAPAPA

MVSALAQAPAPVPVLAPGPPQAVAPPAPKPTQAGEGTLSEALLQLQFDDEDLGA

LLGNSTDPAVFTDLASVDNSEFQQLLNQGIPVAPHTTEPMLMEYPEAITRLVTGA

QRPPDPAPAPLGAPGLPNGLLSGDEDFSSIADMDFSALL)

MyoD1, e.g.,                                                 SEQ ID NO: 17
(MELLSPPLRDIDLTGPDGSLCSFETADDFYDDPCFDSPDLRFFEDLDPRLVHMGA

LLKPEEHAHFPTAVHPGPGAREDEHVRAPSGHHQAGRCLLWACKACKRKTTNA

DRRKAATMRERRRLSKVNEAFETLKRCTSSNPNQRLPKVEILRNAIRYIEGLQAL

LRDQDAAPPGAAAFYAPGPLPPGRGSEHYSGDSDASSPRSNCSDGMMDYSGPPS

GPRRQNGYDTAYYSEAARESRPGKSAAVSSLDCLSSIVERISTDSPAAPALLLAD

APPESPPGPPEGASLSDTEQGTQTPSPDAAPQCPAGSNPNAIYQVL)

RTA, e.g.,                                                      SEQ ID NO: 18
(RDSREGMFLPKPEAGSAISDVFEGREVCQPKRIRPFHPPGSPWANRPLPASLAPTP

TGPVHEPVGSLTPAPVPQPLDPAPAVTPEASHLLEDPDEETSQAVKALREMADTV

IPQKEEAAICGQMDLSHPPPRGHLDELTTTLESMTEDLNLDSPLTPELNEILDTFLN

DECLLHAMHISTGLSIFDTSLF)

SET7, e.g.,                                                 SEQ ID NO: 19
(MDSDDEMVEEAVEGHLDDDGLPHGFCTVTYSSTDRFEGNFVHGEKNGRGKFFF

FDGSTLEGYYVDDALQGQGVYTYEDGGVLQGTYVDGELNGPAQEYDTDGRLIF

KGQYKDNIRHGVCWIYYPDGGSLVGEVNEDGEMTGEKIAYVYPDERTALYGKFI

DGEMIEGKLATLMSTEEGRPHFELMPGNSVYHFDKSTSSCISTNALLPDPYESER

VYVAESLISSAGEGLFSKVAVGPNTVMSFYNGVRITHQEVDSRDWALNGNTLSL

DEETVIDVPEPYNHVSKYCASLGHKANHSFTPNCIYDMFVHPRFGPIKCIRTLRA

VEADEELTVAYGYDHSPPGKSGPEAPEWYQVELKAFQATQQK)

VPR, e.g.,                                                      SEQ ID NO: 20
(EASGSGRADALDDFDLDMLGSDALDDFDLDMLGSDALDDFDLDMLGSDALDD

FDLDMLINSRSSGSPKKKRKVGSQYLPDTDDRHRIEEKRKRTYETFKSIMKKSPFS

GPTDPRPPPRRIAVPSRSSASVPKPAPQPYPFTSSLSTINYDEFPTMVFPSGQISQAS

ALAPAPPQVLPQAPAPAPAPAMVSALAQAPAPVPVLAPGPPQAVAPPAPKPTQA

GEGTLSEALLQLQFDDEDLGALLGNSTDPAVFTDLASVDNSEFQQLLNQGIPVAP

HTTEPMLMEYPEAITRLVTGAQRPPDPAPAPLGAPGLPNGLLSGDEDFSSIADMD

FSALLGSGSGSRDSREGMFLPKPEAGSAISDVFEGREVCQPKRIRPFHPPGSPWAN

RPLPASLAPTPTGPVHEPVGSLTPAPVPQPLDPAPAVTPEASHLLEDPDEETSQAV

KALREMADTVIPQKEEAAICGQMDLSHPPPRGHLDELTTTLESMTEDLNLDSPLT

PELNEILDTFLNDECLLHAMHISTGLSIFDTSLF)

histone acetyltransferase p300, e.g., SEQ ID NO: 21

(KFSAKRLPSTRLGTFLENRVNDFLRRQNHPESGEVTVRVVHASDKTVEVKPGM

KARFVDSGEMAESFPYRTKALFAFEEIDGVDLCFFGMHVQEYGSDCPPPNQRRV

YISYLDSVHFFRPKCLRTAVYHEILIGYLEYVKKLGYTTGHIWACPPSEGDDYIFH

CHPPDQKIPKPKRLQEWYKKMLDKAVSERIVHDYKDIFKQATEDRLTSAKELPY

FEGDFWPNVLEESIKELEQEEEERKREENTSNESTDVTKGDSKNAKKKNNKKTS

KNKSSLSRGNKKKPGMPNVSNDLSQKLYATMEKHKEVFFVIRLIAGPAANSLPPI

VDPDPLIPCDLMDGRDAFLTLARDKHLEFSSLRRAQWSTMCMLVELHTQSQ)

an hydroxylase catalytic domain of a TET family protein (e.g., TET1 hydroxylase catalytic domain), e.g.,
SEQ ID NO: 22

(MSRSRHARPSRLVRKEDVNKKKKNSQLRKTTKGANKNVASVKTLSPGKLKQLI

QERDVKKKTEPKPPVPVRSLLTRAGAARMNLDRTEVLFQNPESLTCNGFTMALR

STSLSRRLSQPPLVVAKSKKVPLSKGLEKQHDCDYKILPALGVKHSENDSVPMQ

DTQVLPDIETLIGVQNPSLLKGKSQETTQFWSQRVEDSKINIPTHSGPAAEILPGPL

EGTRCGEGLFSEETLNDTSGSPKMFAQDTVCAPFPQRATPKVTSQGNPSIQLEEL

GSRVESLKLSDSYLDPIKSEHDCYPTSSLNKVIPDLNLRNCLALGGSTSPTSVIKFL

LAGSKQATLGAKPDHQEAFEATANQQEVSDTTSFLGQAFGAIPHQWELPGADPV

HGEALGETPDLPEIPGAIPVQGEVFGTILDQQETLGMSGSVVPDLPVFLPVPPNPIA

TFNAPSKWPEPQSTVSYGLAVQGAIQILPLGSGHTPQSSSNSEKNSLPPVMAISNV

ENEKQVHISFLPANTQGFPLAPERGLFHASLGIAQLSQAGPSKSDRGSSQVSVTST

VHVVNTTVVTMPVPMVSTSSSSYTTLLPTLEKKKRKRCGVCEPCQQKTNCGECT

YCKNRKNSHQICKKRKCEELKKKPSVVVPLEVIKENKRPQREKKPKVLKADFDN

KPVNGPKSESMDYSRCGHGEEQKLELNPHTVENVTKNEDSMTGIEVEKWTQNK

KSQLTDHVKGDFSANVPEAEKSKNSEVDKKRTKSPKLFVQTVRNGIKHVHCLPA

ETNVSFKKFNIEEFGKTLENNSYKFLKDTANHKNAMSSVATDMSCDHLKGRSNV

LVFQQPGFNCSSIPHSSHSIINHHASIHNEGDQPKTPENIPSKEPKDGSPVQPSLLSL

MKDRRLTLEQVVAIEALTQLSEAPSENSSPSKSEKDEESEQRTASLLNSCKAILYT

VRKDLQDPNLQGEPPKLNHCPSLEKQSSCNTVVFNGQTTTLSNSHINSATNQAST

KSHEYSKVTNSLSLFIPKSNSSKIDTNKSIAQGIITLDNCSNDLHQLPPRNNEVEYC

NQLLDSSKKLDSDDLSCQDATHTQIEEDVATQLTQLASIIKINYIKPEDKKVESTP

TSLVTCNVQQKYNQEKGTIQQKPPSSVHNNHGSSLTKQKNPTQKKTKSTPSRDR

RKKKPTVVSYQENDRQKWEKLSYMYGTICDIWIASKFQNFGQFCPHDFPTVFGK

ISSSTKIWKPLAQTRSIMQPKTVFPPLTQIKLQRYPESAEEKVKVEPLDSLSLFHLK

TESNGKAFTDKAYNSQVQLTVNANQKAHPLTQPSSPPNQCANVMAGDDQIRFQ

QVVKEQLMHQRLPTLPGISHETPLPESALTLRNVNVVCSGGITVVSTKSEEEVCSS

SFGTSEFSTVDSAQKNFNDYAMNFFTNPTKNLVSITKDSELPTCSCLDRVIQKDK

GPYYTHLGAGPSVAAVREIMENRYGQKGNAIRIEIVVYTGKEGKSSHGCPIAKW

VLRRSSDEEKVLCLVRQRTGHHCPTAVMVVLIMVWDGIPLPMADRLYTELTENL

KSYNGHPTDRRCTLNENRTCTCQGIDPETCGASFSFGCSWSMYFNGCKFGRSPSP

```
RRFRIDPSSPLHEKNLEDNLQSLATRLAPIYKQYAPVAYQNQVEYENVARECRLG

SKEGRPFSGVTACLDFCAHPHRDIHNMNNGSTVVCTLTREDNRSLGVIPQDEQL

HVLPLYKLSDTDEFGSKEGMEAKIKSGAIEVLAPRRKKRTCFTQPVPRSGKKRAA

MMTEVLAHKIRAVEKKPIPRIKRKNNSTTTNNSKPSSLPTLGSNTETVQPEVKSET

EPHFILKSSDNTKTYSLMPSAPHPVKEASPGFSWSPKTASATPAPLKNDATASCGF

SERSSTPHCTMPSGRLSGANAAAADGPGISQLGEVAPLPTLSAPVMEPLINSEPST

GVTEPLTPHQPNHQPSFLTSPQDLASSPMEEDEQHSEADEPPSDEPLSDDPLSPAE

EKLPHIDEYWSDSEHIFLDANIGGVAIAPAHGSVLIECARRELHATTPVEHPNRNH

PTRLSLVFYQHKNLNKPQHGFELNKIKFEAKEAKNKKMKASEQKDQAANEGPE

QSSEVNELNQIPSHKALTLTHDNVVTVSPYALTHVAGPYNHWV)
```

LSD1, e.g.,     SEQ ID NO: 23

```
(GMDVTLLEARDRVGGRVATFRKGNYVADLGAMVVTGLGGNPMAVVSKQVN

MELAKIKQKCPLYEANGQAVPKEKDEMVEQEFNRLLEATSYLSHQLDFNVLNN

KPVSLGQALEVVIQLQEKHVKDEQIEHWKKIVKTQEELKELLNKMVNLKEKIKE

LHQQYKEASEVKPPRDITAEFLVKSKHRDLTALCKEYDELAETQGKLEEKLQELE

ANPPSDVYLSSRDRQILDWHFANLEFANATPLSTLSLKHWDQDDDFEFTGSHLT

VRNGYSCVPVALAEGLDIKLNTAVRQVRYTASGCEVIAVNTRSTSQTFIYKCDA

VLCTLPLGVLKQQPPAVQFVPPLPEWKTSAVQRMGFGNLNKVVLCFDRVFWDP

SVNLFGHVGSTTASRGELFLFWNLYKAPILLALVAGEAAGIMENISDDVIVGRCL

AILKGIFGSSAVPQPKETVVSRWRADPWARGSYSYVAAGSSGNDYDLMAQPITP

GPSIPGAPQPIPRLFFAGEHTIRNYPATVHGALLSGLREAGRIADQFLGAMYTLPR

QATPGVPAQQSPSM)
```

CIB1, e.g.,     SEQ ID NO: 24

```
(MGGSGSRLSKELLAEYQDLTFLTKQEILLAHRRFCELLPQEQRSVESSLRAQVPF

EQILSLPELKANPFKERICRVFSTSPAKDSLSFEDFLDLLSVFSDTATPDIKSHYAFR

IFDFDDDGTLNREDLSRLVNCLTGEGEDTRLSASEMKQLIDNILEESDIDRDGTIN

LSEFQHVISRSPDFASSFKIVL)
```

AD2, e.g.,     SEQ ID NO: 25

```
(MNQPQRMAPVGTDKELSDLLDFSMMFPLPVTNGKGRPASLAGAQFGGSGLED

RPSSGSWGSGDQSSSSFDPSRTFSEGTHFTESHSSLSSSTFLGPGLGGKSGERGAY

ASFGRDAGVGGLTQAGFLSGELALNSPGPLSPSGMKGTSQYYPSYSGSSRRRAA

DGSLDTQPKKVRKVPPGLPSSVYPPSSGEDYGRDATAYPSAKTPSSTYPAPFYVA

DGSLHPSAELWSPPGQAGFGPMLGGGSSPLPLPPGSGPVGSSGSSSTFGGLHQHE

RMGYQLHGAEVNGGLPSASSFSSAPGATYGGVSSHTPPVSGADSLLGSRGTTAG

SSGDALGKALASIYSPDHSSNNFSSSPSTPVGSPQGLAGTSQWPRAGAPGALSPSY

DGGLHGLQSKIEDHLDEAIHVLRSHAVGTAGDMHTLLPGHGALASGFTGPMSLG

GRHAGLVGGSHPEDGLAGSTSLMHNHAALPSQPGTLPDLSRPPDSYSGLGRAGA

TAAASEIKREEKEDEENTSAADHSEEEKKELKAPRARTSPDEDEDDLLPPEQKAE
```

REKERRVANNARERLRVRDINEAFKELGRMCQLHLNSEKPQTKLLILHQAVSVIL

NLEQQVRERNLNPKAACLKRREEEKVSGVVGDPQMVLSAPHPGLSEAHNPAGH

M)

CR3, e.g., SEQ ID NO: 26

(MGPTSGPSLLLLLLTHLPLALGSPMYSIITPNILRLESEETMVLEAHDAQGDVPVT

VTVHDFPGKKLVLSSEKTVLTPATNHMGNVTFTIPANREFKSEKGRNKFVTVQA

TFGTQVVEKVVLVSLQSGYLFIQTDKTIYTPGSTVLYRIFTVNHKLLPVGRTVMV

NIENPEGIPVKQDSLSSQNQLGVLPLSWDIPELVNMGQWKIRAYYENSPQQVFST

EFEVKEYVLPSFEVIVEPTEKFYYIYNEKGLEVTITARFLYGKKVEGTAFVIFGIQD

GEQRISLPESLKRIPIEDGSGEVVLSRKVLLDGVQNPRAEDLVGKSLYVSATVILH

SGSDMVQAERSGIPIVTSPYQIHFTKTPKYFKPGMPFDLMVFVTNPDGSPAYRVP

VAVQGEDTVQSLTQGDGVAKLSINTHPSQKPLSITVRTKKQELSEAEQATRTMQ

ALPYSTVGNSNNYLHLSVLRTELRPGETLNVNFLLRMDRAHEAKIRYYTYLIMN

KGRLLKAGRQVREPGQDLVVLPLSITTDFIPSFRLVAYYTLIGASGQREVVADSV

WVDVKDSCVGSLVVKSGQSEDRQPVPGQQMTLKIEGDHGARVVLVAVDKGVF

VLNKKNKLTQSKIWDVVEKADIGCTPGSGKDYAGVFSDAGLTFTSSSGQQTAQR

AELQCPQPAARRRRSVQLTEKRMDKVGKYPKELRKCCEDGMRENPMRFSCQRR

TRFISLGEACKKVFLDCCNYITELRRQHARASHLGLARSNLDEDIIAEENIVSRSEF

PESWLWNVEDLKEPPKNGISTKLMNIFLKDSITTWEILAVSMSDKKGICVADPFE

VTVMQDFFIDLRLPYSVVRNEQVEIRAVLYNYRQNQELKVRVELLHNPAFCSLA

TTKRRHQQTVTIPPKSSLSVPYVIVPLKTGLQEVEVKAAVYHHFISDGVRKSLKV

VPEGIRMNKTVAVRTLDPERLGREGVQKEDIPPADLSDQVPDTESETRILLQGTP

VAQMTEDAVDAERLKHLIVTPSGCGEQNMIGMTPTVIAVHYLDETEQWEKFGLE

KRQGALELIKKGYTQQLAFRQPSSAFAAFVKRAPSTWLTAYVVKVFSLAVNLIAI

DSQVLCGAVKWLILEKQKPDGVFQEDAPVIHQEMIGGLRNNNEKDMALTAFVLI

SLQEAKDICEEQVNSLPGSITKAGDFLEANYMNLQRSYTVAIAGYALAQMGRLK

GPLLNKFLTTAKDKNRWEDPGKQLYNVEATSYALLALLQLKDFDFVPPVVRWL

NEQRYYGGGYGSTQATFMVFQALAQYQKDAPDHQELNLDVSLQLPSRSSKITH

RIHWESASLLRSEETKENEGFTVTAEGKGQGTLSVVTMYHAKAKDQLTCNKFDL

KVTIKPAPEIEKRPQDAKNTMILEICTRYRGDQDATMSILDISMMTGFAPDTDDL

KQLANGVDRYISKYELDKAFSDRNTLIIYLDKVSHSEDDCLAFKVHQYFNVELIQ

PGAVKVYAYYNLEESCTRFYHPEKEDGKLNKLCRDELCRCAEENCFIQKSDDKV

TLEERLDKACEPGVDYVYKTRLVKVQLSNDFDEYIMAIEQTIKSGSDEVQVGQQ

RTFISPIKCREALKLEEKKHYLMWGLSSDFWGEKPNLSYIIGKDTWVEHWPEEDE

CQDEENQKQCQDLGAFTESMVVFGCPN)

GATA4, e.g., SEQ ID NO: 27

(MYQSLAMAANHGPPPGAYEAGGPGAFMHGAGAASSPVYVPTPRVPSSVLGLS

YLQGGGAGSASGGASGGSSGGAASGAGPGTQQGSPGWSQAGADGAAYTPPPVS

PRFSFPGTTGSLAAAAAAAAAREAAAYSSGGGAAGAGLAGREQYGRAGFAGSY

SSPYPAYMADVGASWAAAAAASAGPFDSPVLHSLPGRANPAARHPNLDMFDDF

-continued

SEGRECVNCGAMSTPLWRRDGTGHYLCNACGLYHKMNGINRPLIKPQRRLSAS

RRVGLSCANCQTTTTTLWRRNAEGEPVCNACGLYMKLHGVPRPLAMRKEGIQT

RKRKPKNLNKSKTPAAPSGSESLPPASGASSNSSNATTSSSEEMRPIKTEPGLSSH

YGHSSSVSQTFSVSAMSGHGPSIHPVLSALKLSPQGYASPVSQSPQTSSKQDSWN

SLVLADSHGDIITA)

p53, e.g., SEQ ID NO: 28

(MEEPQSDPSVEPPLSQETFSDLWKLLPENNVLSPLPSQAMDDLMLSPDDIEQWF

TEDPGPDEAPRMPEAAPPVAPAPAAPTPAAPAPAPSWPLSSSVPSQKTYQGSYGF

RLGFLHSGTAKSVTCTYSPALNKMFCQLAKTCPVQLWVDSTPPPGTRVRAMAIY

KQSQHMTEVVRRCPHHERCSDSDGLAPPQHLIRVEGNLRVEYLDDRNTFRHSVV

VPYEPPEVGSDCTTIHYNYMCNSSCMGGMNRRPILTIITLEDSSGNLLGRNSFEVR

VCACPGRDRRTEEENLRKKGEPHHELPPGSTKRALPNNTSSSPQPKKKPLDGEYF

TLQIRGRERFEMFRELNEALELKDAQAGKEPGGSRAHSSHLKSKKGQSTSRHKK

LMFKTEGPDSD)

SP1, e.g., SEQ ID NO: 29

(MSDQDHSMDEMTAVVKIEKGVGGNNGGNGNGGGAFSQARSSSTGSSSSTGGG

GQESQPSPLALLAATCSRIESPNENSNNSQGPSQSGGTGELDLTATQLSQGANGW

QIISSSSGATPTSKEQSGSSTNGSNGSESSKNRTVSGGQYVVAAAPNLQNQQVLT

GLPGVMPNIQYQVIPQFQTVDGQQLQFAATGAQVQQDGSGQIQIIPGANQQIITN

RGSGGNIIAAMPNLLQQAVPLQGLANNVLSGQTQYVTNVPVALNGNITLLPVNS

VSAATLTPSSQAVTISSSGSQESGSQPVTSGTTISSASLVSSQASSSSFFTNANSYST

TTTTSNMGIMNFTTSGSSGTNSQGQTPQRVSGLQGSDALNIQQNQTSGGSLQAG

QQKEGEQNQQTQQQQILIQPQLVQGGQALQALQAAPLSGQTFTTQAISQETLQN

LQLQAVPNSGPIIIRTPTVGPNGQVSWQTLQLQNLQVQNPQAQTITLAPMQGVSL

GQTSSSNTTLTPIASAASIPAGTVTVNAAQLSSMPGLQTINLSALGTSGIQVHPIQG

LPLAIANAPGDHGAQLGLHGAGGDGIHGDTAGGEEGENSPDAQPQAGRRTRRE

ACTCPYCKDSEGRGSGDPGKKKQHICHIQGCGKVYGKTSHLRAHLRWHTGERP

FMCTWSYCGKRFTRSDELQRHKRTHTGEKKFACPECPKRFMRSDHLSKHIKTHQ

NKKGGPGVALSVGTLPLDSGAGSEGSGTATPSALITTNMVAMEAICPEGIARLAN

SGINVMQVADLQSINISGNGF)

MEF2C, e.g., SEQ ID NO: 30

(MGRKKIQITRIMDERNRQVTFTKRKFGLMKKAYELSVLCDCEIALIIFNSTNKLF

QYASTDMDKVLLKYTEYNEPHESRTNSDIVETLRKKGLNGCDSPDPDADDSVGH

SPESEDKYRKINEDIDLMISRQRLCAVPPPNFEMPVSIPVSSHNSLVYSNPVSSLGN

PNLLPLAHPSLQRNSMSPGVTHRPPSAGNTGGLMGGDLTSGAGTSAGNGYGNPR

NSPGLLVSPGNLNKNMQAKSPPPMNLGMNNRKPDLRVLIPPGSKNTMPSVSEDV

DLLLNQRINNSQSAQSLATPVVSVATPTLPGQGMGGYPSAISTTYGTEYSLSSAD

LSSLSGFNTASALHLGSVTGWQQQHLHNMPPSALSQLGACTSTHLSQSSNLSLPS

TQSLNIKSEPVSPPRDRTTTPSRYPQHTRHEAGRSPVDSLSSCSSSYDGSDREDHR

NEFHSPIGLTRPSPDERESPSVKRMRLSEGWAT)

TAX, e.g., (MAHFPGFGQSLLFGYPVYVFGDCVQGDWCPISGGLCSARLHRHALLATCPEHQI

TWDPIDGRVIGSALQFLIPRLPSFPTQRTSKTLKVLTPPITHTTPNIPPSFLQAMRKY

SPFRNGYMEPTLGQHLPTLSFPDPGLRPQNLYTLWGGSVVCMYLYQLSPPITWPL

LPHVIFCHPGQLGAFLTNVPYKRIEELLYKISLTTGALIILPEDCLPTTLFQPARAPV

TLTAWQNGLLPFHSTLTTPGLIWTFTDGTPMISGPCPKDGQPSLVLQSSSFIFHKF

QTKAYHPSFLLSHGLIQYSSFHSLHLLFEEYTNIPISLLFNEKEADDNDHEPQISPG

GLEPPSEKHFRETEV)

SEQ ID NO: 31

PPARγ, e.g., (MGETLGDSPIDPESDSFTDTLSANISQEMTMVDTEMPFWPTNFGISSVDLSVMED

HSHSEDIKPFTTVDFSSISTPHYEDIPFTRTDPVVADYKYDLKLQEYQSAIKVEPAS

PPYYSEKTQLYNKPHEEPSNSLMAIECRVCGDKASGFHYGVHACEGCKGFFRRTI

RLKLIYDRCDLNCRIHKKSRNKCQYCRFQKCLAVGMSHNAIRFGRMPQAEKEKL

LAEISSDIDQLNPESADLRALAKHLYDSYIKSFPLTKAKARAILTGKTTDKSPFVIY

DMNSLMMGEDKIKFKHITPLQEQSKEVAIRIFQGCQFRSVEAVQEITEYAKSIPGF

VNLDLNDQVTLLKYGVHEIIYTMLASLMNKDGVLISEGQGFMTREFLKSLRKPF

GDFMEPKFEFAVKFNALELDDSDLAIFIAVIILSGDRPGLLNVKPIEDIQDNLLQAL

ELQLKLNHPESSQLFAKLLQKMTDLRQIVTEHVQLLQVIKKTETDMSLHPLLQEI

YKDLY)

SEQ ID NO: 32 or

SET9, e.g., (MDSDDEMVEEAVEGHLDDDGLPHGFCTVTYSSTDRFEGNFVHGEKNGRGKFFF

FDGSTLEGYYVDDALQGQGVYTYEDGGVLQGTYVDGELNGPAQEYDTDGRLIF

KGQYKDNIRHGVCWIYYPDGGSLVGEVNEDGEMTGEKIAYVYPDERTALYGKFI

DGEMIEGKLATLMSTEEGRPHFELMPGNSVYHFDKSTSSCISTNALLPDPYESER

VYVAESLISSAGEGLFSKVAVGPNTVMSFYNGVRITHQEVDSRDWALNGNTLSL

DEETVIDVPEPYNHVSKYCASLGHKANHSFTPNCIYDMFVHPRFGPIKCIRTLRA

VEADEELTVAYGYDHSPPGKSGPEAPEWYQVELKAFQATQQK),

SEQ ID NO: 33 or
one or more of the transcriptional activation domains described in Chavez et al., Nat Methods. 2015 April; 12(4): 326-328, which is hereby incorporated by reference in the entirety for any and all purposes including but not limited to activation domain polypeptides and encoding polynucleotides, Cas9 (e.g., dCas9) polypeptides and encoding polynucleotides, and fusion proteins, and complexes (e.g., with sgRNA) thereof.

In some cases, the CRISPR nuclease is fused to one or more affinity tags. For example, the CRISPR nuclease may be a component of a SunTag. Exemplary SunTags or SunTag components include, without limitation, one or more of the affinity tagged CRISPR nucleases or affinity tag ligands, and fusion proteins thereof, described in WO 2016/011070. In one embodiment, the CRISPR nuclease contains one or more affinity tags that are non-covalently bound to one or more ligand-transcriptional activation domain fusion proteins. In such embodiments, the transcriptional activation domain fused to the affinity tag ligand can be, e.g., one or more of the transcriptional activation domains described herein, such as those of SEQ ID NOs:13-33, a transcriptional activation domain described in WO 2016/011070, or a combination or derivative thereof.

As used herein, the terms "Cas9," "Cas9 molecule," and the like, refers to a Cas9 polypeptide or a nucleic acid encoding a Cas9 polypeptide. A "Cas9 polypeptide" is a polypeptide that can form a complex with a guide RNA (gRNA) and bind to a nucleic acid target containing a target domain and, in certain embodiments, a PAM sequence. Cas9 molecules include those having a naturally occurring Cas9 polypeptide sequence and engineered, altered, or modified Cas9 polypeptides that differ, e.g., by at least one amino acid residue, from a reference sequence, e.g., the most similar naturally occurring Cas9 molecule. A Cas9 molecule may be a Cas9 polypeptide or a nucleic acid encoding a Cas9 polypeptide. A Cas9 molecule may be a nuclease (an enzyme that cleaves both strands of a double-stranded nucleic acid), a nickase (an enzyme that cleaves one strand of a double-stranded nucleic acid), or a catalytically inactive (or dead)

Cas9 molecule. A Cas9 molecule having nuclease or nickase activity is referred to as a "catalytically active Cas9 molecule" (a "caCas9" molecule). A Cas9 molecule lacking the ability to cleave or nick target nucleic acid is referred to as a "catalytically inactive Cas9 molecule" (a "ciCas9" molecule) or a "dead Cas9" ("dCas9").

In certain embodiments, a Cas9 molecule meets one or both of the following criteria: it has at least 20, 30, 40, 50, 55, 60, 65, 70, 75, 80, 81, 82, 83, 84, 85, 86, 87, 88, 89, 90, 91, 92, 93, 94, 95, 96, 97, 98, 99, or 100% homology with, or it differs by no more than 1, 2, 3, 4, 5, 6, 7, 8, 9, 10, 11, 12, 13, 14, 15, 16, 17, 18, 19, 20, 25, 30, 35, 40, 35, 50, 55, 60, 65, 70, 75, 80, 85, 90, 95, 100, 150, 200, 250, 300, 350 or 400, amino acid residues from, the amino acid sequence of a reference sequence, e.g., a naturally occurring Cas9 molecule.

In some embodiments, the Cas9 molecule is a *S. pyogenes* Cas9 (SpCas9) or variant thereof. In some embodiments, the Cas9 molecule is a *S. aureus* Cas9 (SaCas9) or variant thereof (see, e.g., FIGS. 7A-11B herein). In some embodiments, the Cas9 molecule is a *Campylobacter jejuni* Cas9 (CjCas9) or variant thereof (see, Kim et al., *Nat. Comm.*, 8, 14500 (2017). In some embodiments, the Cas9 molecule is a *Neisseria meningitides* Cas9 (NmCas9) or variant thereof (see, U.S. Pat. No. 9,074,199). In some embodiments, the Cas9 molecule is a *Streptococcus thermophilus* Cas9 (StCas9) or variant thereof (see, e.g., Xu et al., *CellMolLife Sci.*, 72:383-99 (2014)). In some embodiments, the Cas9 molecule is a dCas9 molecule.

In certain embodiments, the Cas9 molecule is a *S. pyogenes* Cas9 variant. In certain embodiments, the Cas9 variant is the EQR variant. In certain embodiments, the Cas9 variant is the VRER variant. In certain embodiments, the dCas9 molecule is a *S. pyogenes* Cas9 variant. In certain embodiments, the Cas9 variant is the EQR variant. In certain embodiments, the Cas9 variant is the VRER variant. In certain embodiments, a Cas9 system comprises a Cas9 molecule, e.g., a Cas9 molecule described herein, e.g., the Cas9 EQR variant or the Cas9 VRER variant.

In certain embodiments, the Cas9 molecule is a *S. aureus* Cas9 variant. In certain embodiments, the Cas9 variant is the KKH (E782K/N968K/R1015H) variant (see, e.g., Kleinstiver et al., Nature 523, 481-485 (23 Jul. 2015); and Leenay et al. Molecular Cell, Vol. 62, Issue 1, 2016, p. 137), the entire contents of which are expressly incorporated herein by reference and especially with regard to Cas (e.g., Cas9) variants such as those having altered PAM specificities). In certain embodiments, the Cas9 variant is the E782K/K929R/R1015H variant (see, e.g., Kleinstiver 2015). In certain embodiments, the Cas9 variant is the E782K/K929R/N968K/R1015H variant (see, e.g., Kleinstiver 2015). In certain embodiments the Cas9 variant comprises one or more mutations in one of the following residues: E782, K929, N968, R1015. In certain embodiments the Cas9 variant comprises one or more of the following mutations: E782K, K929R, N968K, R1015H and R1015Q (see, e.g., Kleinstiver 2015). In certain embodiments, a Cas9 system comprises a Cas9 molecule, e.g., a Cas9 molecule described herein, e.g., the Cas9 KKH variant.

As used herein, the terms "Cpf1," "Cpf1 molecule," and the like, refers to a Cpf1 polypeptide or a nucleic acid encoding a Cpf1 polypeptide. A "Cpf1 polypeptide" is a polypeptide that can form a complex with a guide RNA (gRNA) and bind to a nucleic acid target containing a target domain and, in certain embodiments, a PAM sequence. Cpf1 molecules include those having a naturally occurring Cpf1 polypeptide sequence and engineered, altered, or modified Cpf1 polypeptides that differ, e.g., by at least one amino acid residue, from a reference sequence, e.g., the most similar naturally occurring Cpf1 molecule. A Cpf1 molecule may be a Cpf1 polypeptide or a nucleic acid encoding a Cpf1 polypeptide. Examplary Cpf1 polypeptides include those isolated from *Prvotella, Francsella novicida* (FnCpf1), *Lachnospiraceae* bacterium (LbCpf1) and *Acidacminococcus* sp. (AsCpf1) (see, e.g., Toth et al., *Biology Direct*, 11:46 (2016).

In certain embodiments, a Cpf1 molecule meets one or both of the following criteria: it has at least 20, 30, 40, 50, 55, 60, 65, 70, 75, 80, 81, 82, 83, 84, 85, 86, 87, 88, 89, 90, 91, 92, 93, 94, 95, 96, 97, 98, 99, or 100% homology with, or it differs by no more than 1, 2, 3, 4, 5, 6, 7, 8, 9, 10, 11, 12, 13, 14, 15, 16, 17, 18, 19, 20, 25, 30, 35, 40, 35, 50, 55, 60, 65, 70, 75, 80, 85, 90, 95, 100, 150, 200, 250, 300, 350 or 400, amino acid residues from, the amino acid sequence of a reference sequence, e.g., a naturally occurring Cpf1 molecule.

As used herein, the term "gRNA molecule" or "gRNA" refers to a guide RNA which is capable of targeting a CRISPR nuclease to a target nucleic acid. In one embodiment, the term "gRNA molecule" refers to a guide ribonucleic acid. In another embodiment, the term "gRNA molecule" refers to a nucleic acid encoding a gRNA. In one embodiment, a gRNA molecule is non-naturally occurring. In one embodiment, a gRNA molecule is a synthetic gRNA molecule.

The guide RNA can be a scaffold RNA that binds to one or more protein or nucleic acid ligands (scaffold RNA ligands). The ligands can be fused or otherwise covalently or non-covalently linked to transcriptional activation domains. In an alternative embodiment, the scaffold RNA is not a guide RNA in that it does not specifically associate with a CRISPR nuclease. Exemplary scaffold RNAs, and CRISPR nuclease/scaffold RNA complexes, and methods of making and using such, are described in, e.g., WO 2016/054106 (describing CRISPR-associating and CRISPR independent scaffold RNAs) and Zhang et al., Scientific Reports 5, Article No. 16277 (2015); Konermann et al., 2015, Nature 517:583-8 (describing CRISPR/gRNA-directed synergistic activation mediators (SAM)).

"Subject," as used herein, may mean either a human or non-human animal. The term includes, but is not limited to, mammals (e.g., humans, other primates, pigs, rodents (e.g., mice and rats or hamsters), rabbits, guinea pigs, cows, horses, cats, dogs, sheep, and goats). In an embodiment, the subject is a human. In another embodiment, the subject is poultry. In another embodiment, the subject is piscine. In certain embodiments, the subject is a human, and in certain of these embodiments the human is an infant, child, young adult, or adult.

As used herein, the terms "target nucleic acid" or "target gene" refer to a nucleic acid which is being targeted for binding, e.g., by a CRISPR nuclease in complex with a guide RNA, a guide-RNA, or a scaffold RNA. In certain embodiments, a target nucleic acid comprises one gene, or a promoter or enhancer region operably linked to one gene. In certain embodiments, a target nucleic acid may comprise one or more genes, e.g., two genes, three genes, four genes, or five genes, or promoters or enhancer regions operably linked to one or more genes. In one embodiment, a target nucleic acid may comprise a promoter region, or control region, of a gene. In one embodiment, a target nucleic acid may comprise an intron of a gene. In another embodiment, a target nucleic acid may comprise an exon of a gene. In one embodiment, a target nucleic acid may comprise a coding region of gene. In one embodiment, a target nucleic acid may comprise a non-coding region of a gene. In some embodiments, the target nucleic acid is a control region, promoter, enhancer, intron, exon, transcription start site, coding region, or non-coding region of a gene listed in Table 1 herein.

In some embodiments, the target nucleic acid is a control region, promoter, enhancer, intron, exon, transcription start site, coding region, or non-coding region of a gene in the same pathway as a gene listed in Table 1 herein. The target nucleic acid can, e.g., be a control region, promoter, enhancer, intron, exon, transcription start site, coding region, or non-coding region of a gene upstream and in the same pathway as a gene listed in Table 1 herein. Additionally, where two or more genes or positions are targeted, or alternatively, the target nucleic acid can, e.g., be a control region, promoter, enhancer, intron, exon, transcription start site, coding region, or non-coding region of a gene downstream and in the same pathway as a gene listed in Table 1 herein. Additionally, where two or more genes or positions are targeted, or alternatively, the target nucleic acid can, e.g., be a control region, promoter, enhancer, intron, exon, transcription start site, coding region, or non-coding region of a gene in a parallel pathway as a gene listed in Table 1 herein. Exemplary genes in the same pathway or a parallel pathway as one or more of the genes listed in Table 1 are described e.g., in the KEGG pathway database (available at www.genome.jp/kegg/pathway.html).

"Target position" as used herein, refers to a site on a target nucleic acid that is hybridized to a guide RNA (e.g., in complex with a CRISPR nuclease) or scaffold RNA. Optimized target positions include, without limitation, one or more target positions optimized for transcriptional activation that are described in WO 2016/011080.

"Episomal vector" or "episomally propagating vector" refers to a plasmid or viral vector that persists or propagates in a mammalian cell as an episomal element. Episomal vectors described herein can encode one or more components (e.g., CRISPR nuclease, guide RNA, zinc finger nuclease, TALEN, TAL effector, scaffold RNA, transcriptional activator, affinity element, or combination thereof) for treatment of a disease or condition by transcriptional activation (e.g., a disease or condition of Table 1). Episomal vectors include, but are not limited to, Adeno-associated virus (AAV) vectors, and Epstein-barr virus (EBV) vectors. Suitable AAV vectors and methods for making and using such AAV vectors, e.g., for delivering the vectors into target cells are described in Samulski R et al. (1987), J. Virol. 61: 3096-3101; Walsh et al., Proc. Soc. Exp. Biol. Med. 204: 289-300 (1993); Fisher K J et al. (1996), J. Virol. 70: 520-532; Samulski R et al. (1989), J. Virol. 63: 3822-3826; U.S. Pat. Nos. 5,252,479; 5,139,941; 5,436,146; International Patent Application No. WO 94/13788; and International Patent Application No. WO 93/24641, the entire disclosures of which are herein incorporated by reference.

As used herein, the term "Zinc Finger Nuclease" refers to a zinc finger DNA binding protein (or zinc finger DNA binding domain within a larger protein) that binds DNA in a sequence-specific manner through one or more zinc fingers, which are regions of amino acid sequence within the zinc finger binding domain whose structure is stabilized through coordination of a zinc ion. The term zinc finger DNA binding protein is often abbreviated as zinc finger nuclease or ZFN.

As used herein, the term "transcription activator-like effector nuclease" refers to a protein, that includes a transcription activator-like effector DNA-binding domain fused to a DNA cleavage domain, that binds DNA in a sequence-specific manner. The term transcription activator-like effector nuclease is often abbreviated to TALEN.

DETAILED DESCRIPTION OF THE INVENTION

Introduction

Described herein are methods and compositions for treating a disease in a mammalian subject associated with, exacerbated by, or caused by reduced transcription of a gene, reduced amount of a gene product, or reduced activity of a gene product by increasing transcription of a target gene. Such methods and compositions can be useful, e.g., for treating a haploinsufficiency disease in the subject. Haploinsufficiency diseases that can be treated by the methods and compositions described herein include, without limitation, one or more of the diseases listed in Table 1. Table 1 provides the Entrez Gene ID (column 2) from the national center for bioinformatics (NCBI) and corresponding gene symbol (column 1) provided by the human genome nomenclature committee (HGNC), a pubmed ID (PMID) citation to a supporting reference (column 4), and a brief description of the associated disorder (column 5). The table is adapted from Supplementary Table 1 of Dang et al., *European Journal of Human Genetics* (2008) 16, 1350-57 and the ClinVar (https://www.ncbi.nlm.hih.gov/clinvar) and ClinGen (https://www.clinicalgenome.org) databases.

Nucleases

In some embodiments of the methods described herein, a host cell is contacted with one or more nucleases. In some embodiments, the nuclease is a endonuclease, site-specific recombinase, transposase, topoisomerase, zinc finger nuclease, TALEN, and includes modified derivatives and variants thereof.

In some embodiments, a nuclease is capable of targeting a designated nucleotide or region within the target site. In some embodiments, the nuclease is capable of targeting a region positioned between the 5' and 3' regions of the target site. In another embodiment, the nuclease is capable of targeting a region positioned upstream or downstream of the 5' and 3' regions of the target site (e.g., upstream or downstream of the transcription start site (TSS)). A recognition sequence is a polynucleotide sequence that is specifically recognized and/or bound by the nuclease. The length of the recognition site sequence can vary, and includes, for example, nucleotide sequences that are at least 10, 12, 14, 16, 18, 19, 20, 21, 22, 23, 24, 25, 26, 27, 28, 29, 30, 35, 40, 45, 50, 55, 60, 65, 70 or more nucleotides in length. In some embodiments, the recognition sequence is palindromic, i.e., the sequence on one DNA strand reads the same in the opposite direction on the complementary DNA strand. In some embodiments, the target site of the nuclease is within the recognition sequence.

Zinc Finger Nuclease

In some embodiments, the nuclease is a zinc-finger nuclease (ZFN). ZFNs typically comprise a zinc finger DNA binding domain and a nuclease domain. Generally, ZFNs include two zinc finger arrays (ZFAs), each of which is fused to a single subunit of a non-specific endonuclease, such as the nuclease domain from the FokI enzyme, which becomes active upon dimerization. Typically, a single ZFA consists of 3 or 4 zinc finger domains, each of which is designed to recognize a specific nucleotide triplet (GGC, GAT, etc.). A ZFN composed of two "3-finger" ZFAs is therefore capable of recognizing an 18 base pair target site (i.e., recognition sequence); an 18 base pair recognition sequence is generally unique, even within large genomes such as those of humans and plants. By directing the co-localization and dimerization of the two FokI nuclease monomers, ZFNs generate a functional site-specific endonuclease that can target a particular locus (e.g., gene, promotor or enhancer).

Zinc-finger nucleases useful in the methods disclosed herein include those that are known and ZFN that are engineered to have specificity for one or more target sites described herein (e.g., promotor or enhancer nucleotide sequence). Zinc finger domains are amenable for designing polypeptides which specifically bind a selected polynucleotide recognition sequence within a target site of the host cell genome. ZFN can comprise an engineered DNA-binding zinc finger domain linked to a non-specific endonuclease domain, for example, a nuclease domain from a Type IIs endonuclease such as HO or FokI. In some examples, a zinc finger DNA binding domain can be fused to a site-specific recombinase, transposase, or a derivative thereof that retains DNA nicking and/or cleaving activity.

In a preferred embodiment, additional functionalities can be fused to the zinc-finger binding domain, including but not limited to, transcriptional activator domains (such as VP16, VP48, VP64, VP160 and the like) or transcription repressor domains (such as KRAB). In one embodiment, the zinc finger nuclease is engineered such that the zinc finger nuclease comprises a transcriptional activator domain selected from VP16, VP48, VP64 or VP160. In one embodiment, the zinc finger nuclease is engineered such that the zinc finger nuclease comprises a transcriptional activator domain selected from HSF1, VP16, VP64, p65, RTA, MyoD1, SET7, VPR, histone acetyltransferase p300, TET1 hydroxylase catalytic domain, LSD1, CIB1, AD2, CR3, GATA4, p53, SP1, MEF2C, TAX, PPAR-gamma, and SET9. For example, engineered zinc finger transcriptional activator that interact with a promoter region of the gamma-globulin gene was shown to enhance fetal hemoglobin production in primer adult erythroblasts (Wilber et al., *Blood,* 115(15): 3033-3041). Other polydactyl zinc-finger transcription factors are also known in the art, including those disclosed in Beerli and Barbas (see, *Nature Technology,* (2002) 20:135-141).

Each zinc finger domain recognizes three consecutive base pairs in the target DNA. For example, a three finger domain recognizes a sequence of nine contiguous nucleotides, with a dimerization requirement of the nuclease, two sets of zinc finger triplets are used to bind a 18 nucleotide recognition sequence. Useful zinc finger modules include those that recognize various GNN and ANN triplets (Dreier et al., (2001) *J Biol Chem* 276:29466-78; Dreier et al., (2000) *J Mol Biol* 303:489-502; Liu et al., (2002) *J Biol Chem* 277:3850-6), as well as those that recognize various CNN or TNN triplets (Dreier et al., (2005) *J Biol Chem* 280:35588-97; Jamieson et al., (2003) *Nature Rev Drug Discovery* 2:361-8). See also, Durai et al., (2005) *Nucleic Acids Res* 33:5978-90; Segal, (2002) *Methods* 26:76-83; Porteus and Carroll, (2005) *Nat Biotechnology* 23:967-73; Pabo et al., (2001) *Ann Rev Biochem* 70:313-40; Wolfe et al., (2000) *Ann Rev Biophys Biomol Struct* 29:183-212; Segal and Barbas (2001) *Curr Opin Biotechnol* 12:632-7; Segal et al., (2003) *Biochemistry* 42:2137-48; Beerli and Barbas, (2002) *Nat Biotechnol* 20:135-41; Carroll et al., (2006) *Nature Protocols* 1:1329; Ordiz et al., (2002) *Proc Natl Acad Sci USA* 99:13290-5; Guan et al., (2002) *Proc Natl Acad Sci USA* 99:13296-301; WO2002099084; WO00/42219; WO02/42459; WO2003062455; US20030059767; US Patent Application Publication Number 2003/0108880; U.S. Pat. Nos. 6,140,466, 6,511,808 and 6,453,242. Useful zinc-finger nucleases also include those described in WO03/080809; WO05/014791; WO05/084190; WO08/021207; WO09/042186; WO09/054985; and WO10/065123.

In some embodiments, a ZFN comprises a fusion protein having a cleavage domain of a Type IIS restriction endonuclease fused to an engineered zinc finger binding domain, wherein the binding domain further comprises one or more transcriptional activators. In some embodiments, the type IIS restriction endonuclease is selected from a HO endonuclease or a FokI endonuclease. In some embodiments, the zinc finger binding domain comprises 3, 4, 5 or 6 zinc fingers. In another embodiment, the zinc finger binding domain specifically binds to a recognition sequence corresponding to a promoter or enhancer disclosed herein (e.g., SIM1, MC4R, PKD1, SETD5, THUMPD3, SCN2A and PAX6 promotor or enhancer). In one embodiment, the one or more transcriptional activators is selected from VP16, VP48, VP64, or VP160. Generally, the DNA-binding domain of a ZFN contains between 3 and 6 individual zinc finger repeats and can recognize between 9 and 18 contiguous nucleotides. Each ZFN can be designed to target a specific target site in the host cell genome, e.g., a promotor sequence, an enhancer sequence, or exon/intron within a gene.

TALENs

In some embodiments of the methods, the nuclease is a TALEN. TAL effectors (TALEs) are proteins secreted by *Xanthomonas* bacteria and play an important role in disease or triggering defense mechanisms, by binding host DNA and activating effector-specific host genes. see, e.g., Gu et al. (2005) *Nature* 435:1122-5; Yang et al., (2006) *Proc. Natl. Acad. Sci. USA* 103:10503-8; Kay et al., (2007) *Science* 318:648-51; Sugio et al., (2007) *Proc. Natl. Acad. Sci. USA* 104:10720-5; Romer et al., (2007) *Science* 318:645-8; Boch et al., (2009) *Science* 326(5959):1509-12; and Moscou and Bogdanove, (2009) 326(5959):1501. A TALEN comprises a TAL effector DNA-binding domain fused to a DNA cleavage domain. The DNA binding domain interacts with DNA in a sequence-specific manner through one or more tandem repeat domains. The repeated sequence typically comprises 33-34 highly conserved amino acids with divergent $12^{th}$ and $13^{th}$ amino acids. These two positions, referred to as the Repeat Variable Diresidue (RVD) are highly variable and show a strong correlation with specific nucleotide recognition (Boch et al., (2009) *Science* 326(5959): 1509-12; and Moscou and Bogdanove, (2009) 326(5959):1501). This relationship between amino acid sequence and DNA recognition sequence has allowed for the engineering of specific DNA-binding domains by selecting a combination of repeat segments containing the appropriate RVDs.

The TAL-effector DNA binding domain can be engineered to bind to a target DNA sequence and fused to a nuclease domain, e.g., a Type IIS restriction endonuclease, such as FokI (see e.g., Kim et al. (1996) *Proc. Natl. Acad. Sci. USA* 93:1156-1160). In some embodiments, the nuclease domain can comprises one or more mutations (e.g., FokI variants) that improve cleavage specificity (see, Doyon et al., (2011) *Nature Methods,* 8 (1): 74-9) and cleavage activity (Guo et al., (2010) *Journal of Molecular Biology,* 400 (1): 96-107). Other useful endonucleases that can be used as the nuclease domain include, but are not limited to, HhaI, HindIII, Nod, BbvCI, EcoRI, BglI, and AlwI. In some embodiments, the TALEN can comprise a TAL effector DNA binding domain comprising a plurality of TAL effector repeat sequences that bind to a specific nucleotide sequence (i.e., recognition sequence) in the target DNA. While not to be construed as limiting, TALENs useful for the methods provided herein include those described in WO10/079430 and U.S. Patent Application Publication No. 2011/0145940.

In some embodiments, the TAL effector DNA binding domain can comprise 10 or more DNA binding repeats, and preferably 15 or more DNA binding repeats. In some embodiments, each DNA binding repeat comprises a RVD that determines recognition of a base pair in the target DNA, and wherein each DNA binding repeat is responsible for recognizing one base pair in the target DNA. In some embodiments, the RVD comprises one or more of: HD for recognizing C; NG for recognizing T; NI for recognizing A; NN for recognizing G or A; NS for recognizing A or C or G or T; N* for recognizing C or T, where * represents a gap in the second position of the RVD; HG for recognizing T; H* for recognizing T, where * represents a gap in the second position of the RVD; IG for recognizing T; NK for recognizing G; HA for recognizing C; ND for recognizing C; HI for recognizing C; HN for recognizing G; NA for recognizing G; SN for recognizing G or A; and YG for recognizing T.

In a preferred embodiment, the TALEN is engineered such that the TAL effector comprises one or more transcriptional activator domains (e.g., VP16, VP48, VP64 or VP160). For example, engineered TAL effectors having a transcriptional activator domain at the c-terminus of the TAL effector were shown to modulate transcription of Sox2 and Klf4 genes in human 293FT cells (Zhang et al., *Nature Biotechnology*, 29(2): 149-153 (2011). Other TAL effector transcription factors (TALE-TFs) are also known in the art, including those disclosed in Perez-Pinera et al., (*Nature Methods*, (2013) 10(3):239-242) that demonstrated modulation of IL1RN, KLK3, CEACAM5 and ERBB2 genes in human 293T cells using TALE-TFs. In some embodiments, the one or more transcriptional activator domains are located adjacent to the nuclear localization signal (NLS) present in the C-terminus of the TAL effector. In another embodiment, the TALE-TFs can bind nearby sites upstream or downstream of the transcriptional start site (TSS) for a target gene. In one embodiment, the TAL effector comprises a transcriptional activator domain selected from VP16, VP48, VP64 or VP160. In another embodiment, the TAL effector comprises a transcriptional activator domain selected from HSF1, VP16, VP64, p65, RTA, MyoD1, SET7, VPR, histone acetyltransferase p300, TET1 hydroxylase catalytic domain, LSD1, CIB1, AD2, CR3, GATA4, p53, SP1, MEF2C, TAX, PPAR-gamma, and SET9.

In some embodiments, the TALEN comprises a TAL effector DNA-binding domain fused to a DNA cleavage domain, wherein the TAL effector comprises a transcriptional activator. In some embodiments, the DNA cleavage domain is of a Type IIS restriction endonuclease selected from a HO endonuclease or a FokI endonuclease. In some embodiments, the TAL effector DNA-binding domain specifically binds to a recognition sequence corresponding to a promoter region or enhancer region disclosed herein (e.g., SIM1, MC4R, PKD1, SETD5, THUMPD3, SCN2A and PAX6 promotor or enhancer). Generally, the DNA-binding domain of a TALEN is designed to target a specific target site in the host cell, e.g., a promotor sequence or an enhancer sequence.

In some embodiments, the target site for the zinc finger nuclease or TALEN is endogenous to the host cell, such as a native locus in the host cell genome. In some embodiments, the target site is selected according to the type of nuclease to be utilized in the method. If the nuclease to be utilized is a zinc finger nuclease, optimal target sites may be selected using a number of publicly available online resources. See, e.g., Reyon et al., *BMC Genomics* 12:83 (2011), which is hereby incorporated by reference in its entirety. Publicly available methods for engineering zinc finger nucleases include: (1) Context-dependent Assembly (CoDA), (2) Oligomerized Pool Engineering (OPEN), (3) Modular Assembly, (4) ZiFiT (internet-accessible software for the design of engineered zinc finger arrays), (5) ZiFDB (internet-accessible database of zinc fingers and engineered zinc finger arrays), and (6) ZFNGenome. For example, OPEN is a publicly available protocol for engineering zinc finger arrays with high specificity and in vivo functionality, and has been successfully used to generate ZFNs that function efficiently in plants, zebrafish, and human somatic and pluripotent stem cells. OPEN is a selection-based method in which a pre-constructed randomized pool of candidate ZFAs is screened to identify those with high affinity and specificity for a desired target sequence. Additionally, ZFNGenome is a GBrowse-based tool for identifying and visualizing potential target sites for OPEN-generated ZFNs. ZFNGenome provides a compendium of potential ZFN target sites in sequenced and annotated genomes of model organisms. ZFNGenome includes more than 11 million potential ZFN target sites, mapped within the fully sequenced genomes of seven model organisms; *S. cerevisiae, C. reinhardtii, A. thaliana, D. melanogaster, D. rerio, C. elegans*, and *H. sapiens*. ZFNGenome provides information about each potential ZFN target site, including its chromosomal location and position relative to transcription initiation site(s). Users can query ZFNGenome using several different criteria (e.g., gene ID, transcript ID, target site sequence).

In some embodiments, if the nuclease is a TALEN, optimal target sites may be selected in accordance with the methods described by Sanjana et al., *Nature Protocols*, 7:171-192 (2012), which is hereby incorporated by reference in its entirety. TALENs function as dimers, and a pair of TALENs, referred to as the left and right TALENs, target sequences on opposite strands of DNA. TALENs are engineered as a fusion of the TALE DNA-binding domain and a monomeric FokI catalytic domain. To facilitate Fold dimerization, the left and right TALEN target sites are generally selected with a spacing of approximately 14-20 bases.

In some embodiments, the one or more nucleases useful for the methods described herein are provided, e.g., delivered into the host cell as a purified protein. In some embodiments, the one or more nucleases are provided via polynucleotide(s) comprising a nucleic acid encoding the nuclease. In another embodiment, the one or more nucleases can be introduced into the host cell as purified RNA which can be directly translated in the host cell nucleus. In a preferred embodiment, the polynucleotide comprising a nucleic acid encoding the nuclease comprises an expression vector that allows for the expression of the nuclease within a host cell. Suitable expression vectors include episomal vectors.

In some embodiments, where the nuclease functions as a dimer requiring the separate expression of each monomer, e.g., zinc finger nucleases and TALENs, each monomer of the dimer may be expressed from the same episomal vector or from different episomal vectors. In another embodiment, where multiple nucleases are introduced to the cell to introduce double-strand breaks at different target sites, the nucleases can be encoded on a single episomal vector or on separate episomal vectors.

In one aspect, the present invention provides a method of treating a haploinsufficiency disease in a mammalian subject, the method comprising contacting a cell of the subject with a composition comprising a zinc finger nuclease or TALEN that, under conditions present in a nucleus of the cell, the zinc finger nuclease or TALEN specifically hybridizes to a promoter region or an enhancer region; wherein the contacting forms a complex comprising the DNA binding domain of the zinc finger nuclease or TALEN, and the promoter region or enhancer region, wherein the complex activates transcription of the wild-type copy of the haploinsufficient gene in an amount and for a duration sufficient to treat the haploinsufficiency disease in the subject. In some embodiments, the promoter or enhancer region corresponds to a promoter or enhancer region (i.e., control region) of any of the genes listed in Table 1.

In some embodiments, the contacting comprises contacting the cell with an episomal vector encoding the zinc finger nuclease or TALEN. In some embodiments, the episomal vector(s) are non-integrating. In some embodiments, the zinc finger nuclease or TALEN has been modified to comprises one or more transcriptional activation domains. In one embodiment, the one or more transcriptional activation domains is selected from the group consisting of HSF1, VP16, VP64, p65, MyoD1, RTA, SET7/9, VPR, histone acetyltransferase p300, an hydroxylase catalytic domain of a TET family protein (e.g., TET1 hydroxylase catalytic domain), LSD1, CIB1, AD2, CR3, EKLF1, GATA4, PRVIE, p53, SP1, MEF2C, TAX, and PPARγ. In some embodiments, the transcriptional activation domain is VP64. In some embodiments, the haploinsufficient gene is SIM1, Leptin, Leptin receptor, MC4R, SCN2A, SETD5, PAX6, PKD1, MC3R, POMC, STAT3, STAT5, SOCS3, GHR, NPY, NPY1R, NPY2R, NPY5R, PYY, AMPK (PRKAA1, PRKAA2, PRKAB1, PRKAB2, PRKAG1, PRKAG2, PRKAG3), OXT, JAK2, SHP2, NOS3, NROB2, BRS3, CARTPT, FABP4, HTR2C, IL6, NHLH2, NMU, NPB, NPBWRI, PNPLA2, UCP3, ADIPOQ, APOA5, ARNT2, ASIP, C1QTNF2, C3AR1, CCK, CPT1B, CSF2, DGAT1, DGAT2, GHRL, GHSR, HSD11B1, HTR7, INSIG1, INSIG2, LIPC, NMURI, NMUR2, NPBWR2, NTS, PPARGC1A, PPY, RETN, SIRT1, TGFBR2, WDTC1, or FOXO1.

TABLE 1

Genes Associated With Haploinsufficiency Diseases

| Gene Symbol | Entrez Gene ID | Chromosome | PubMed (PMID) | Disorder/Syndrome |
|---|---|---|---|---|
| TP73 | 7161 | 1 | 11454718 | prostate hyperplasia and prostate cancer |
| DFFB | 1677 | 1 | 16156899 | oligodendroglioma development |
| KCNAB2 | 8514 | 1 | 11580756 | characteristic craniofacial abnormalities, mental retardation, and epilepsy with 1p36 deletion syndrome |
| CHD5 | 26038 | 1 | — | monosomy 1p36 syndrome |
| CAMTA1 | 23261 | 1 | 15709179 | tumors development |
| PINK1 | 65018 | 1 | 15349860 | sporadic early-onset parkinsonism |
| SAM68 | 10657 | 1 | 17927519 | mammary tumor onset and tumor multiplicity |
| KCNQ4 | 9132 | 1 | — | DEAFNESS, AUTOSOMAL DOMINANT NONSYNDROMIC SENSORINEURAL 2 |
| GLUT1 | 6513 | 1 | 12029447, 11477212, 11136715, 16497725 | Facilitated glucose transporter protein type 1 (GLUT1) deficiency syndrome |
| MYH | 4595 | 1 | 16292541 | hepatocellular carcinoma and cholangiocarcinom |
| FOXE3 | 2301 | 1 | 11980846 | anterior segment dysgenesis similar to Peters' anomaly |
| HUD | 1996 | 1 | 16278682 | poor prognosis |
| INK4C | 1031 | 1 | 16260494 | medulloblastoma formation |
| NFIA | 4774 | 1 | 17530927 | Complex central nervous system (CNS) malformations and urinary tract defects |
| CCN1 | 3491 | 1 | 17023674 | delayed formation of the ventricular septum in the embryo and persistent ostium primum atrial septal defects |
| ABCA4 | 24 | 1 | — | Stargardt disease, retinitis pigmentosa-19, and macular degeneration age-related 2 |
| WNT2B | 7482 | 1 | 17351355 | mental retardation, short stature and colobomata |
| ADAR | 103 | 1 | 16536805 | dyschromatosis symmetrica hereditaria |
| ATP1A2 | 477 | 1 | — | familial hemiplegic migraine type 2 |
| MPZ | 4359 | 1 | — | neurologic diseases, including CHN, DSS, and CMT1B |
| MYOC | 4653 | 1 | — | hereditary juvenile-onset open-angle glaucoma |
| HRPT2 | 79577 | 1 | 16458039 | Ossifying fibroma (progressive enlargement of the affected jaw) |

TABLE 1-continued

Genes Associated With Haploinsufficiency Diseases

| Gene Symbol | Entrez Gene ID | Chromosome | PubMed (PMID) | Disorder/Syndrome |
|---|---|---|---|---|
| LRH-1 | 2494 | 1 | 17670946, 15684064 | inflammatory bowel disease |
| IRF6 | 3664 | 1 | — | van der Woude syndrome and popliteal pterygium syndrome |
| PROX1 | 5629 | 1 | — | Lymphatic vascular defects, adult-onset obesity |
| TP53BP2 | 7159 | 1 | — | no suppression of tumor growth |
| NLRP3 | 114548 | 1 | — | CINCA syndrome |
| ID2 | 3398 | 2 | 15569159 | Congenital hydronephrosis |
| MYCN | 4613 | 2 | 15821734 | reduced brain size and intestinal atresias in Feingold syndrome |
| GCKR | 2646 | 2 | 9570959 | one form of maturity onset diabetes of the young |
| SPAST | 6683 | 2 | — | SPASTIC PARAPLEGIA 4 |
| MSH6 | 2956 | 2 | 10751599 | limitation of mismatch repair |
| FSHR | 2492 | 2 | 14502087 | degenerative changes in the central nervous system |
| SPR | 6697 | 2 | 15241655 | dopa-responsive dystonia |
| PAX8 | 7849 | 2 | — | congenital hypothyroidism |
| SMADIP1 | 9839 | 2 | 11595972, 16688751 | syndromic Hirschsprung disease |
| RPRM | 56475 | 2 | 15592418 | tumorigenesis, no suppression of tumor growth |
| SCN1A | 6323 | 2 | 16865694, 16075041 | Severe myoclonic epilepsy of infancy (SMEI) or Dravet syndrome |
| HOXD13 | 3239 | 2 | 12900906 | foot malformations |
| COL3A1 | 1281 | 2 | — | Ehlers-Danlos syndrome type IV, and with aortic and arterial aneurysms |
| SLC40A1 | 30061 | 2 | 16135412 | ferroportin disease |
| SATB2 | 23314 | 2 | — | craniofacial dysmorphologies, cleft palate |
| SUMO1 | 7341 | 2 | 17606301, 16990542 | nonsyndromic cleft lip and palate |
| BMPR2 | 659 | 2 | 11115378 | primary pulmonary hypertension |
| XRCC5 | 7520 | 2 | 16325483 | retarded growth, increased radiosensitivity, elevated p53 levels and shortened telomeres |
| PAX3 | 5077 | 2 | 12070244, 9731536 | developmental delay and autism |
| STK25 | 10494 | 2 | 15521982 | mild-to-moderate mental retardation with an Albright hereditary osteodystrophy-like phenotype |
| CHL1 | 10752 | 3 | — | 3p deletion (3p−) syndrome |
| SRGAP3 | 9901 | 3 | 12195014 | severe mental retardation |
| VHL | 7428 | 3 | 16061637 | increased lung cancer susceptibility |
| GHRL | 51738 | 3 | — | GHRELIN POLYMORPHISM |
| PPARG | 5468 | 3 | 15073042 | susceptibility to mammary, ovarian and skin carcinogenesis |
| SRG3 | 6599 | 3 | 17255092 | proteasomal degradation |
| RASSF1A | 11186 | 3 | 11585766 | pathogenesis of a variety of cancers, no suppression of tumor growth |
| TKT | 7086 | 3 | — | reduced adipose tissue and female fertility |
| MITF | 4286 | 3 | 10952390, 9170159 | Waardenburg syndrome type 2 |
| FOXP1 | 27086 | 3 | — | tumors development |
| ROBO1 | 6091 | 3 | — | predispose to dyslexia |
| DIRC2 | 84925 | 3 | — | onset of tumor growth |
| ATP2C1 | 27032 | 3 | 15811312, 17597066 | orthodisease, skin disorder |
| FOXL2 | 668 | 3 | 11468277 | blepharophimosis syndrome associated with ovarian dysfunction |
| ATR | 545 | 3 | 15282542 | mismatch repair-deficient |
| SI | 6476 | 3 | — | SUCRASE-ISOMALTASE DEFICIENCY, CONGENITAL |
| TERC | 7012 | 3 | 16284252, 15326392 | Autosomal dominant dyskeratosis congenita (AD DC), a rare inherited bone marrow failure syndrome |
| SOX2 | 6657 | 3 | 16529618, 15503273 | hippocampal malformations and epilepsy |
| OPA1 | 4976 | 3 | 16735988, 11017080 | optic atrophy |

TABLE 1-continued

Genes Associated With Haploinsufficiency Diseases

| Gene Symbol | Entrez Gene ID | Chromosome | PubMed (PMID) | Disorder/Syndrome |
|---|---|---|---|---|
| TFRC | 7037 | 3 | — | stressed erythropoiesis and neurologic abnormalities |
| FGFR3 | 2261 | 4 | 9199352 | a variety of skeletal dysplasias, including the most common genetic form of dwarfism, achondroplasia |
| LETM1 | 3954 | 4 | 16719275 | Wolf Hirshhorn syndrome |
| SH3BP2 | 6452 | 4 | — | Wolf-Hirschhorn syndrome |
| MSX1 | 4487 | 4 | 14630905 | oligodontia |
| RBPJ | 3516 | 4 | — | embryonic lethality and formation of arteriovenous malformations |
| PHOX2B | 8929 | 4 | — | predispose to Hirschsprung disease |
| ENAM | 10117 | 4 | 15649948 | Amelogenesis imperfecta (inherited defects of dental enamel formation) |
| MAPK10 | 5602 | 4 | — | epileptic encephalopathy of the Lennox-Gaustaut type |
| PKD2 | 5311 | 4 | 16720597, 10615132 | Autosomal dominant polycystic kidney disease |
| SNCA | 6622 | 4 | 12477695 | familial Parkinson's disease |
| RIEG | 5308 | 4 | 9480756 | Rieger syndrome (RIEG) characterized by malformations of the anterior segment of the eye, failure of the periumbilical skin to involute, and dental hypoplasia |
| ANK2 | 287 | 4 | — | arrhythmia |
| MAD2L1 | 4085 | 4 | 17038523 | optimal hematopoiesis |
| PLK4 | 10733 | 4 | 16025114 | mitotic infidelity and carcinogenesis |
| FBXW7 | 55294 | 4 | — | cancer (breast, ovary) tumors development |
| TERT | 7015 | 5 | — | DYSKERATOSIS CONGENITA |
| SEMA5A | 9037 | 5 | 9464278 | abnormal brain development |
| GDNF | 2668 | 5 | 11774071 | complex human diseases (Hirschsprung-like intestinal obstruction and early-onset lethality) |
| FGF10 | 2255 | 5 | 16476029, 15654336 | craniofacial development and developmental disorders |
| PIK3R1 | 5295 | 5 | 10829070 | insulin resistance |
| APC | 324 | 5 | 14691304 | familial adenomatous polyposis |
| RAD50 | 10111 | 5 | 16474176 | hereditary breast cancer susceptibility associated with genomic instability |
| SMAD5 | 4090 | 5 | 12064918 | secondary myelodysplasias and acute myeloid leukemias |
| EGR1 | 1958 | 5 | 17420284 | development of myeloid disorders |
| TCOF1 | 6949 | 5 | 17552945, 16465596, 15930015, 15249688 | depletion of neural crest cell precursors, Treacher Collins syndrome |
| NPM1 | 4869 | 5 | 16341035, 16007073 | myelodysplasias and leukemias |
| NKX2-5 | 1482 | 5 | 16470726, 10398271, 15368344 | microcephaly and congenital heart disease |
| MSX2 | 4488 | 5 | 10742104 | pleiotropic defects in bone growth and ectodermal organ formation |
| NSD1 | 64324 | 5 | 16970856, 16547423, 15720303, 15640245, 15539801, 14631206, 14517949, 12687502, 12676901, 11896389 | Sotos syndrome |
| FOXC1 | 2296 | 6 | 14564054, 11170889 | Axenfeld-Rieger anomaly of the anterior eye chamber |
| DSP | 1832 | 6 | 11841538, 11476106, 10594734, 17475244 | skin fragility/woolly hair syndrome; disruption of tissue structure, integrity and changes in keratinocyte proliferation |
| EEF1E1 | 9521 | 6 | — | no suppression of tumor growth |
| TNXA | 7146 | 6 | 15733269 | Ehlers-Danlos syndrome |

TABLE 1-continued

Genes Associated With Haploinsufficiency Diseases

| Gene Symbol | Entrez Gene ID | Chromosome | PubMed (PMID) | Disorder/Syndrome |
|---|---|---|---|---|
| TNX | 7148 | 6 | 15733269 | Elastic fiber abnormalities in hypermobility type Ehlers-Danlos syndrome |
| HMGA1 | 3159 | 6 | — | insulin resistance and diabetes |
| RUNX2 | 860 | 6 | 16270353, 16187316, 15952089, 15566413, 10204840, 9690033, 9207800 | cleidocranial dysplasia |
| CD2AP | 23607 | 6 | 12764198 | glomerular disease susceptibility |
| ELOVL4 | 6785 | 6 | 17311087, 17254625 | defective skin permeability barrier function and neonatal lethality |
| NT5E | 4907 | 6 | 12805562 | Neuropathy target esterase deficiency |
| SIM1 | 6492 | 6 | 16728530, 10587584 | impaired melanocortin-mediated anorexia and activation of paraventricular nucleus neurons |
| COL10A1 | 1300 | 6 | — | Schmid type metaphyseal chondrodysplasia and Japanese type spondylometaphyseal dysplasia |
| PARK2 | 5071 | 6 | — | PARKINSON DISEASE 2 |
| TWIST1 | 7291 | 7 | 16540516, 16237669, 17003487, 15829502, 11854168 | coronal synostosis |
| GLI3 | 2737 | 7 | 15739154, 14608643, 9054938 | Greig cephalopolysyndactyly and Pallister-Hall syndromes |
| GCK | 2645 | 7 | — | non-insulin dependent diabetes mellitus (NIDDM), maturity onset diabetes of the young, type 2 (MODY2) and persistent hyperinsulinemic hypoglycemia of infancy (PHHI) |
| FKBP6 | 8468 | 7 | 15770126 | Williams-Beuren syndrome |
| ELN | 2006 | 7 | 14556246, 10198167, 16820942, 16784071, 16476938, 12016585, 11735026, 10942104, 10885576, 10780788 | cardiovascular disease and connective tissue abnormalities |
| LIMK1 | 3984 | 7 | 9637430 | Williams syndrome (WS), a neurodevelopmental disorder |
| RFC2 | 5982 | 7 | — | growth deficiency as well as developmental disturbances in Williams syndrome |
| GTF3 | 9569 | 7 | 10573005 | abnormal muscle fatiguability |
| GTF2I | 2969 | 7 | — | Williams-Beuren syndrome |
| NCF1 | 653361 | 7 | 15626477 | autosomal recessive chronic granulomatous disease |
| KRIT1 | 889 | 7 | 12404106 | Cerebral Cavernous Malformations (vascular malformations characterised by abnormally enlarged capillary cavities) |
| COL1A2 | 1278 | 7 | 17898012 | subtle symptoms like recurrent joint subluxation or hypodontia |
| SHFM1 | 7979 | 7 | 17230488 | severe mental retardation, short stature, microcephaly and deafness |
| RELN | 5649 | 7 | 16376115, 11592844 | Cognitive disruption and altered hippocampus synaptic function |
| FOXP2 | 93986 | 7 | 16470794 | Speech and language impairment and oromotor dysprax |
| CAV1 | 857 | 7 | 15816560, 14981899 | 17beta-estradiol-stimulated mammary tumorigenesis |
| ST7 | 7982 | 7 | — | no suppression of tumor growth |
| BRAF | 673 | 7 | — | Cardiofaciocutaneous (CFC) syndrome |
| SHH | 6469 | 7 | 10852374 | Holoprosencephaly, sacral anomalies, and situs ambiguus |
| HLXB9 | 3110 | 7 | 14663834, 12116275 | Currarino syndrome including a presacral mass, sacral agenesis, and anorectal malformation |

TABLE 1-continued

Genes Associated With Haploinsufficiency Diseases

| Gene Symbol | Entrez Gene ID | Chromosome | PubMed (PMID) | Disorder/Syndrome |
|---|---|---|---|---|
| GATA4 | 2626 | 8 | 10096597 | congenital heart disease |
| NKX3-1 | 4824 | 8 | 15734999 | prostate cancer |
| FGFR1 | 2260 | 8 | — | Pfeiffer syndrome, Jackson-Weiss syndrome, Antley-Bixler syndrome, osteoglophonic dysplasia, and autosomal dominant Kallmann syndrome 2 |
| CHD7 | 55636 | 8 | — | CHARGE syndrome |
| CSN5 | 10987 | 8 | 15735686 | TRC8 hereditary kidney cancer |
| EYA1 | 2138 | 8 | — | branchiootorenal dysplasia syndrome, branchiootic syndrome, and sporadic cases of congenital cataracts and ocular anterior segment anomalies |
| TRPS1 | 7227 | 8 | 11285235 | dominantly inherited tricho-rhino-phalangeal (TRP) syndromes |
| DMRT1 | 1761 | 9 | — | failure of testicular development and feminization in male |
| DMRT2 | 10655 | 9 | — | defective testis formation in karyotypic males and impaired ovary function in karyotypic females |
| MLLT3 | 4300 | 9 | — | neuromotor developmental delay, cerebellar ataxia, and epilepsy |
| ARF | 1029 | 9 | 16199529, 12019208 | acute myeloid leukemia |
| CDKN2B | 1030 | 9 | 10388473 | syndrome of cutaneous malignant melanoma and nervous system tumors |
| BAG1 | 573 | 9 | 15560850 | lung tumorigenesis |
| PAX5 | 5079 | 9 | — | pathogenesis of lymphocytic lymphomas |
| GCNT1 | 2650 | 9 | 16778138 | T lymphoma cells resistant to cell death |
| ROR2 | 4920 | 9 | 17632781 | basal cell nevus syndrome (BCNS) |
| PTCH1 | 5727 | 9 | 11922389, 14500378 | Primitive neuroectodermal tumors formation |
| NR5A1 | 2516 | 9 | 14594453 | impaired testicular development, sex reversal, and adrenal failure |
| LMX1B | 4010 | 9 | 15774843, 11668639, 9837817 | nail-patella syndrome |
| ENG | 2022 | 9 | 15718503, 16470589 | Hereditary hemorrhagic telangiectasia type 1 |
| TSC1 | 7248 | 9 | 14633685 | transitional cell carcinoma of the bladder |
| COL5A1 | 1289 | 9 | 16431952, 11391664, 10777716 | Structural abnormalities of the cornea and lid |
| NOTCH1 | 4851 | 9 | 16601454 | aortic valve disease (cardiac malformation and aortic valve calcification) |
| EHMT1 | 79813 | 9 | 16826528, 15805155 | 9q34 subtelomeric deletion syndrome |
| KLF6 | 1316 | 10 | 17297474 | cellular growth dysregulation and tumorigenesis |
| GATA3 | 2625 | 10 | 17046739, 16817354, 15994092, 15705923, 11577985, 11389161 | HDR (hypoparathyroidism, deafness and renal dysplasia) syndrome |
| ANX7 | 310 | 10 | 14608035 | tumorigenesis |
| PTEN | 5728 | 10 | 16938570, 16793127, 16738322, 16288012, 16027169, 15466193, 15001465, 12569555, 12461751, 11553783, 9697695, 12011252 | prostate cancer high-grade prostatic intra-epithelial neoplasias |
| PAX2 | 5076 | 10 | 14569086 | renal-coloboma syndrome |
| FGF8 | 2253 | 10 | 17448458 | several human craniofacial disorders |
| BUB3 | 9184 | 10 | 16600919 | short life span that is associated with the early onset of aging-related features |
| CDKN1C | 1028 | 11 | 10424812 | Beckwith-Wiedemann syndrome |

TABLE 1-continued

Genes Associated With Haploinsufficiency Diseases

| Gene Symbol | Entrez Gene ID | Chromosome | PubMed (PMID) | Disorder/Syndrome |
|---|---|---|---|---|
| NUP98 | 4928 | 11 | — | destruction of securin in mitosis |
| PAX6 | 5080 | 11 | 16866875, 16719277, 16717455, 15480875, 15057935, 12782766, 12552561, 11920832, 11431688, 16646034 | eye diseases |
| WT1 | 7490 | 11 | 8827067, 17931563 | congenital genitourinary (GU) anomalies and/or bilateral disease and tumorigenesis |
| EXT2 | 2132 | 11 | 11137991 | type II form of multiple exostoses |
| ALX4 | 60529 | 11 | 15057119, 9636085 | Tibial aplasia, lower extremity mirror image polydactyly, brachyphalangy, craniofacial dysmorphism and genital hypoplasia |
| FEN1 | 2237 | 11 | 16978612 | neuromuscular and neurodegenerative diseases |
| SF1 | 7536 | 11 | 17940071, 17200175 | mild gonadal dysgenesis and impaired androgenization |
| FGF3 | 2248 | 11 | 17656375 | otodental syndrome |
| FZD4 | 8322 | 11 | 17103440 | complex chromosome rearrangement with multiple abnormalities including growth retardation, facial anomalies, exudative vitreoretinopathy (EVR), cleft palate, and minor digital anomalies |
| ATM | 472 | 11 | 10571946, 10363981 | High incidence of cancer |
| H2AX | 3014 | 11 | 12914700 | genomic instability, early onset of various tumors |
| FLI1 | 2313 | 11 | 15525489 | Paris-Trousseau thrombopenia |
| NFRKB | 4798 | 11 | 11920839 | cellular immunodeficiency, pancytopenia, malformations |
| PHB2 | 11331 | 12 | — | enhanced estrogen receptor function |
| ETV6 | 2120 | 12 | 16643428 | a paediatric pre-B acute lymphoblastic leukaemia |
| CDKN1B | 1027 | 12 | 16951165, 11042700, 10935480 | ErbB2-induced mammary tumor growth |
| COL2A1 | 1280 | 12 | 10819645 | Stickler syndrome |
| KRT5 | 3852 | 12 | — | epidermolysis bullosa simplex |
| MYF6 | 4618 | 12 | 11053684 | myopathy and severe course of Becker muscular dystrophy |
| IGF1 | 3479 | 12 | 15769976 | subtle inhibition of intrauterine and postnatal growth |
| SERCA2 | 488 | 12 | 17116488, 16204033, 11389134 | colon and lung cancer |
| TBX5 | 6910 | 12 | 15289437, 12789647, 12736217, 11572777 | maturation failure of conduction system morphology and function in Holt-Oram syndrome |
| TBX3 | 6926 | 12 | 17265068, 16896345, 12668170, 12376101, 12116211 | ulnar-mammary syndrome |
| HNF1A | 6927 | 12 | 14633861, 12530534 | reduced serum apolipoprotein M levels |
| BRCA2 | 675 | 13 | 15172125 | predisposed to breast, ovarian, pancreatic and other cancers |
| FKHR | 2308 | 13 | 15489287 | Alveolar rhabdomyosarcomas |
| RB1 | 5925 | 13 | 12531801 | Metaphase cytogenetic abnormalities |
| ZIC2 | 7546 | 13 | 11699604, 11285244 | neurological disorderss, behavioral abnormalities |
| LIG4 | 3981 | 13 | — | LIG4 syndrome, nonlymphoid tumorigenesis |
| COCH | 1690 | 14 | 16078052 | unknown |
| NPAS3 | 64067 | 14 | 12746393 | schizophrenia |
| NKX2-1 | 7080 | 14 | — | Choreoathetosis, hypothyroidism, pulmonary alterations, neurologic phenotype and secondary hyperthyrotropinemia, and diseases due to transcription factor defects |

TABLE 1-continued

Genes Associated With Haploinsufficiency Diseases

| Gene Symbol | Entrez Gene ID | Chromosome | PubMed (PMID) | Disorder/Syndrome |
|---|---|---|---|---|
| PAX9 | 5083 | 14 | 16479262, 16333316, 11941488, 11781684 | posterior tooth agenesis |
| BMP4 | 652 | 14 | 16835935 | a contiguous gene syndrome comprising anophthalmia, pituitary hypoplasia, and ear anomalies |
| GCH1 | 2643 | 14 | — | malignant hyperphenylalaninemia and dopa-responsive dystonia |
| SIX6 | 4990 | 14 | 10512683 | bilateral anophthalmia and pituitary anomalies |
| RAD51B | 5890 | 14 | 16778173 | centrosome fragmentation and aneuploidy |
| BCL11B | 64919 | 14 | 17306224 | suppression of lymphomagenesis and thymocyte development |
| SPRED1 | 161742 | 15 | — | neurofibromatosis type 1-like syndrome |
| BUBR1 | 701 | 15 | 14744753 | enhanced tumor development |
| DLL4 | 54567 | 15 | — | embryonic lethality due to major defects in arterial and vascular development |
| FBN1 | 2200 | 15 | — | Marfan syndrome, isolated ectopia lentis, autosomal dominant Weill-Marchesani syndrome, MASS syndrome, and Shprintzen-Goldberg craniosynostosis syndrome |
| ALDH1A2 | 8854 | 15 | — | facilitate posterior organ development and prevent spina bifida |
| TPM1 | 7168 | 15 | — | type 3 familial hypertrophic cardiomyopathy |
| P450SCC | 1583 | 15 | 11502818 | 46, XY sex reversal and adrenal insufficiency |
| BLM | 641 | 15 | 12242442 | the autosomal recessive disorder Bloom syndrome |
| COUP-TFII | 7026 | 15 | 15384084 | several malformations, pre- and postnatal growth retardation and developmental |
| SOX8 | 30812 | 16 | — | the mental retardation found in ATR-16 syndrome |
| TSC2 | 7249 | 16 | 16027168, 12100629 | differential cancer susceptibility |
| PKD1 | 5310 | 16 | — | autosomal dominant polycystic kidney disease |
| CBP | 1387 | 16 | 11962765 | Rubinstein-Taybi syndrome |
| SOCS1 | 8651 | 16 | 15197228 | severe liver fibrosis and hepatitis-induced carcinogenesis |
| PRM2 | 5620 | 16 | — | infertility |
| PRM1 | 5619 | 16 | — | infertility |
| ABCC6 | 368 | 16 | — | pseudoxanthoma elasticum |
| ERAF | 51327 | 16 | — | subtle erythroid phenotype |
| SALL1 | 6299 | 16 | 16429401 | Townes-Brocks syndrome |
| CBFB | 865 | 16 | 17022082 | delayed cranial ossification, cleft palate, congenital heart anomalies, and feeding difficulties |
| CTCF | 10664 | 16 | 17962299, 15761865 | loss of imprinting of insulin-like growth factor-II in Wilms tumor |
| WWOX | 51741 | 16 | 17575124 | initiation of tumor development |
| FOXF1 | 2294 | 16 | 11943666 | defects in formation and branching of primary lung buds |
| FOXC2 | 2303 | 16 | 16910099, 16081467, 15624441, 12719382, 11694548, 11078474 | the lymphatic/ocular disorder Lymphedema-Distichiasis |
| YWHAE | 7531 | 17 | — | pathogenesis of small cell lung cancer |
| HIC1 | 3090 | 17 | 16724116 | Miller-Dieker syndrome |
| LIS1 | 5048 | 17 | 17148952, 16642511, 9760204 | abnormal cell proliferation, migration and differentiation in the adult dentate gyrus |
| P53 | 7157 | 17 | 15583690, 12517413, 12467136, 11695559, 11532857, 11319275 | male oral squamous cell carcinomas |

TABLE 1-continued

Genes Associated With Haploinsufficiency Diseases

| Gene Symbol | Entrez Gene ID | Chromosome | PubMed (PMID) | Disorder/Syndrome |
|---|---|---|---|---|
| PMP22 | 5376 | 17 | 15955700 | hereditary neuropathy with liability to pressure palsies |
| COPS3 | 8533 | 17 | 10851253 | Circadian rhythm abnormalities of melatonin in Smith-Magenis syndrome |
| RAI1 | 10743 | 17 | 17041942, 17024248, 16845274, 15690371, 15565467 | Smith-Magenis syndrome |
| TOP3A | 7156 | 17 | — | Smith-Magenis syndrome |
| SHMT1 | 6470 | 17 | — | Smith-Magenis syndrome |
| RNF135 | 84282 | 17 | 17632510 | phenotypic abnormalities including overgrowth |
| NF1 | 4763 | 17 | 16893911, 16835260, 15804420, 15676286, 15103551, 12124168, 9187663, 17103458 | neurofibromatosis type 1 |
| SUZ12 | 23512 | 17 | — | mental impairment in constitutional NF1 microdeletions |
| MEL-18 | 7703 | 17 | 12196719 | breast carcinogenesis |
| KLHL10 | 317719 | 17 | — | disrupted spermiogenesis |
| STAT5B | 6777 | 17 | 15870688 | striking amelioration of IL-7-induced mortality and disease development |
| STAT5A | 6776 | 17 | 15870688 | striking amelioration of IL-7-induced mortality and disease development |
| BECN1 | 8678 | 17 | — | autophagy function, and tumor suppressor function |
| BRCA1 | 672 | 17 | 17420720, 17404506, 15289302 | shortened life span and ovarian tumorigenesis |
| PGRN | 2896 | 17 | 17168647, 16862115 | neurodegeneration |
| MAPT | 4137 | 17 | — | neuronal cell death, neurodegenerative disorders such as Alzheimer's disease, Pick's disease, frontotemporal dementia, cortico-basal degeneration and progressive supranuclear palsy |
| CSH1 | 1442 | 17 | 14642004 | Silver-Russell syndrome |
| POLG2 | 11232 | 17 | — | mtDNA deletions causes COX deficiency in muscle fibers and results in the clinical phenotype |
| PRKAR1A | 5573 | 17 | 15371594 | Carney complex, a familial multiple neoplasia syndrome |
| SOX9 | 6662 | 17 | 17142326, 11606049, 8894698, 8001137 | skeletal dysplasias |
| NHERF1 | 9368 | 17 | 17078868 | breast tumours |
| FSCN2 | 25794 | 17 | 16043865 | photoreceptor degeneration, autosomal dominant retinitis pigmentosa |
| DSG1 | 1828 | 18 | 17194569 | diseases of epidermal integrity |
| DSG2 | 1829 | 18 | — | ARRHYTHMOGENIC RIGHT VENTRICULAR DYSPLASIA |
| TCF4 | 6925 | 18 | 17478476 | Pitt-Hopkins syndrome, a syndromic mental disorder |
| FECH | 2235 | 18 | 10068685 | protoporphyria |
| MC4R | 4160 | 18 | 12851322, 12639913, 10598807 | increased adiposity and linear growth |
| GALR1 | 2587 | 18 | — | uncontrolled proliferation and neoplastic transformation |
| SALL3 | 27164 | 18 | — | 18q deletion syndrome |
| LKB1 | 6794 | 19 | 12218179 | Peutz-Jeghers syndrome |
| PNPLA6 | 10908 | 19 | 15094302 | organophosphorus-induced hyperactivity and toxicity |
| RYR1 | 6261 | 19 | — | malignant hyperthermia susceptibility, central core disease, and minicore myopathy with external ophthalmoplegia |
| TGFB1 | 7040 | 19 | 17114585 | Aggressive pancreatic ductal adenocarcinoma |

TABLE 1-continued

Genes Associated With Haploinsufficiency Diseases

| Gene Symbol | Entrez Gene ID | Chromosome | PubMed (PMID) | Disorder/Syndrome |
|---|---|---|---|---|
| RPS19 | 6223 | 19 | — | Diamond-Blackfan anemia |
| DMPK | 1760 | 19 | 10021468 | cardiac disease in myotonic dystrophy |
| CRX | 1406 | 19 | 10892846 | photoreceptor degeneration, Leber congenital amaurosis type III and the autosomal dominant cone-rod dystrophy 2 |
| PRPF31 | 26121 | 19 | — | retinitis pigmentosa with reduced penetrance |
| JAG1 | 182 | 20 | 11861489, 11139239, 10590916, 17786115, 11152664, 10534349 | Alagille syndrome |
| PAX1 | 5075 | 20 | 12774041 | Klippel-Feil syndrome |
| GDF5 | 8200 | 20 | 16532400, 12357473 | Multiple-synostosis syndrome |
| HNF4A | 3172 | 20 | 10905494 | monogenic autosomal dominant non-insulin-dependent diabetes mellitus type I |
| SALL4 | 57167 | 20 | 16790473 | Okihiro syndrome |
| MC3R | 4159 | 20 | — | susceptibility to obesity |
| RAE1 | 8480 | 20 | 16355229 | premature separation of sister chromatids, severe aneuploidy and untimely degradation of securin |
| GNAS | 2778 | 20 | 17652219, 15579796 | reduced activation of a downstream target in epithelial tissues |
| EDN3 | 1908 | 20 | — | Hirschsprung disease |
| KCNQ2 | 3785 | 20 | 12700166 | epilepsy susceptibility |
| SOX18 | 54345 | 20 | 17290276 | mental retardation |
| SLC5A3 | 6526 | 21 | — | brain inositol deficiency |
| RUNX1 | 861 | 21 | 17394134, 16364766, 15339695, 15061191, 11830488, 11721958, 15297309, 14556655, 11756147, 10684580 | The 8p11 myeloproliferative syndrome |
| DYRK1A | 1859 | 21 | 12192061 | neurological defects, developmental delay |
| COL6A1 | 1291 | 21 | — | autosomal dominant disorder, Bethlem myopathy |
| PRODH | 5625 | 22 | 17028864 | 22q11 Deletion syndrome |
| DGCR2 | 9993 | 22 | — | DiGeorge syndrome |
| HIRA | 7290 | 22 | 9063745, 8111380 | DiGeorge syndrome (cranio-facial, cardiac and thymic malformations) |
| TBX1 | 6899 | 22 | 16969581, 16684884, 15778864, 12539040, 12351571, 11242049 | 22q11 deletion syndrome and schizophrenia |
| COMT | 1312 | 22 | 16848928 | 22q11.2 deletion syndrome |
| RTN4R | 65078 | 22 | — | schizophrenia susceptibility (schizoaffective disorders are common features in patients with DiGeorge/velocardiofacial syndrome) |
| PCQAP | 51586 | 22 | 11414760 | DiGeorge syndrome |
| LZTR1 | 8216 | 22 | — | DiGeorge syndrome |
| INI1 | 6598 | 22 | 16912184 | pituitary tumorigenesis |
| MYH9 | 4627 | 22 | 16162639 | hematological abnormalities |
| SOX10 | 6663 | 22 | 11641219 | the etiology of Waardenburg/Hirschsprung disease |
| FBLN1 | 2192 | 22 | — | limb malformations |
| PPARA | 5465 | 22 | — | prostate cancer |
| PROSAP2 | 85358 | 22 | 11431708, 12065602 | The terminal 22q13.3 deletion syndrome, characterized by severe expressive-language delay, mild mental retardation, hypotonia, joint laxity, dolichocephaly, and minor facial dysmorphisms |

TABLE 1-continued

Genes Associated With Haploinsufficiency Diseases

| Gene Symbol | Entrez Gene ID | Chromosome | PubMed (PMID) | Disorder/Syndrome |
| --- | --- | --- | --- | --- |
| SHOX | 6473 | X | 17881654, 17726696, 16776105, 16319696, 15356038, 15173321, 15118270, 14981722, 14557470, 14513876, 14513875, 12673642, 12510982, 12439897, 12116254, 12035792, 11889214, 11701728, 11546827, 11523902, 11503163, 11408757, 11134233, 10905666, 10878753, 10842291, 10798359, 10749976, 10599728 | congenital form of growth failure, the aetiology of "idiopathic" short stature and the growth deficits and skeletal anomalies in Leri Weill, Langer and Turner syndrome |
| P2RY8 | 286530 | X | 15466006 | mentally retarded males |
| NLGN4X | 57502 | X | — | autism and Asperger syndrome |
| TRAPPC2 | 6399 | X | — | spondyloepiphyseal dysplasia tarda |
| RPS4X | 6191 | X | — | unknown |
| CSF2RA | 1438 | X | 8950669 | growth deficiency |
| CHRDL1 | 91851 | X | 3196642 | topographic retinotectal projection and in the regulation of retinal angiogenesis in response to hypoxia |
| SF3B4 | 10262 | 1 | 24003905, 27127115, | Nager syndrome, Hepatocellular carcinoma and Rodriguez Acrofacial Dysotosis |
| CTNND2 | 1501 | 5 | 29127138, 25839933 | Intellectual disability, epilepsy |
| AAGAB | 79719 | 15 | 26608363, 25771163 | Buschke-Fischer-Brauer and punctate palmoplantar keratoderma |
| ABCD1 | 215 | X | 26454440, 29136088 | adrenoleukodystrophy |
| AKT3 | 10000 | 1 | 28969385, 27297869 | Developmental disorders and breast cancer |
| ANKRD11 | 29123 | 16 | 28422132, 27605097 | KBG syndrome |
| ANOS1 | 3730 | X | 28780519, 25892360 | Kallmann syndrome |
| AP1S2 | 8905 | X | 17617514, 23756445, | Mental retardation |
| AR | 367 | X | 29051026 | Kennedy's disease and androgen insensitivity |
| ARSE | 415 | X | 20301713, 23470839 | chondrodysplasia punctata |
| ARX | 170302 | X | 25044608 | cognitive disability and epilepsy |
| ASXL1 | 171023 | 20 | 27616637 | myelodysplastic syndromes and chronic myelomonocytic leukemia |
| ATP7A | 538 | X | 22992316, 24754450 | Menkes disease, X-linked distal spinal muscular atrophy, and occipital horn syndrome |
| ATP8A2 | 51761 | 13 | 20683487 | cerebellar ataxia and cognitive disabilities |
| ATRX | 546 | X | 20301622 | cognitive disabilities as well as alpha-thalassemia (ATRX) syndrome |
| AUTS2 | 26053 | 7 | 26717414 | autism spectrum disorders, intellectual disability, and developmental delay |
| AVPR2 | 554 | X | 27565746, 27117808 | Nephrogenic Diabetes Insipidus (NDI) |
| BAG3 | 9531 | 10 | 28211974 | cardiomyopathy |
| BCL11A | 53335 | 2 | 28891213 | Autism and intellectual development |
| BCOR | 54880 | X | 26573325 | sarcoma of the kidney |
| BMPR1A | 657 | 10 | 26383923 | Intellectual disability |
| BRWD3 | 254065 | X | 24462886, 17668385 | cognitive disabilities and X-linked macrocephaly |
| BTK | 695 | X | 19039656 | agammaglobulinemia |
| CACNA1C | 775 | 12 | 28493952, 26204268 | Autism |
| CASK | 8573 | X | 28783747, 24927672 | FG syndrome 4, intellectual disability and microcephaly |
| CDH1 | 999 | 16 | 26182300 | breast, colorectal, thyroid, gastric and ovarian cancer |
| CDKL5 | 6792 | X | 27265524, 26701947 | infantile spasm syndrome (ISSX), also known as X-linked West syndrome, and Rett syndrome (RTT). |

TABLE 1-continued

Genes Associated With Haploinsufficiency Diseases

| Gene Symbol | Entrez Gene ID | Chromosome | PubMed (PMID) | Disorder/Syndrome |
| --- | --- | --- | --- | --- |
| CHD2 | 1106 | 15 | 26677509 | Neurodevelopmental disorders |
| CHD8 | 57680 | 14 | 26921529, 25989142, 2673379 | Autism |
| CHM | 1121 | X | 27820636 | choroideremia |
| CHRM3 | 1131 | 1 | 26959877 | Schizophrenia |
| CLCN5 | 1184 | X | 27117801, 29058463 | Dent disease and renal tubular disorders complicated by nephrolithiasis |
| CNKSR2 | 22866 | X | 22511892 | Intellectual disability |
| CNTN4 | 152330 | 3 | 21308999 | autism spectrum disorders |
| CNTNAP2 | 26047 | 7 | 27439707 | neurodevelopmental disorders, including Gilles de la Tourette syndrome, schizophrenia, epilepsy, autism, ADHD and intellectual disability |
| COL11A1 | 1301 | 1 | 21035103 | Fibrochondrogenesis, Stickler syndrome and with Marshall syndrome |
| COL1A1 | 1277 | 17 | 28102596 | imperfecta types I-IV, Ehlers-Danlos syndrome type VIIA, Ehlers-Danlos syndrome Classical type, Caffey Disease and idiopathic osteoporosis |
| CREBBP | 1387 | 16 | 27342041 | Rubinstein-Taybi syndrome (RTS) and acute myeloid leukemia |
| CRYBB2 | 1415 | 22 | 25489230, 25964531, | Cataracts and prostate cancer |
| CUL4B | 8450 | X | 24898194 | Intellectual disability |
| CYBB | 1536 | X | 27917630 | chronic granulomatous disease (CGD |
| DCX | 1641 | X | 25868952 | pilepsy, cognitive disability, subcortical band heterotopia and lissencephaly syndrome |
| DICER1 | 23405 | 14 | 24761742 | familial tumor susceptibility syndrome |
| DKC1 | 1736 | X | 27570172, 25499969 | X-linked dyskeratosis congenita |
| DLG3 | 1741 | X | 19795139 | cognitive disability |
| DMD | 1756 | X | 28247318 | uchenne muscular dystrophy (DMD), Becker muscular dystrophy (BMD), and cardiomyopathy |
| DSC2 | 1824 | 18 | 26310507 | arrhythmogenic right ventricular dysplasia-11, and cancer |
| EBP | 10682 | X | 22121851 | Chondrodysplasia punctata 2 |
| EDNRB | 1910 | 13 | 8852658 | Hirschsprung disease type 2 |
| EDA | 1896 | X | 25846883 | X-linked hypohidrotic ectodermal dysplasia |
| EFNB1 | 1947 | X | 15959873 | craniofrontonasal syndrome |
| EFTUD2 | 9343 | 17 | 26507355 | mandibulofacial dysostosis with microcephaly |
| EMX2 | 2018 | 10 | 8528262 | schizencephaly |
| EP300 | 2033 | 22 | 25712426 | Rubinstein-Taybi syndrome and epithelial cancer |
| ERF | 2077 | 19 | 26097063 | craniosynostosis |
| ERMARD | 55780 | 6 | 24056535 | Periventricular nodular heterotopia |
| EXT1 | 2131 | 8 | 24009674 | Multiple osteochondromas |
| EYA4 | 2070 | 6 | 15735644 | Cardiomyopathy and hearing loss |
| F8 | 2157 | X | 28777843 | hemophilia A |
| F9 | 2158 | X | 28007939 | hemophilia B or Christmas disease |
| FAM58A | 92002 | X | 18297069 | STAR syndrome |
| FANCB | 2187 | X | 21910217 | VACTERL syndrome |
| FAS | 355 | 10 | 21490157 | Autoimmune lympho-proliferative syndrome |
| FGD1 | 2245 | X | 27199457 | dysplasia in Aarskog-Scott syndrome and a syndromatic form of X-linked cognitive disability |
| FLCN | 201163 | 17 | 28970150 | Birt-Hogg-Dube syndrome |
| FLG | 2312 | 1 | 21514438 | ichthyosis vulgaris |

TABLE 1-continued

Genes Associated With Haploinsufficiency Diseases

| Gene Symbol | Entrez Gene ID | Chromosome | PubMed (PMID) | Disorder/Syndrome |
| --- | --- | --- | --- | --- |
| FLNA | 2316 | X | 22238415 | Periventricular nodular heterotopias, otopalatodigital syndromes, frontometaphyseal dysplasia, Melnick-Needles syndrome, and X-linked congenital idiopathic intestinal pseudoobstruction |
| FOXG1 | 2290 | 14 | 28851325 | Rett syndrome |
| FRMD7 | 90167 | X | 25678693 | congenital nystagmus |
| FTSJ1 | 24140 | X | 18401546 | cognitive disability |
| GATA2 | 2624 | 3 | 21670465, 21892158 | monocytopenia and mycobacterial infection syndrome and Emberger syndrome |
| GATA6 | 2627 | 18 | 25706805 | congenital defects and cardiomyopathy |
| GDI1 | 2664 | X | 21736009 | cognitive disability |
| GJA5 | 2702 | 1 | 25992486 | atrial fibrillation |
| GJA8 | 2703 | 1 | 28526010 | zonular pulverulent cataracts, nuclear progressive cataracts, and cataract-microcornea syndrome |
| GK | 2710 | X | 10851254 | glycerol kinase deficiency |
| GLA | 2717 | X | 28723748 | Fabry disease |
| GLI2 | 2736 | 2 | 25974718 | Greig cephalopolysyndactyly syndrome, Pallister-Hall syndrome, preaxial polydactyly type IV, postaxial polydactyly types A1 and B |
| GLMN | 11146 | 1 | 15689436 | glomuvenous malformations |
| GPC3 | 2719 | X | 28371070 | Simpson-Golabi-Behmel syndrome |
| GRIA3 | 2892 | X | 19449417 | Intellectual disability |
| GRIN2A | 2903 | 16 | 27683935 | epilepsy and speech disorder |
| GRIN2B | 2904 | 12 | 27818011 | neurodevelopmental disorders autism, attention deficit hyperactivity disorder, epilepsy and schizophrenia |
| HCCS | 3052 | X | — | microphthalmia syndrome |
| HDAC4 | 9759 | 2 | 20691407 | Mental retardation |
| HMGA2 | 8091 | 12 | 25809938 | Silver-Russell syndrome |
| HNF1B | 6928 | 17 | 27838256 | Intellectual disability |
| HNRNPK | 3190 | 9 | 26173930 | Intellectual disability |
| HPRT1 | 3251 | X | 29185864 | Lesch-Nyhan syndrome or gout |
| HNRNPU | 3192 | 1 | 28393272 | epileptic encephalopathy and intellectual disability |
| IDS | 3423 | X | 27246110 | Hunter syndrome |
| IGF1R | 3480 | 15 | 21811077 | Familial short statute |
| IKBKG | 8517 | X | 27037530 | inncontinentia pigmenti, hypohidrotic ectodermal dysplasia, and immunodeficiencies |
| IL1RAPL1 | 11141 | X | 21933724 | intellectual disability |
| KANSL1 | 284058 | 17 | 20301783 | intellectual disability |
| KAT6B | 23522 | 10 | 26334766 | Say-Barber-Biesecker/Young-Simpson syndrome |
| KCNH2 | 3757 | 7 | 24530480 | long QT syndrome type 2 |
| KDM5C | 8242 | X | 25666439 | cognitive disability |
| KDM6A | 7403 | X | 23076834 | Kabuki syndrome |
| KIAA2022 | 340533 | X | 27358180 | cognitive disability and epilepsy |
| KIF11 | 3832 | 10 | 22653704 | microcephaly |
| KMT2A | 4297 | 11 | 28911906 | Acute lymphoid leukemias and acute myeloid leukemias |
| KMT2D | 8085 | 12 | 27530205 | Kabuki syndrome |
| L1CAM | 3897 | X |  | Masa syndrome and L1 syndrome |
| LAMP2 | 3920 | X | 28627787 | Danon disease |
| LDLR | 3949 | 19 | 28873201 | Familial hypercholesterolemia |
| LEMD3 | 23592 | 12 | 26694706 | Buschke-Ollendorff syndrome and melorheostosis |
| LHX4 | 89884 | 1 | 25871839 | hypopituitarism |
| LMNA | 4000 | 1 | 20127487 | cardiomyopathy |
| LRP5 | 4041 | 11 | 27228167 | familial exudative vitreoretinopathy |
| MAGEL2 | 54551 | 15 | 26365340, | Prader-Willi syndrome (PWS) |

TABLE 1-continued

Genes Associated With Haploinsufficiency Diseases

| Gene Symbol | Entrez Gene ID | Chromosome | PubMed (PMID) | Disorder/Syndrome |
| --- | --- | --- | --- | --- |
| MAGT1 | 84061 | X | 24130152 | intellectual disability |
| MAOA | 4128 | X | 8211186 | Mental retardation |
| MAP2K2 | 5605 | 19 | 25487361 | cardiofaciocutaneous syndrome |
| MBD5 | 55777 | | 27786435, 25271084, 24885232 | Microcephaly, intellectual disabilities, speech impairment, and seizures |
| MECP2 | 4204 | X | 29141583 | Rett syndrome |
| MED13L | 23389 | 12 | 28371282, 28645799 | Intellectual disability |
| MEF2C | 4208 | 5 | 27255693 | cognitive disability, epilepsy, and cerebral malformation |
| MEIS2 | 4212 | 15 | 25712757 | Intellectual disability |
| MEN1 | 4221 | 11 | 9510467, 15105049, 21763627 | Multiple Endocrine Neoplasia type 1 |
| MID1 | 4281 | X | 25304119 | Opitz syndrome |
| MLH1 | 4292 | 3 | 15942939 | colon cancer |
| MNX1 | 3110 | 7 | 24095820 | Currarino syndrome |
| MSH2 | 4436 | 2 | 26498247 | hereditary nonpolyposis colon cancer |
| MSH6 | 2956 | 2 | 6099011 | hereditary nonpolyposis colon cancer, colorectal cancer, and endometrial cancer |
| MTAP | 4507 | 9 | 22464254 | diaphyseal medullary stenosis with malignant fibrous histiocytoma (DMSMFH). |
| MTM1 | 4534 | X | 21488203 | X-linked myotubular myopathy |
| MYBPC3 | 4607 | 11 | 27348999 | familial hypertrophic cardiomyopathy |
| MYLK | 4638 | 3 | 28602422 | Megacystis Microcolon Intestinal Hypoperistalsis Syndrome |
| MYT1L | 23040 | 2 | 22547139 | schizophrenia |
| NDP | 4693 | X | 27217716 | Norrie disease |
| NF2 | 4771 | 22 | 11159946 | neurofibromatosis type II |
| NFIX | 4784 | 19 | 26200704 | Marshall-Smith syndrome or Sotos-like syndrome |
| NHS | 4810 | X | 28557584 | Nance-Horan syndrome |
| NIPBL | 25836 | 5 | 26701315 | Cornelia de Lange syndrome |
| NODAL | 4838 | 10 | 19064609 | Cardiovascular malformations |
| NOG | 9241 | 17 | 25391606 | symphalangism (SYM1) and multiple synostoses syndrome (SYNS1) |
| NR0B1 | 190 | X | 25968435 | congenital adrenal hypoplasia and hypogonadotropic hypogonadism |
| NRXN1 | 9378 | 2 | 26279266 | Pitt-Hopkins-like syndrome-2 and schizophrenia |
| NSDHL | 50814 | X | 26014843 | CHILD syndrome |
| NXF5 | 55998 | X | 11566096 | Mental retardation |
| NYX | 60506 | X | 26234941 | X-linked congenital stationary night blindness |
| OCRL | 4952 | X | 27059748 | oculocerebrorenal syndrome of Lowe and also Dent disease |
| OFD1 | 8481 | X | 28371265 | oral-facial-digital syndrome type I and Simpson-Golabi-Behmel syndrome type 2 |
| OPHN1 | 4983 | X | 17845870 | X-linked cognitive disability |
| OTC | 5009 | X | 26446336 | Hyperammonemia |
| OTX2 | 5015 | 14 | 27299576, 28388256 | syndromic microphthalmia 5 and pituitary hormone deficiency 6 |
| PAFAH1B1 | 5048 | 17 | 11754098 | Lissencephaly |
| PAK2 | 5062 | 3 | 21841781 | intellectual disability |
| PAK3 | 5063 | X | 18523455 | intellectual disability |
| PCDH19 | 57526 | X | 27179713 | epileptic encephalopathy and autism |
| PDHA1 | 5160 | X | 10679936 | X-linked Leigh syndrome |
| PGK1 | 5230 | X | 16567519 | neurological impairment |
| PHEX | 5251 | X | 27840894 | Hypophosphatemic rickets |
| PHF6 | 84295 | X | 22190899 | cognitive disability and epilepsy |
| PHF8 | 23133 | X | 17594395 | Mental retardation and cleft palate |
| PIGA | 5277 | X | 24706016 | encephalopathies |

TABLE 1-continued

Genes Associated With Haploinsufficiency Diseases

| Gene Symbol | Entrez Gene ID | Chromosome | PubMed (PMID) | Disorder/Syndrome |
|---|---|---|---|---|
| PITX3 | 5309 | 10 | 16565358 | Ocular and neurological disorders |
| PKP2 | 5318 | 12 | 27030002 | cardiomyopathy |
| PLP1 | 5354 | X | 27793435 | Pelizaeus-Merzbacher disease and spastic paraplegia type 2 |
| POLR1D | 51082 | 13 | 24603435 | Treacher Collins syndrome (TCS) |
| PORCN | 64840 | X | 23696273 | focal dermal hypoplasia |
| PQBP1 | 10084 | X | 21204222 | cognitive disability |
| PRPS1 | 5631 | X | 26089585 | Charcot-Marie-Tooth disease and Arts syndrome |
| PRRT2 | 112476 | 16 | 22744660 | paroxysmal kinesigenic dyskinesias |
| PTHLH | 5744 | 12 | 26733284 | osteochondroplasia |
| PTPN11 | 5781 | 12 | 28328117 | Noonan syndrome |
| RAB39B | 116442 | X | 20159109 | cognitive disability, epilepsy, and macrocephaly |
| RASA1 | 5921 | 5 | 26969842 | capillary malformations and Parkes Weber syndrome |
| RBFOX1 | 54715 | 16 | 26174448 | Epilepsy |
| RET | 5979 | 10 | — | Hirschsprung disease |
| RP2 | 6102 | X | 16969763 | Retinal dystrophies |
| RPS17 | 6218 | 15 | 23812780 | Diamond-Blackfan anemia |
| RPS24 | 6229 | 10 | 17186470 | Diamond-Blackfan anemia |
| RPS26 | 6231 | 12 | 22045982 | Diamond-Blackfan anemia |
| RPS6KA3 | 6197 | X | 26297997 | Coffin-Lowry syndrome |
| RS1 | 6247 | X | 26043410 | retinoschisis |
| SCN2A | 6326 | 2 | 26291284 | Epilepsy and autism |
| SCN5A | 6331 | 3 | 28069705 | Long QT syndrome type 3 |
| SDHAF2 | 54949 | 11 | 21224366 | paraganglioma |
| SDHB | 6390 | 1 | 27839933 | paraganglioma |
| SDHC | 6391 | 1 | 26652933 | paraganglioma |
| SDHD | 6392 | 11 | 28924001 | paraganglioma |
| SETBP1 | 26040 | 18 | 28346496 | Schinzel-Giedion syndrome |
| SETD5 | 55209 | 3 | 27375234 | Intellectual disability |
| SGCE | 8910 | 7 | 26783545 | Myoclonus dystonia |
| SH2B1 | 25970 | 16 | 23160192 | Maladaptive behaviors and obesity |
| SH2D1A | 4068 | X | — | Lymphoproliferative syndrome |
| SIX3 | 6496 | 2 | 19346217 | holoprosencephaly |
| SLC16A12 | 387700 | 10 | 18304496 | Juvenile cataracts and renal glucosuria |
| SLC16A2 | 6567 | X | 27805744 | Allan-Herndon-Dudley syndrome |
| SLC2A1 | 6513 | 1 | 25532859 | Paroxysmal exertion-induced dyskinesia |
| SLC4A10 | 57282 | 2 | 18413482 | Epilepsy and mental retardation |
| SLC6A8 | 6535 | X | 24137762 | Mental retardation |
| SLC9A6 | 10479 | X | 25044251 | cognitive disability |
| SMAD3 | 4088 | 15 | 22803640 | Cardiovascular malformations and aneurysms |
| SMAD4 | 4089 | 18 | 18823382 | pancreatic cancer, juvenile polyposis syndrome, and hereditary hemorrhagic telangiectasia syndrome |
| SMARCA4 | 6597 | 19 | 23775540 | Rhabdoid tumor predisposition syndrome |
| SMARCB1 | 6598 | 22 | 28338502 | Rhabdoid tumor predisposition syndrome |
| SMS | 6611 | X | 23696453 | intellectual disability |
| SNURF | 8926 | 15 | 22511895 | Prader-Willi Syndrome |
| SOX11 | 6664 | 2 | 6543202 | Autism and mental retardation |
| SOX5 | 6660 | 12 | 23498568 | Mental retardation |
| SPINK1 | 6690 | 5 | 27159572 | hereditary pancreatitis and tropical calcific pancreatitis |
| SRY | 6736 | Y | 7987333 | gonadal dysgenesis |
| STK11 | 6794 | 19 | 29141581 | Peutz-Jeghers syndrome and cancer |
| STS | 412 | X | 26421812 | X-linked ichthyosis (XLI) |
| STXBP1 | 6812 | 9 | 26865513 | infantile epileptic encephalopathy-4 |
| SYN1 | 6853 | | 22807112 | neuronal degeneration such as Rett syndrome |
| SYNGAP1 | 8831 | 6 | 23161826 | intellectual disability and autism |

TABLE 1-continued

Genes Associated With Haploinsufficiency Diseases

| Gene Symbol | Entrez Gene ID | Chromosome | PubMed (PMID) | Disorder/Syndrome |
|---|---|---|---|---|
| TAB2 | 23118 | 6 | 25940952 | congenital heart defects |
| TBX20 | 57057 | 7 | 26118961 | cardiac pathologies |
| TBX22 | 50945 | X | 22851992 | Cleft palate |
| TBX4 | 9496 | 17 | 15106123 | Small patella syndrome |
| TCF12 | 6938 | 15 | 26068201 | Anaplastic oligodendroglioma |
| TDGF1 | 6997 | 3 | 12073012 | forebrain defects |
| TFAP2B | 7021 | 6 | 24507797 | Char syndrome |
| TGFBR1 | 7046 | 9 | 21358634 | Ferguson-Smith disease (FSD) |
| TGFBR2 | 7048 | 3 | 28344185 | Syndrome, Loeys-Deitz Aortic Aneurysm Syndrome |
| TGIF1 | 7050 | 18 | 16962354 | holoprosencephaly type 4 |
| TIMM8A | 1678 | X | 20301359 | Jensen syndrome |
| TNNI3 | 7137 | 19 | 18006163 | cardiomyopathy |
| TP63 | 8626 | 3 | 11462173 | ectodermal dysplasia, cleft lip/palate, and split-hand/foot malformation |
| TSPAN7 | 7102 | X | 19339915 | cognitive disability and neuropsychiatric diseases |
| UBE2A | 7319 | X | 16909393 | cognitive disability |
| UBE3A | 7337 | 15 | 28559284 | autism |
| UPF3B | 65109 | X | 22609145 | Mental retardation |
| VEGFA | 7422 | 6 | 20420808 | Cardiovascular defects |
| WDR45 | 11152 | X | 27030146 | neurodegeneration |
| XIAP | 331 | X | 26182687 | dysgammaglobulinemia |
| YAP1 | 10413 | 11 | 24462371 | hearing loss, intellectual disability, hematuria, and orofacial clefting |
| ZC4H2 | 55906 | X | 23623388 | cognitive disability |
| ZDHHC9 | 51114 | X | 28687527 | cognitive disability |
| ZEB2 | 9839 | 2 | 15121779 | Mowat-Wilson syndromw |
| ZFPM2 | 23414 | | 24769157 | Cardiovascular malformations |
| ZIC1 | 7545 | 3 | 24782033 | Hepatocellular carcinoma |
| ZIC3 | 7547 | X | 24123890 | X-linked visceral heterotaxy |
| ZIC4 | 84107 | 3 | 21204220 | Danny-Walker malformation |
| ZNF41 | 7592 | X | 14628291 | cognitive disability |
| ZNF674 | 641339 | X | 22126752 | cognitive disability |
| ZNF711 | 7552 | X | 21384559 | cognitive disability |
| CACNA1A | 773 | 19 | | Neurological disorders |

Compositions

Episomal Vectors

Described herein are compositions useful as components for targeting transcriptional activation domains to genetic control elements to increase transcription of an endogenous gene and thereby treat a disease or condition associated with, exacerbated by, or caused by reduced transcription of a gene, reduced amount of a gene product, or reduced activity of a gene product. The components include guide RNAs, scaffold RNAs, scaffold RNA ligands, CRISPR nucleases, transcriptional activation domains, affinity tag(s), affinity tag ligand(s), fusion proteins of one or more thereof, and combinations thereof. The components also include episomal vectors that encode one or more guide RNAs, scaffold RNAs, scaffold RNA ligands, CRISPR nucleases, transcriptional activation domains, affinity tag(s), affinity tag ligand(s), fusion proteins of one or more thereof, and combinations thereof. The episomal vectors can be single- or double-stranded DNA, single-stranded RNA, or double-stranded RNA.

In one embodiment, an episomal vector encoding a CRISPR nuclease, such as a catalytically inactive CRISPR nuclease is be provided. In some cases, the episomal vector encodes a CRISPR nuclease fused to one or more transcriptional activation domains. In some cases, the episomal vector encodes a CRISPR nuclease fused to one or more affinity tags. In some cases, the episomal vector encodes a CRISPR nuclease fused to one or more affinity tags and one or more transcriptional activation domains. CRISPR nuclease fusion proteins can contain transcriptional activator domain(s) and/or affinity tag(s) fused at the amino-terminus of the CRISPR nuclease, at the carboxy terminus, or a combination thereof. Additionally or alternatively, the CRISPR nuclease can be modified by the insertion of transcriptional activator domain(s) and/or affinity tag(s) within a surface loop. The episomal vector (e.g., AAV vector) can contain a promoter that is operably linked to the CRISPR nuclease or CRISPR nuclease fusion protein. The promoter can be a promoter that is endogenous to a viral source from which the episomal vector is derived. For example, where the episomal vector is an AAV vector, the promoter can be an endogenous AAV promoter. Alternatively, the promoter can be a promoter that is heterologous to the viral source form which the episomal vector is derived. For example, where the episomal vector is an AAV vector, the promoter can be a non-AAV promoter. The promoter can be a promoter of a gene targeted for transcriptional activation (e.g., a gene selected from Table 1) or a promoter that is heterologous to the targeted gene. The promoter can be constitutive (e.g., a CMV promoter, CAG promoter, CBA promoter, EFla promoter, PGK promoter, etc.), tissue specific (e.g., a synapsin, camKIIa, GFAP, RPE, ALB, TBG, MBP, MCK, TNT, or aMHC, promoter, and the like), or inducible (e.g., tetracycline inducible).

In one embodiment, an episomal vector encoding a zinc finger nuclease is provided. In some cases, the episomal vector encodes a zinc finger nuclease fused to one or more transcriptional activation domains. In some cases, the episomal vector encodes a zinc finger nuclease fused to one or more affinity tags. In some cases, the episomal vector encodes a zinc finger nuclease fused to one or more affinity tags and one or more transcriptional activation domains. Zinc finger nuclease fusion proteins can contain transcriptional activator domain(s) and/or affinity tag(s) fused at the amino-terminus of the zinc finger nuclease, at the carboxy terminus, or a combination thereof. The episomal vector (e.g., AAV vector) can contain a promoter that is operably linked to the zinc finger nuclease or zinc finger nuclease fusion protein. The promoter can be a promoter that is endogenous to a viral source from which the episomal vector is derived. For example, where the episomal vector is an AAV vector, the promoter can be an endogenous AAV promoter. Alternatively, the promoter can be a promoter that is heterologous to the viral source form which the episomal vector is derived. For example, where the episomal vector is an AAV vector, the promoter can be a non-AAV promoter. The promoter can be a promoter of a gene targeted for transcriptional activation (e.g., a gene selected from Table 1) or a promoter that is heterologous to the targeted gene. The promoter can be constitutive (e.g., a CMV promoter, CAG promoter, CBA promoter, EFla promoter, PGK promoter, etc.), tissue specific (e.g., a synapsin, camKIIa, GFAP, RPE, ALB, TBG, MBP, MCK, TNT, or aMHC, promoter, and the like), or inducible (e.g., tetracycline inducible).

In one embodiment, an episomal vector encoding a TALEN is provided. In some cases, the episomal vector encodes a TALEN fused to one or more transcriptional activation domains. In some cases, the episomal vector encodes a TALEN fused to one or more affinity tags. In some cases, the episomal vector encodes a TALEN fused to one or more affinity tags and one or more transcriptional activation domains. TALENs can contain transcriptional activator domain(s) and/or affinity tag(s) fused at the amino-terminus, at the carboxy terminus, or a combination thereof. The episomal vector (e.g., AAV vector) can contain a promoter that is operably linked to the TALEN. The promoter can be a promoter that is endogenous to a viral source from which the episomal vector is derived. For example, where the episomal vector is an AAV vector, the promoter can be an endogenous AAV promoter. Alternatively, the promoter can be a promoter that is heterologous to the viral source form which the episomal vector is derived. For example, where the episomal vector is an AAV vector, the promoter can be a non-AAV promoter. The promoter can be a promoter of a gene targeted for transcriptional activation (e.g., a gene selected from Table 1) or a promoter that is heterologous to the targeted gene. The promoter can be constitutive (e.g., a CMV promoter, CAG promoter, CBA promoter, EFla promoter, PGK promoter, etc.), tissue specific (e.g., a synapsin, camKIIa, GFAP, RPE, ALB, TBG, MBP, MCK, TNT, or aMHC, promoter, and the like), or inducible (e.g., tetracycline inducible).

In one embodiment, an episomal vector encoding a guide RNA is provided. The guide RNA can be a small guide RNA. The guide RNA can be a component of a synergistic activation mediator (e.g., as described in Zhang et al., Scientific Reports 5, Article No. 16277 (2015); and Konermann et al., 2015, Nature 517:583-8). The episomal vector (e.g., AAV vector) can contain a promoter that is operably linked to the guide RNA. The promoter can be a promoter that is endogenous to a viral source from which the episomal vector is derived. For example, where the episomal vector is an AAV vector, the promoter can be an endogenous AAV promoter. Alternatively, the promoter can be a promoter that is heterologous to the viral source form which the episomal vector is derived. For example, where the episomal vector is an AAV vector, the promoter can be a non-AAV promoter. The promoter can be a promoter of a gene targeted for transcriptional activation (e.g., a gene selected from Table 1) or a promoter that is heterologous to the targeted gene. The promoter can be constitutive (e.g., a CMV promoter, CAG promoter, CBA promoter, EFla promoter, PGK promoter, etc.), tissue specific (e.g., a synapsin, camKIIa, GFAP, RPE, ALB, TBG, MBP, MCK, TNT, or aMHC, promoter, and the like), or inducible (e.g., tetracycline inducible).

In some embodiments, the episomal vector encodes both a CRISPR nuclease and a guide RNA. In some cases, the CRISPR nuclease is operably linked to a promoter and the guide RNA is operably linked to a different promoter. In some cases, the two promoters are the same. In some cases, the two promoters are different. In some cases, both promoters are inducible. In some cases, both promoters are tissue specific. In some cases, both promoters are constitutive. In some cases, one promoter is constitutive and the other promoter is tissue specific. In some cases, one promoter is constitutive and the other promoter is inducible. In some cases, one promoter is tissue specific and the other is inducible.

In some embodiments, the episomal vector encodes a scaffold RNA, such as a scaffold RNA described in WO 2016/054106. In some embodiments, the episomal vector also encodes a CRISPR nuclease. Additionally or alternatively, the episomal vector can also encode one or more transcriptional activation domain(s). In some cases, the transcriptional activation domain(s) are fused to a binding element that binds to the scaffold RNA (e.g., binds to an ms2, f6, PP7, com, or L7a sequence of a scaffold RNA).

In some embodiments, two or more different episomal vector are provided. For example, an episomal vector encoding a CRISPR nuclease and a separate episomal vector encoding a guide RNA can be provided. Alternatively, an episomal vector encoding a CRISPR nuclease and a guide RNA can be provided and a separate episomal vector encoding one or more transcriptional activation domain(s) can be provided. In some cases, the one or more transcriptional activation domains are fused to a binding element that binds a scaffold RNA (e.g., binds a guide RNA of an SAM). In some cases, the one or more transcriptional activation domains are fused to a binding element that binds an affinity tag of a CRISPR nuclease. In some embodiments, an episomal vector encoding a scaffold RNA is provided and a separate episomal vector is provided that encodes one or more transcriptional activation domain(s) fused to a binding element that binds the scaffold RNA.

In some embodiments, the episomal vector encodes a zinc finger nuclease or TALEN that hybridizes to or specifically hybridizes to (e.g., under stringent hybridization conditions) a gene listed in Table 1, or a gene in the same pathway or a parallel pathway as a gene listed in Table 1. In some cases, the episomal vector encodes a zinc finger nuclease or TALEN that hybridizes to or specifically hybridizes to (e.g., under stringent hybridization conditions) a control region (e.g., promoter region or enhancer region) of a gene listed in Table 1, or a gene in the same pathway or a parallel pathway as a gene listed in Table 1.

In some cases, the episomal vector encodes a zinc finger nuclease or TALEN that hybridizes to or specifically hybridizes to (e.g., under stringent hybridization conditions) to SIM1, Leptin, Leptin receptor, MC4R, SCN2A, SETD5, PAX6, PKD1, MC3R, POMC, STAT3, STAT5, SOCS3, GHR, NPY, NPY1R, NPY2R, NPY5R, PYY, AMPK (PRKAA1, PRKAA2, PRKAB1, PRKAB2, PRKAG1, PRKAG2, PRKAG3), OXT, JAK2, SHP2, NOS3, NROB2, BRS3, CARTPT, FABP4, HTR2C, IL6, NHLH2, NMU, NPB, NPBWRI, PNPLA2, UCP3, ADIPOQ, APOA5, ARNT2, ASIP, C1QTNF2, C3AR1, CCK, CPT1B, CSF2, DGAT1, DGAT2, GHRL, GHSR, HSD11B1, HTR7, INSIG1, INSIG2, LIPC, NMURI, NMUR2, NPBWR2, NTS, PPARGC1A, PPY, RETN, SIRT1, TGFBR2, WDTC1, or FOXO1.

In some cases, the episomal vector encodes a zinc finger nuclease or TALEN that hybridizes to or specifically hybridizes to (e.g., under stringent hybridization conditions) a control region (e.g., promoter region or enhancer region) of SIM1, Leptin, Leptin receptor, MC4R, SCN2A, SETD5, PAX6, PKD1, MC3R, POMC, STAT3, STAT5, SOCS3, GHR, NPY, NPY1R, NPY2R, NPY5R, PYY, AMPK (PRKAA1, PRKAA2, PRKAB1, PRKAB2, PRKAG1, PRKAG2, PRKAG3), OXT, JAK2, SHP2, NOS3, NROB2, BRS3, CARTPT, FABP4, HTR2C, IL6, NHLH2, NMU, NPB, NPBWRI, PNPLA2, UCP3, ADIPOQ, APOA5, ARNT2, ASIP, C1QTNF2, C3AR1, CCK, CPT1B, CSF2, DGAT1, DGAT2, GHRL, GHSR, HSD11B1, HTR7, INSIG1, INSIG2, LIPC, NMURI, NMUR2, NPBWR2, NTS, PPARGC1A, PPY, RETN, SIRT1, TGFBR2, WDTC1, or FOXO1.

In some cases, the episomal vector encodes a zinc finger nuclease or TALEN that hybridizes to or specifically hybridizes to (e.g., under stringent hybridization conditions) a control region (e.g., promoter region or enhancer region) of SIM1. In some cases, the the episomal vector encodes a zinc finger nuclease or TALEN that hybridizes to or specifically hybridizes to (e.g., under stringent hybridization conditions) a promoter region of SIM1. In some cases, the episomal vector encodes a zinc finger nuclease or TALEN that hybridizes to or specifically hybridizes to (e.g., under stringent hybridization conditions) an enhancer region of SIM1. In some cases, the episomal vector encodes a zinc finger nuclease or TALEN that hybridizes to or specifically hybridizes to (e.g., under stringent hybridization conditions) a control region (e.g., promoter region or enhancer region) of MC4R. In some cases, the episomal vector encodes a zinc finger nuclease or TALEN that hybridizes to or specifically hybridizes to (e.g., under stringent hybridization conditions) a promoter region of MC4R. In some cases, the episomal vector encodes a zinc finger nuclease or TALEN that hybridizes to or specifically hybridizes to (e.g., under stringent hybridization conditions) an enhancer region of MC4R. In some cases, the episomal vector encodes a zinc finger nuclease or TALEN that hybridizes to or specifically hybridizes to (e.g., under stringent hybridization conditions) a control region (e.g., promoter region or enhancer region) of PDK1. In some cases, the the episomal vector encodes a zinc finger nuclease or TALEN that hybridizes to or specifically hybridizes to (e.g., under stringent hybridization conditions) a promoter region of PDK1. In some cases, the episomal vector encodes a zinc finger nuclease or TALEN that hybridizes to or specifically hybridizes to (e.g., under stringent hybridization conditions) an enhancer region of PDK1. In some cases, the episomal vector encodes a zinc finger nuclease or TALEN that hybridizes to or specifically hybridizes to (e.g., under stringent hybridization conditions) a control region (e.g., promoter region or enhancer region) of SETD5. In some cases, the episomal vector encodes a zinc finger nuclease or TALEN that hybridizes to or specifically hybridizes to (e.g., under stringent hybridization conditions) a promoter region of SETD5. In some cases, the episomal vector encodes a zinc finger nuclease or TALEN that hybridizes to or specifically hybridizes to (e.g., under stringent hybridization conditions) an enhancer region of SETD5. In some cases, the episomal vector encodes a zinc finger nuclease or TALEN that hybridizes to or specifically hybridizes to (e.g., under stringent hybridization conditions) a control region (e.g., promoter region or enhancer region) of SCN2A. In some cases, the episomal vector encodes a zinc finger nuclease or TALEN that hybridizes to or specifically hybridizes to (e.g., under stringent hybridization conditions) a promoter region of SCN2A. In some cases, the episomal vector encodes a zinc finger nuclease or TALEN that hybridizes to or specifically hybridizes to (e.g., under stringent hybridization conditions) an enhancer region of SCN2A. In some cases, the episomal vector encodes a zinc finger nuclease or TALEN that hybridizes to or specifically hybridizes to (e.g., under stringent hybridization conditions) a control region (e.g., promoter region or enhancer region) of PAX6. In some cases, the episomal vector encodes a zinc finger nuclease or TALEN that hybridizes to or specifically hybridizes to (e.g., under stringent hybridization conditions) a promoter region of PAX6. In some cases, the episomal vector encodes a zinc finger nuclease or TALEN that hybridizes to or specifically hybridizes to (e.g., under stringent hybridization conditions) an enhancer region of PAX6.

In some embodiments, the episomal vector encodes a guide or scaffold RNA that hybridizes to or specifically hybridizes to (e.g., under stringent hybridization conditions) a gene listed in Table 1, or a gene in the same pathway or a parallel pathway as a gene listed in Table 1. In some cases, the episomal vector encodes a guide or scaffold RNA that hybridizes to or specifically hybridizes to (e.g., under stringent hybridization conditions) a control region (e.g., promoter region or enhancer region) of a gene listed in Table 1, or a gene in the same pathway or a parallel pathway as a gene listed in Table 1.

In some cases, the episomal vector encodes a guide or scaffold RNA that hybridizes to or specifically hybridizes to (e.g., under stringent hybridization conditions) to SIM1, Leptin, Leptin receptor, MC4R, SCN2A, SETD5, PAX6, PKD1, MC3R, POMC, STAT3, STAT5, SOCS3, GHR, NPY, NPY1R, NPY2R, NPY5R, PYY, AMPK (PRKAA1, PRKAA2, PRKAB1, PRKAB2, PRKAG1, PRKAG2, PRKAG3), OXT, JAK2, SHP2, NOS3, NROB2, BRS3, CARTPT, FABP4, HTR2C, IL6, NHLH2, NMU, NPB, NPBWRI, PNPLA2, UCP3, ADIPOQ, APOA5, ARNT2, ASIP, C1QTNF2, C3AR1, CCK, CPT1B, CSF2, DGAT1, DGAT2, GHRL, GHSR, HSD11B1, HTR7, INSIG1, INSIG2, LIPC, NMURI, NMUR2, NPBWR2, NTS, PPARGC1A, PPY, RETN, SIRT1, TGFBR2, WDTC1, or FOXO1.

In some cases, the episomal vector encodes a guide or scaffold RNA that hybridizes to or specifically hybridizes to (e.g., under stringent hybridization conditions) a control region (e.g., promoter region or enhancer region) of SIM1, Leptin, Leptin receptor, MC4R, SCN2A, SETD5, PAX6, PKD1, MC3R, POMC, STAT3, STAT5, SOCS3, GHR, NPY, NPY1R, NPY2R, NPY5R, PYY, AMPK (PRKAA1, PRKAA2, PRKAB1, PRKAB2, PRKAG1, PRKAG2, PRKAG3), OXT, JAK2, SHP2, NOS3, NROB2, BRS3, CARTPT, FABP4, HTR2C, IL6, NHLH2, NMU, NPB, NPBWRI, PNPLA2, UCP3, ADIPOQ, APOA5, ARNT2, ASIP, C1QTNF2, C3AR1, CCK, CPT1B, CSF2, DGAT1, DGAT2, GHRL, GHSR, HSD11B1, HTR7, INSIG1, INSIG2, LIPC, NMURI, NMUR2, NPBWR2, NTS, PPARGC1A, PPY, RETN, SIRT1, TGFBR2, WDTC1, or FOXO1.

In some cases, the episomal vector encodes a guide or scaffold RNA that hybridizes to or specifically hybridizes to (e.g., under stringent hybridization conditions) a control region (e.g., promoter region or enhancer region) of SIM1. In some cases, the the episomal vector encodes a guide or scaffold RNA that hybridizes to or specifically hybridizes to (e.g., under stringent hybridization conditions) a promoter region of SIM1. In some cases, the episomal vector encodes a guide or scaffold RNA that hybridizes to or specifically hybridizes to (e.g., under stringent hybridization conditions) an enhancer region of SIM1. In some cases, the episomal vector encodes a guide or scaffold RNA that hybridizes to or specifically hybridizes to (e.g., under stringent hybridization conditions) a control region (e.g., promoter region or enhancer region) of MC4R. In some cases, the episomal vector encodes a guide or scaffold RNA that hybridizes to or specifically hybridizes to (e.g., under stringent hybridization conditions) a promoter region of MC4R. In some cases, the episomal vector encodes a guide or scaffold RNA that hybridizes to or specifically hybridizes to (e.g., under stringent hybridization conditions) an enhancer region of MC4R. In some cases, the episomal vector encodes a guide or scaffold RNA that hybridizes to or specifically hybridizes to (e.g., under stringent hybridization conditions) a control region (e.g., promoter region or enhancer region) of PDK1. In some cases, the the episomal vector encodes a guide or scaffold RNA that hybridizes to or specifically hybridizes to (e.g., under stringent hybridization conditions) a promoter region of PDK1. In some cases, the episomal vector encodes a guide or scaffold RNA that hybridizes to or specifically hybridizes to (e.g., under stringent hybridization conditions) an enhancer region of PDK1. In some cases, the episomal vector encodes a guide or scaffold RNA that hybridizes to or specifically hybridizes to (e.g., under stringent hybridization conditions) a control region (e.g., promoter region or enhancer region) of SETD5. In some cases, the episomal vector encodes a guide or scaffold RNA that hybridizes to or specifically hybridizes to (e.g., under stringent hybridization conditions) a promoter region of SETD5. In some cases, the episomal vector encodes a guide or scaffold RNA that hybridizes to or specifically hybridizes to (e.g., under stringent hybridization conditions) an enhancer region of SETD5. In some cases, the episomal vector encodes a guide or scaffold RNA that hybridizes to or specifically hybridizes to (e.g., under stringent hybridization conditions) a control region (e.g., promoter region or enhancer region) of SCN2A. In some cases, the episomal vector encodes a guide or scaffold RNA that hybridizes to or specifically hybridizes to (e.g., under stringent hybridization conditions) a promoter region of SCN2A. In some cases, the episomal vector encodes a guide or scaffold RNA that hybridizes to or specifically hybridizes to (e.g., under stringent hybridization conditions) an enhancer region of SCN2A. In some cases, the episomal vector encodes a guide or scaffold RNA that hybridizes to or specifically hybridizes to (e.g., under stringent hybridization conditions) a control region (e.g., promoter region or enhancer region) of PAX6. In some cases, the episomal vector encodes a guide or scaffold RNA that hybridizes to or specifically hybridizes to (e.g., under stringent hybridization conditions) a promoter region of PAX6. In some cases, the episomal vector encodes a guide or scaffold RNA that hybridizes to or specifically hybridizes to (e.g., under stringent hybridization conditions) an enhancer region of PAX6.

In some cases, the targeting region of the guide RNA is encoded by, specifically hybridizes to, or is fully complementary to: SEQ ID NO: 1 (GACACGGAATTCATTGCCAG), SEQ ID NO:2 (CTGCGGGTTAGGTCTACCGG), SEQ ID NO:3 (GTTGAGCGCTCAGTCCAGCG), SEQ ID NO:4 (TCCCGACGTCGTGCGCGACC), or SEQ ID NO:5 (GCTCTGAATCTTACTACCCG). In some cases, the targeting region of the guide RNA is encoded by, specifically hybridizes to, or is fully complementary to: SEQ ID NO:6 (GCTGTTAACTAAAGACAGGG), SEQ ID NO:7 (GTGGTCTGGGTGATCTCATG), SEQ ID NO:8 (GACAAAGGAACATCTGAGAGG), SEQ ID NO:9 (GTGATCTCATGGGGAAGAGG), or SEQ ID NO:10 (GGCTTTGATCGTGGTCTGGG). In some cases, the targeting region of the guide RNA is encoded by, specifically hybridizes to, or is fully complementary to: SEQ ID NO: 11 (GCGAGCCCAGTCGCGTGGGG), SEQ ID NO: 12 (GCCAAGAATTGGCCAAAGGG), SEQ ID NO:34 (GTCAAAGGGGCATATGGAAGG), SEQ ID NO:35 (GGGAAGAAAGCCCCACTTGG), SEQ ID NO:36 (GCCCAGTCGCGTGGGGGGGG), or SEQ ID NO:37 (GGAGCGCGAGTGTCACTCGG). In another embodiment, the targeting region of the guide RNA is encoded by, specifically hybridizes to, or is fully complementary to: SEQ ID NO:38 (GCTCACTGTAGGACCCGAGCC), SEQ ID NO:39 (GACGCGGCGCTCATTGGCCAA), SEQ ID NO:40 (CGAGCCGCGAGCCCAGTCGCG), SEQ ID NO:41 (TCCCCCCCCCCCCCCACGCGA), SEQ ID NO:42 (GTCACTCACCCCGATTGGCCA), or SEQ ID NO:43 (CGCGAGCCCAGTCGCGTGGGG). In some embodiments, the targeting region of the guide RNA is encoded by, specifically hybridizes to, or is fully complementary to: SEQ ID NO:44 (GTTGGCTTATCCAAACATCTC), SEQ ID NO:45 (ATGTTAAGCAAGGGTAATAGA), SEQ ID NO:46 (CTGTGAAAGGAATACAATTCA), SEQ ID NO: 47 (GCCAATTCTTGGCAACCGAGC), SEQ ID NO:48 (GAATTGGCCAAAGGGAGGGGT), or SEQ ID NO:49 (AATTAGCAGACAGCTTGGTAC). In some embodiments, the targeting region of the guide RNA is encoded by, specifically hybridizes to, or is fully complementary to: SEQ ID NO: 50 (CTGGCTGATTCCCGAGGATTT), SEQ ID NO: 51 (CACTGAATACGGATTGGTCAG), SEQ ID NO:52 (GATGTCTCAGAACCACTGAAT), SEQ ID NO:53 (AACCACTGAATACGGATTGGT), or SEQ ID NO:54 (ACCAATCCGTATTCAGTGGTT). In some embodiments, the targeting region of the guide RNA is encoded by, specifically hybridizes to, or is fully complementary to: SEQ ID NO:55 (GGCGCGGGGCGGACGGGGCGA), SEQ ID NO:56 (GCGCCCCGGGAACGCGTGGGG), SEQ ID NO:57 (CGCCCCGCGCCGCGCGGGGAG), SEQ ID NO:58 (TCCGCCCCGCGCCGCGCGGGG), SEQ ID NO:59 (GGAACGCGTGGGGCGGAGCTT), SEQ ID NO:60 (GCCCCGCGCCGCGCGGGGAGG), SEQ ID NO:61 (TGCGCCCCGGGAACGCGTGGG), SEQ ID NO:62 (GAACGCGTGGGGCGGAGCTTC), SEQ ID NO:63 (GCGGCGCGGGGCGGACGGGGC), or SEQ ID NO:64 (CCCGTCCGCCCCGCGCCGCGC). In some embodiments, the targeting region of the guide RNA is encoded by, specifically hybridizes to, or is fully complementary to: SEQ ID NO:65 (GGCCCACTCGCCGCCAATCAG), SEQ ID NO:66 (GGAAGCCGCCGGGGCCGCCTA), SEQ ID NO:67 (TGATTGGCGGCGAGTGGGCCA), SEQ ID NO:68: (GCCGCCAATCAGCGGAAGCCG), SEQ ID NO:69: (GGCGGCTTCCGCTGATTGGCG), SEQ ID NO:70: (CCGCCAATCAGCGGAAGCCGC), SEQ ID NO:71: (AGCCGCCGGGGCCGCCTAGAG), SEQ ID NO:72: (GCTTCCGCTGATTGGCGGCGA), SEQ ID NO:73:

(CGGCGAGTGGGCCAATGGGTG), or SEQ ID NO:74: (CCAATGGGTGCGGGGCGGTGG). In some embodiments, the targeting region of the guide RNA is encoded by or specifically hybridizes to: SEQ ID NO:75 (GGCTGCCGGGGCCGCCTAAAG), SEQ ID NO:76 (GGAGGCTGCCGGGGCCGCCTA), SEQ ID NO:77 (GCCGCCAATCAGCGGAGGCTG), SEQ ID NO:78 (CCGCCAATCAGCGGAGGCTGC), SEQ ID NO:79 (TGGCCGGTGCGCCGCCAATCA), SEQ ID NO:80 (GGCCGGTGCGCCGCCAATCAG), SEQ ID NO:81 (CGGCGCACCGGCCAATAAGTG), SEQ ID NO:82 (ATAAGTGTGGGGCGGTGGGCG), SEQ ID NO:83 (CCAATAAGTGTGGGGCGGTGG), or SEQ ID NO:84 (CAATAAGTGTGGGGCGGTGGG). In some embodiments, the targeting region of the guide RNA is encoded by or specifically hybridizes to: SEQ ID NO:85: CCTTTC-TATGACCTAGTCGG, SEQ ID NO:86: CAGAATCAGTAACGCACTGT, SEQ ID NO:87: GAAACCAGGAGAGATAACCC, SEQ ID NO:88: GGACCCCAGATATTCTGGAA, SEQ ID NO:89: TTAT-TGTTGACTTAACGAAG, SEQ ID NO:90: AAAAAGAAGCAAATAGCTAA, or SEQ ID NO:91: (AGAATCAGTAACGCACTGTA). In some embodiments, the targeting region of the guide RNA is encoded by, specifically hybridizes to, or is fully complementary to: SEQ ID NO:92 (TGTTGGTTTATTGGACCCCAGATATTC), SEQ ID NO: 93 (TGTTGGAGAAAATTAACTTAGTG-CATA), or SEQ ID NO:94 (TGTTGGTATAACTGC-CACTAGAGGGCT). In some embodiments, the targeting region of the guide RNA is encoded by, specifically hybridizes to, or is fully complementary to SEQ ID NO:95 (AGGAGCCGGGACCCACCGG).

In some cases, the targeting region of the guide RNA is encoded by, specifically hybridizes to, or is fully complementary to a sequence that is orthologous and/or homologous to a region of a mouse or human genome corresponding to, or targeted by an sgRNA comprising, one of SEQ ID NOs: 1-12, or 34-95. In some cases, the guide RNA is encoded by, specifically hybridizes to, or is fully complementary to a sequence that is 90%, 95%, or 99% identical to, or differs by 1, 2, or 3 nucleotides from, or is 1, 2, or 3 nucleotides longer or shorter at a 5' and/or 3' end than one of SEQ ID NOs: 1-12, or 34-95.

One or more of the episomal vectors described herein can be provided as a kit for treatment of a disease in a mammalian subject associated with, exacerbated by, or caused by reduced transcription of a gene, reduced amount of a gene product, or reduced activity of a gene product. For example, an episomal vector encoding a CRISPR nuclease, a zinc finger nuclease, a TALEN, a TAL effector, a guide RNA, a transcriptional activation domain, a scaffold RNA, a scaffold RNA ligand, an affinity tag ligand, fusion proteins of one or more thereof, or a combination thereof, can be provided as a component of a kit containing an episomal vector packaging plasmid, cell line, or helper virus, or a combination thereof.

In some cases, an episomal vector in which the encoded polypeptide(s) and/or RNA(s) are flanked by AAV inverted terminal repeats is provided as a component of a kit containing additional materials for packaging the episomal vector into functional AAV particles. Such additional materials can include one or more plasmids encoding AAV rep and cap genes, one or more plasmids encoding adenovirus helper factors E1A, E1B, E2A, E4ORF6 and VA, adenovirus, or a combination thereof. In some cases, the trans-activating elements and/or helper elements for AAV packaging are provided in a stable cell line as a component of the kit.

In some embodiments, the cap gene is an AAV-DJ, AAV1, AAV2, AAV3, AAV4, AAV5, AAV6, AAV7, AAV8, or AAV9 cap gene. In some embodiments, the cap gene is an AAV-DJ, AAV1, AAV2, AAV5, AAV7, AAV8 or AAV9 cap gene. In some embodiments, the cap gene is an AAV2 cap gene. In some embodiments, the cap gene is an AAV-DJ cap gene. In some embodiments, the inverted terminal repeats (ITRs) are AAV1, AAV2, AAV3, AAV4, AAV5, AAV6, AAV7, AAV8, or AAV9 ITRs. In some embodiments, the ITRs are AAV1, AAV2, AAV5, AAV7, AAV8 or AAV9 ITRs. In some embodiments, the ITRs are AAV2 ITRs. In some cases, the capsid protein encoded by the cap gene is the same serotype as the ITRs. For example, the cap gene can be an AAV2 cap gene and the ITRs can be AAV2 ITRs. In some cases, the capsid protein encoded by the cap gene is a different serotype from the serotype of the ITRs. Thus, for example, the cap gene can be an AAV5 cap gene and the ITRs can be AAV2 ITRs. As another example, the cap gene can be an AAV-DJ cap gene and the ITRs can be AAV2 ITRs.

In some cases, the episomal vector can be in a target cell or cell of the target tissue. In some cases, the target cell or cell of a target tissue is a dividing cell. In some cases, the cell is a non-dividing cell. In some cases, the cell is a neuron. In some cases, the cell is a cell of the hypothalamus. In some cases, the target cell or cell of the target tissue is a mammalian cell that contains a genome having at least one functional copy of a target gene, wherein the functional cop(y/ies) in the absence of transcriptional activation by a heterologous complex do not produce enough of a corresponding gene product to produce a wild-type phenotype in an organism. In some cases, the mammalian cell further comprises a scaffold RNA encoded by an episomal vector described herein, a guide RNA encoded by an episomal vector described herein, a CRISPR nuclease encoded by an episomal vector described herein, a SunTag encoded by an one or more episomal vectors described herein, a synergistic activation mediator (SAM) encoded by one or more episomal vectors described herein, a transcriptional activation domain encoded by an episomal vector described herein, an affinity tag ligand encoded by an episomal vector described herein, a fusion of one or more polypeptides described herein encoded by an episomal vector described herein, or a combination thereof.

In some cases, the episomal vector in a target cell or a cell of a target tissue is converted to a circular form, a circular concatemer, or a linear concatemer, e.g., through recombination of repeat elements, such as ITRs. In some cases, the episomal vector in the target cell or the cell of a target tissue is converted from a single-stranded DNA vector into a double-stranded DNA. In some cases, the double-stranded DNA is converted into a circular form, a circular concatemer, or a linear concatemer. In some cases, the episomal vector in the target cell or cell of the target tissue persists as an episomal element providing persistent transgene (e.g., CRISPR nuclease, transcriptional activator, guide RNA, scaffold RNA, etc.) expression. In some cases, the episomal elements is one of the foregoing circular forms, circular concatemers, or linear concatemers.

Viral Particles

One or more of the foregoing episomal vectors can be packaged in a viral particle. For example, the viral particle can contain an episomal vector encoding a CRISPR nuclease, a guide RNA, a scaffold RNA, a transcriptional activator, an affinity tag, an affinity tag ligand, a scaffold RNA ligand, a fusion protein of one or more thereof, or a combination of one or more thereof. The viral particle can be a viral particle that is capable of delivering the episomal vector to a target cell or tissue, such that the episomal vector enter the nucleus of a target cell or a cell of a target tissue and do not, or do not substantially integrate into the genome of the cell.

In some cases, the viral particle delivers the episomal vector to the target cell or cell of the target tissue and the episomal vector is converted to a circular form, a circular concatemer, or a linear concatemer, e.g., through recombination of repeat elements, such as ITRs. In some cases, the episomal vector delivered by the viral particle is converted from a single-stranded DNA vector into a double-stranded DNA. In some cases, the double-stranded DNA is converted into a circular form, a circular concatemer, or a linear concatemer. In some cases, the viral particle delivers an episomal vector to a target cell or cell of the target tissue, and the episomal vector persists as an episomal element providing persistent transgene expression.

The viral particles can be EBV or AAV viral particles. In some cases, the viral particles are AAV viral particles. In some cases, the viral particles are AAV-DJ, AAV1, AAV2, AAV3, AAV4, AAV5, AAV6, AAV7, AAV8, or AAV9 viral particles. In some cases, the viral particles are AAV-DJ, AAV1, AAV2, AAV5, AAV7, AAV8 or AAV9 viral particles. In some cases, the viral particles are AAV2 viral particles. In some cases, the viral particles are AAV-DJ viral particles. The genome packed in the viral particle and encoding the one or more transgenes (the episomal vector) can be an AAV1, AAV2, AAV3, AAV4, AAV5, AAV6, AAV7, AAV8, or AAV9 genome. In some cases, the genome is an AAV1, AAV2, AAV5, AAV7, AAV8 or AAV9 genome. In some cases, the genome is an AAV2 genome. In some cases the genome is the same serotype as the viral particle in which it is packaged. In other cases, the genome and viral particle are of different serotypes. For example, the capsid can be AAV5 serotype and the episomal vector can be AAV2 serotype. As another example, the capsid can be an AAV-DJ serotype and the episomal vector can be an AAV2 serotype.

One or more of the viral particles described herein can be provided as a kit for treatment of a disease in a mammalian subject associated with, exacerbated by, or caused by reduced transcription of a gene, reduced amount of a gene product, or reduced activity of a gene product. For example, an episomal vector encoding a CRISPR nuclease, a guide RNA, a transcriptional activation domain, a scaffold RNA, a scaffold RNA ligand, an affinity tag ligand, fusion proteins of one or more thereof, or a combination thereof, can be packaged into one or more viral particles and provided as a component of a kit containing a suitable pharmaceutical excipient, carrier, diluent, or buffer for delivery to a subject.

In one embodiment, the viral particles are in a suitable pharmaceutical excipient, carrier, diluent, or buffer for delivery to a subject. Such excipients, carriers, diluents, and buffers include any pharmaceutical agent that can be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins Pharmaceutical Dosage Forms and Drug Delivery Systems (1999) H. C. Ansel et al., eds., 7$^{th}$ ed., Lippincott, Williams, & Wilkins and Handbook of Pharmaceutical Excipients (2000) A. H. Kibbe et al., eds., 3$^{rd}$ ed. Amer. Pharmaceutical Assoc.

Methods

Described herein are methods for treating a disease in a mammalian subject associated with, exacerbated by, or caused by reduced transcription of a gene, reduced amount of a gene product, or reduced activity of a gene product by increasing transcription of a target gene. The methods generally include contacting a target cell or a cell of a target tissue with one or more of the foregoing episomal vectors. In some embodiments, the episomal vectors are non-integrating or substantially non-integrating. In some embodiments, the episomal vectors are packaged into viral particles and the viral particles are contacted with the target cell or the cell of a target tissue. In some cases, the contacting is performed in vivo. In some cases, the contacting is performed in vitro (e.g., using primary cells obtained from the subject) and the contacted cells are delivered to a subject, or optionally cultured and delivered to the subject.

The episomal vectors (e.g., packaged into viral particles) can be delivered by any means known in the art. In some cases, the episomal vectors are contacted with a cell in vivo by systemic delivery (e.g., intravenous delivery). In some cases, the episomal vectors (e.g., packaged into viral particles) are contacted with a cell in vivo by site-specific delivery to an affected cell or tissue. For example, viral particles in which episomal vectors are packaged can be injected into a site of an affected cell or tissue. In some cases, two or more episomal vectors are packaged into viral particles such that each viral particle contains a single copy of one of the two or more episomal vectors or is empty (contains no genome or a genome that lacks a functional transgene). Such viral particles can be delivered as a mixture or individually. In some cases, the particles are delivered simultaneously. In some cases, the particles are delivered sequentially. Typically, the particles are delivered such that the delivered transgenes encoded by the episomal vectors are co-expressed in the subject such that a disease is treated.

In one embodiment, one or more different viral particles (e.g., viral particles having the same capsid but containing vectors that encode different transgenes) are injected into a brain of a subject. In some cases, the one or more viral particles are injected into a hypothalamus of a subject. The viral particles can be delivered to an anterior portion of the hypothalamus, a posterior portion of the hypothalamus, a ventromedial portion of the hypothalamus, or a combination thereof. The viral particles can be delivered bilaterally (e.g., via bilateral injections to a hypothalamus of a subject). In some cases, the one or more viral particles are delivered to a neuron of the subject. In some case, the one or more viral particles are delivered by stereotactic injection.

The dose of viral particle delivered to a subject can be from $1 \times 10^3$ viral particles/kg subject to $1 \times 10^{20}$ viral particles/kg subject. The dose of episomal vector delivered to a subject can be from $1 \times 10^3$ vector molecules/kg subject to $1 \times 10^{20}$ vector molecules/kg subject. In some cases, the dose is from $1 \times 10^4$ to $1 \times 10^{18}$, from $1 \times 10^5$ to $1 \times 10^{16}$, from $1 \times 10^6$ to $1 \times 10^{15}$ viral particles/kg subject or vector molecules/kg subject. In some cases, the dose is at least $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, or $1 \times 10^{15}$ viral particles/kg subject or vector molecules/kg subject. In some cases, vector molecules are in the form of viral genomes delivered in a viral particle. In some cases, the dose is a dose of delivered viral genome (e.g., packaged in a viral particle) encoding a CRISPR nuclease (e.g., dCas9 fused to an activation domain) and a guide RNA (e.g., sgRNA). In some cases, the dose is a dose of delivered viral genome (e.g., packaged in a viral particle) encoding a CRISPR nuclease (e.g., dCas9 fused to an activation domain), and a second dose, such as one or more of the foregoing doses is a dose of delivered viral genome (e.g., packaged in a viral particle) encoding guide RNA (e.g., sgRNA).

In some cases, a systemic does can be higher as compared to a dose applied directly to a tissue or organ to be treated. For example, for treatment of obesity dysregulated by a haploinsufficient sim1 gene in hypothalamus tissue or cell, a lower dose can be delivered to the hypothalamus as compared to a systemic dose. In humans, systemic delivery can, e.g., be about $6.7 \times 10^{13}$-$2.0 \times 10^{14}$ viral genomes (vg)/kg (see, clinicaltrials.gov/ct2/show/NCT02122952) and neurosurgical delivery can, e.g., be about $7.5 \times 10^{11}$-$8.8 \times 10^{12}$ vg/kg (see clinicaltrials.gov/ct2/show/NCT01973543).

A dose can be administered once, or multiple times. In some cases, the dose is delivered at least once within a period of 30 days, 60 days, 90 days, 120 days, or 180 days. In some cases, a dose is delivered at least once every 10 weeks, 20 weeks, 30 weeks, 40 weeks, 52 weeks, or 75 weeks, or 100 weeks. In some cases, a dose is delivered at least once every 6 months, 12 months, 18 months, 2 years, 3 years, 5 years, or 10 years. In some cases, a single dose or 2, or 3, or 4 doses results in persistent and sufficient expression of the otherwise haploinsufficient target gene to treat at least one symptom of a disease or condition caused by the haploinsufficiency for a period of months or years. In some cases, a dose is administered, the sufficiency of expression of a target haploinsufficient gene (e.g., a gene in Table 1 such as sim1) is assessed (e.g., in a target tissue such as hypothalamus) and additional doses are delivered as needed by the same or different route. In some cases, one or more doses of viral particles as described herein are delivered, in sufficient amount to increase transcription of a target gene and thereby treat at least one symptom of a disease associated with, exacerbated by, or caused by reduced transcription of a gene, reduced amount of a gene product, or reduced activity of a gene product, and one or more doses are re-administered when transcription of the target gene has reduced from its maximal expression by at least 10%, 25%, 50%, 75%, 90%, or more.

EXAMPLES

Rescue of Haploinsufficiency-caused Obesity
I. Introduction

Over 300 genes are known to cause human disease due to haploinsufficiency (1, 2), leading to a wide range of phenotypes that include cancer, neurological diseases, developmental disorders, immunological diseases, metabolic disorders, infertility, kidney disease, limb malformations and many others (1). Large-scale exome sequencing analyses estimate that a total of 3,230 human genes could be heterozygous loss-of-function (LoF) intolerant (3). Gene therapy holds great promise in correcting haploinsufficient diseases, by inserting a functional recombinant copy or copies of the mutant gene. Currently, there are a total of 2,300 clinical trials underway for gene therapy, the majority of them using adeno-associated virus (AAV) to deliver the recombinant gene (4). AAV is a preferred gene delivery method due to its ability to deliver DNA without integrating into the genome, not causing pathogenicity and providing long lasting gene expression of the transgene (5). However, AAV has an optimal 4.7 kilo base (kb) packaging capacity, limiting its gene therapy use for genes longer than 3.5 kb (taking into account additional regulatory sequences needed for its stable expression). Analysis of the 3,230 heterozygous LoF genes finds 715 (22%) of them to have coding sequence longer than 3.5 kb, rendering them not suitable for AAV gene therapy.

CRISPR gene editing can potentially fix haploinsufficient mutations, however it would require the need to custom tailor the editing strategy for each mutation. Moreover, it's not a feasible therapy for heterozygous LoF micro-deletions. To address these challenges, we devised a novel therapeutic strategy for haploinsufficiency using CRISPR activation (CRISPRa). CRISPRa takes advantage of the RNA-guided targeting ability of CRISPR to direct a nuclease deficient Cas9 (dCas9) along with a transcriptional activator to regulatory element/s of a specific gene, thus increasing its expression (6-10). Here, we tested whether we can use this system to increase the transcription of the unaffected endogenous gene in a haploinsufficient disease to rescue the disease phenotype.

SIM1 is a transcription factor that is expressed in the developing kidney and central nervous system, and is essential for the formation of the supraoptic (SON) and paraventricular (PVN) nuclei of the hypothalamus (11). It is also thought to play a major role in the leptin pathway (12). In humans, haploinsufficiency of SIM1 due to chromosomal aberrations (12, 13) results in hyperphagic obesity (13) and SIM1 coding mutations, many of them being loss-of-function, are thought to be a major cause of severe obesity in humans (14-16). Sim1 homozygous null mice die perinatally, while Sim1 heterozygous mice ($Sim1^{+/-}$) survive, are hyperphagic and develop early-onset obesity with increased linear growth, hyperinsulinemia and hyperleptinemia (17). A postnatal conditional knockout of hypothalamic Sim1 leads to a similar phenotype in heterozygous mice (18), implicating Sim1 to be an important regulator of energy homeostasis. Overexpression of SIM1, using a human bacterial artificial chromosome in mice, rescues diet-induced obesity and reduced food intake (19), suggesting a potential role for Sim1 as a general therapeutic target for obesity. Here, we used Sim1 as our proof of concept model for our CRISPRa therapeutic strategy. We tested the ability of CRISPRa to rescue the obesity phenotype in $Sim1^{+/-}$ mice using both transgenic and AAV based approaches targeting the Sim1 promoter or its hypothalamus specific enhancer. Our results present a novel therapeutic approach for treating haploinsufficient diseases, or other diseases caused by altered gene dosage.

II. Results
A. Upregulation of Sim1 In Vitro

Figure 1B:
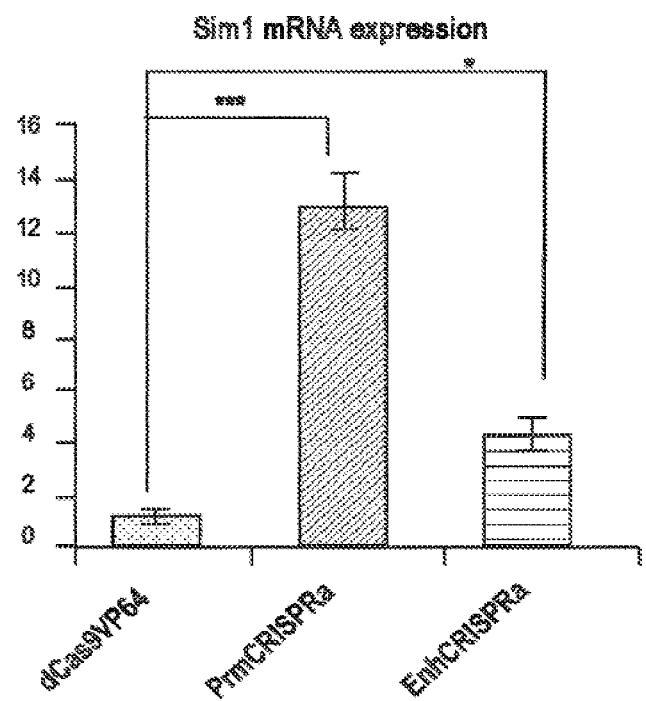
Figure 8A:
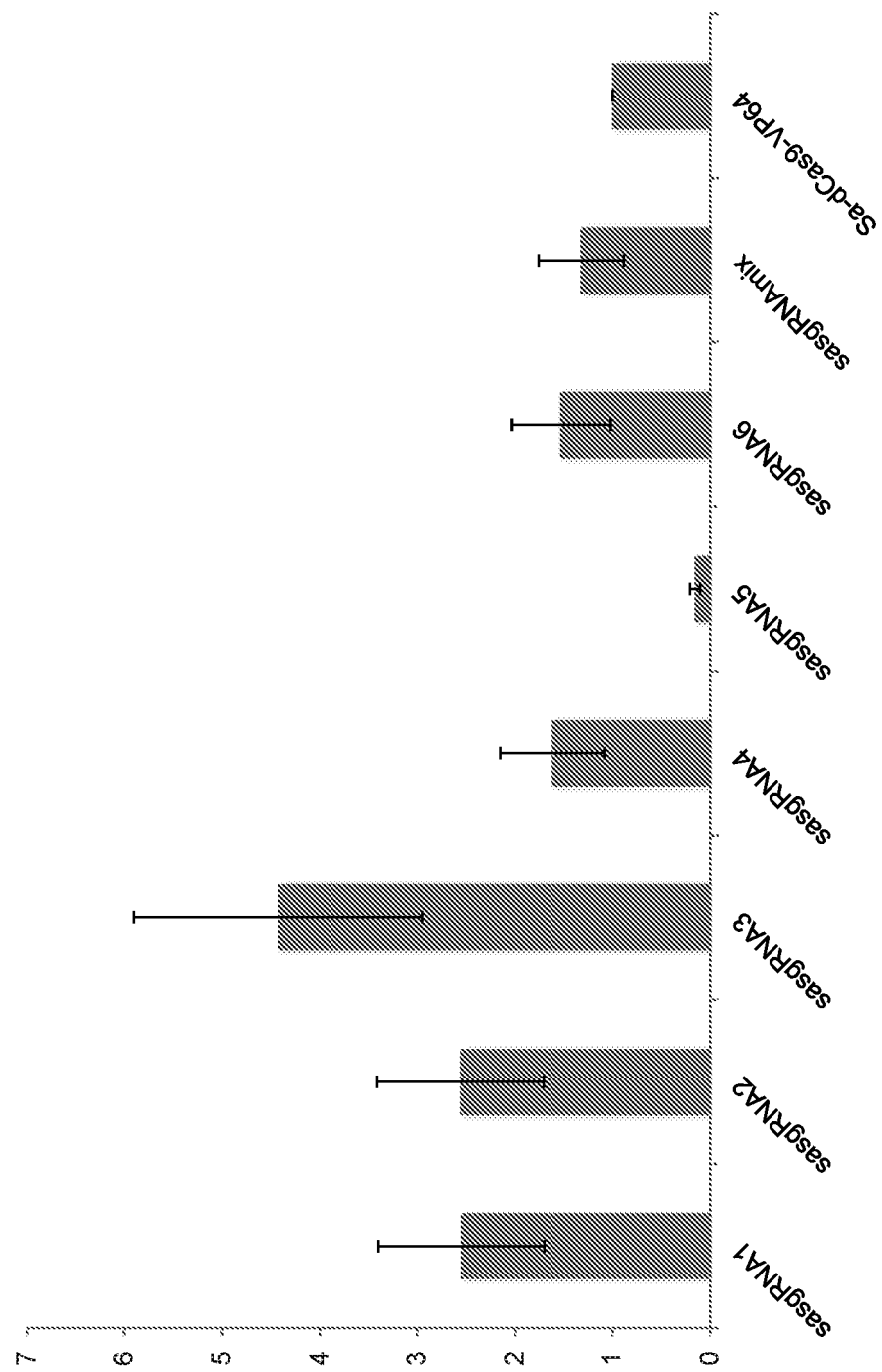

We first set out to optimize our CRISPRa conditions in vitro. SIM1 has a well characterized promoter (20) and distant hypothalamus enhancer (~270 kb from the transcription start site), Sim1 candidate enhancer 2 (SCE2 (21)), both of which were chosen as targets for CRISPRa (FIG. 1A). We designed sgRNAs for either the Sim1 promoter or enhancer (SCE2). Using these guides we tested if dCas9 fused to VP64 (dCas9-VP64), a transcriptional activator that carries four tandem copies of VP16 (a herpes simplex virus type 1 transcription factor) (22), can overexpress Sim1 in mouse neuroblastoma cells (Neuro-2a). This activator was chosen due to its lower activation levels compared to other known activators (23), as we wanted to obtain therapeutic Sim1 dosage levels in vivo that are similar to wild-type. Cells were transfected with dCas9-VP64 and the various guides and following 48 hours Sim1 mRNA levels were measured using quantitative PCR (qPCR). We identified one sgRNA for either promoter or SCE2 that was able to overexpress endogenous Sim1 by 13 and 4 fold respectively (FIG. 1B). Additionally, we identified four sgRNAs for the Sim1 promoter that were able to overexpress endogenous Sim1 by over 4-fold (FIG. 7A) and at least one sgRNA for SCE2 that was able to overexpress endogenous Sim1 by over 2-fold (FIG. 8A).

B. Transgenic CRISPRa Rescues Obesity

Figure 1C:
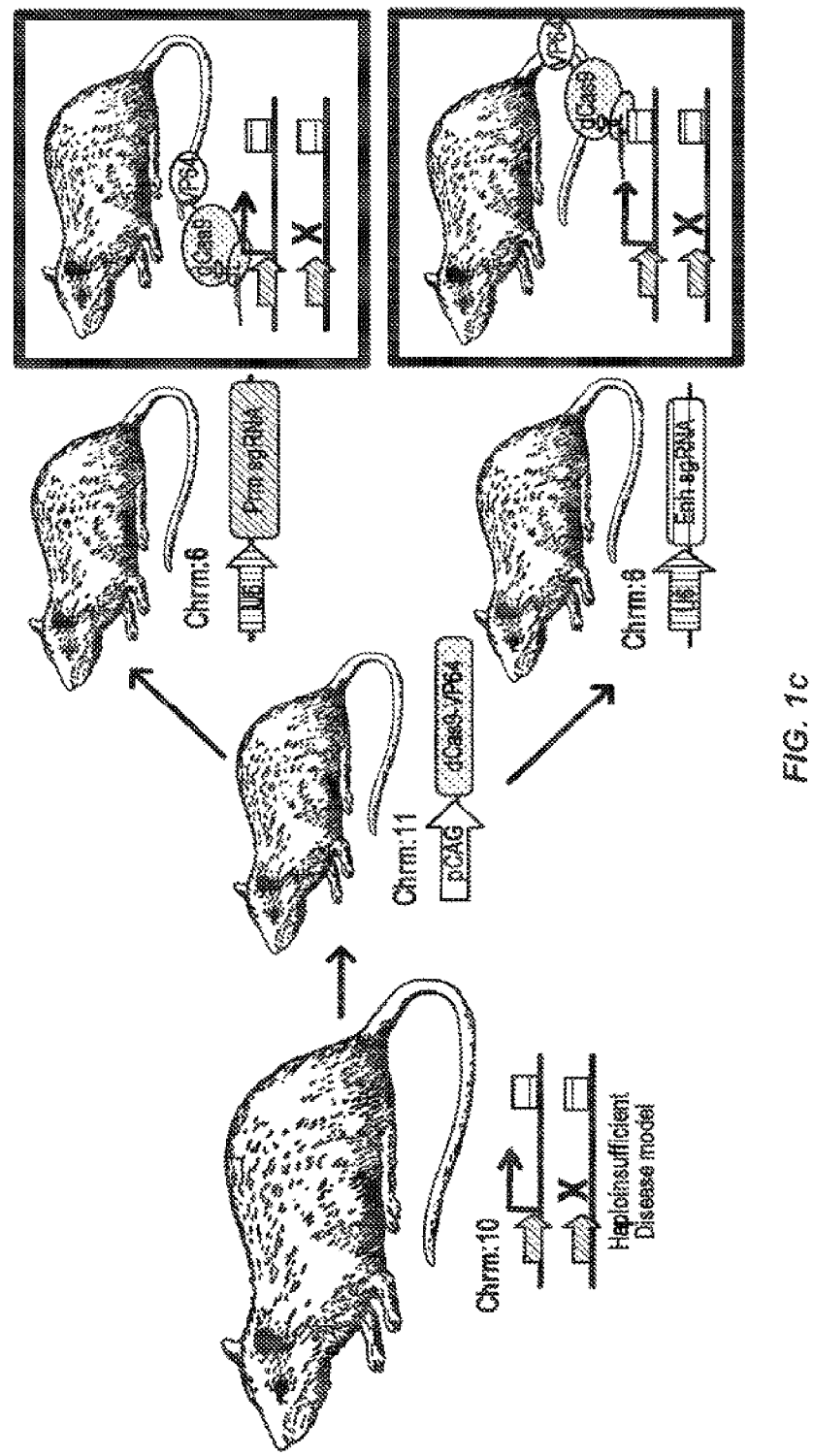
Figure 1D:
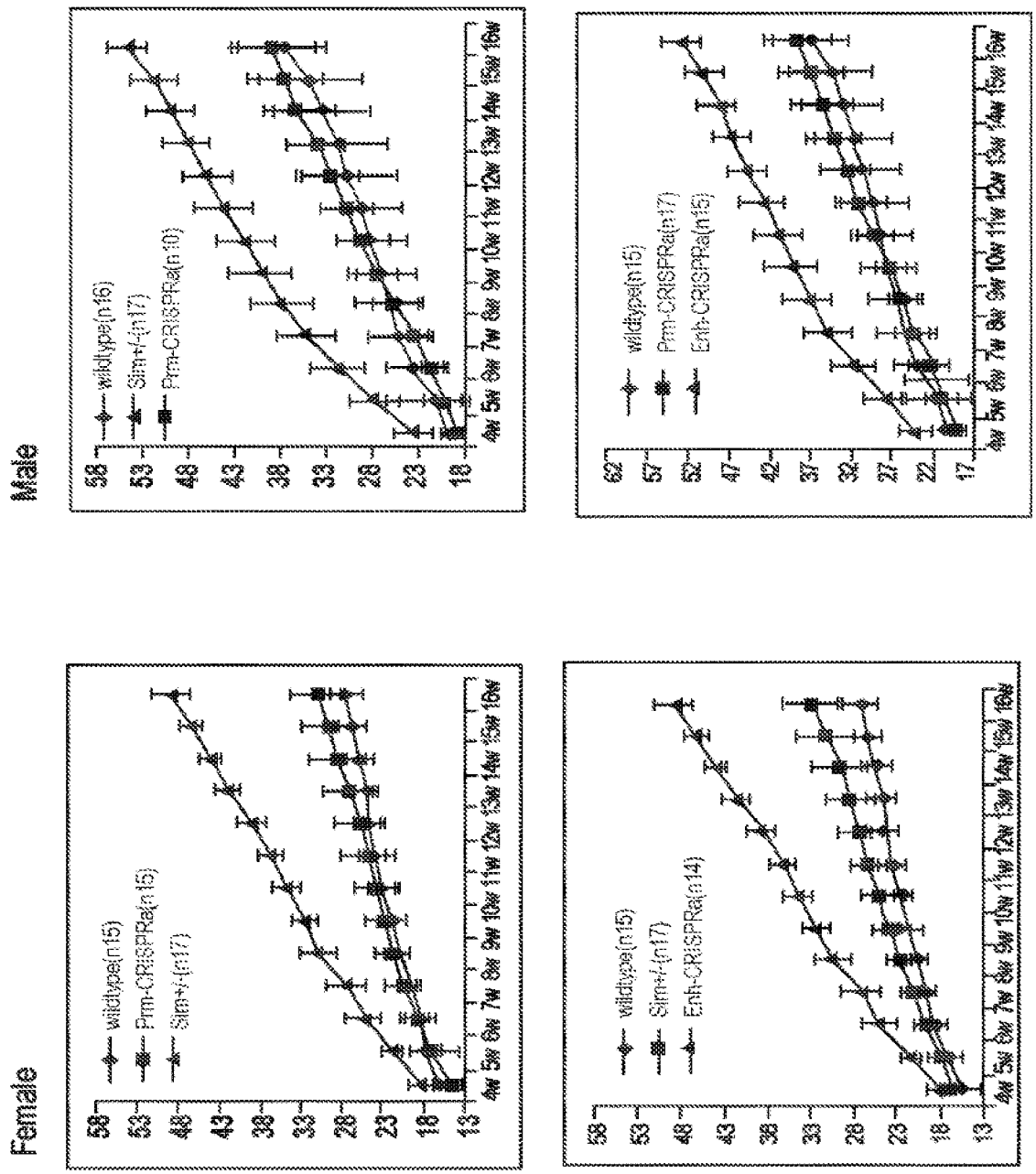
Figure 1E:
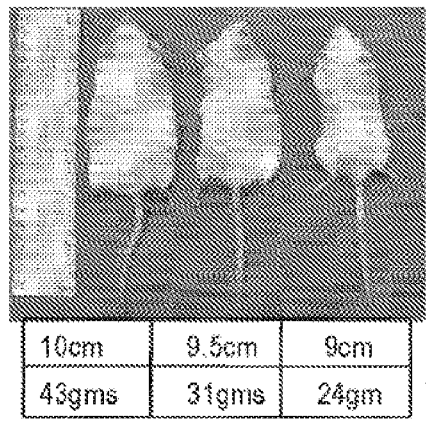
Figure 1F:
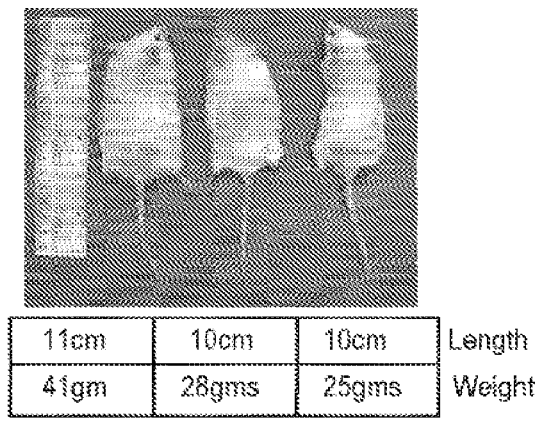

To test the ability of our CRISPRa system to activate Sim1 in vivo, we generated knockin mouse lines using TARGATT technology (24) that have dCas9-VP64 inserted into the mouse Hipp11 ($H11P^{CAG-dCas9-VP64}$) locus and either sgRNA, targeting the Sim1 promoter ($ROSA26^{Sim1Pr-sgRNA}$) or SCE2 ($ROSA26^{SCE2En-sgRNA}$), in the Rosa26 locus (FIG. 1C). We then crossed these mice to $Sim1^{+/-}$ mice that develop severe obesity (17). Mice having all three alleles ($Sim1^{+/-}$ X $H11P^{CAG-dCas9-VP64}$ and $ROSA26^{Sim1Pr-sgRNA}$ or $ROSA26^{SCE2En-sgRNA}$) were maintained using breeders chow (picodiet-5058) and weighed on a weekly basis until 16 weeks of age along with wild-type littermates and $Sim1^{+/-}$ X $H11P^{CAG-dCas9-VP64}$ mice and $Sim1^{+/-}$, both of which become severely obese (negative controls). Analysis of at least seven females and seven males per condition showed that $Sim1^{+/-}$ mice carrying both dCas9-VP64 and either Sim1 promoter or enhancer sgRNA have a significant reduction in body weight compared to $Sim1^{+/-}$ X $H11P^{CAG-dCas9-VP64}$ and $Sim1^{+/-}$ littermates (FIGS. 1D-F).

C. CRISPRa Corrects $Sim1^{+/-}$ Metabolic Profile

Figure 2A:
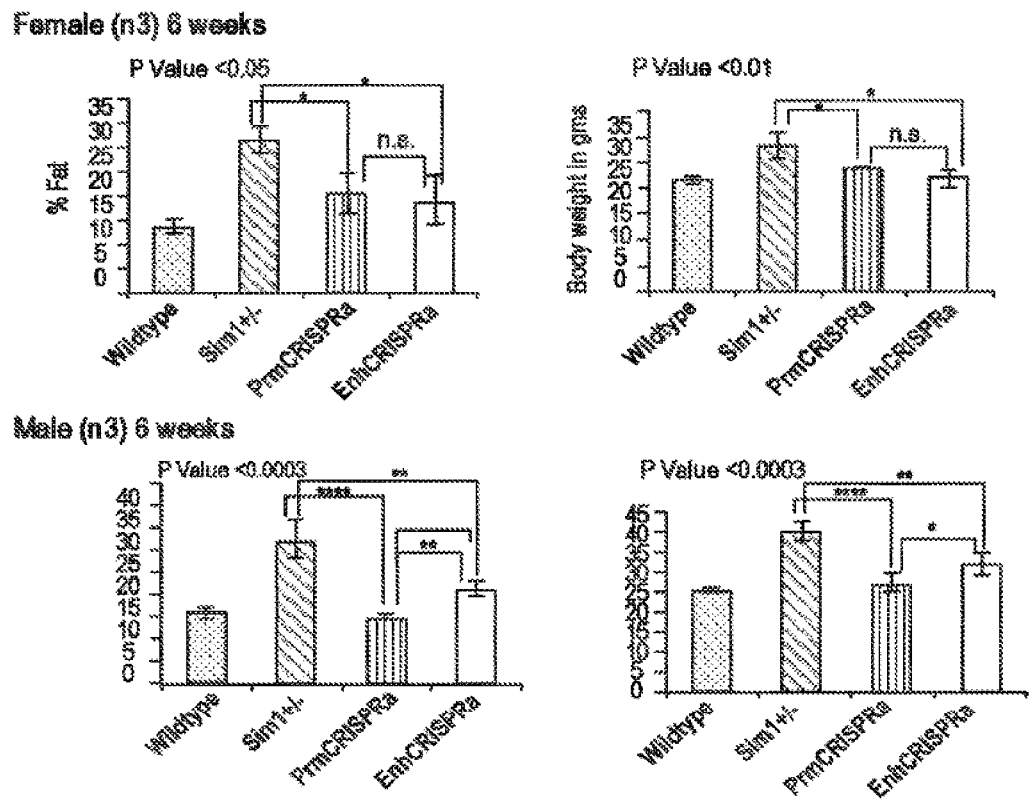
Figure 2B:
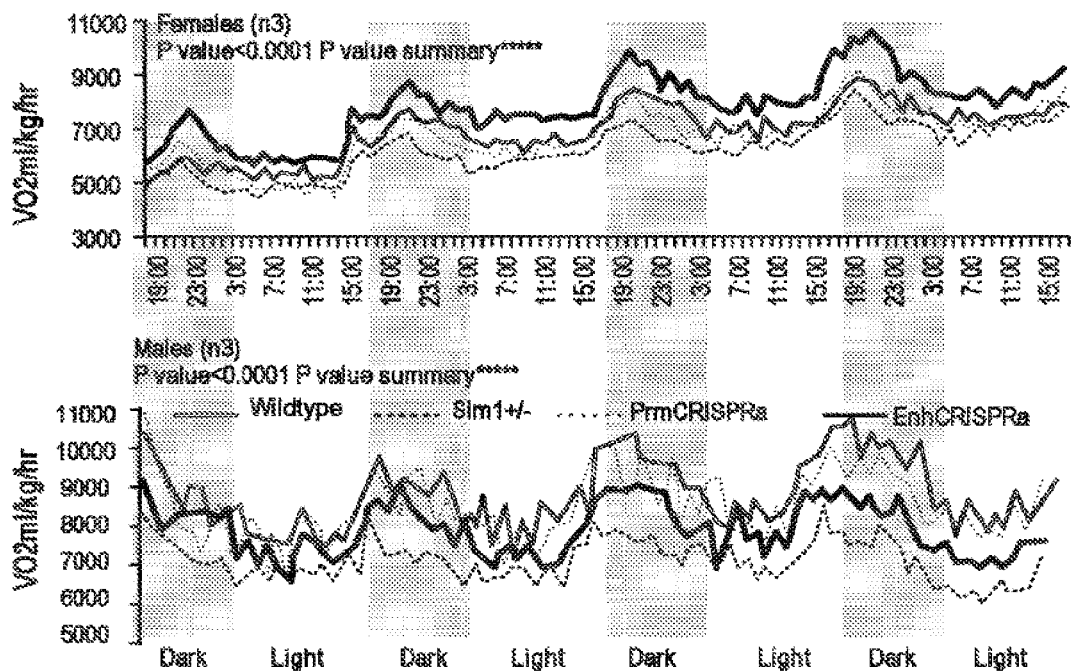

To relate body weight reduction with body composition and metabolic parameters, we next performed metabolic profiling for $Sim1^{+/-}$ X $H11P^{CAG-dCas9-VP64}$ X $ROSA26^{Sim1Pr-sgRNA}$ (Prm CRISPRa) $Sim1^{+/-}$ X $H11P^{CAG-dCas9-VP64}$ X $ROSA26^{SCE2En-sgRNA}$ (Enh-CRISPRa) and our other mouse lines. Three mice for each genotype were analyzed for body composition and metabolic profiling, right at the onset of the obesity phase, 6-8 weeks of age. Both Prm-CRISPRa and Enh-CRISPRa mice showed a significant reduction in body fat content compared to $Sim1^{+/-}$ in both females and males (FIG. 2A). Metabolic chamber analyses of other hallmarks of $Sim1^{+/-}$ obese mice such as oxygen consumption and food intake showed a shift towards wild-type metabolic parameters in the Prm-CRISPRa and Enh-CRISPRa mice (FIG. 2B-C). In addition, their respiratory exchange ratio (RER; VCO2/VO2), an indirect method of defining basic metabolic rate, also showed parameters similar to their wild-type littermates (FIG. 2D). However, we did not observe any significant differences for their physical activity in individual chambers. Combined, these results show that both Prm-CRISPRa and Enh-CRISPRa mice have less body fat and demonstrate an improvement in their metabolic parameters that contribute towards a reduction in their overall body weight.

D. Sim1 Activation is Tissue-Specific

Figure 3:
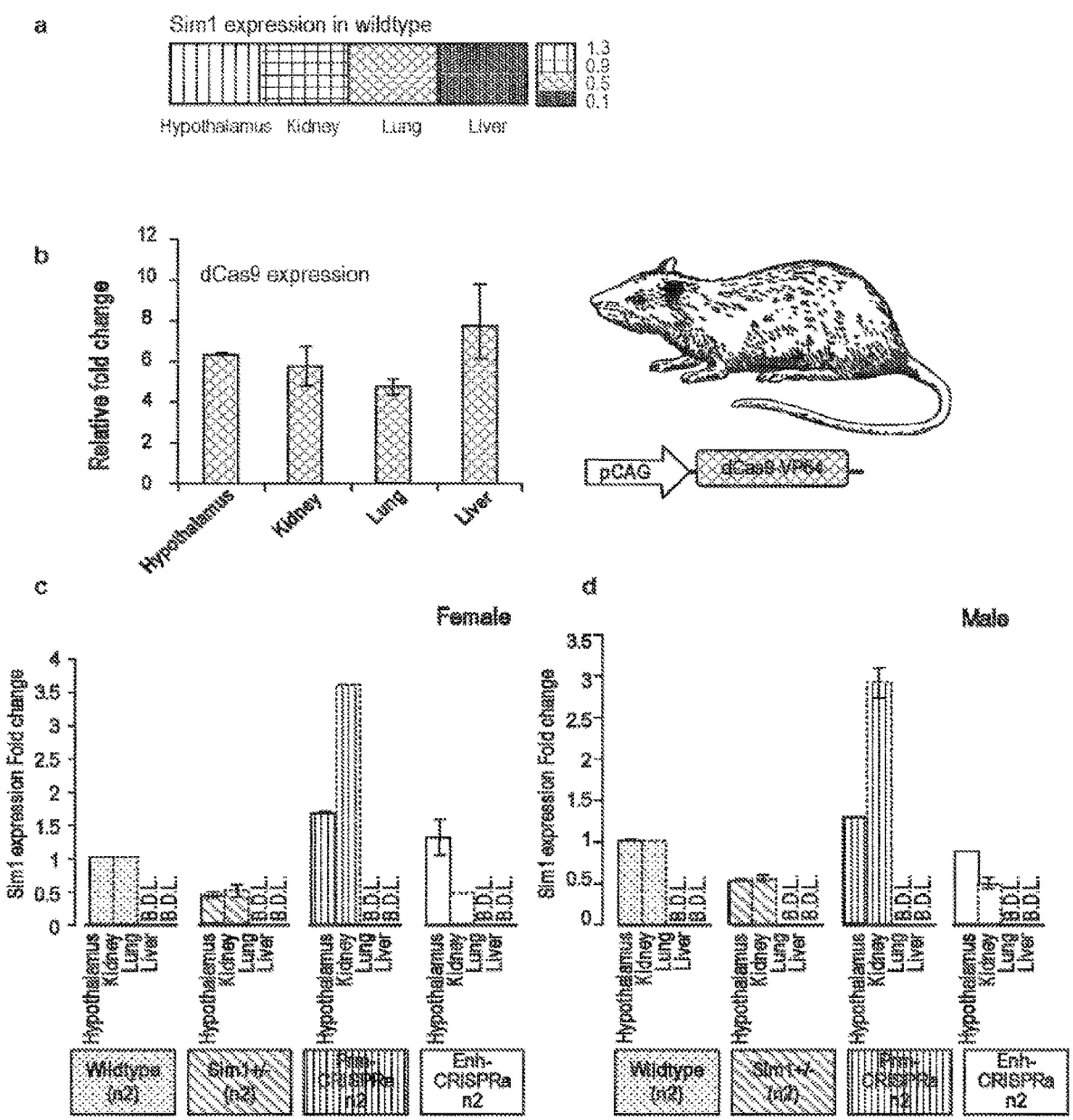
FIGS. 3A-D dCas9 and Sim1 mRNA expression levels in CRISPRa transgenic mice. A, Heatmap of Sim1 tissue expression. Red and grey filled squares signify tissues where Sim1 is expressed and not expressed, respectively as determined in our wild-type mice. B, dCas9 mRNA expression in the hypothalamus, kidney, lung and liver from 4 Sim1$^{+/-}$ X H11P$^{CAG\text{-}dCas9\text{-}VP64}$ mice. The mean values±s.d were determined based on mRNA fold-increase normalized to beta-actin (for hypothalamus) and Rpl38 (for kidney, lung, liver) using the ΔΔCT method. C-D, Sim1 mRNA expression in the hypothalamus, kidney, lung and liver for the following genotypes: wild-type littermates, Sim1$^{+/-}$, H11P$^{CAG\text{-}dCas9\text{-}VP64}$ X ROSA26$^{Sim1Pr\text{-}sgRNA}$ (Prm-CRISPRa) and H11P$^{CAG\text{-}dCas9\text{-}VP64}$ X ROSA26$^{SCE2En\text{-}sgRNA}$ (Enh-CRISPRa) from 2 females (C) and 2 male (D). The mean values±s.d were determined based on mRNA fold-increase compared to wild-type littermates and normalized to beta-actin or Rpl38 using the ΔΔCT method. B.D.L=below detected levels.

To test for Sim1 activation levels and tissue-specificity in our mice, we measured its mRNA expression levels in different tissues. We selected two tissues where Sim1 is known to be expressed, hypothalamus and kidney, and two tissues where it is not expressed, lung and liver (25) (FIG. 3A). We first measured dCas9 expression, and found it to be expressed in all four tissues, as expected, since we used a ubiquitous CMV enhancer chicken beta-Actin (CAG) promoter to drive its expression (FIG. 3B). In contrast, for Sim1, we observed significantly higher mRNA levels in the hypothalamus and kidney in Prm-CRISPRa mice and only in the hypothalamus of Enh-CRISPRa mice compared to $Sim1^{+/-}$ mice (FIG. 3C-D). Since we did not observe any significant differences between the obesity phenotype of Prm-CRISPRa and Enh-CRISPRa mice, we could speculate that the activation of Sim1 in the hypothalamus is sufficient to rescue the $Sim1^{+/-}$ obesity phenotype. Interestingly, in tissues where Sim1 is not expressed (i.e. liver and lung), we could not detect Sim1 expression in Prm-CRISPRa or Enh-CRISPRa mice despite observing Cas9 expression. These results imply that in the in vivo conditions of our study, dCas9-VP64 could only upregulate expression in tissues where the cis-regulatory elements of its target gene are active. This suggests that cis-regulatory elements could be used to determine the tissue-specificity of CRISPRa.

E. CRISPRa AAV Reduces $Sim1^{+/-}$ Weight Gain

Figure 4:
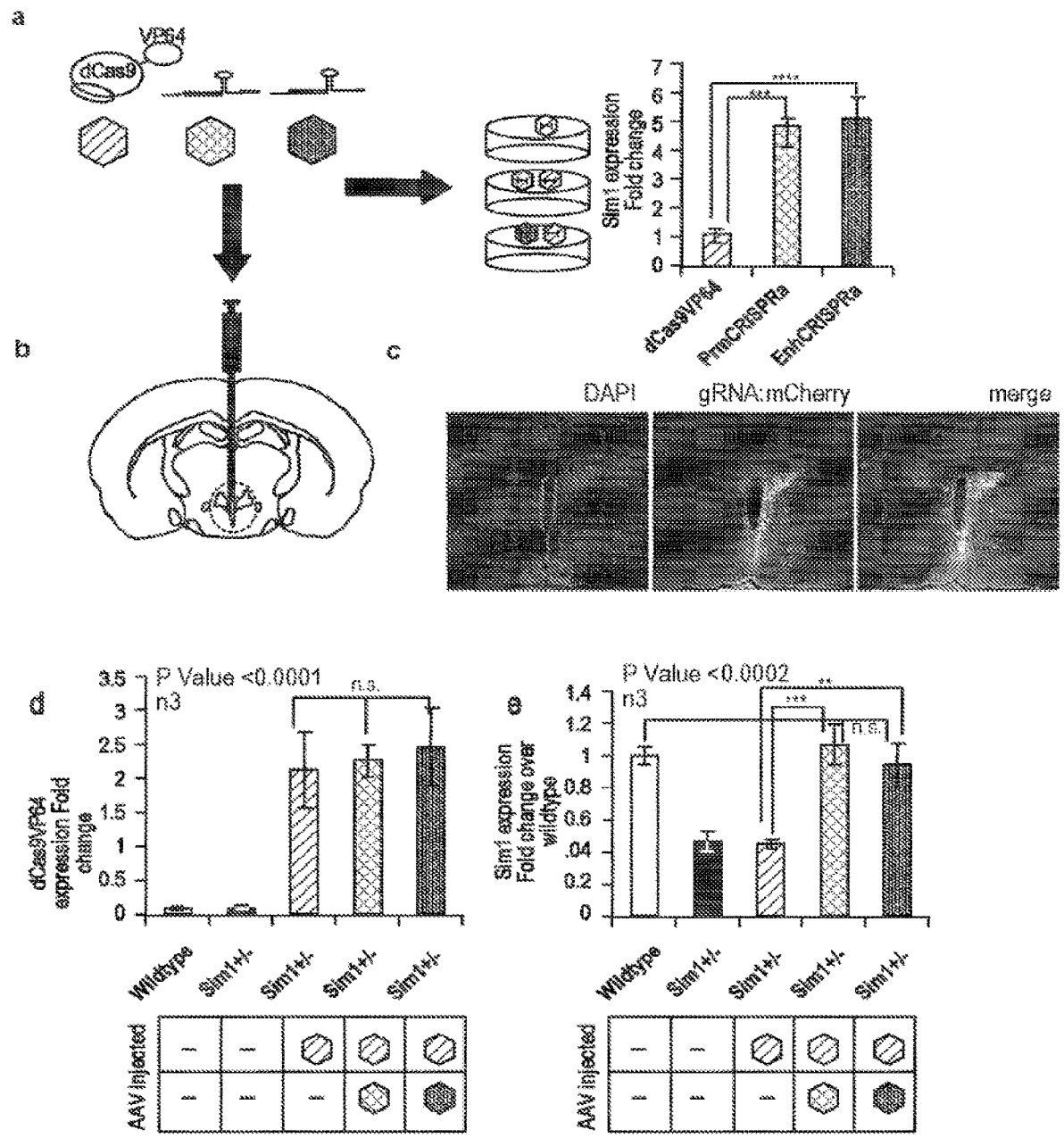
FIGS. 4A-E CRISPRa Sim1 overexpression in vitro and in vivo using AAV. A, AAV CRISPRa in Neuro-2A cells using virons containing: pCMV-dCas9-VP64 (dCas9-VP64), pCMV-dCas9-VP64 along with pSim1Pr-mCherry (PrmCRIPSRa) and pCMV-dCas9-VP64 along with pSCE2En-mCherry (EnhCRISPRa). Results are expressed as mRNA fold-increase normalized to beta-actin using the ΔΔCT method. The mean values±s.d. were obtained from 3 independent experiments. ***=p-value<0.0005 (ANOVA, Tukey test). B, Schema showing the PVN injected region. C, Immunohistochemistry of pSim1Pr-mCherry injected hypothalamus from 20 week old mice showing mCherry expression in the PVN. D-E, Cas9 (d) and Sim1 (e) mRNA expression from pCMV-dCas9-VP64 (dCas9-VP64), pCMV-dCas9-VP64+pSim1Pr-mCherry (PrmCRIPSRa, n=3) and pCMV-dCas9-VP64+pSCE2En-mCherry (EnhCRISPRa, n=4) from injected mice. The mean values±s.d were determined based on mRNA fold-increase compared to Sim1$^{+/-}$ mice and normalized to beta-actin using the ΔΔCT method.

To further translate this approach to a therapeutic strategy for haploinsufficiency, we took advantage of AAV to deliver CRISPRa into the hypothalamus of $Sim1^{+/-}$ mice. We generated the following three AAV vectors: 1) dCas9-VP64 driven by a cytomegalovirus (CMV) promoter (pCMV-dCas9-VP64); 2) Sim1 promoter sgRNA along with mCherry (pU6-Sim1Pr-CMV-mCherry); 3) SCE2 sgRNA along with mCherry (pU6-SCE2-CMV-mCherry). For the pCMV-dCas9-VP64 vector, due to the size of dCas9-VP64 expression cassette, we obtained a 5.4 kb insert. While this insert size is above the 4.7 kb limit, it was shown that going above 5 kb reduces transgene expression levels but still could be used for delivery (26). These vectors were packaged individually into AAV-DJ serotype, which is a chimera of type 2, 8 and 9 that was shown to achieve high expression levels in multiple tissues (27) (FIG. 4A). We did observe lower but usable viral titers for pCMV-dCas9-VP64 AAV (see methods). We first tested if of our AAV CRISPRa vectors could overexpress Sim1 in vitro using Neuro-2a cells. We observed a 4 and 5 fold upregulation of Sim1 mRNA expression when targeting the promoter or enhancer respectively (FIG. 4A). Using additional sgRNAs (SEQ ID NOS:38, 40 or 42), we observed that our AAV CRISPRa vectors could overexpress Sim1 in vitro using Neuro-2a cells. We observed a 2-fold to 6-fold upregulation of Sim1 mRNA expression when targeting the promoter (FIG. 7B) and a 2-fold to 4.5-fold upregulation of Sim1 mRNA expression when targeting the enhancer (SCE2) (FIG. 8B).

Figure 5:
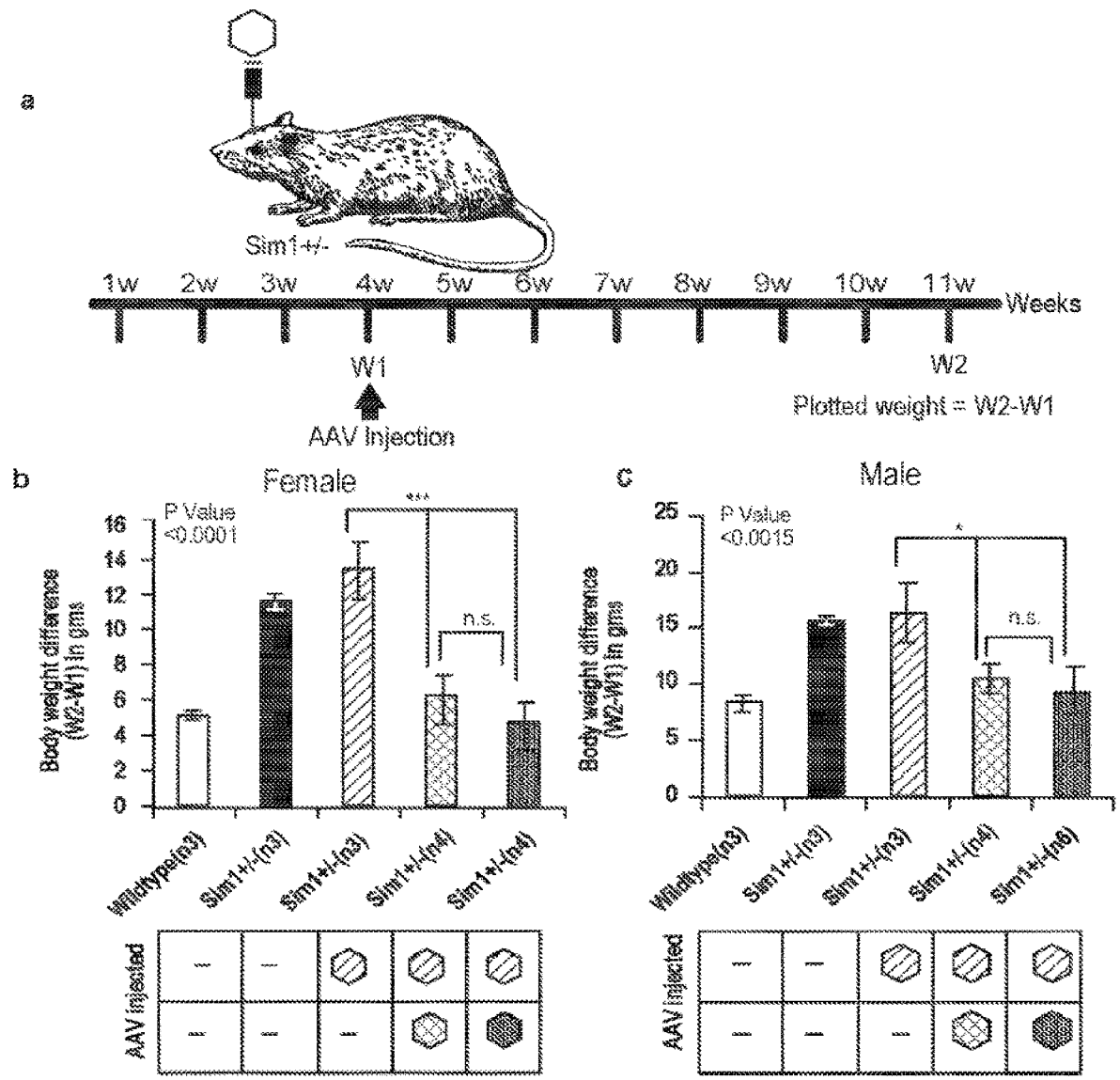
FIGS. 5A-C CRISPRa-AAV injection in PVN reduces weight gain in Sim1+/− mice. A, Timeline for weight measurement post CRISPRa-AAV injection in PVN. B-C, Weight gain determined over a 7 week period from Sim1$^{+/-}$ mice injected with pCMV-dCas9-VP64 (dCas9-VP64), pCMV-dCas9-VP64+pSim1Pr-mCherry (Prm-CRIPSRa) pCMV-dCas9-VP64+pSCE2En-mCherry (Enh-CRISPRa) compared to un-injected wild-type littermates and Sim1$^{+/-}$ mice. Mean values±s.d are shown from 3 females (B) and 3 males (C). *=p-value<0.001 ***=p-value<0.0005 n.s=non-significant; (ANOVA, Tukey test).

Next, we performed stereotactic injections to deliver virus carrying pCMV-dCas9-VP64 and either pU6-Sim1Pr-CMV-mCherry (Prm-CRISPRa-AAV) or pU6-SCE2-CMV-mCherry (Enh-CRISPRa-AAV) into the PVN of the hypothalamus of $Sim1^{+/-}$ mice at four weeks of age, before they start developing obesity. As negative controls, we also injected $Sim1^{+/-}$ mice with pCMV-dCas9-VP64 virus only. We tested for the expression of our sgRNA-CMV-mCherry cassette by performing immunostaining on the hypothalamus of injected mice and found it to be expressed in the PVN (FIG. 4B-C). To test whether Sim1 expression levels were increased by delivering CRISPRa-AAV to the hypothalamus of $Sim1^{+/-}$ mice, we measured mRNA expression levels for both dCas9 and Sim1 from 11 week old AAV injected mice. dCas9 was found to be expressed in the hypothalamus of all our pCMV-dCas9-VP64 AAV injected mice (FIG. 4D). Sim1 upregulation was observed in both Prm-CRISPRa-AAV and Enh-CRISPRa-AAV injected hypothalami, but not in mice injected with only pCMV-dCas9-VP64-AAV (FIG. 4E). The injected mice were measured for body weight up to 11 weeks of age (FIG. 5A). We observed a significant weight reduction in the Prm-CRISPRa-AAV or Enh-CRISPRa-AAV injected mice compared to the Sim1$^{+/-}$ or pCMV-dCas9-VP64-AAV injected Sim1$^{+/-}$ mice (FIG. 5B-C). These results show that CRISPRa-AAV mediated upregulation could be used as a viable gene therapy tool to treat haploinsufficiency.

F. Upregulation of Mc4r In Vitro

Over 70% of obesity that has genetic basis is caused by defects in the leptin pathway. MC4R is part of the leptin pathway and mutations in it are the most commonly found mutations in obese individuals (~5% of the 1 percentile obese population). Since it is a downstream factor, upregulation of MC4R and SIM1 could possibly rescue obesity caused by mutations in these other leptin pathway genes. Here, we have shown that we can upregulate MC4R by targeting its promoter and have also shown that upregulation of SIM1 can increase MC4R expression. We were also able to rescue the obesity phenotype in Mc4r heterozygos mice (performed essentially as set forth in the upregulation of Sim1 in vitro, discussed above). As such, MC4R upregulation could be used as therapy for obesity.

We designed sgRNAs for the Mc4r promoter (See, SEQ ID NOS:50-54). Using these guides we tested if dCas9 fused to VP64 (dCas9-VP64) can overexpress Mc4r in mouse neuroblastoma cells (Neuro-2a). Cells were transfected with dCas9-VP64 and the various guides and following 48 hours Mc4r mRNA levels were measured using quantitative PCR (qPCR). We identified one sgRNA for the Mc4r promoter that was able to overexpress endogenous Mc4r by 7-fold (FIG. 9A).

G. CRISPRa AAV Induces Upregulation of Mc4r

We next tested if of our AAV CRISPRa vectors (prepared essentially as described under Sim1 CRISPRa AAV, above) containing sgRNAs, SEQ ID NOS:51, 52 or 54, could overexpress Mc4r in vitro using Neuro-2a cells. We observed between a 3.4-fold and 6.6-fold upregulation of Mc4r mRNA expression when targeting the promoter (FIG. 9B).

H. Upregulation of SCN2A In Vitro

Mutations in SCN2A are the most commonly found mutations in individuals with autism spectrum disorder (ASD) and epilepsy. The majority of mutations are loss of function leading to ASD due to haploinsufficiency. Here, we have shown that we can upregulate SCN2A by targeting its promoter. As such, SCN2A upregulation could be used as therapy for ASD and epilepsy.

Figure 12A:
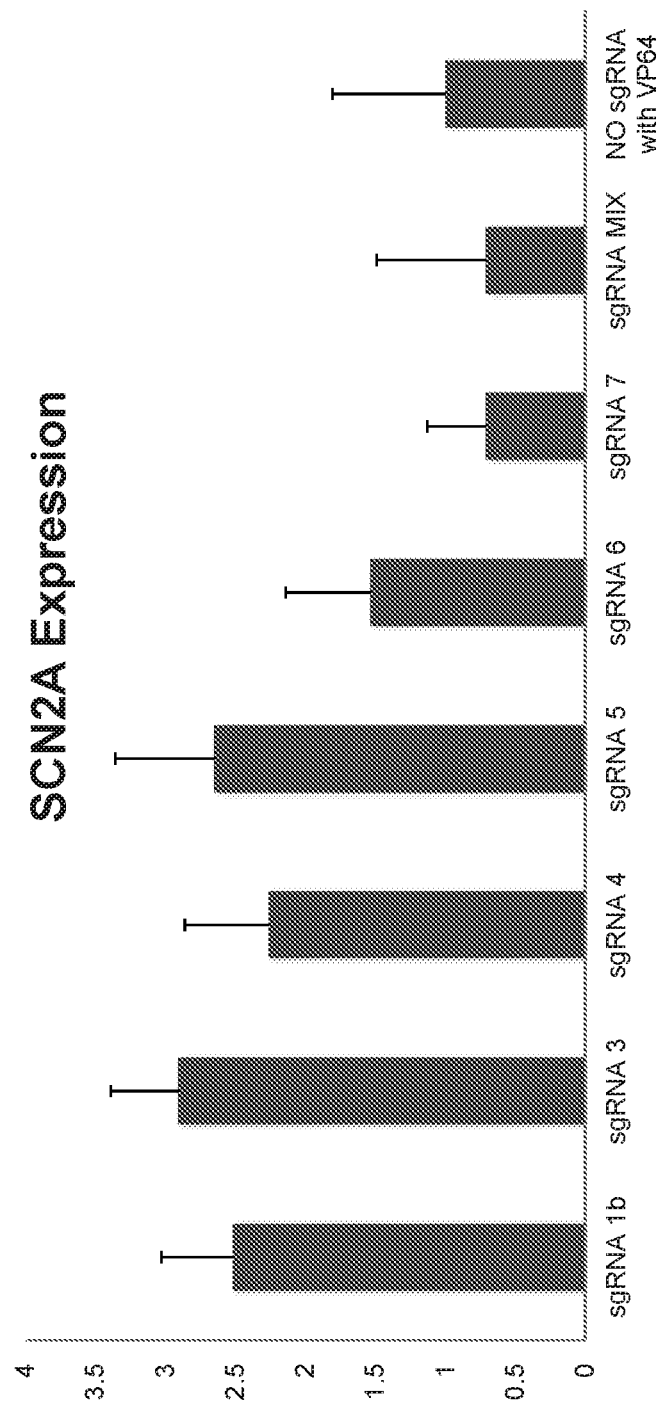

We designed sgRNAs for the Scn2a promoter (See, SEQ ID NOS:85-91). Using these guides we tested if dCas9 fused to VP64 (dCas9-VP64) can overexpress Scn2a in mouse neuroblastoma cells (Neuro-2a). Cells were transfected with dCas9-VP64 and the various guides and following 48 hours Scn2a mRNA levels were measured using quantitative PCR (qPCR). We identified four sgRNAs for the Scn2a promoter that were able to overexpress endogenous Scn2a by over 2-fold (FIG. 12A).

I. CRISPRa AAV Induces Upregulation of Scn2A

We next tested if of our AAV CRISPRa vectors (prepared essentially as described under Sim1 CRISPRa AAV, above) containing sgRNAs, SEQ ID NOS:92-94, could overexpress Scn2a in vitro using Neuro-2a cells. Two different multiplicity of infection (MOI) were used: 5,000 and 1,750 viral genome (vg/ml). We observed a slight upregulation of Scn2a mRNA expression when targeting the promoter with a MOI of 5,000 viral genomes per ml (FIG. 12B).

J. Upregulation of SETD5 In Vitro

Mutations in SETD5 lead to mental retardation-23 (OMIM #615761) which include intellectual disability and dysmorphic features. Here, we have shown that we can upregulate SETD5 by targeting its promoter. As such, SETD5 upregulation could be used as therapy for intellectual disability.

We designed sgRNAs for the Setd5 promoter (See, SEQ ID NOS:75-84). Using these guides we tested if dCas9 fused to VP64 (dCas9-VP64) can overexpress Setd5 in mouse neuroblastoma cells (Neuro-2a). Cells were transfected with dCas9-VP64 and the various guides and following 48 hours Setd5 mRNA levels were measured using quantitative PCR (qPCR). We identified two sgRNAs for the Setd5 promoter that were able to overexpress endogenous Setd5 by over 1.5-fold (FIG. 11B).

Next, we designed sgRNAs for the SETD5 promoter in humans (See, SEQ ID NOS:65-74). Using these guides we tested if dCas9 fused to VP64 (dCas9-VP64) can overexpress SETD5 in human HEK293T cells. Cells were transfected with dCas9-VP64 and the various guides and following 48 hours SETD5 mRNA levels were measured using quantitative PCR (qPCR). We identified at least one sgRNA for the SETD5 promoter that was able to overexpress endogenous SETD5 by over 2.5-fold (FIG. 11A).

K. Upregulation of PKD1 In Vitro

Mutations in PKD1 lead to autosomal dominant polycystic kidney disease (ADPKD; OMIM #173900) which is the most frequent hereditary kidney disorder affecting 1 to 400-1000 individuals. 85% of ADPKD is caused by mutations in PKD1, the majority of which are loss-of-function. PKD1 is 13 kb long and as such cannot be packaged in standard gene therapy vectors. Using the CRISPRa technology disclosed herein, we have shown that we can upregulate PKD1 by targeting its promoter. As such, PKD1 upregulation could be used as therapy for autosomal dominant polycystic kidney disease.

We designed sgRNAs for the PKD1 promoter in humans (See, SEQ ID NOS:55-64). Using these guides we tested if dCas9 fused to VP64 (dCas9-VP64) can overexpress PKD1 in human HEK293T cells. Cells were transfected with dCas9-VP64 and the various guides and following 48 hours PKD1 mRNA levels were measured using quantitative PCR (qPCR). We identified at least three sgRNAs for the PKD1 promoter that were able to overexpress endogenous PKD1 by over 2-fold (FIG. 10).

L. Upregulation of PAX6 In Vitro

Loss-of-function mutations in PAX6 lead to Aniridia 1 (OMIM #106210) due to haploinsufficiency. Here, we have shown that we can upregulate PAX6 by targeting its promoter. As such, PAX6 upregulation could be used as therapy for aniridia 1.

We designed one sgRNA for the PAX6 promoter in humans (SEQ ID NO:95). Using this guide we tested if dCas9 (*S. pyogenes*) fused to VP64 (dCas9-VP64) can overexpress PAX6 in Human H1-ESC cells differentiated into neurons. Cells were infected with lentivirus carrying the guide, and following 48 hours PAX6 mRNA levels were measured using quantitative PCR (qPCR). Our exemplary sgRNA for the PAX6 promoter was able to overexpress endogenous PAX6 by over 6-fold (FIG. 13). FIG. 13 also demonstrates that additional neuronal markers (e.g., NES) were also capable of neural induction of H1-ESCs.

III. Discussion

CRISPR-based gene editing is a promising therapeutic technology to correct genetic mutations. However, it currently is not a feasible technology for haploinsufficiency, limited by low non-homologous end joining (NHEJ) efficiencies (i.e. editing only a small portion of cells) and the need to custom tailor specific guides and donor sequences for each individual mutation. In addition, it is not a feasible therapeutic strategy for micro-deletions, over 200 of which are known to cause human disease (28), primarily due to haploinsufficiency. In this study, we used a novel approach to tackle these hurdles and show how a haploinsufficient disease could be corrected by increasing the transcriptional output from the existing functional allele via CRISPRa.

Figure 6:
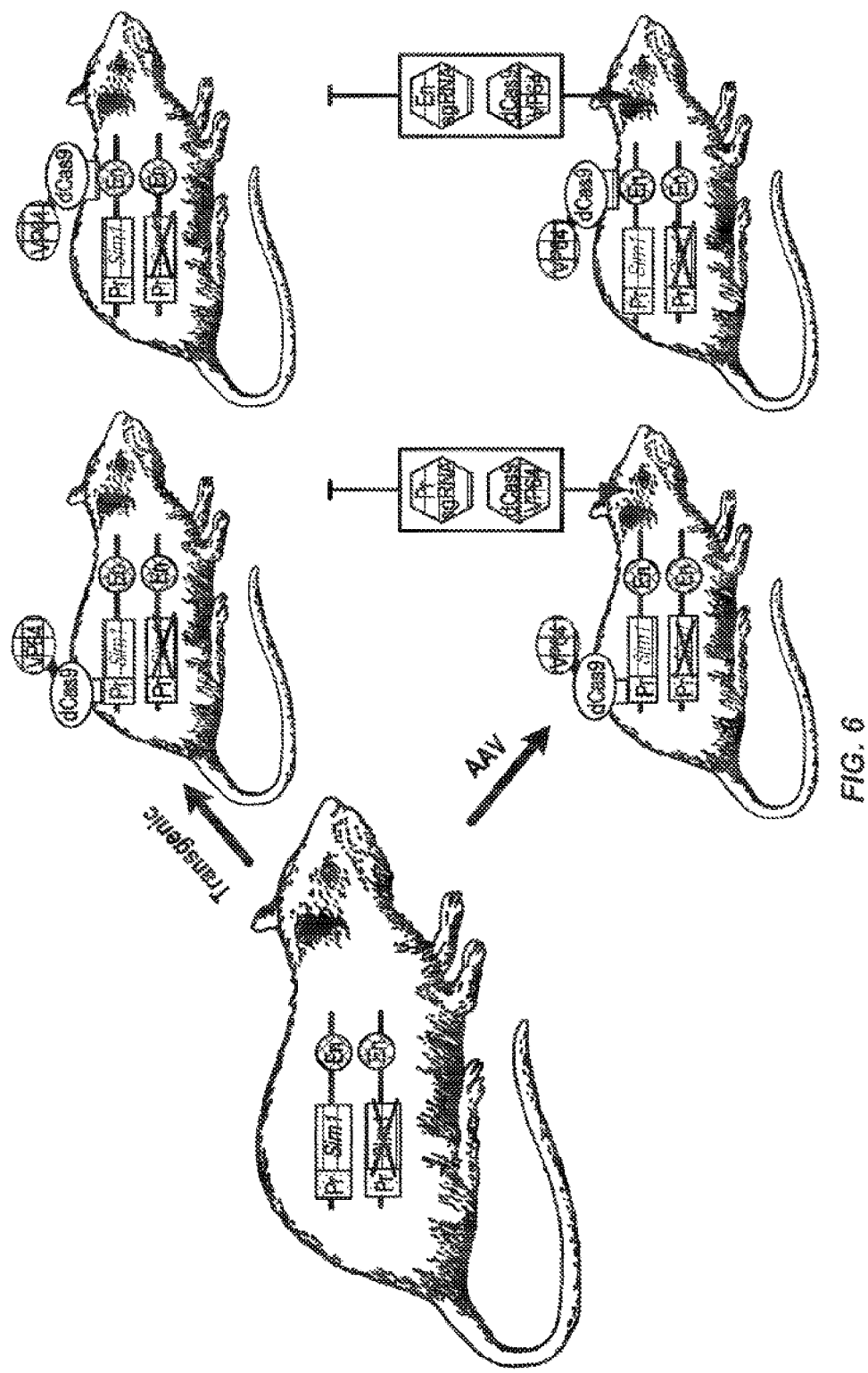
FIG. 6 Schema of CRISPRa haploinsufficiency rescue experiments. The obesity phenotype in Sim1$^{+/-}$ mice was rescued via CRISPRa by targeting either the Sim1 promoter or enhancer using both a transgenic and postnatal AAV approach.

Using CRISPRa targeting for either the promoter or enhancer of Sim1, we were able to rescue the obesity phenotype in a tissue-specific manner in mice that are haploinsufficient for Sim1 (FIG. 6). As this therapeutic approach takes advantage of the existing functional allele, it has several benefits: 1) It overcomes the need to custom tailor CRISPR gene editing approaches for different haploinssufficient causing mutations in the same gene. 2) This approach could potentially be used to target two or more genes. As such, it could pose as a potential therapeutic strategy for micro-deletions related-diseases that are caused by the heterozygous LoF of more than one gene. 3) CRISPRa-AAV could be used to rescue haploinsufficient diseases caused by genes that are longer than its optimal packaging capability. 4) CRISPR-based therapies can take advantage of cis-regulatory elements to guide tissue-specificity. The availability of large-scale tissue-specific maps of gene regulatory elements could provide ample candidates to use for this therapeutic approach. We observed distinct difference in tissue specific activation of Sim1 in our study, which can be attributed to chromatin accessibility of the locus in various tissues. Previous large-scale Cas9 and dCas9 cell culture screens have shown a targeting preference for regions with low nucleosome occupancy (29). Active promoters or enhancers would have lower nucleosome occupancy, thus being more amenable to dCas9 targeting.

Our dCas9-VP64 mouse and AAV vectors can be a useful tool for targeted gene activation in vivo by delivering sgRNA/s targeted to a specific gene/s in certain tissues/cell types. This approach could be used to assess gene-gene interactions or for the identification of the target gene/s of a specific regulatory element in vivo by measuring its expression level following activation. Another potential area of study could be neuronal circuit manipulation. Discrepancies between acute and chronic neuronal circuit manipulations have been observed (30) which can be addressed by our AAV-CRISPRa and Transgenic-CRISPRa strategies respectively.

Haploinsufficiency of Sim1 causes obesity both in mice (17) and humans (13). Whether this is caused by the reduction in PVN size during development that is observed in Sim1$^{+/-}$ mice (17) or by disturbed energy homeostasis during adulthood was an area of major research. The obesity phenotype observed in the postnatal conditional knockout of hypothalamic Sim1 (18), reinforced the hypothesis that Sim1 does indeed have a role in energy homeostasis later during adulthood. Our ability to rescue the obesity phenotype via CRISPRa AAV injections into the hypothalamus of 4 week old mice, further corroborates this role. Abrogation of melanocortin 4 receptor (Mc4r) signaling is the hallmark of most polygenic and monogeneic obesity phenotypes. Conditional postnatal deficiency of Sim1 leads to reduced levels of Mc4r signaling. As Sim1 was shown to be an integral downstream component of the leptin-Mc4r pathway (18), Sim1 CRISPRa targeting could provide a potential therapy for conditions that disrupt the leptin signaling pathway.

Despite technological advances in CRISPR-based therapeutic intervention, our understanding of the long-term side effects of CRISPR expression and its off-targeting effects in-vivo still remains largely unknown, which also holds true for our current study. Anti-CRISPR genes (31) or conditional activation or silencing of our CRISPRa system could be able to address these concerns in future. Furthermore, there is also a need to develop CRISPRa/i tools to modulate gene dosage, so as to be able to optimize transcriptional output for certain diseases where higher or lower activation levels might be needed. In this study, we used VP64 as our activator, due to its known weak activation capacity (23) which fit with our need to obtain levels of gene expression that are similar to having two normal alleles. CRISPRa based gene activation is dependent upon the nature of the fused activator (23), sgRNA target (29) and may require optimization of the CRISPR system and delivery method.

As demonstrated in this study, CRISPRa can be used to activate genes not only by targeting their promoters, but by also targeting distal cis-regulatory elements such as enhancers. Previous studies have shown that these elements can be viable therapeutic targets. For example, by targeting a globin enhancer with zinc finger nucleases fused to a chromatin looping factor, the LIM domain binding 1 (LDB1) gene, activation of fetal hemoglobin was achieved in vitro, providing a potential therapy for sickle cell disease (37). In another study, re-activation of fetal hemoglobin was achieved by deactivating the enhancer of its repressor B-cell CLL/lymphoma 11A (BCL11A) using CRISPR gene editing (38). Our study provides a novel approach that also takes advantage of cis-regulatory elements for therapeutic purposes. There are numerous diseases that are caused by lower gene dosage that could potentially be treated with CRISPRa therapy. In addition, several human diseases could potentially be rescued by the activation of another gene with a similar function. These could include for example Utrophin for Duchenne Muscular Dystrophy (39), survival of motor neuron 2 (SMA2) for Spinal Muscular Atrophy (SMA; (40)) or the aforementioned fetal globin for sickle cell disease. Further development of this technology could provide a viable therapy for patients inflicted with these diseases.

III. Materials and Methods

Plasmids

The pMSCV-LTR-dCas9-VP64-BFP vector, encoding a mammalian codon-optimized *Streptococcus pyogenes* dCas9 fused to two C-terminal SV40 NLSs and tagBFP along with a VP64 domain and the U6-sgRNA-CMV-mCherry-T2A-Puro plasmids were used for cell line transfections (both kind gifts from Dr. Stanley Qi). sgRNAs were cloned using the In-Fusion HD-cloning kit (Clontech) following the manufacturer's protocol into the BstXI and Aho sites. Mouse knockin vectors were generated by cloning dCas9-VP64 and U6-sgRNA-CMV-mCherry expression cassettes from the aforementioned vectors into the TAR-GATT (CAG+Poly A) plasmid (Applied StemCell). pcDNA-dCas9-VP64 (Addgene 47107), and U6-sgRNA-CMV-mCherry-WPRE-pA were cloned replacing the Ef1a-FAS-hChR2(H134R)-mCherry-WPRE-pA with that of our U6-sgRNA-CMV-mCherry-WPREpA into the backbone of pAAV-Ef1a-FAS-hChR2(H134R)-mCherry-WPRE-pA (Addgene 37090).

AAV Production

AAV DJ serotype particles were produced using the Stanford Neuroscience viral vector core. The packaging load for pCMV-dCas9-VP64 was 5.4 kb and for pU6-Sim1Pr-CMV-mCherry and pU6-SCE2-CMV-mCherry 2.5 kb. Genomic titers were ascertained by WPRE and ITR probes to be $1.40E1^0$ viral genome (vg)/ml for pCMV-dCas9-VP64 and around $3.30E^{13}$ vg/ml for pU6-Sim1Pr-CMV-mCherry and $2.20\ E1^3$ vg/ml for pU6-SCE2-CMV-mCherry.

Cell Culture

Neuroblastoma 2a cells (Neuro-2a; ATCC® CCL-131) were grown following ATCC guidelines. Plasmids were transfected into Neuro-2a cells using X-tremeGENE HP DNA transfection reagent (Roche) following the manufacturer's protocol. AAV particles were infected into Neuro2a cells at different MOIs. Neuro2a cells were harvested 48 hours post transfection and 5 days post infection to isolate RNA for qRT-PCR analysis.

Human HEK293T cells were grown following ATCC guidelines. Plasmids were transfected into these cells using X-tremeGENE HP DNA transfection reagent (Roche) following the manufacturer's protocol.

Quantitative Reverse-Transcription PCR

RNA was isolated from cells or tissues using RNeasy Mini Kit (Qiagen) following the manufacturer's protocol. For mice, animals were euthanized and tissues were harvested directly into the RNA lysis buffer of the RNeasy Mini Kit. The hypothalamus was dissected using a mouse Brain Matrix and slicers from Zivic Instruments. cDNA was prepared using SuperScript III First-Strand Synthesis System (Invitrogen) using the manufacturer's protocol along with DNaseI digestion. qPCR was performed using SsoFast EvaGreen Supermix (Biorad). The results were expressed as fold-increase mRNA expression of the gene of interest normalized to either beta-actin, Rpl38 or Elf3 expression by the $\Delta\Delta$CT method followed by ANOVA and Tukey test for statistical analysis. Reported values are the mean and standard error of the mean from three independent experiments performed on different days (N=3) with technical duplicates that were averaged for each experiment.

Mice $Sim1^{+/-}$ mice (17) on a mixed genetic background were obtained as a kind gift from Dr. Jacques Michaud lab. In these mice, a 1 kb fragment containing 750 bp of the 5' region, the initiation codon, and the sequence coding for the basic domain (the first 17 amino acids) was replaced by a Pgk-neo cassette, that was used for genotyping using KAPA mouse genotyping kit (KAPA Biosystems). To generate dCas9-VP64 and sgRNA mice we used TARGATT technology (24). DNA for injection was prepared and purified as mini-circles using the TARGATT Transgenic Kit, V6 (Applied StemCell). The injection mix contained 3 ng/µL DNA and 48 ng/L of in vitro transcribed φC31o mRNA in microinjection TE buffer (0.1 mM EDTA, 10 mM Tris, pH 7.5) and injections were done using standard mouse transgenic protocols (41). dCas9-VP64 was inserted into the mouse Hipp11 locus and sgRNAs into the Rosa26 locus. Mice were genotyped using the using the KAPA mouse genotyping kit. F0 TARGATT knock-ins were assessed using PCR7+8, PCR1 described in (PMID: 21464299) along with vector insertion specific dCas9-VP64 primers as well as mCherry specific primers. All mice were fed ad libitum Picolab mouse diet 20, 5058 containing 20% protein, 9% fat, 4% fibre for whole study. Calories provided by: Protein, % 23.210 Fat (ether extract), % 21.559 Carbohydrates, % 55.231. All animal work was approved by the UCSF Institutional Animal Care and Use Committee.

Mouse Body Weight Measurements.

$H11P^{CAG-dCas9-VP64}$, $ROSA26^{Sim1Pr-sgRNA}$ and $ROSA26^{SCE2En-sgRNA}$ mice were mated with FVB mice for 3-5 generations to assess germline transmission. Three independent integrants were used from each line to set up matings. $H11P^{CAG-dCas9-VP64}$ were mated with $Sim1^{+/-}$ and subsequent $Sim1^{+/-}$ X $H11P^{CAG-dCas9-VP64}$ mice were rossed with either $ROSA26^{Sim1Pr-sgRNA}$ or $ROSA26^{SCE2En-sgRNA}$ to generate mice having all three unlinked alleles. Mice were maintained at Picodiet 5058 throughout the study and at least 6 females and 6 males from all genotypes (wild-type littermates, $Sim1^{+/-}$, $Sim1^{+/-}$ X $H11P^{CAG-dCas9-VP64}$, $Sim1^{+/-}$ X $H11P^{CAG-dCas9-VP64}$ X $ROSA26^{Sim1Pr-sgRNA}$, $Sim1^{+/-}$ X $H11P^{CAG-dCas9-VP64}$ X $ROSA26^{SCE2En-sgRNA}$) were measured for their body weights from 4-16 weeks of age on a weekly basis.

Mouse Metabolic Profiling

Metabolic rates from individual mice were measured using the Columbus Instruments Comprehensive Lab Animal Monitoring System (CLAMS; Columbus Instruments). Mice were single housed and acclimatized on powdered picodiet 5058 for 3-4 days before performing the metabolic monitoring. We individually housed mice in CLAMS units and measurements were carried out over 4-5 days. The temperature was maintained at 22° C. and oxygen and carbon dioxide were calibrated with 'Air reference' set at 20.901 and 0.0049. Three males and three females from each genotype: wild-type littermates, $Sim1^{+/-}$, $Sim1^{+/-}$ X $H11P^{CAG-dCas9-VP64}$ X $ROSA26^{Sim1Pr-sgRNA}$, $Sim1^{+/-}$ X $H11P^{CAG-dCas9-VP64}$ X $ROSA26^{SCE2En-sgRNA}$ were measured. with metabolic parameter (VCO2, VO2, RER, food intake, and activity monitoring). Metabolic data was analyzed using CLAX support software (Columbus Instruments).

Body Composition Analysis

Body composition was measured using either Dual Energy X-ray Absorptiometry (DEXA) or Echo Magnetic Resonance Imaging (EchoMRI; Echo Medical System). For DEXA, mice anesthetized using isoflurane were measured for bone mineral density and tissue composition (fat mass and lean mass) using the Lunar PIXImus. EchoMRI (Echo Medical System) was used to measure whole body composition parameters such as total body fat, lean mass, body fluids, and total body water in live mice without the need for anesthesia or sedation.

Stereotaxic Injections

Four week-old $Sim1^{+/-}$ males or females, weighing between 22 and 26 g, were housed individually in cages for at least 2 days before surgical interventions. Mice were anesthetized with a 100 mg/kg Avertin intraperitoneal injection. The skull was immobilized in a stereotaxic apparatus (David Kopf Instruments). The stereotaxic coordinates for injection into the PVN were 0.80 mm caudal to bregma, 0 mm at the midline, and 5.2 mm below the surface of the skull. A 1.5 mm hole was created in the cranium by circular movements using hand-held Dumont 5-45 tweezers (Fine Science Tools). Using a 31 gauge 1 ul Hamilton microsyringe, we injected a dose of $0.5 \times 10^7$ vg/ml of sgRNA-AAV along with $2.5 \times 10^6$ vg/kg of dCas-VP64-AAV, in a total injection volume of 1 ul per animal into the PVN unilaterally over a 10 minute period. After AAV delivery, the needle was left in place for 20 minutes to prevent reflux and slowly withdrawn in several steps, over 10 minutes. Mice were administered two doses of buprenorphine (100 mg/kg) before and 24 hours post surgery. Immunostaining for mCherry, as described below, was used to validate PVN injection coordinates 2-12 weeks following injection in several mice. Mice were maintained on a picodiet 5058 and weighed on a weekly basis.

Immunostaining

For immunostaining, mice were anesthetized with pentobarbital (7.5 mg/0.15 ml, i.p.) and transcardially perfused with 10 ml of heparinized saline (10 U/ml, 2 ml/min) followed by 10 ml of phosphate-buffered 4% paraformaldehyde (PFA). Brains were removed, postfixed for 24 hours in 4% PFA, and then equilibrated in 30% sucrose in PBS for 72 hours. Brains were coronally sectioned (35 microns for immunostaining, 50 m for stereology) on a sliding microtome (Leica SM 2000R). Immunohistochemistry was performed as previously described (19, 42, 43). Coronal brain sections that had been stored in PBS at 4° C. were permeabilized and blocked in 3% normal goat serum/0.3% Triton X-100 for 1 hour and incubated at 4° C. overnight using an mCherry antibody at a dilution of 1:500 (Abcam ab167453). Sections were placed in 4,6-diamidino-2-phenylindole (DAPI) (0.2 g/ml; 236276; Roche) for 10 minutes and then mounted on plus coated slides and coverslipped using Vectashield (H-1000; Vector Laboratories). Images of sections containing PVN were captured on a Zeiss Apotome.

REFERENCES

1 Dang, V. T., Kassahn, K. S., Marcos, A. E. & Ragan, M. A. Identification of human haploinsufficient genes and their genomic proximity to segmental duplications. *Eur J Hum Genet.* 16, 1350-1357. doi: 1310.1038/ejhg.2008.1111. Epub 2008 June 1354. (2008).
2 Huang, N., Lee, I., Marcotte, E. M. & Hurles, M. E. Characterising and predicting haploinsufficiency in the human genome. *PLoS Genet.* 6, e1001154. doi: 1001110.1001371/journal.pgen.1001154. (2010).
3 Lek, M. et al. Analysis of protein-coding genetic variation in 60,706 humans. *Nature.* 536, 285-291. doi: 210.1038/nature19057. (2016).
4 Bender, E. Gene therapy: Industrial strength. *Nature.* 537, S57-59. doi: 10.1038/1537S1057a. (2016).
5 Kotterman, M. A. & Schaffer, D. V. Engineering adeno-associated viruses for clinical gene therapy. *Nat Rev Genet.* 15, 445-451. doi: 410.1038/nrg3742. Epub 2014 May 1020. (2014).
6 Gilbert, L. A. et al. CRISPR-mediated modular RNA-guided regulation of transcription in eukaryotes. *Cell.* 154, 442-451. doi: 410.1016/j.cell.2013.1006.1044. Epub 2013 July 1011. (2013).
7 Perez-Pinera, P. et al. RNA-guided gene activation by CRISPR-Cas9-based transcription factors. *Nat Methods.* 10, 973-976. doi: 910.1038/nmeth.2600. Epub 2013 July 1025. (2013).
8 Konermann, S. et al. Genome-scale transcriptional activation by an engineered CRISPR-Cas9 complex. *Nature* (2014).
9 Hilton, I. B. et al. Epigenome editing by a CRISPR-Cas9-based acetyltransferase activates genes from promoters and enhancers. *Nat Biotechnol.* 33, 510-517. doi: 510.1038/nbt.3199. Epub 2015 April 1036. (2015).
10 Chavez, A. et al. Highly efficient Cas9-mediated transcriptional programming. *Nat Methods.* 12, 326-328. doi: 310.1038/nmeth.3312. Epub 2015 March 1032. (2015).
11 Michaud, J. L., Rosenquist, T., May, N. R. & Fan, C. M. Development of neuroendocrine lineages requires the bHLH-PAS transcription factor SIM1. *Genes Dev* 12, 3264-3275 (1998).
12 Beckers, S., Zegers, D., Van Gaal, L. F. & Van Hul, W. The role of the leptin-melanocortin signalling pathway in the control of food intake. *Crit Rev Eukaryot Gene Expr.* 19, 267-287. (2009).
13 Holder, J. L., Jr., Butte, N. F. & Zinn, A. R. Profound obesity associated with a balanced translocation that disrupts the SIM1 gene. *Hum Mol Genet* 9, 101-108 (2000).
14 Ahituv, N. et al. Medical sequencing at the extremes of human body mass. *Am J Hum Genet.* 80, 779-791. (2007).
15 Ramachandrappa, S. et al. Rare variants in single-minded 1 (SIM1) are associated with severe obesity. *J Clin Invest.* 123, 3042-3050. doi: 3010.1172/JCI68016. Epub 62013 June 68017. (2013).
16 Bonnefond, A. et al. Loss-of-function mutations in SIM1 contribute to obesity and Prader-Willi-like features. *J Clin Invest.* 123, 3037-3041. doi: 3010.1172/JCI68035. Epub 62013 June 68017. (2013).
17 Michaud, J. L. et al. Sim1 haploinsufficiency causes hyperphagia, obesity and reduction of the paraventricular nucleus of the hypothalamus. *Hum Mol Genet* 10, 1465-1473 (2001).
18 Tolson, K. P. et al. Postnatal Sim1 deficiency causes hyperphagic obesity and reduced Mc4r and oxytocin expression. *J* 30, 3803-3812. (2010).
19 Kublaoui, B. M., Holder, J. L., Jr., Tolson, K. P., Gemelli, T. & Zinn, A. R. SIM1 overexpression partially rescues agouti yellow and diet-induced obesity by normalizing food intake. *Endocrinology.* 147, 4542-4549. Epub 2006 May 4518. (2006).
20 Yang, C., Boucher, F., Tremblay, A. & Michaud, J. L. Regulatory interaction between arylhydrocarbon receptor and SIM1, two basic helix-loop-helix PAS proteins involved in the control of food intake. *J Biol Chem.* 279, 9306-9312. Epub 2003 December 9301. (2004).
21 Kim, M. J., Oksenberg, N., Hoffmann, T. J., Vaisse, C. & Ahituv, N. Functional characterization of SIM1-associated enhancers. *Hum Mol Genet* (2013).
22 Flint, J. & Shenk, T. Viral transactivating proteins. *Annu Rev Genet.* 31, 177-212. (1997).
23 Chavez, A. et al. Comparison of Cas9 activators in multiple species. *Nat Methods.* 13, 563-567. doi: 510.1038/nmeth.3871. Epub 2016 May 1023. (2016).
24 Tasic, B. et al. Site-specific integrase-mediated transgenesis in mice via pronuclear injection. *Proc Natl Acad Sci USA.* 108, 7902-7907. doi: 7910.1073/pnas.1019507108. Epub 1019502011 April 1019507104. (2011).
25 Su, A. I. et al. A gene atlas of the mouse and human protein-encoding transcriptomes. *Proc Natl Acad Sci USA.* 101, 6062-6067. Epub 2004 April 6069. (2004).
26 Wu, Z., Yang, H. & Colosi, P. Effect of genome size on AAV vector packaging. *Mol Ther.* 18, 80-86. doi: 10.1038/mt.2009.1255. Epub 2009 November 1010. (2010).
27 Zincarelli, C., Soltys, S., Rengo, G. & Rabinowitz, J. E. Analysis of AAV serotypes 1-9 mediated gene expression and tropism in mice after systemic injection. *Mol Ther.* 16, 1073-1080. doi: 1010.1038/mt.2008.1076. Epub 2008 April 1015. (2008).
28 Weise, A. et al. Microdeletion and microduplication syndromes. *J Histochem Cytochem.* 60, 346-358. doi: 310.1369/0022155412440001. Epub 0022155412442012 March 0022155412440006. (2012).
29 Horlbeck, M. A. et al. Nucleosomes impede Cas9 access to DNA and. *Elife.* 5., e12677. doi: 12610.17554/eLife.12677. (2016).
30 Otchy, T. M. et al. Acute off-target effects of neural circuit manipulations. *Nature.* 528, 358-363. doi: 310.1038/nature16442. Epub 12015 December 16449. (2015).
31 Bondy-Denomy, J., Pawluk, A., Maxwell, K. L. & Davidson, A. R. Bacteriophage genes that inactivate the CRISPR/Cas bacterial immune system. *Nature.* 493, 429-432. doi: 410.1038/nature11723. Epub 12012 December 11716. (2013).
32 Wang, D. et al. Adenovirus-Mediated Somatic Genome Editing of Pten by CRISPR/Cas9 in Mouse Liver in Spite of Cas9-Specific Immune Responses. *Hum Gene Ther.* 26, 432-442. doi: 410.1089/hum.2015.1087. (2015).
33 Chew, W. L. et al. A multifunctional AAV-CRISPR-Cas9 and its host response. *Nat Methods.* 13, 868-874. doi: 810.1038/nmeth.3993. Epub 2016 September 1035. (2016).
34 Donsante, A. et al. AAV vector integration sites in mouse hepatocellular carcinoma. *Science.* 317, 477. (2007).
35 Chandler, R. J. et al. Vector design influences hepatic genotoxicity after adeno-associated virus gene therapy. *J Clin Invest.* 125, 870-880. doi: 810.1172/JCI79213. Epub 72015 January 79220. (2015).
36 Nault, J. C. et al. Recurrent AAV2-related insertional mutagenesis in human hepatocellular carcinomas. *Nat Genet.* 47, 1187-1193. doi: 1110.1038/ng.3389. Epub 2015 August 1124. (2015).
37 Deng, W. et al. Reactivation of developmentally silenced globin genes by forced chromatin looping. *Cell.* 158, 849-860. doi: 810.1016/j.cell.2014.1005.1050. (2014).
38 Canver, M. C. et al. BCL11A enhancer dissection by Cas9-mediated in situ saturating mutagenesis. *Nature.* 527, 192-197. doi: 110.1038/nature15521. Epub 12015 September 15516. (2015).
39 Hirst, R. C., McCullagh, K. J. & Davies, K. E. Utrophin upregulation in Duchenne muscular dystrophy. *Acta Myol.* 24, 209-216. (2005).
40 Sproule, D. M. & Kaufmann, P. Therapeutic developments in spinal muscular atrophy. *Ther Adv Neurol Disord.* 3, 173-185. doi: 110.1177/1756285610369026. (2010).
41 Nagy, A., Gertsenstein, M., Vintersten, K. & Behringer, R. Manipulating the mouse embryo: A laboratory manual. 3rd edition edn, (Cold Spring Harbor, 2002).
42 Beuckmann, C. T. et al. Expression of a poly-glutamine-ataxin-3 transgene in orexin neurons induces narcolepsy-cataplexy in the rat. *J Neurosci.* 24, 4469-4477. (2004).
43 Kublaoui, B. M., Gemelli, T., Tolson, K. P., Wang, Y. & Zinn, A. R. Oxytocin deficiency mediates hyperphagic obesity of Sim1 haploinsufficient mice. *Mol Endocrinol.* 22, 1723-1734. doi: 1710.1210/me.2008-0067. Epub 2008 May 1721. (2008).

Although the foregoing invention has been described in some detail by way of illustration and example for purposes of clarity of understanding, one of skill in the art will appreciate that certain changes and modifications may be practiced within the scope of the appended claims. All patents, patent applications, and other publications, including GenBank Accession Numbers, Entrez Gene IDs, and publications referred to by pubmed ID (PMID), cited in this application are incorporated by reference in the entirety for all purposes.

What is claimed is:

1. A method of treating a haploinsufficiency disease in a mammalian subject, the method comprising contacting a cell of the subject with a composition comprising:
   i) a catalytically inactive CRISPR nuclease fused to a transcriptional activation domain, and
   ii) a guide RNA, wherein the guide RNA comprises:
      a) a targeting region that, under conditions present in a nucleus of the cell, specifically hybridizes to a promoter region or an enhancer region operably linked to a wild-type copy of a haploinsufficient gene; and
      b) a binding region that specifically binds the catalytically inactive CRISPR nuclease under conditions present in a nucleus of the cell,
   wherein the contacting forms a complex comprising the catalytically inactive CRISPR nuclease bound to the guide RNA, wherein the targeting region of the guide RNA in the complex is hybridized to the promoter or enhancer of the wild-type copy of the haploinsufficient gene; and
   wherein the complex activates transcription of the wild-type copy of the haploinsufficient gene in an amount and for a duration sufficient to treat the haploinsufficiency disease in the subject.

2. The method of claim 1, wherein the contacting comprises:
   (a) contacting the cell with an episomal vector encoding the guide RNA or the catalytically inactive CRISPR nuclease; or
   (b) contacting the cell with an episomal vector encoding the guide RNA and the catalytically inactive CRISPR nuclease; or
   (c) contacting the cell with an episomal vector encoding the guide RNA and a second episomal vector encoding the catalytically inactive CRISPR nuclease; or
   (d) injection of nucleic acid encoding the guide RNA and/or the catalytically inactive CRISPR nuclease into a region of a brain containing a hypothalamus; or
   (e) injection of an adeno-associated viral vector comprising nucleic acid encoding the guide RNA and/or the catalytically inactive CRISPR nuclease into a region of a brain containing a hypothalamus.

3. The method of claim 2, wherein the episomal vector(s):
(a) are non-integrating; and/or
(b) are non-replicating; and/or
(c) are adeno-associated virus (AAV) vectors; and/or
(d) independently comprise a first and a second end, wherein the first end and second end each independently comprise an AAV inverted terminal repeat.

4. The method of claim 1, wherein the catalytically inactive CRISPR nuclease comprises (i) a nuclease domain that has been modified to eliminate nuclease and nicking activity and (ii) a transcriptional activation domain, and/or a D10A, H840A *S. pyogenes* dCas9.

5. The method of claim 1, wherein the catalytically inactive CRISPR nuclease is a catalytically inactive CRISPR nuclease-VP64 fusion polypeptide.

6. The method of claim 1, wherein the haploinsufficient gene is SCN1A, SCN2A, SIM1, or MC4R.

7. The method of claim 1, wherein the cell is a non-dividing cell, a neuron, or a hypothalamus cell.

8. The method of claim 1, wherein the haploinsufficiency disease is selected from the group consisting of obesity, autism, epilepsy, intellectual disability, aniridia, and polycystic kidney disease.

\* \* \* \* \*